US012624070B2

(12) United States Patent
Stoveken et al.

(10) Patent No.: US 12,624,070 B2
(45) Date of Patent: May 12, 2026

(54) HIGH CONTRAST PHOTOCONVERTIBLE FLUORESCENT PROTEINS AND METHODS OF USE

(71) Applicant: Board of Regents, The University of Texas System, Austin, TX (US)

(72) Inventors: Brian J. Stoveken, San Antonio, TX (US); James D. Lechleiter, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 981 days.

(21) Appl. No.: 17/619,382

(22) PCT Filed: Jun. 19, 2020

(86) PCT No.: PCT/US2020/038749
§ 371 (c)(1),
(2) Date: Dec. 15, 2021

(87) PCT Pub. No.: WO2020/257659
PCT Pub. Date: Dec. 24, 2020

(65) Prior Publication Data
US 2022/0259271 A1     Aug. 18, 2022

Related U.S. Application Data

(60) Provisional application No. 62/863,517, filed on Jun. 19, 2019.

(51) Int. Cl.
*C07K 14/435*          (2006.01)
(52) U.S. Cl.
CPC .............................. *C07K 14/43504* (2013.01)
(58) Field of Classification Search
CPC ................................................ C07K 14/43504
See application file for complete search history.

(56) References Cited

FOREIGN PATENT DOCUMENTS

WO      WO-2018/132842 A1      7/2018

OTHER PUBLICATIONS

Wiedenmann et al., "EosFP, a fluorescent marker protein with UV-inducible green-to-red fluorescence conversion", PNAS, 2004, vol. 101, No. 45, pp. 15905-15910.*
Alieva et al., "Diversity and evolution of coral fluorescent proteins", PLoS One, 3:E2680-E2680 (2008).*
Nienhaus et al., "Structural basis for photo-induced protein cleavage and green-to-red conversion of fluorescent protein EosFP", PNAS, 2005, vol. 102, No. 26, pp. 9156-9159.*
Carter et al., "Cloning of anthozoan fluorescent protein genes", Comp. Biochem. Physiol., Part C; 2004, vol. 138, pp. 259-270.*

Sun et al., "Biophysical characterization of natural and mutant fluorescent proteins cloned from zooxanthellate corals", FEBS Lett., 2004, vol. 570, Iss. 1-3, pp. 175-183.*
U.S. Appl. No. 62/863,517, filed Jun. 19, 2019, Brian J. Stoveken.
PCT, PCT/US2020/038749 (WO 2020/257659), Jun. 19, 2020 (Dec. 24, 2020), Brian J. Stoveken (Board of Regents, The University of Texas System).
Adam, V., et al. Structural Basis of Enhanced Photoconversion Yield in Green Fluorescent Protein-like Protein Dendra2. Biochemistry 48, 4905-4915 (2009).
Annibale, P., et al. Photoactivatable Fluorescent Protein mEos2 Displays Repeated Photoactivation after a Long-Lived Dark State in the Red Photoconverted Form. J. Phys. Chem. Lett. 1, 1506-1510 (2010).
Annibale, P., et al. Quantitative Photo Activated Localization Microscopy: Unraveling the Effects of Photoblinking. PLOS One 6, e22678 (2011).
Avilov, S. et al. In cellulo Evaluation of Phototransformation Quantum Yields in Fluorescent Proteins Used As Markers for Single-Molecule Localization Microscopy. PLOS One 9, (2014).
Baldering, T. N. et al. Synthetic and genetic dimers as quantification ruler for single-molecule counting with PALM. Mol. Biol. Cell mbcE18100661 (2019).
Berardozzi, R., et al. Arginine 66 Controls Dark-State Formation in Green-to-Red Photoconvertible Fluorescent Proteins. J. Am. Chem. Soc. 138, 558-565 (2016).
Betzig, E. et al. Imaging intracellular fluorescent proteins at nanometer resolution. Science 313, 1642-1645 (2006).
Bhattacharjee, N. & Biswas, P. Position-specific propensities of amino acids in the β-strand. BMC Struct. Biol. 10, 29 (2010).
Chudakov, D. M. et al. Photoswitchable cyan fluorescent protein for protein tracking. Nat. Biotechnol. 22, 1435-1439 (2004).
De Zitter, E. et al. Mechanistic investigation of mEos4b reveals a strategy to reduce track interruptions in sptPALM. bioRxiv 475939 (2018).
Duan, C. et al. Structural Evidence for a Two-Regime Photobleaching Mechanism in a Reversibly Switchable Fluorescent Protein. J. Am. Chem. Soc. 135, 15841-15850 (2013).
Duan, C. et al. Rational design of enhanced photoresistance in a photoswitchable fluorescent protein. Methods Appl. Fluoresc. 3, 014004 (2015).
Ehrig, T., et al. Green-fluorescent protein mutants with altered fluorescence excitation spectra. FEBS Lett. 367, 163-166 (1995).
Fricke, F., et al. One, two or three? Probing the stoichiometry of membrane proteins by single-molecule localization microscopy. Sci. Rep. 5, 14072 (2015).
Fron, E. et al. Revealing the Excited-State Dynamics of the Fluorescent Protein Dendra2. J. Phys. Chem. B 117, 2300-2313 (2013).
Goedhart, J. et al. Structure-guided evolution of cyan fluorescent proteins towards a quantum yield of 93%. Nat. Commun. 3, 751 (2012).

(Continued)

*Primary Examiner* — Suzanne M Noakes
(74) *Attorney, Agent, or Firm* — BALLARD SPAHR LLP

(57) ABSTRACT

Disclosed herein, are photoconvertible fluorescent proteins or analogs thereof, and in particular, green-to-red photoconvertible fluorescent proteins or analogs thereof of the EosFP family; and compositions comprising the same and methods for analyzing a physiologically active substance in a cell wherein the fluorescent proteins are expressed in the cell.

13 Claims, 70 Drawing Sheets

Specification includes a Sequence Listing.

(56)                    References Cited

OTHER PUBLICATIONS

Goedhart, J. et al. Bright cyan fluorescent protein variants identified by fluorescence lifetime screening. Nat. Methods 7, 137-139 (2010).

Habuchi, S., et al. mKikGR, a Monomeric Photoswitchable Fluorescent Protein. PLOS One 3, e3944 (2008).

Heim, R., et al. Wavelength mutations and posttranslational autoxidation of green fluorescent protein. Proc. Natl. Acad. Sci. U. S. A. 91, 12501-12504 (1994).

Henderson, J. N., et al. Structural basis for reversible photobleaching of a green fluorescent protein homologue. Proc. Natl. Acad. Sci. 104, 6672-6677 (2007).

Hense, et al. Exploring color tuning strategies in red fluorescent proteins, Photochem. Photobiol. Sci., Feb. 2015, vol. 14, No. 2, pp. 200-212.

Hoi, H. et al. A Monomeric Photoconvertible Fluorescent Protein for Imaging of Dynamic Protein Localization. J. Mol. Biol. 401, 776-791 (2010).

Kremers, G.-J. & Piston, D. Photoconversion of Purified Fluorescent Proteins and Dual-probe Optical Highlighting in Live Cells. JoVE J. Vis. Exp. e1995 (2010).

Lambert, T. J. FPbase: a community-editable fluorescent protein database. Nat. Methods 16, 277 (2019).

Lee, S.-H., et al. Counting single photoactivatable fluorescent molecules by photoactivated localization microscopy (PALM). Proc. Natl. Acad. Sci. U. S. A. 109, 17436-17441 (2012).

Lewis, A. K. et al. Oxidation increases the strength of the methionine-aromatic interaction. Nat. Chem. Biol. 12, 860-866 (2016).

Mcevoy, A. L. et al. mMaple: A Photoconvertible Fluorescent Protein for Use in Multiple Imaging Modalities. PLoS One 7, (2012).

Paez Segala, M. G. et al. Fixation-resistant photoactivatable fluorescent proteins for correlative light and electron microscopy. Nat. Methods 12, 215-218 (2015).

Pal, D. & Chakrabarti, P. Non-hydrogen bond interactions involving the methionine sulfur atom. J. Biomol. Struct. Dyn. 19, 115-128 (2001).

Reid, K. S. C., et al. Sulphur-aromatic interactions in proteins. FEBS Lett. 190, 209-213 (1985).

Sanders, D. W. et al. Distinct tau prion strains propagate in cells and mice and define different tauopathies. Neuron 82, 1271-1288 (2014).

Shu, X., et al. Novel Chromophores and Buried Charges Control Color in mFruits,.Biochemistry 45, 9639-9647 (2006).

Studier, F. W. Protein production by auto-induction in high density shaking cultures. Protein Expr. Purif. 41, 207-234 (2005)).

Subach, F. V. et al. Photoactivation mechanism of PAmCherry based on crystal structures of the protein in the dark and fluorescent states. Proc. Natl. Acad. Sci. U. S. A. 106, 21097-21102 (2009).

Takaba, K. et al. Subatomic resolution X-ray structures of green fluorescent protein. IUCrJ 6, 387-400 (2019).

Thédié, D., et al. Photoswitching of Green mEos2 by Intense 561 nm Light Perturbs Efficient Green-to-Red Photoconversion in Localization Microscopy. J. Phys. Chem. Lett. 8, 4424-4430 (2017).

Tsutsui, H., et al. Semi-rational engineering of a coral fluorescent protein into an efficient highlighter. EMBO Rep. 6, 233-238 (2005).

Turkowyd Bartosz et al. A General Mechanism of Photoconversion of Green-to-Red Fluorescent Proteins Based on Blue and Infrared Light Reduces Phototoxicity in Live-Cell Single-Molecule Imaging. Angew. Chem. Int. Ed. 56, 11634-11639 (2017).

Valley, C. C. et al. The Methionine-aromatic Motif Plays a Unique Role in Stabilizing Protein Structure. J. Biol. Chem. 287, 34979-34991 (2012).

Wachter, R. M. Chromogenic Cross-Link Formation in Green Fluorescent Protein. Acc. Chem. Res. 40, 120-127 (2007).

Wang, S., et al. Characterization and development of photoactivatable fluorescent proteins for single-molecule-based superresolution imaging. Proc. Natl. Acad. Sci. U. S. A. 111, 8452-8457 (2014).

International Search Report and Written Opinion were mailed on Nov. 24, 2020 by the International Searching Authority for International Application No. PCT/US2020/038749, filed on Jun. 19, 2020 and published as WO/2020/257659 on Dec. 24, 2020 (Applicant—Board of Regents, The University of Texas System) (10 Pages).

* cited by examiner

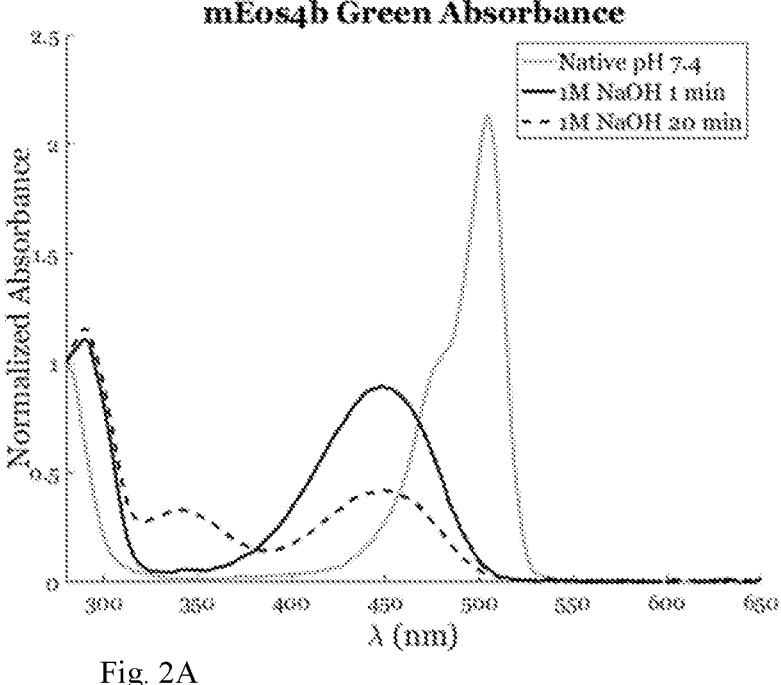
Fig. 2A
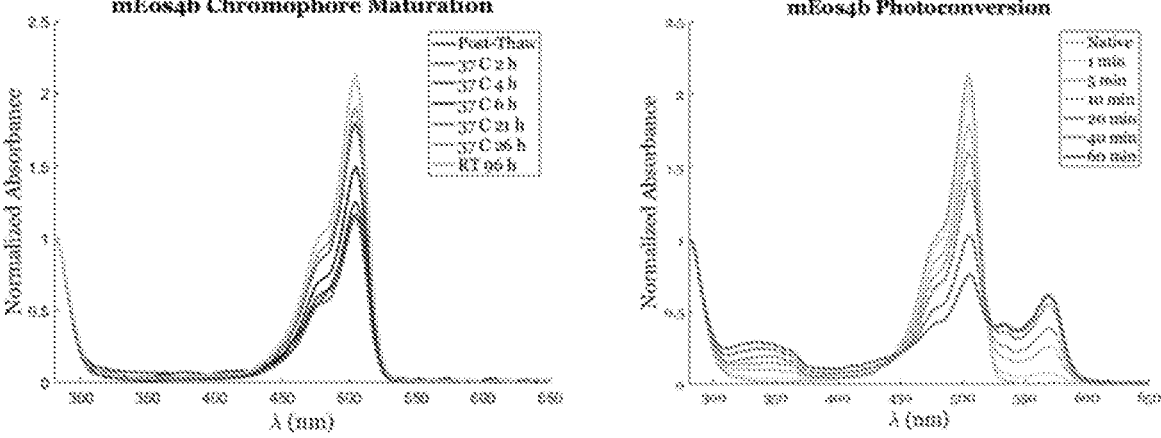
Fig. 2B                                        Fig. 2C mEos2 mEos2
-A69T mEos2

KikGR mEos2

Fig. 11A
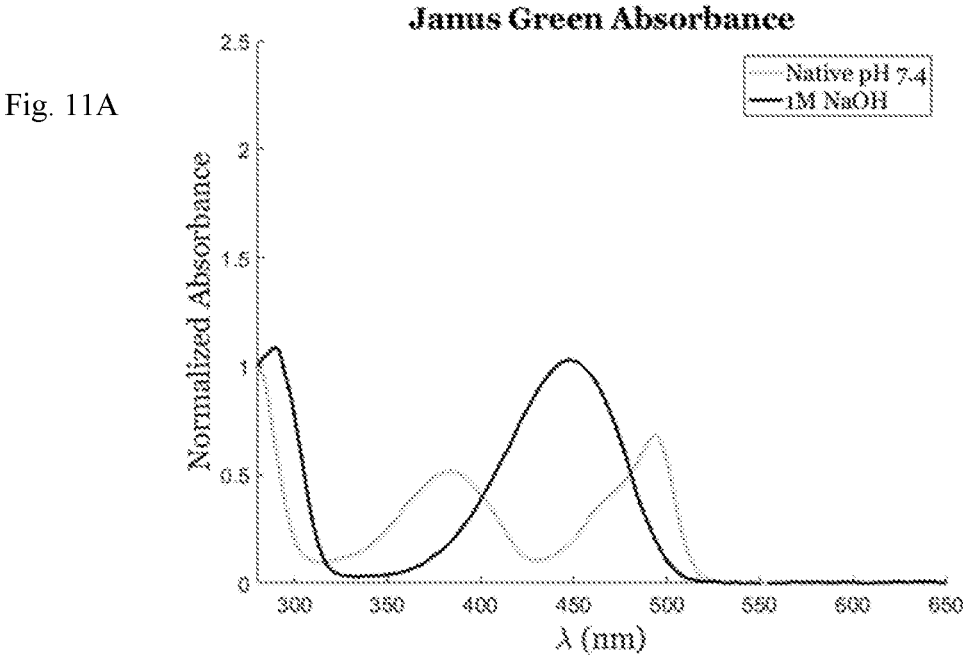
Fig. 11B
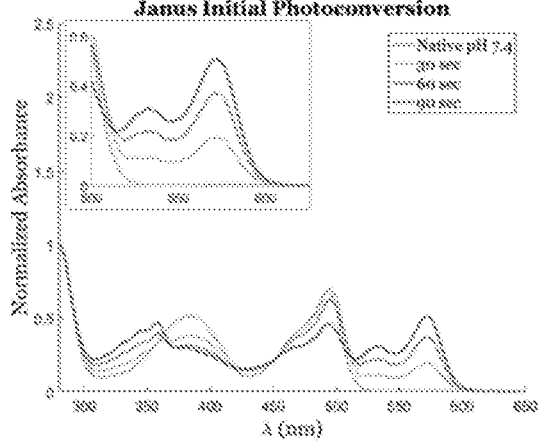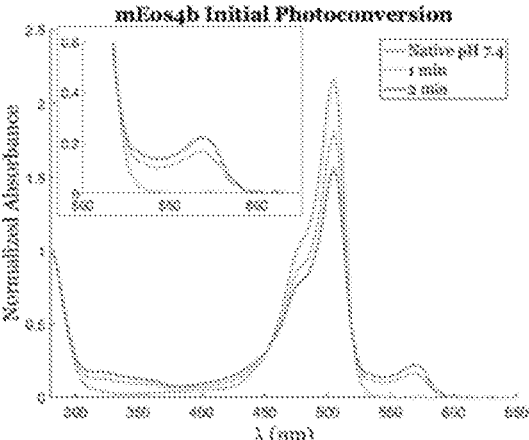

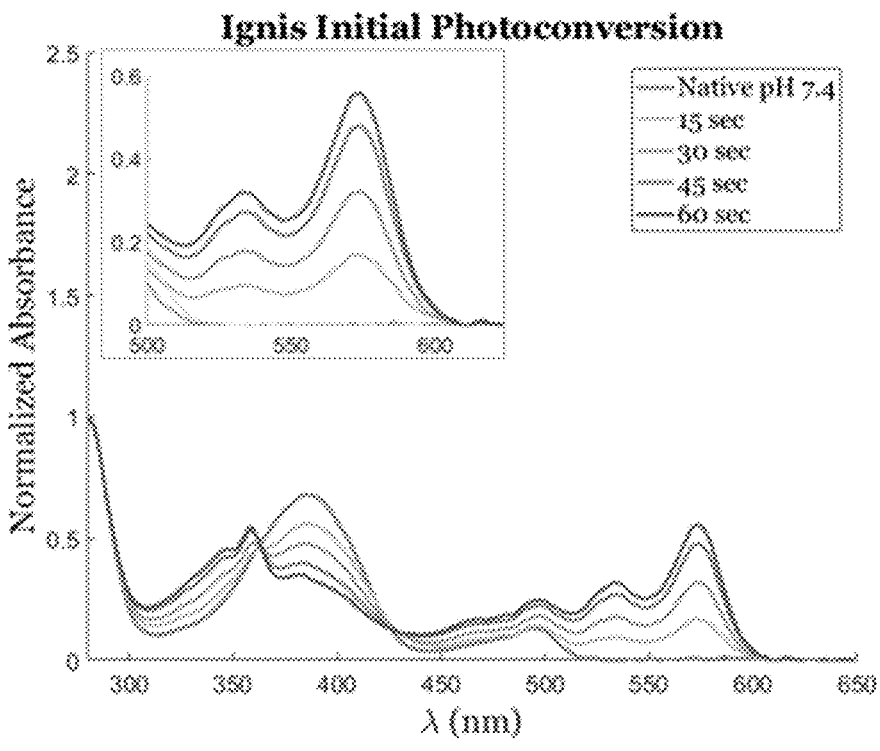
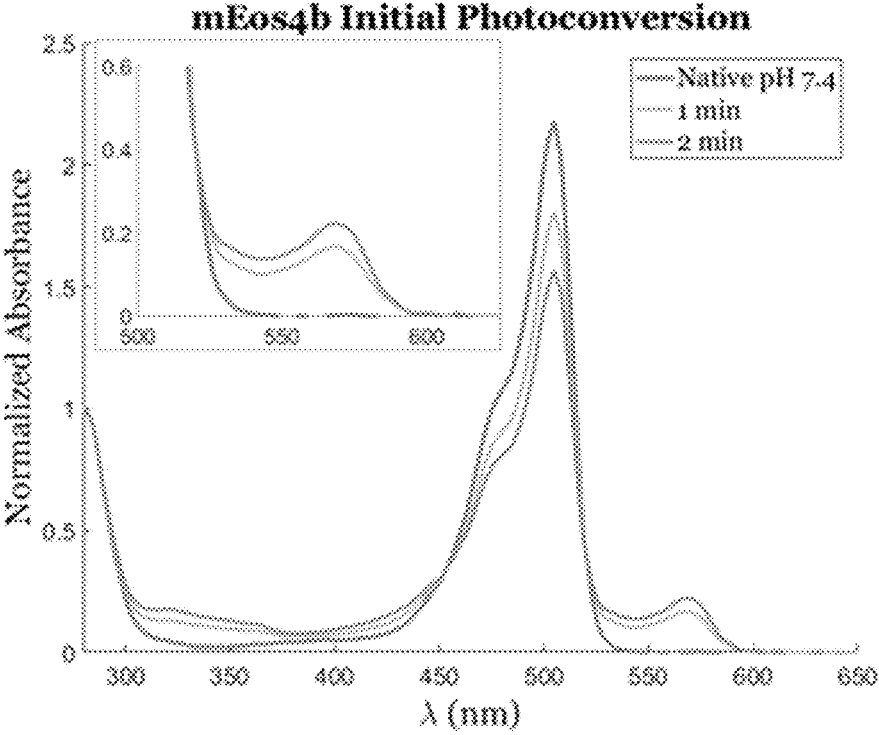
Fig. 15B

Janus Photoconversion Contrast mEos4b Photoconversion Contrast

Sum of Frames
(Z-Projection)

PALM
Rendering

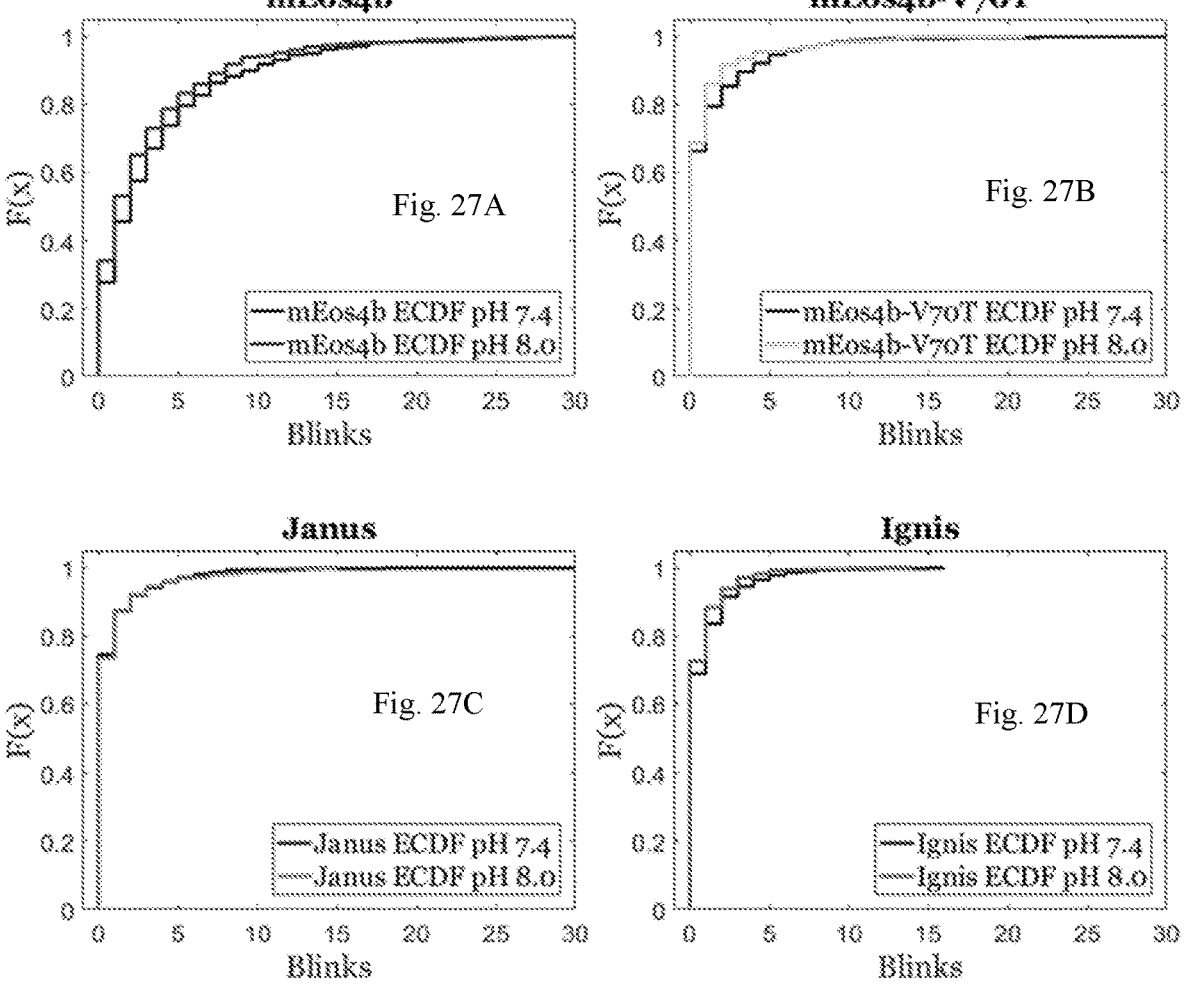

Fig. 32A                                    Fig. 32B
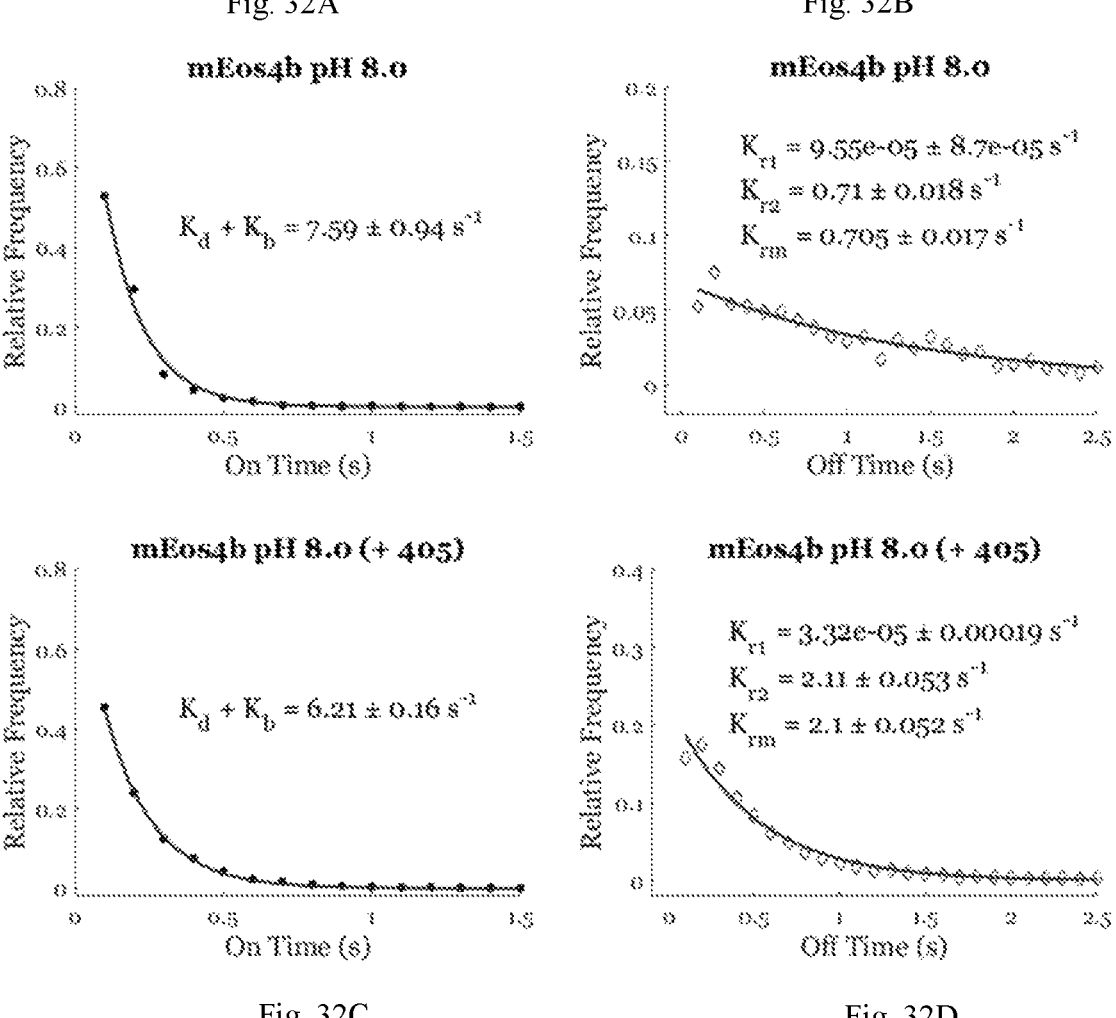
Fig. 32C                                    Fig. 32D

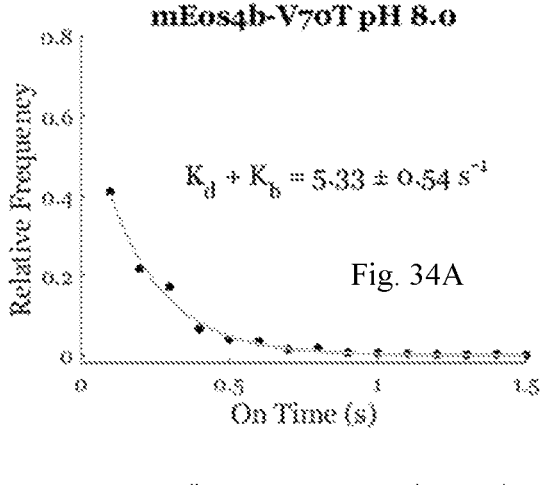
mEos4b-V70T pH 8.0
$K_d + K_b = 5.33 \pm 0.54\ s^{-1}$
Fig. 34A
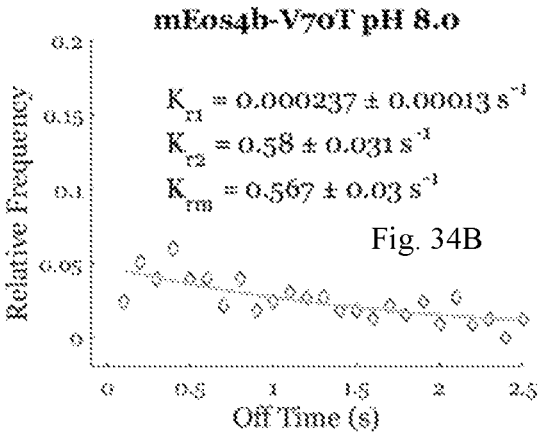
mEos4b-V70T pH 8.0
$K_{r1} = 0.000237 \pm 0.00013\ s^{-1}$
$K_{r2} = 0.58 \pm 0.031\ s^{-1}$
$K_{rm} = 0.567 \pm 0.03\ s^{-1}$
Fig. 34B
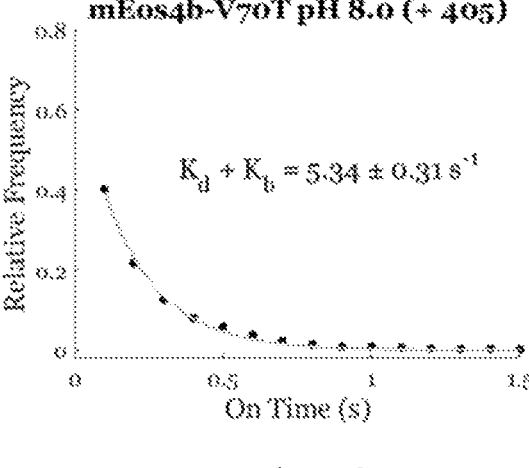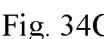
mEos4b-V70T pH 8.0 (+ 405)
$K_d + K_b = 5.34 \pm 0.31\ s^{-1}$
Fig. 34C
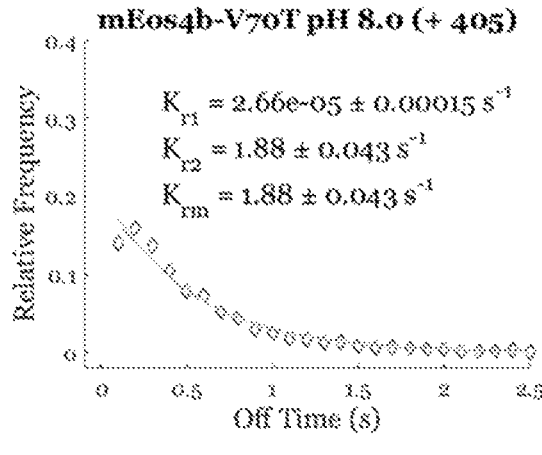
mEos4b-V70T pH 8.0 (+ 405)
$K_{r1} = 2.66e{-}05 \pm 0.00015\ s^{-1}$
$K_{r2} = 1.88 \pm 0.043\ s^{-1}$
$K_{rm} = 1.88 \pm 0.043\ s^{-1}$
Fig. 34D

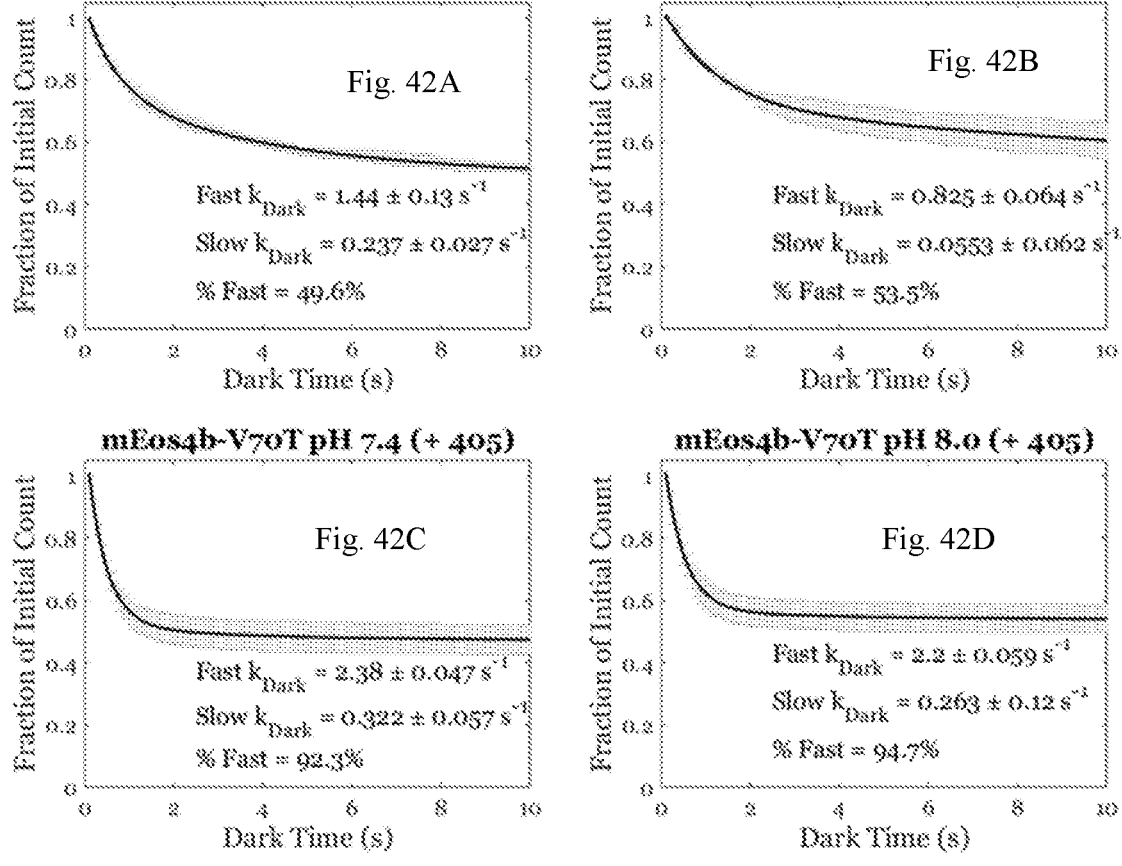

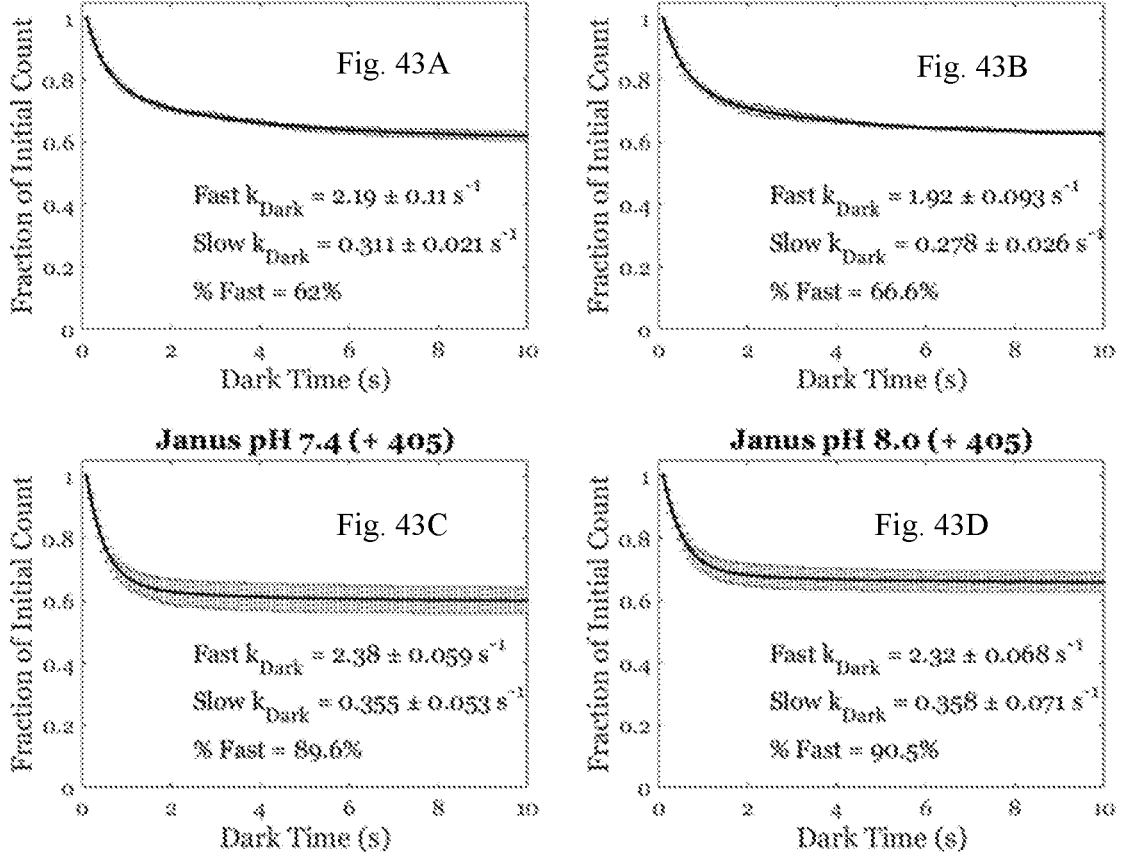

Ignis pH 7.4

Fast $k_{Dark}$ = 2.6 ± 0.085 s$^{-1}$
Slow $k_{Dark}$ = 0.322 ± 0.023 s$^{-1}$
% Fast = 76.1%

Ignis pH 8.0

Fast $k_{Dark}$ = 2.18 ± 0.089 s$^{-1}$
Slow $k_{Dark}$ = 0.256 ± 0.028 s$^{-1}$
% Fast = 74.1%

Ignis pH 7.4 (+ 405)

Fast $k_{Dark}$ = 2.54 ± 0.085 s$^{-1}$
Slow $k_{Dark}$ = 0.347 ± 0.029 s$^{-1}$
% Fast = 78.3%

Ignis pH 8.0 (+ 405)

Fast $k_{Dark}$ = 2.43 ± 0.065 s$^{-1}$
Slow $k_{Dark}$ = 0.372 ± 0.025 s$^{-1}$
% Fast = 78.7%

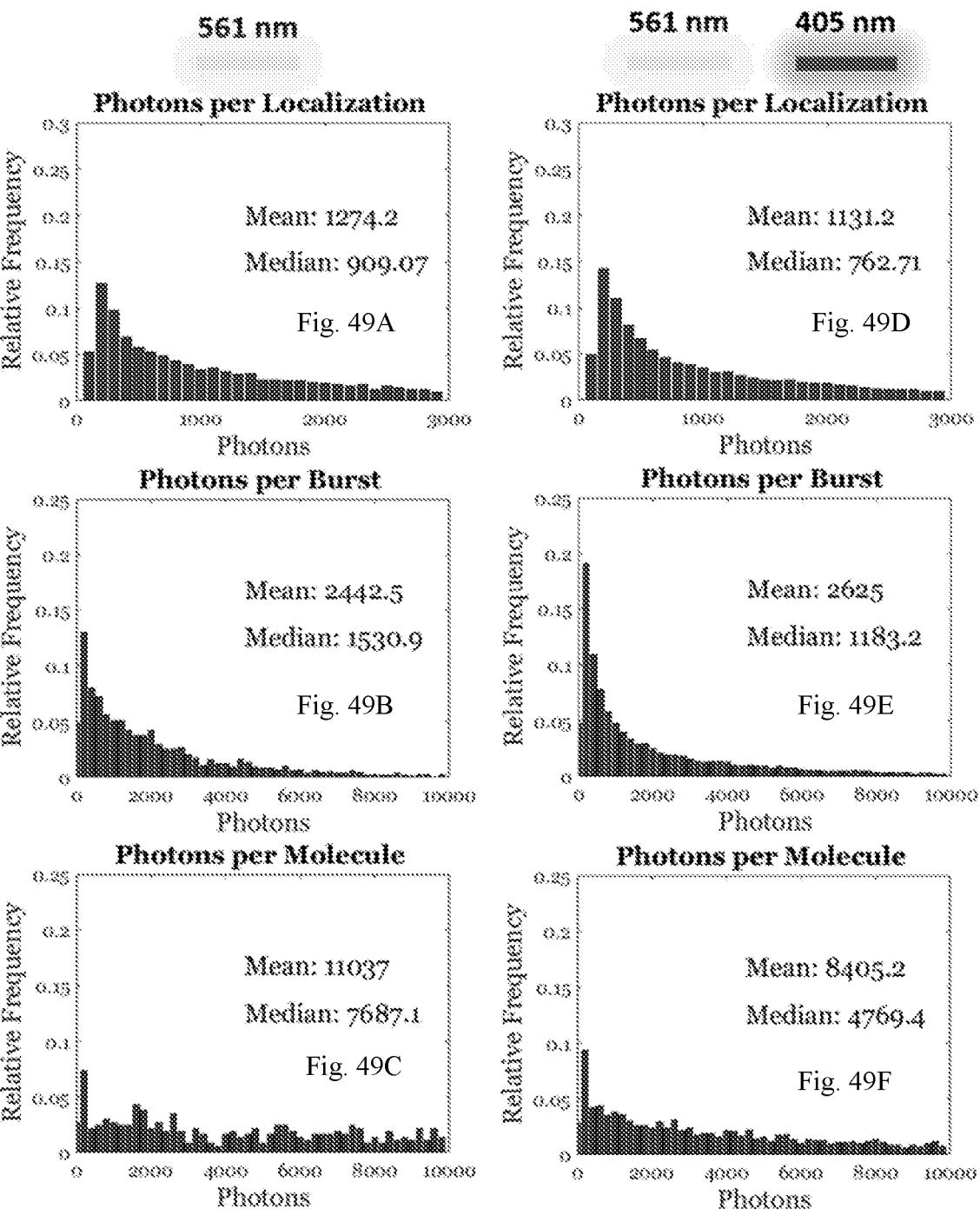

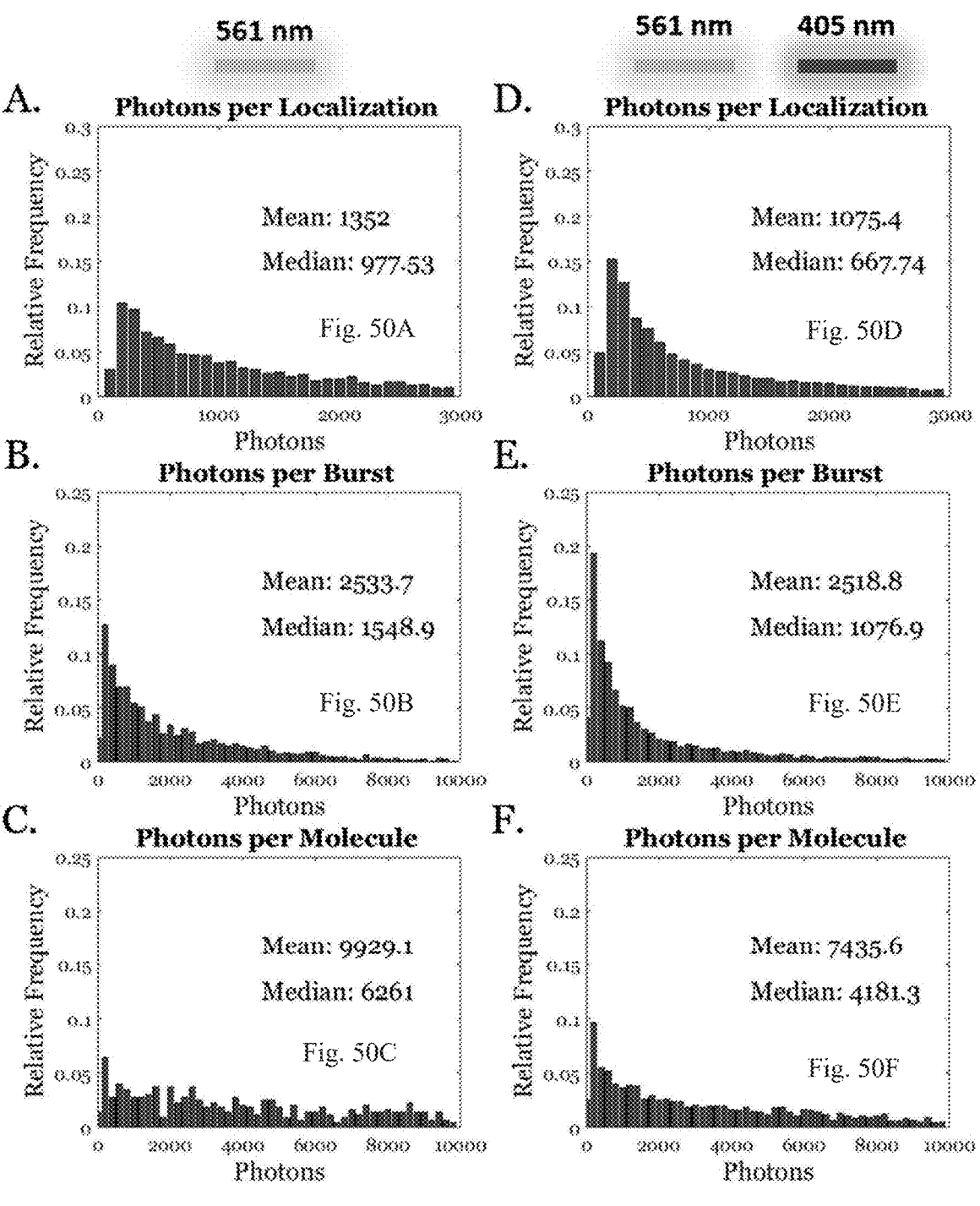

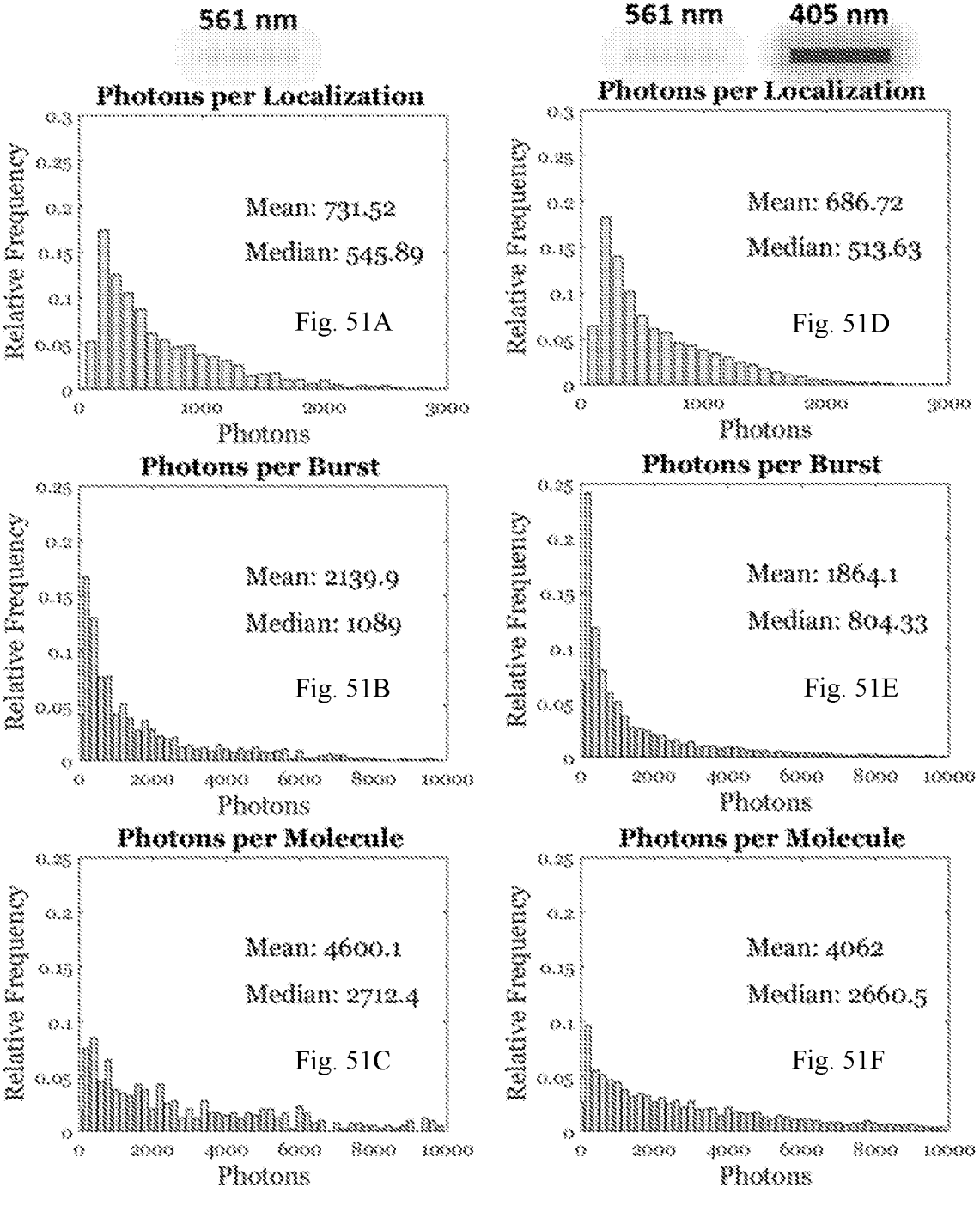

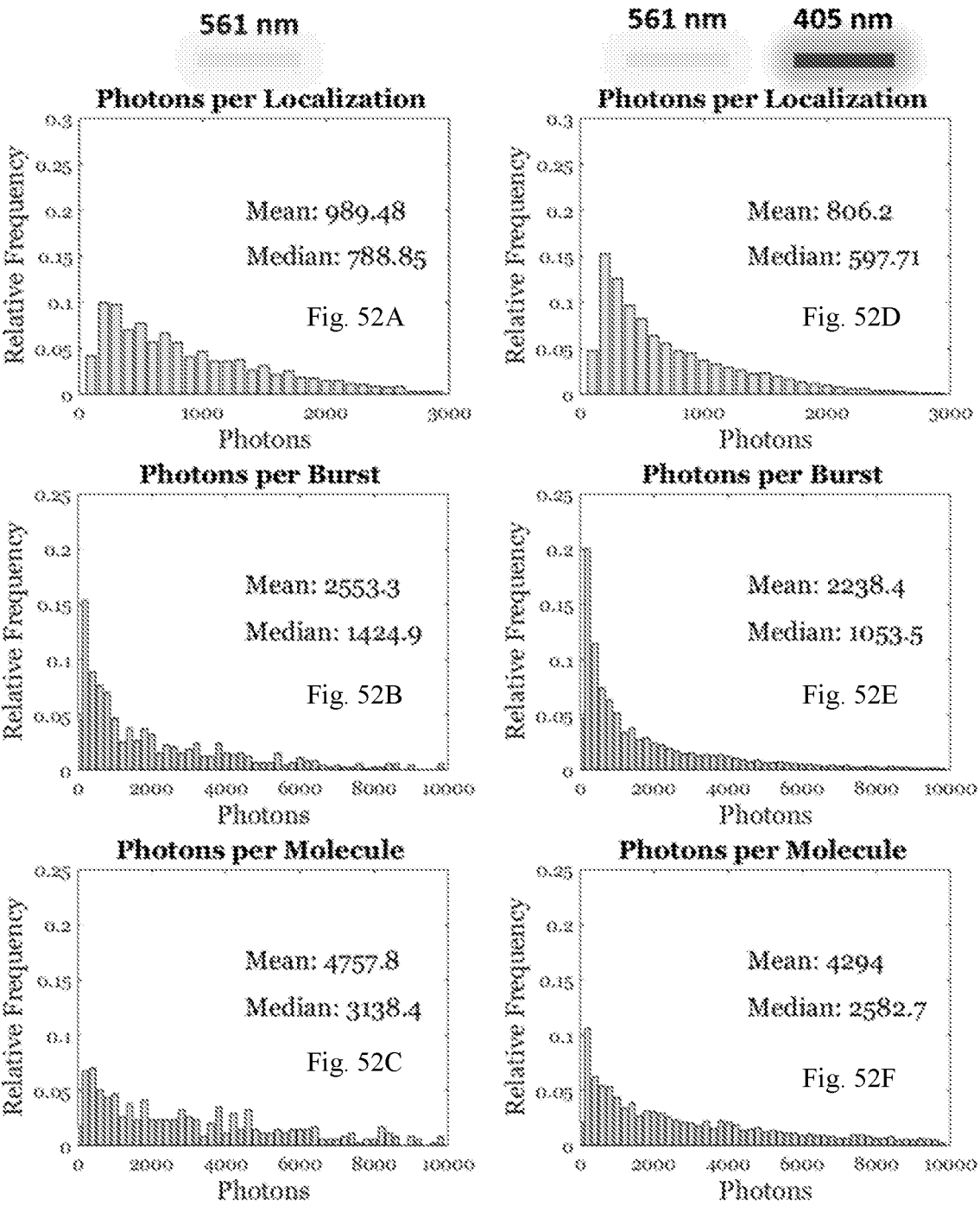

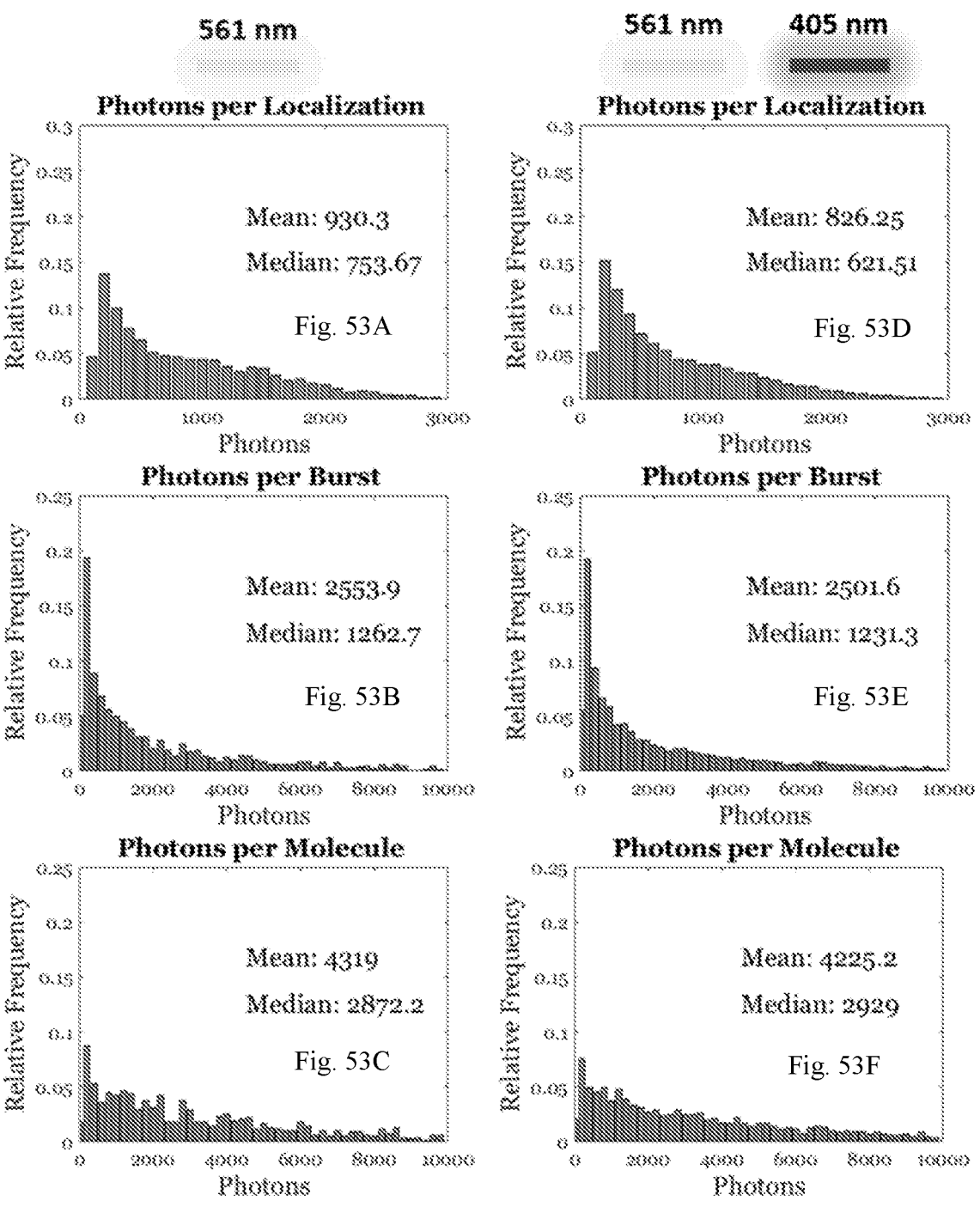

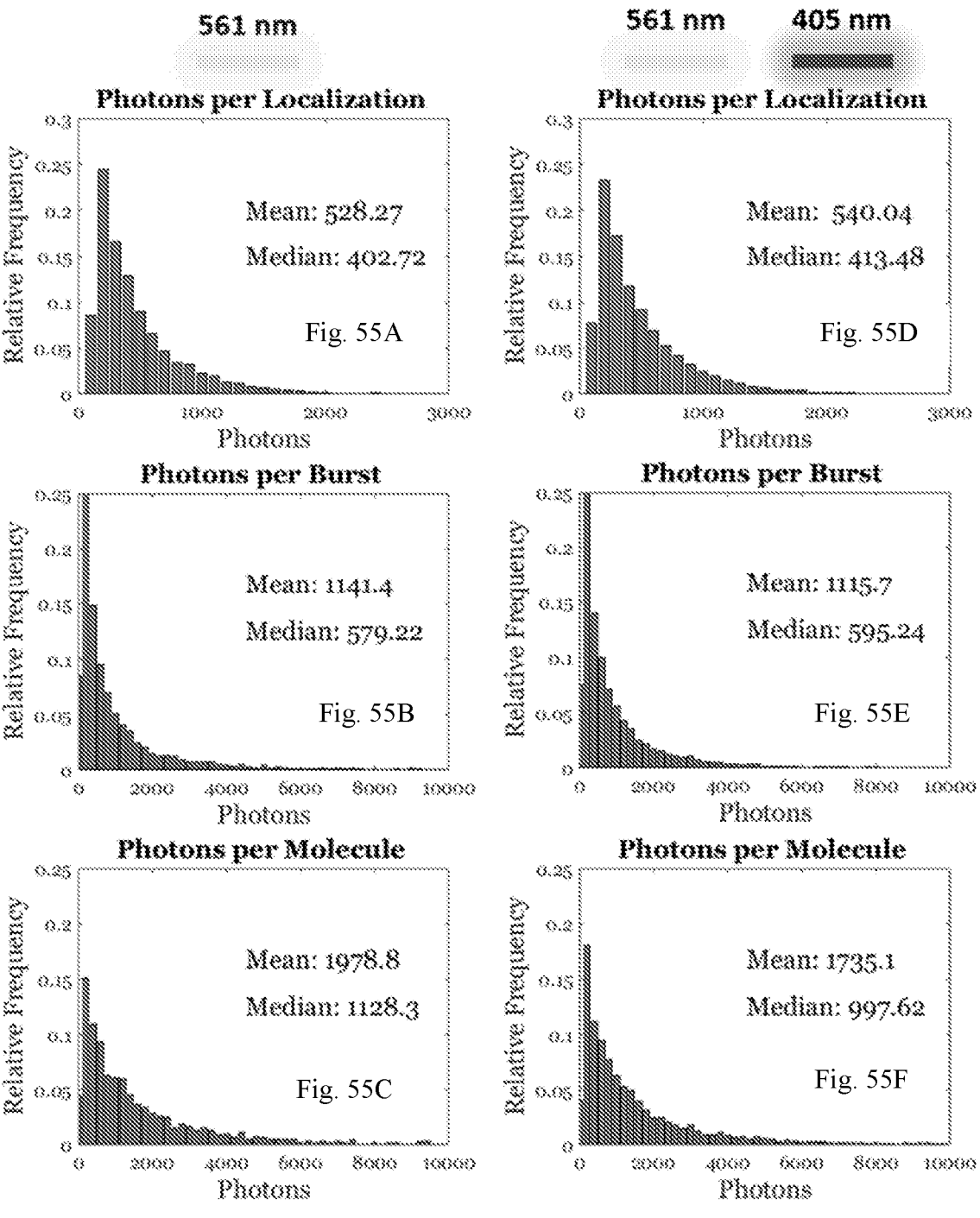

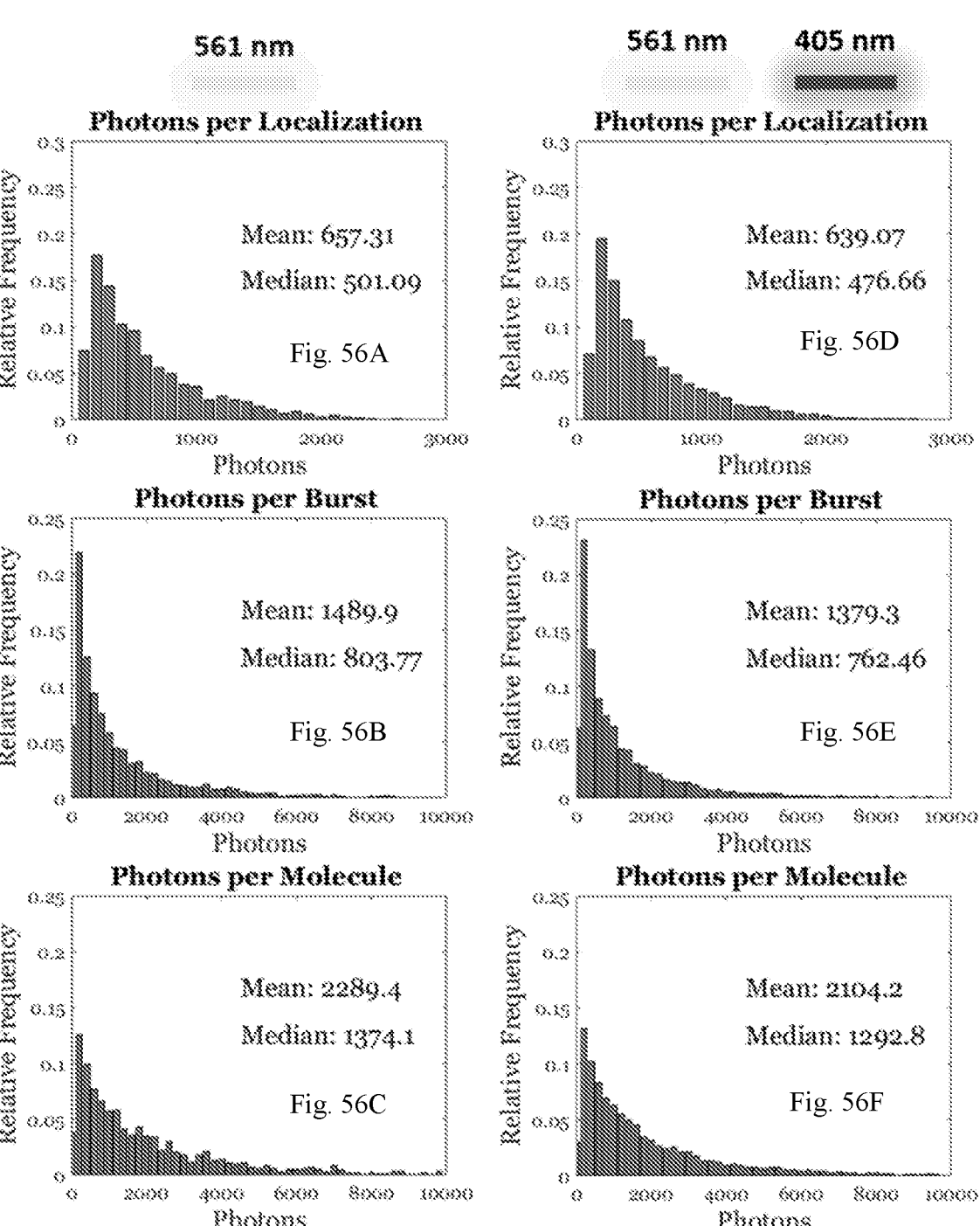

HIGH CONTRAST PHOTOCONVERTIBLE FLUORESCENT PROTEINS AND METHODS OF USE

CROSS-REFERENCE TO RELATED APPLICATIONS

This application is a national phase application under 35 U.S.C. § 371 of International Application No. PCT/US2020/038749, filed Jun. 19, 2020 and claims the benefit of the filing date of U.S. Provisional Application No. 62/863,517, filed on Jun. 19, 2019. The content of these earlier filed applications is hereby incorporated by reference in its entirety.

REFERENCE TO SEQUENCE LISTING

The Sequence Listing submitted herein as a text file named "21105_0072U2_SL.txt," created on Dec. 14, 2021, and having a size of 28,672 bytes is hereby incorporated by reference pursuant to 37 C.F.R. § 1.52 (e)(5).

BACKGROUND

Genetically-encoded photoconvertible fluorescent proteins are important tools for single molecule photoactivated localization microscopy, a technique that permits imaging below the diffraction limit with nanometer precision. Certain characteristics such as poor photoconversion contrast and high photoblinking of the bright, fixation-resistant, green-to-red photoconvertible fluorescent protein, mEos4b, limit its utility in quantitative applications. Alternative photoconvertible fluorescent proteins are desired that can enhance single molecule photoactivated localization microscopy and that can address the limitations of currently available photoconvertible fluorescent proteins.

SUMMARY

Disclosed herein are photoconvertible fluorescent proteins comprising one or more mutations or substitutions of the mEos4b protein coding sequence (SEQ ID NO: 1).

Disclosed herein are photoconvertible fluorescent proteins, wherein the photoconvertible fluorescent proteins comprise the coding region of the mEos4b protein, wherein the coding region comprises at least one or more mutations or substitutions.

Disclosed herein are photoconvertible fluorescent proteins, wherein the photoconvertible fluorescent proteins comprise the coding region of the mEos4b protein, wherein the coding region comprises a mutation or a substitution at residues 41 and 70, wherein the mutation or substitution at residue 41 is a methionine to an isoleucine residue mutation or substitution (Met4Ile); and the mutation or substitution at residue 70 is a valine to a threonine residue mutation or substitution (Val70Thr).

Disclosed herein are photoconvertible fluorescent proteins, wherein the photoconvertible fluorescent proteins comprise the coding region of the mEos4b protein, wherein the coding region comprises a mutation or a substitution at residues 41, 70 and 197, wherein the mutation or substitution at residue 41 is a methionine to an isoleucine residue mutation or substitution (Met41Ile); and the mutation or substitution at residue 70 is valine to a threonine residue mutation or substitution (Val70Thr); and the mutation or substitution at residue 197 is an isoleucine to a methionine residue mutation or substitution (Ile197Met).

BRIEF DESCRIPTION OF THE DRAWINGS

FIG. 1A shows the excitation and emission spectra of green mEos4b. FIG. 1B shows the excitation and emission spectra of red mEos4b after 385 nm LED photoconversion.

FIGS. 2A-C show the absorbance and photoconversion properties of mEos4b.

FIG. 2A) shows native (green) and alkali-denatured absorbance spectra of equimolar mEos4b solutions. Note the decay in absorbance of the denatured chromophore over time. FIG. 2B shows maturation of mEos4b chromophore absorbance. Peak absorbance at 505 nm increased with incubation at 37 C and room temperature (RT). Peak absorbance is achieved by 96 hours at room temperature. FIG. 2C shows progressive photoconversion of mEos4b in vitro with 385 nm LED illumination.

FIG. 3A shows the titration of the green mEos4b chromophore, and corresponding fit to the Henderson-Hasselbalch relationship. N=5. Mean±SD. Inset: Absorbance spectrum of mEos4b at each pH. Note sub-maximal absorbance since titrations were performed thawed solutions (see, FIG. 11). FIG. 3B shows the titration of the red mEos4b chromophore. N=3. Mean±SD.

FIG. 4A shows the photoconversion contrast of mEos4b (N=9), mEos3.2 (N=4), and Dendra2 (N=4) in Hela cells. Mean field average of contrast in individual cells ± SD. ****=p<0.001 by two-way ANOVA with Tukey's post-hoc test for multiple comparisons. FIG. 4B shows green state decay of mEos4b, mEos3.2 and Dendra2 in the same experiment. FIG. 4C shows the representative wide-field images of green channel (FITC filter set) and red channel (TRITC filter set, magenta pseudocolor). Note the increased intensity of mEos4b and mEos3.2 after 30 seconds of photoconversion.

FIG. 5A shows red Dendra2 fluorescence vs. initial green fluorescence. FIG. 5B shows a model of photoconversion pathways suggested by widefield results. FIG. 5C shows red mEos3.2 fluorescence vs. initial green fluorescence. 30 sec (blue) and 5 min (red). FIG. 5D shows red mEos3.2 fluorescence at 5 minutes vs. peak green fluorescence. FIG. 5E shows red mEos4b fluorescence vs. initial green fluorescence. 30 sec (blue) and 5 min (red). FIG. 5F shows red mEos4b fluorescence at 5 minutes vs. peak green fluorescence.

FIG. 7A shows Arg66-chromophore interaction in mEos2. Note hydrogen bond with imidazolinone carbonyl (PDB code: 3S05). FIG. 7B shows the disruption of Arg66-chromophore interaction by Arg66-Thr69 interaction in mEos2-A69T (PDB code: 5DTL). FIG. 7C shows the hydrophobic trio (Ile196-Leu210-Met40) lining the chromophore histidine in mEos2. FIG. 7D shows the flipped hydrophobic trio (Met199-Leu213-Val41) in KikGR (PDB code: 4P76). FIG. 7E show the distances between the Met40 thioether and chromophore histidine in mEo2 in two conformations.

FIG. 8A shows the titration of the green mEos4b-V70T chromophore, and corresponding fit to the Henderson-Hasselbalch relationship. N=3. Mean±SD. FIG. 8B shows the titration of the red mEos4b-V70T chromophore. N=3. Mean±SD.

FIG. 9A show the absorbance of equimolar solutions of native (green) and alkali-denatured mEos4b-V70T (black) in its green state. Note the prominent absorbance band of the neutral chromophore with peak at 385 nm. FIG. 9B shows the 385 nm LED photoconversion of mEos4b-V70T at early time points to screen for improved photoconversion. Note that mEos4b-V70T does not exhibit an increase in red chromophore absorbance in comparison to mE0s4b at the same time points.

FIG. 10A shows the absorbance of mEos4b-M41I in its native and photoconverted states (colored curves) vs. mEos4b (black curve). Note the substantially reduced green state absorbance of mEos4b-M41I. The variant retains photoconversion capability. FIG. 10B shows the green chromophore titration of mEos4b-M41I. N=4. Mean±SD.

FIGS. 11A-B show the absorbance and photoconversion properties of Janus. FIG. 11A shows the absorbance spectra of equimolar solutions of native and alkali-denatured Janus in its green state. FIG. 11B shows the enhanced photoconversion of Janus in vitro with 385 nm LED illumination. Note the more rapid accumulation of anionic red chromophore at 571 nm compared to mEos4b. mEos4b spectrum is a reproduction of data in FIG. 18B.

FIG. 12A shows the progressive photoconversion of Janus under 385 nm LED illumination. Note the increase and slight red shift in the absorbance maximum near 496 nm in the 1 minute spectrum. Additionally, the absorbance of neutral band in this experiment is reduced compared to FIG. 20, concomitant with slower red chromophore accumulation as a result of the slightly more alkaline buffer at pH 7.8. FIG. 12B shows progressive photoconversion of mEos4b under 385 nm LED illumination.

FIG. 13A shows the excitation and emission spectra of Janus in its green form. FIG. 13B shows the excitation and emission spectra of Janus in its red form after photoconversion with 385 nm LED illumination.

FIG. 14A shows the titration of the green Janus chromophore. N=3. Mean±SD. FIG. 14B shows the titration of the red Janus chromophore. N=3 Mean±SD.

FIGS. 15A-B show the absorbance and photoconversion properties of Ignis. FIG. 15A shows the absorbance of native (green curve) and alkali-denatured Ignis (dashed-black curve) in its green form. Note that that the majority of absorbance is accounted for by the neutral chromophore species with peak near 385 nm. FIG. 15B shows the photoconversion of Ignis relative to mEos4b. Note that absorbance of the red Ignis species accumulates nearly four times faster than mEos4b under identical conditions (insets).

FIG. 16A shows the titration of the green Ignis chromophore. N=3. Mean±SD. FIG. 16B the titration of the red Ignis chromophore. N=3. Mean±SD.

FIG. 17A shows the excitation and emission spectra of Ignis in its green form. FIG. 17B show the excitation and emission spectra of Ignis in its red form after photoconversion under 385 nm LED illumination.

FIG. 19A shows a representative confocal laser scanning micrographs of mEos4b and Janus protein droplets during progressive photoconversion by 405 nm laser illumination. FIG. 19B shows the quantification of red mEos4b fluorescence normalized to peak green fluorescence intensity. N=8. Mean±SD at each time point. FIG. 19C shows the quantification of red Janus fluorescence normalized to peak green fluorescence intensity. N=5. Mean±SD at each time point. FIG. 19D shows correlations between peak red and peak green fluorescence intensities of mEos4b (blue) and Janus (red) with 95% confidence intervals of the linear regression fits.

FIG. 20A shows fluorescence photoconversion contrast of Janus protein droplets. FIG. 20B show the fluorescence photoconversion contrast of mEos4b protein droplets. Inset: Expanded view of contrast values below 1.0.

FIG. 21A shows representative ratiometric micrographs of live HeLa cells expressing N-Myr-DmrB:PC-FP fusion proteins after 150 second and 300 seconds of 405 laser-mediated photoconversion, as well as histograms from independent measurement days. FIG. 21B shows the quantification of the average photoconversion contrast per field (sampled from multiple cells per field). N=16 (mEos3.2), 14 (Dendra2), 15 (mEos4b), 16 (mEos4b-V70T) and 15 (Janus). **=p<0.001, one-way ANOVA with Tukey's post hoc test for multiple comparisons. FIG. 21C** shows the mean initial green state fluorescence of each field analyzed. No significant differences, despite a weak trend toward lower Dendra2 fluorescence (p=0.182).

FIGS. 23A-B show PALM illumination schemes and the experimental overview. FIG. 23A shows two schemes with 405 nm pre-illumination followed by 561 nm excitation (Scheme 1) and concurrent illumination with both 561 and 405 nm laser light. FIG. 23B shows a representative in vitro PALM experiment illustrating spatially and temporally well-isolated signals from recombinant mEos4b molecules deposited on a clean glass coverslip.

FIGS. 27A-D show the comparison of PC-FP ECDFs at pH 8.0 and pH 7.4.ECDFs at pH 8.0 (colored lines) vs. pH 7.4 (black lines) for A) mEos4b, B) mEos4b-V70T, C) Janus, and D) Ignis.

FIG. 30A shows a representative fluorescence kymograph and corresponding intensity trace from a single mEos4b molecule, demonstrating multiple on and off states. FIG. 30B shows a simple kinetic model of on and off (dark) state transitions in green-t0-red, Kaede-like PC-FPs. Native (green) PC-FPs transition to red states upon absorption of U.V./violet light at $k_{PC}$, and irreversibly photobleach at $k_b$. Converted molecules can enter transient dark states at $k_d$, and return to the fluorescent red state at $k_r$.

FIGS. 31A and C show the on-time distributions of mEos4b molecules at pH7.4 in the presence and absence of 405 nm light, along with the monophasic exponential fit parameter, $k_{on}=(k_d+k_b)$. FIGS. 31B and D show the off-time distributions of mEos4b molecules at pH 7.4 in the presence and absence of 405 nm light, with biphasic exponential fit parameters, $k_{r1}$ and $k_{r2}$, as well as the monophasic exponential fit parameter $k_{rm}$.

FIGS. 32A-D show the distributions of mEos4b on and off times (pH 8.0). FIGS. 32A and C show the on-time distributions of mEos4b molecules at pH 8.0 in the presence and absence of 405 nm light, along with the monophasic exponential fit parameter, $k_{on}=(k_d+k_b)$.

FIGS. 32B and D show the off-time distributions of mEos4b molecules at pH 8.0 in the presence and absence of 405 nm light, with biphasic exponential fit parameters, $k_{r1}$ and $k_{r2}$, as well as the monophasic exponential fit parameter $k_{rm}$.

FIGS. 33A and C show the on-time distributions of mEos4b-V70T molecules at pH7.4 in the presence and absence of 405 nm light, along with the monophasic exponential fit parameter, $k_{on}=(k_d+k_b)$. FIGS. 33B and D show the off-time distributions of mEos4b-V70T molecules at pH 7.4 in the presence and absence of 405 nm light, with biphasic exponential fit parameters, $k_{r1}$ and $k_{r2}$, as well as the monophasic exponential fit parameter $k_{rm}$.

FIGS. 34A-D show the distributions of mEos4b-V70T on and off times (pH 8.0). FIGS. 34A and C show the on-time distributions of mEos4b-V70T molecules at pH 8.0 in the presence and absence of 405 nm light, along with the monophasic exponential fit parameter, $k_{on}=(k_d+k_b)$. FIGS. 34B and D show the off-time distributions of mEos4b-V70T molecules at pH 8.0 in the presence and absence of 405 nm light, with biphasic exponential fit parameters, $k_{r1}$ and $k_{r2}$, as well as the monophasic exponential fit parameter $k_{rm}$.

FIGS. 35A and C show the on-time distributions of Janus molecules at pH7.4 in the presence and absence of 405 nm light, along with the monophasic exponential fit parameter, $k_{on}=(k_d+k_b)$. FIGS. 35B and D show the off-time distributions of Janus molecules at pH 7.4 in the presence and absence of 405 nm light, with biphasic exponential fit parameters, $k_{r1}$ and $k_{r2}$, as well as the monophasic exponential fit parameter $k_{rm}$.

FIGS. 36A and C show the on-time distributions of Janus molecules at pH 8.0 in the presence and absence of 405 nm light, along with the monophasic exponential fit parameter, $k_{on}=(k_d+k_b)$. FIGS. 36B and D show the off-time distributions of Janus molecules at pH 8.0 in the presence and absence of 405 nm light, with biphasic exponential fit parameters, $k_{r1}$ and $k_{r2}$, as well as the monophasic exponential fit parameter $k_{rm}$.

FIGS. 37A and C show the on-time distributions of Janus molecules at pH7.4 in the presence and absence of 405 nm light, along with the monophasic exponential fit parameter, $k_{on}=(k_d+k_b)$. FIGS. 37B and D show the off-time distributions of Ignis molecules at pH 7.4 in the presence and absence of 405 nm light, with biphasic exponential fit parameters, $k_{r1}$ and $k_{r2}$, as well as the monophasic exponential fit parameter $k_{rm}$.

FIGS. 38A and C show the on-time distributions of Ignis molecules at pH8.0 in the presence and absence of 405 nm light, along with the monophasic exponential fit parameter, $k_{on}=(k_d+k_b)$. FIGS. 38B and D show the off-time distributions of Ignis molecules at pH 8.0 in the presence and absence of 405 nm light, with biphasic exponential fit parameters, $k_{r1}$ and $k_{r2}$, as well as the monophasic exponential fit parameter $k_{rm}$.

FIG. 39A shows a representative kymograph and fluorescence intensity trace from mEos4b, showing seven blinks and eight fluorescence emissions. An appropriate dark time ($T_{D1}$, red) links temporally distinct emissions, correctly assigning them to the same molecule. A shorter dark time ($T_{D2}$, blue) over-estimates the number of molecules as three rather than one. FIG. 39B shows the decay of total molecule counts vs. allowed $T_D$, and identification of 95% dark time.

FIGS. 40A and C show PC-FP 95% dark times at pH 7.4 in the absence and presence of 405 nm light. N=3 for each protein. FIGS. 40B and D show PC-FP 95% dark times at pH 8.0 in the absence and presence 405 nm light. N=12 (mEos4b pH 7.4+405), N=9 (mEos4b pH 8.0+405), N=11 (mEos4b-V70T pH 7.4+405), N=9 (mEos4b-V70T pH 8.0+405), N=9 (Janus and Ignis pH 7.4 and 8.0+405). P values calculated by one way ANOVA with Tukey's post hoc test for multiple comparisons.

FIGS. 41A-D show mEos4b molecule counts vs. dark time ($T_D$). Plots of total mEos4b molecule counts vs. $T_D$ (normalized to the count at $T_D$=0), with biphasic exponential fit (black curve) and fit parameters. FIG. 41A shows pH 7.4 without 405 nm light. FIG. 41B shows pH 8.0 without 405 nm light. FIG. 41C shows pH 7.4+405 nm light. FIG. 41D shows pH 8.0+405 nm light.

FIGS. 42A-D show mEos4b-V70T molecule counts vs. dark time ($T_D$). Plots of total mEos4b-V70T molecule counts vs. $T_D$ (normalized to the count at $T_D$=0), with biphasic exponential fit (black curve) and fit parameters. FIG. 42A shows pH 7.4 without 405 nm light. FIG. 42B shows pH 8.0 without 405 nm light. FIG. 42C shows pH 7.4+405 nm light. FIG. 42D shows pH 8.0+405 nm light.

FIGS. 43A-D show Janus molecule counts vs. dark time ($T_D$). Plots of total Janus molecule counts vs. $T_D$ (normalized to the count at $T_D$=0), with biphasic exponential fit (black curve) and fit parameters. FIG. 43A shows pH 7.4 without 405 nm light. FIG. 43B shows pH 8.0 without 405 nm light. FIG. 43A shows pH 7.4+405 nm light. FIG. 43D shows pH 8.0+405 nm light.

FIG. 44A shows pH 7.4 without 405 nm light. FIG. 44B shows pH 8.0 without 405 nm light. FIG. 44C shows pH 7.4+405 nm light. FIG. 44D shows pH 8.0+405 nm light.

FIG. 45A shows the photoconversion at pH 7.4 (N=12). FIG. 45B shows the photoconversion at pH 8.0 (N=9).

FIG. 46A shows the photoconversion at pH 7.4 (N=11). FIG. 46B shows the photoconversion at pH 8.0 (N=9).

FIG. 47A shows the photoconversion at pH 7.4 (N=9). FIG. 47B shows the photoconversion at pH 8.0 (N=9).

FIG. 48A shows the photoconversion at pH 7.4 (N=9). FIG. 48B shows the photoconversion at pH 8.0 (N=9).

FIGS. 49A-F show mEos4b photon distributions at pH 7.4. Mean and median mEos4b photon counts per localization, burst, and molecule in the absence (A, B, C) and presence (D, E, F) of 2 W/cm$^2$ 405 nm photoconversion laser at 2 W/cm$^2$.

FIGS. 50A-F show mEos4b photon distributions at pH 8.0. Mean and median mEos4b photon counts per localization, burst, and molecule in the absence (A, B, C) and presence (D, E, F) of 2 W/cm$^2$ 405 nm photoconversion laser at 2 W/cm$^2$.

FIGS. 51A-F show mEos4b-V70T photon distributions at pH 7.4. Mean and median mEos4b-V70T photon counts per localization, burst, and molecule in the absence (A, B, C) and presence (D, E, F) of 2 W/cm$^2$ 405 nm photoconversion laser at 2 W/cm$^2$.

FIGS. 52A-F show mEos4b-V70T photon distributions at pH 8.0. Mean and median mEos4b-V70T photon counts per localization, burst, and molecule in the absence (A, B, C) and presence (D, E, F) of 2 W/cm$^2$ 405 nm photoconversion laser at 2 W/cm$^2$.

FIGS. 53A-F show Janus photon distributions at pH 7.4. Mean and median Janus photon counts per localization, burst, and molecule in the absence (A, B, C) and presence (D, E, F) of 2 W/cm$^2$ 405 nm photoconversion laser at 2 W/cm$^2$.

FIGS. 54A-F show Janus photon distributions at pH 8.0. Mean and median Janus photon counts per localization, burst, and molecule in the absence (A, B, C) and presence (D, E, F) of 2 W/cm$^2$ 405 nm photoconversion laser at 2 W/cm$^2$.

FIGS. 55A-F show Janus photon distributions at pH 7.4. Mean and median Iginss photon counts per localization, burst, and molecule in the absence (A, B, C) and presence (D, E, F) of 2 W/cm$^2$ 405 nm photoconversion laser at 2 W/cm$^2$.

FIGS. 56A-F show Ignis photon distributions at pH 8.0. Mean and median Ignis photon counts per localization, burst, and molecule in the absence (A, B, C) and presence (D, E, F) of 2 W/cm$^2$ 405 nm photoconversion laser at 2 W/cm$^2$.

DETAILED DESCRIPTION

Figure 1A:
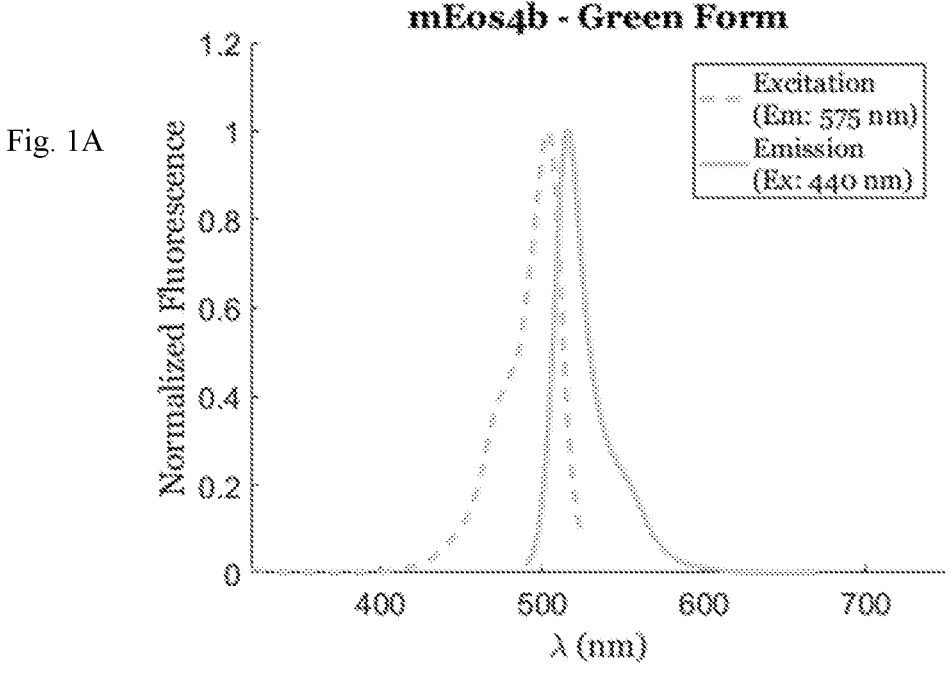
FIGS. 1A-B shows the fluorescence spectra of mEos4b.
Figure 1B:
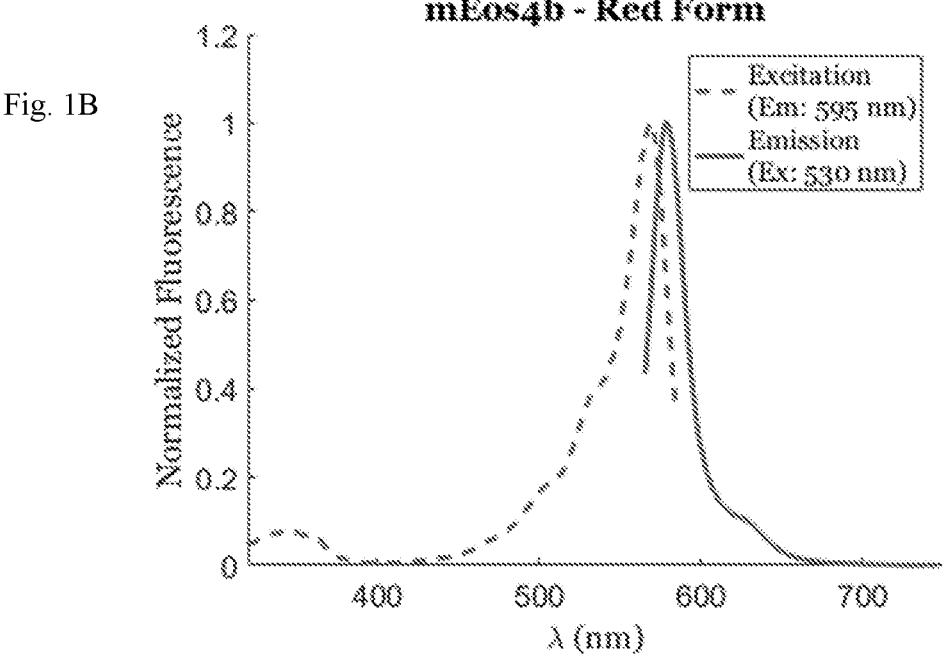
Figure 3A:
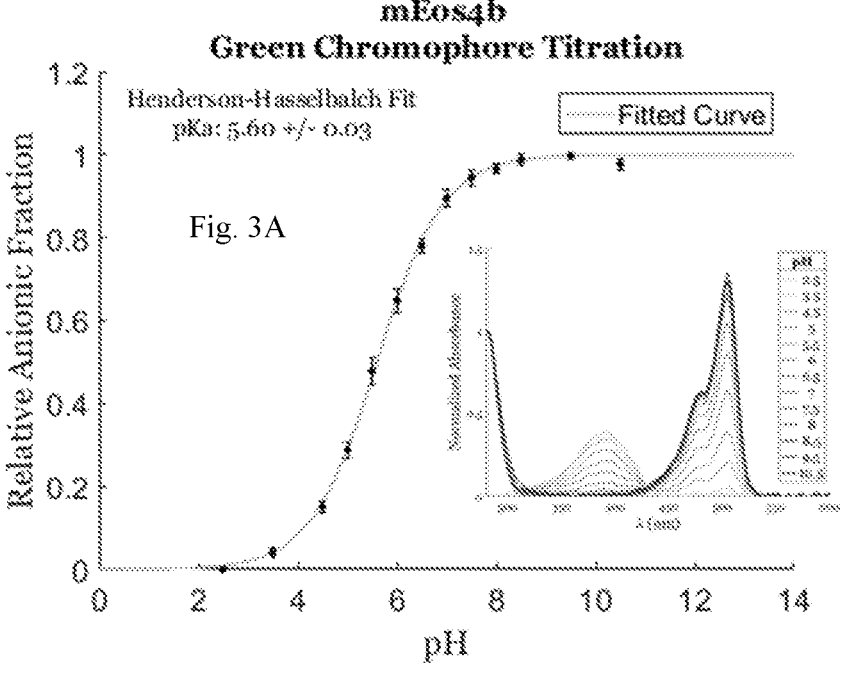
FIGS. 3A-B shows the chromophore acidities of green and red mEos4b.
Figure 3B:
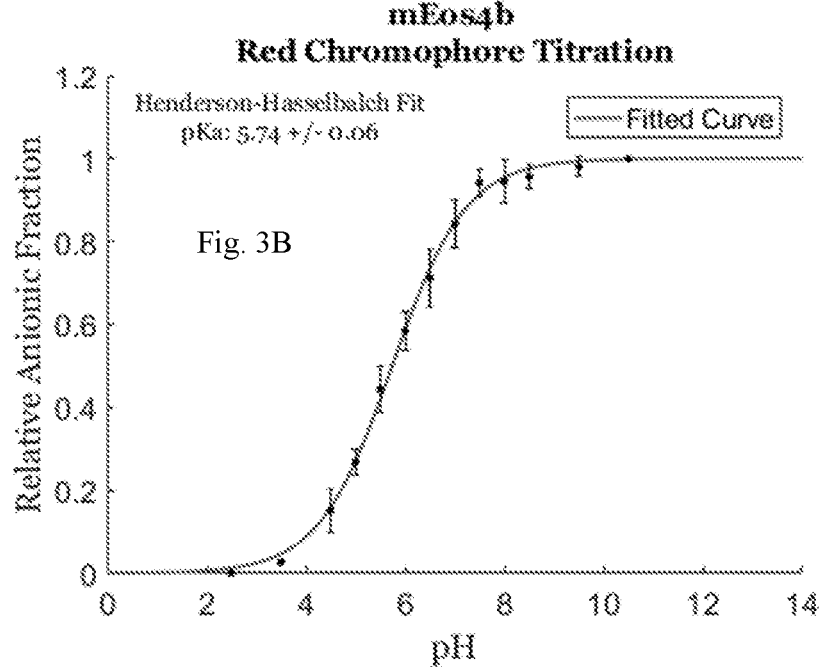
Figures 4A, 4B, 4C:
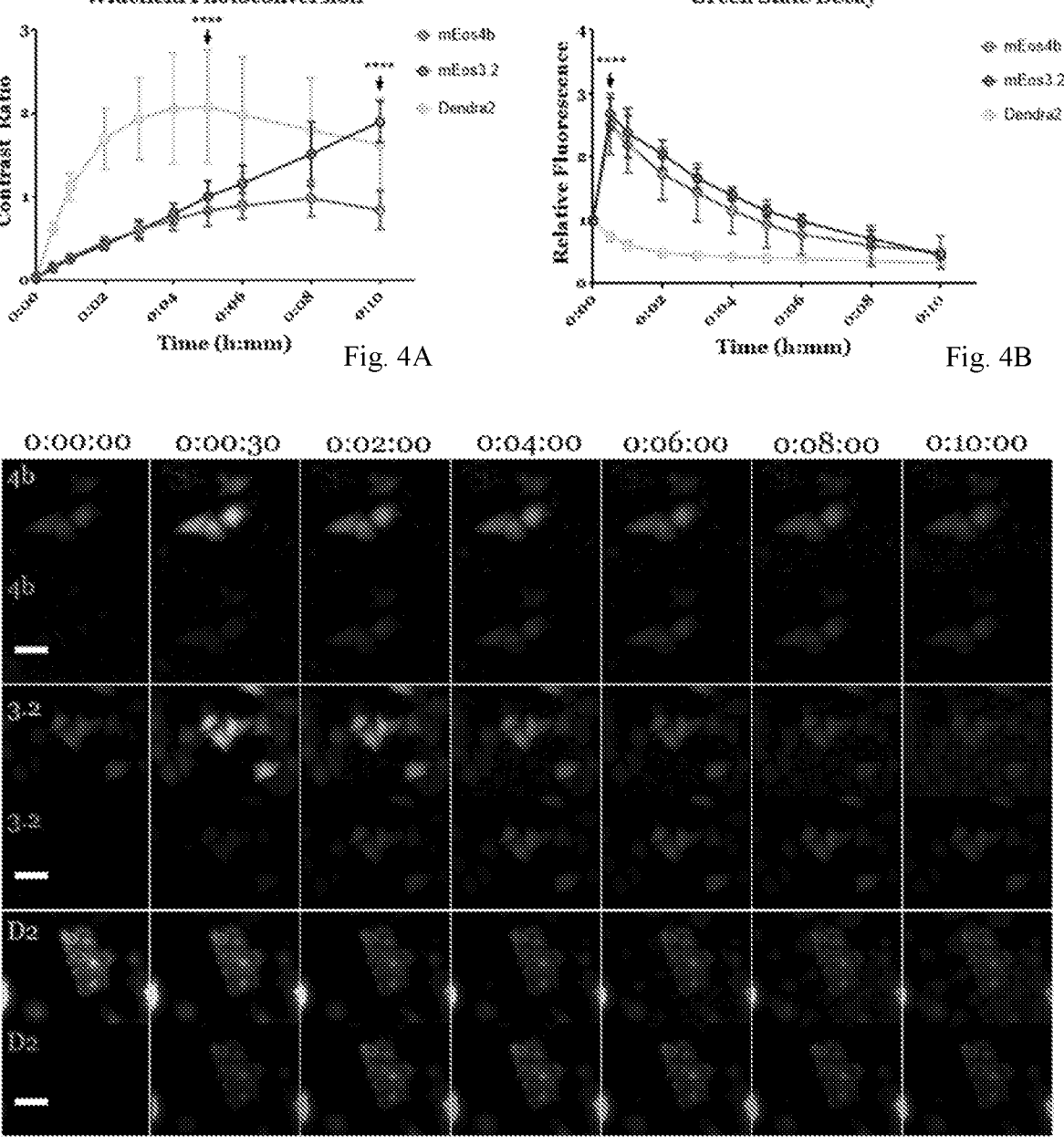
FIGS. 4A-C show widefield photoconversion of PC-FPs in cellulo.
Figure 5A:
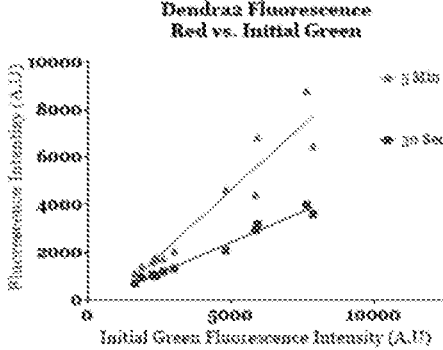
FIGS. 5A-F show the estimated relative widefield photoconversion yields.
Figure 5B:
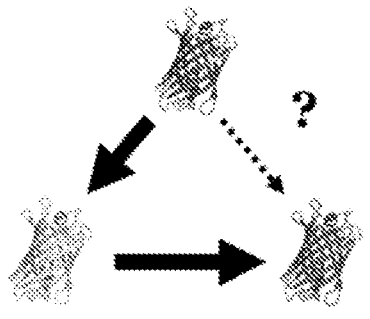
Figure 5C:
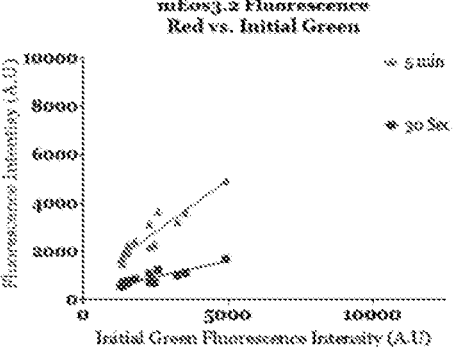
Figure 5D:
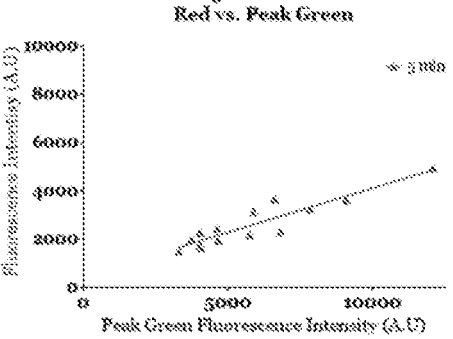
Figure 5E:
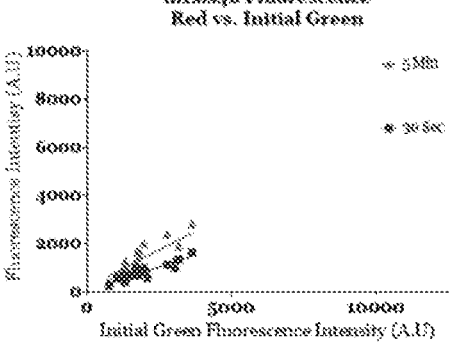
Figure 5F:
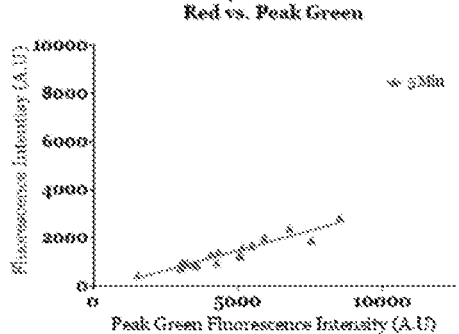
Figure 6:
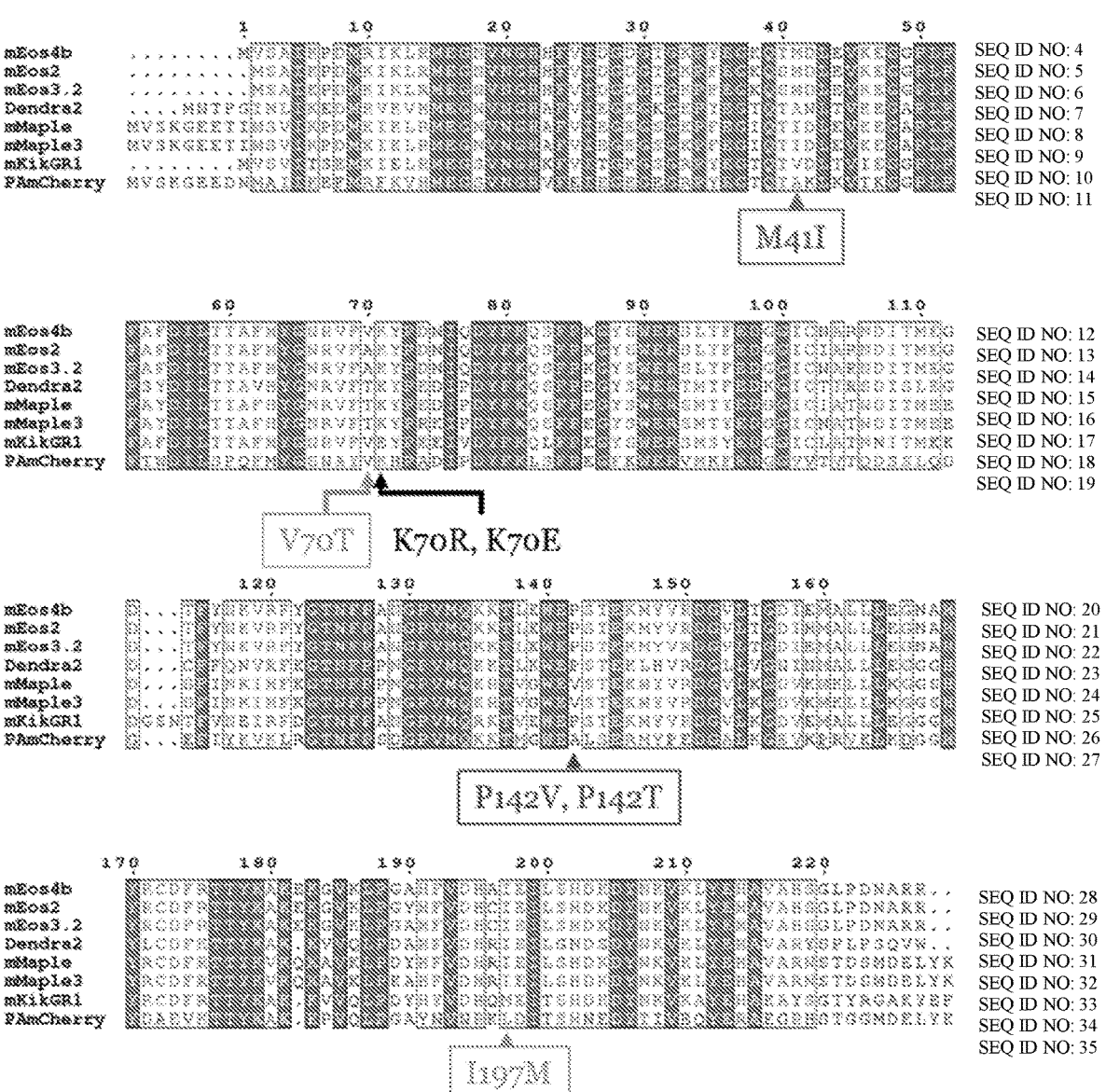
FIG. 6 shows the alignment of PC-FPs and residues evaluated. Positions of amino acid substitutions within mEos4b are indicated by arrows. Mutations chosen to impact the green state chromophore are colored green. Mutations chosen that principally impact the red state chromophore are colored red. Purple signifies mutations of unknown effect chosen due to chromophore proximity and putative role in β-strand stabilization.nK70R and K70E are hypothesized to confer further fixation resistance by virtue of their position relative to the V70/R67 interaction.
Figures 7A, 7B, 7C, 7D, 7E:
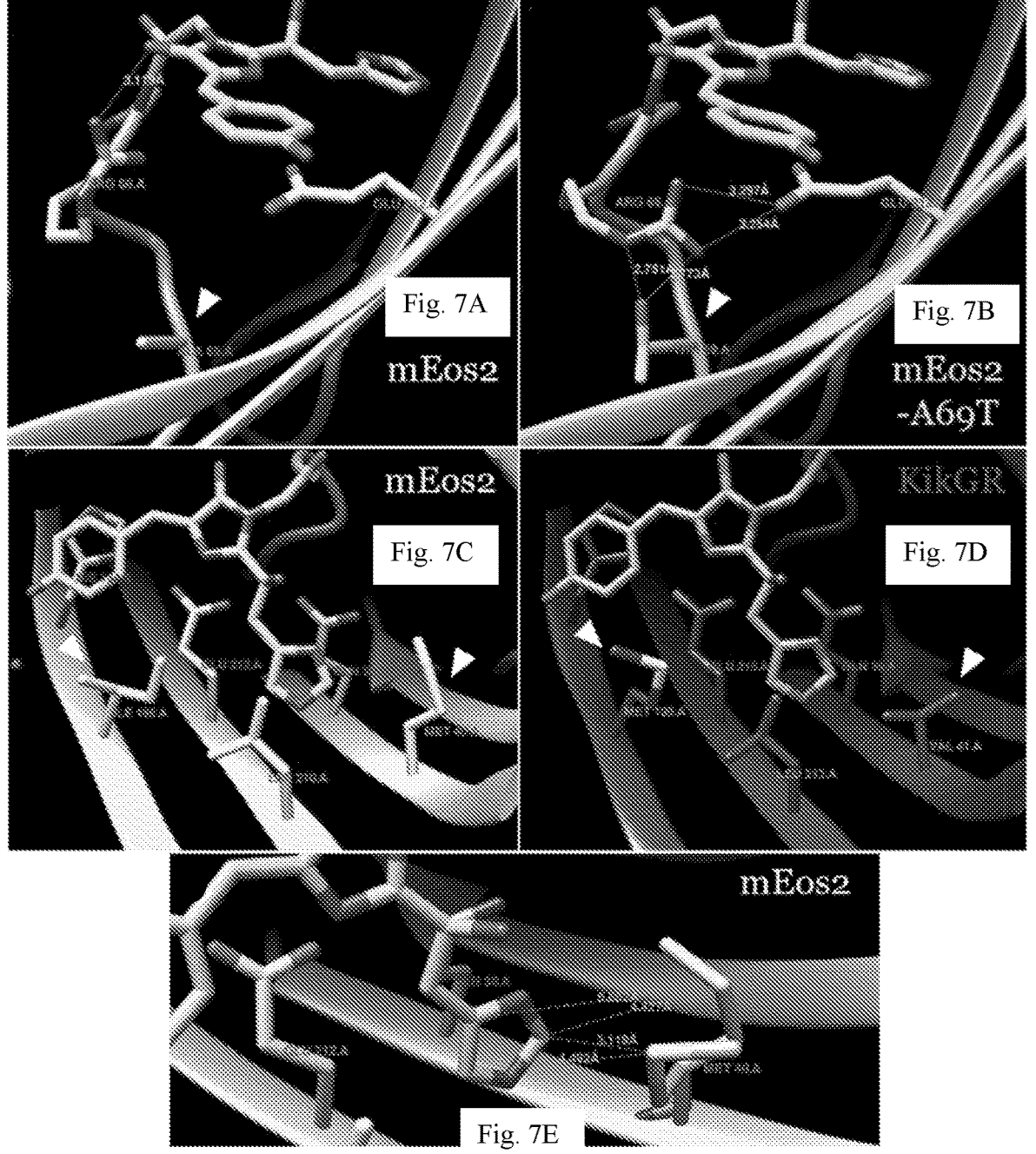
FIGS. 7A-E show the structural rationale for mEos4b mutations.
Figure 8A:
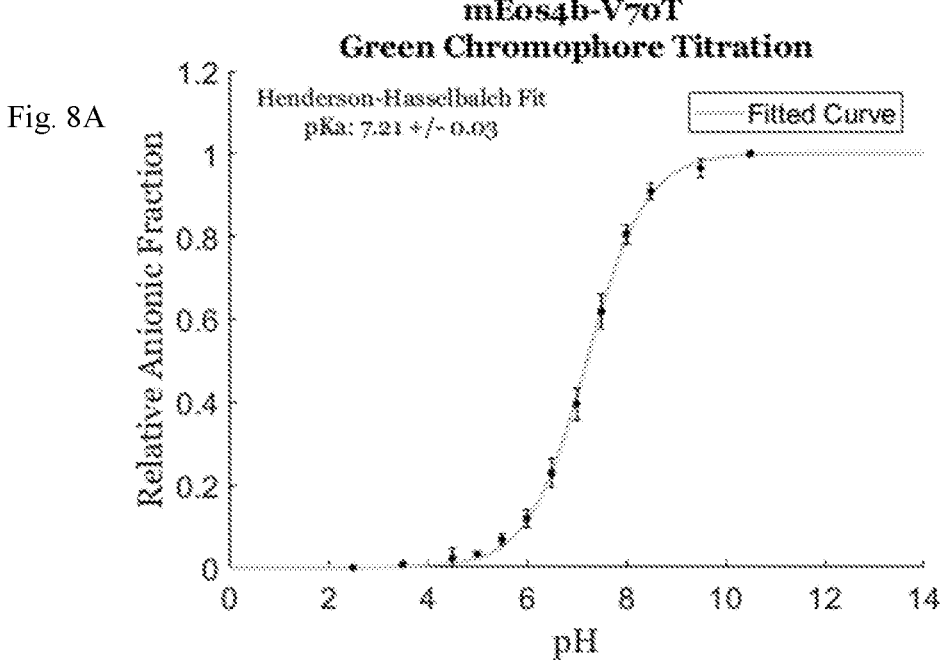
FIGS. 8A-B show the chromophore acidities of green and red mEos4b-V70T.
Figure 8B:
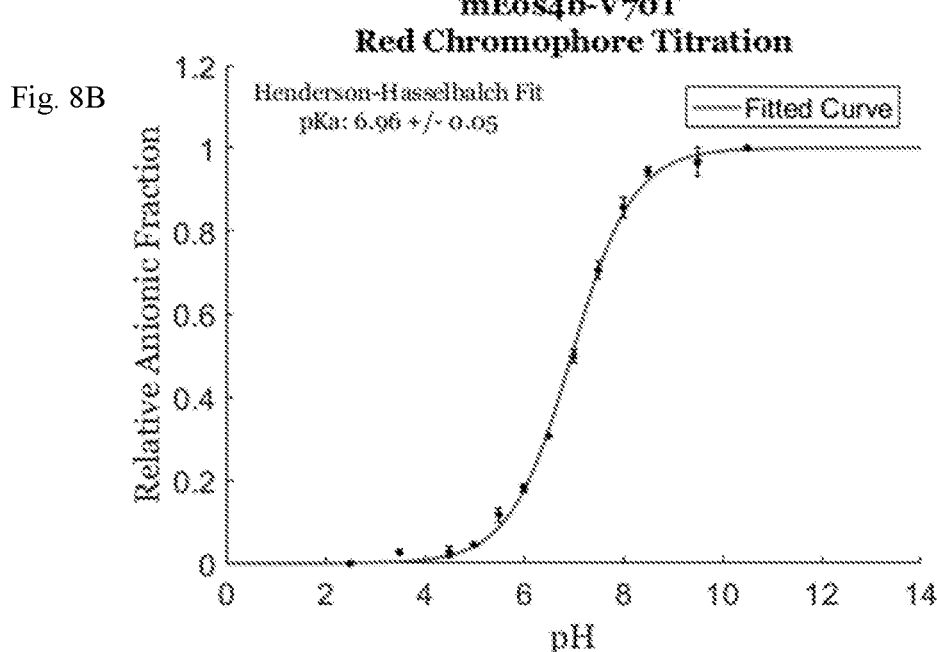
Figure 9A:
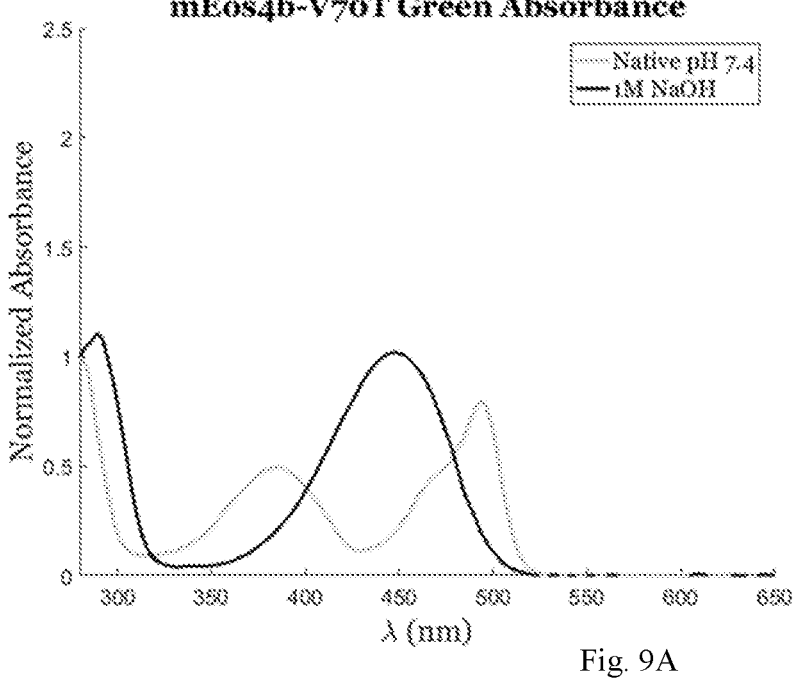
FIGS. 9A-B show the absorbance and photoconversion properties of mEos4b-V70T.
Figure 9B:
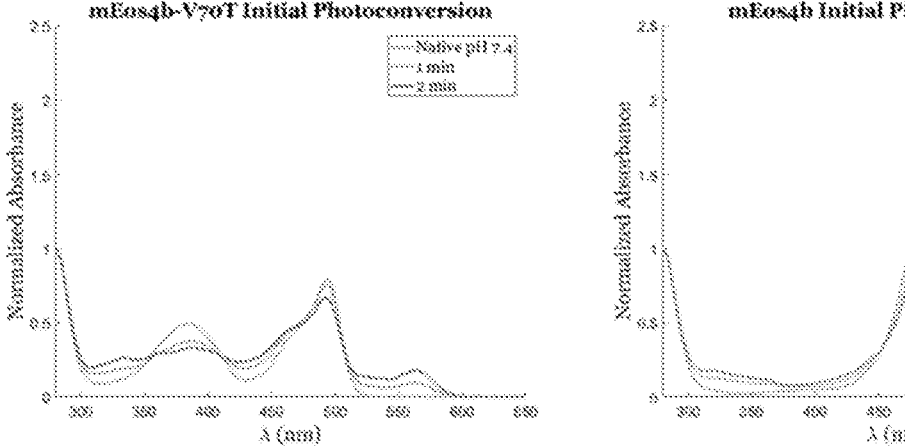

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "comprising" can include the aspects "consisting of" and "consisting essentially of."

As used herein the terms "amino acid" and "amino acid identity" refers to one of the 20 naturally occurring amino acids or any non-natural analogues that may be in any of the antibodies, variants, or fragments disclosed. Thus "amino acid" as used herein means both naturally occurring and synthetic amino acids. For example, homophenylalanine, citrulline and norleucine are considered amino acids for the purposes of the invention. "Amino acid" also includes amino acid residues such as proline and hydroxyproline. The side chain may be in either the (R) or the (S) configuration.

In some aspects, the amino acids are in the D or L-configuration. If non-naturally occurring side chains are used, non-amino acid substituents may be used, for example to prevent or retard in vivo degradation.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

The term "fragment" can refer to a portion (e.g., at least 4, 5, 6, 7, 8, 9, 10, 11, 12, 13, 14, 15, 16, 17, etc. amino acids) of a peptide that is substantially identical to a reference peptide and retains the biological activity of the reference. In some aspects, the fragment or portion retains at least 50%, 75%, 80%, 85%, 90%, 95% or 99% of the biological activity of the reference peptide described herein. Further, a fragment of a referenced peptide can be a continuous or contiguous portion of the referenced polypeptide (e.g., a fragment of a peptide that is ten amino acids long can be any 2-9 contiguous residues within that peptide).

A "variant" can mean a difference in some way from the reference sequence other than just a simple deletion of an N-and/or C-terminal amino acid residue or residues. A "variant" can include a substitution. Where the variant includes a substitution of an amino acid residue, the substitution can be considered conservative or non-conservative. Conservative substitutions are those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cystic acid is acidic, and ornithine is basic. Proline may be substituted with hydroxyproline and retain the conformation conferring properties of proline.

As used herein, a "photoconvertible fluorescent protein or variant thereof" refers to a fluorescent protein that controllably transitions between spectrally distinct fluorescent states. In some aspects, this transition can be irreversible, and its efficiency can be dependent on certain conditions, for example, protonation of the chromophore and irradiation with ultraviolet wavelengths.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

As disclosed herein, mEos4b was engineered to produce variants with improved photoconversion contrast for optical highlighting and reduced single molecule photoblinking propensity. Compound substitutions lining the Kaede-like chromophore resulted in a markedly faster single molecule photoconversion rates and synergistic effects not observed in other photoconvertible fluorescent protein variants bearing individual substitutions. Initial applications in protein counting tests demonstrated positive identification of dimeric protein complexes in the plasma membrane using relatively a simple spatiotemporal merging method. Overall the results described herein provide insights into mechanisms of photoconversion in Kaede family photoconvertible fluorescent proteins.

More specifically, disclosed herein are photoconvertible fluorescent proteins referred to as "Janus" and "Ignis". Both photoconvertible fluorescent proteins are green-to-red photoconvertible fluorescent proteins (PC-FPs) of the EosFP family, generated through site directed mutagenesis of the mEos4b protein coding sequence at amino acid positions 41 and 70 (Janus) and positions 41, 70 and 197 (Ignis) relative to the start codon ATG. Methionine at position 41 has been mutated to isoleucine (Met41Ile) and valine at position 70 has been mutated to threonine (Val70Thr) in both photoconvertible fluorescent proteins. The Ignis photoconvertible fluorescent protein contains the additional mutation, isoleucine at position 197 to methionine (Ile197Met). The genotype of Janus is therefore mEos4b-Met41Ile-Val70Thr, and Ignis is mEos4b-Met41Ile-Val70ThrIle197Met. Ignis is Janus with an additional Ile197Met mutation.

Janus Fluorescent Protein. Janus was derived from the pure monomer, mEos4b, without modification of surface residues that confer monomeric character. It can behave as a monomer with indistinguishable performance to documented monomeric PC-FPs, mEos3.2 and mEos4b, in challenging fusion constructs (membrane-localized fusion proteins CTLA4 and N-myristoylated DmrB) in the experiments described herein.

The excitation and emission spectra of green-state Janus are blue-shifted relative to mEos4b like mEos4bV70T. This improves its excitation under commonly-employed 488 nm laser illumination, compensating for its lower peak excitation coefficient. (mEos4b is only about 55% maximally excited at this wavelength whereas Janus is nearer its excitation maximum). As such, Janus is bright in green channel confocal applications. However, the Janus red state retains longer-wavelength spectral peaks, with excitation maximum at 571 nm and emission maximum at 585 nm. This is one of the largest red Stokes-shifts among available PC-FPs. The excitation spectrum in the red form also permits convenient and efficient excitation under both 561 and 568 nm laser illumination commonly employed in confocal and super-resolution experiments. These findings are superior to both fluorescent proteins, mKikGR and Dendra2, which have red excitation peaks considerably above and below 561 and 568 nm.

Relative to commonly-used PC-FPs in the EosFP family, Janus displays exceptional photoconversion contrast and red state brightness in ensemble photoconversion experiments, both in vitro (purified Janus protein) and in cellulo (over-expressed Janus protein in cultured cells). It has bright fluorescent green and red states noted above, which make it attractive for optical highlighting applications. Photoconversion from green to red states requires lower intensity and/or less duration of phototoxic ultraviolet/violet light in the range of 365-405 nm available in common lamp and laser light sources. Janus photoconversion also appears to escape dark and/or protonated-state shelving observed in mEos4b and mEos4b-V70T, producing its red state on a shorter time scale in ensemble photoconversion measurements.

Janus is useful as a probe in super-resolution, photoactivated localization microscopy (PALM), because it has a high single molecule photon yield and low photoblinking tendency (<25% of molecules exhibit reversible dark state transitions under concurrent 405 and 561 illumination). Undesirable blinking is a common characteristic of popular photoconvertible fluorescent proteins with His-Tyr-Gly chromophores (mEos2, mEos3.2, mEos4b, mMaple1-3), and can cause systematic artifacts in PALM data. PC-FPs with lower reported blinking tendencies (Dendra2, mKikGR and A69T variant of mEos2) suffer from reduced molecular brightness (Dendra2, mEos2-A69T) or documented residual dimerization tendency (mKikGR).

The Janus photoconvertible fluorescent protein has advantages over other commercially available products in that it has an exceptional photoconversion contrast. Other advantages include generating a bright red state fluorescence for ensemble and single-molecule measurements; having a low photoblinking rate in single molecule localization microscopy; and is highly monomeric.

In some aspects, Janus fluorescent proteins can be used in applications for optical highlighting, super-resolution, and photoactivated localization microscopy (PALM).

In summary, along with its excellent performance as a fusion tag and optical highlighter, these photophysical characteristics translate to better localization precision and minimal overcounting error in single molecule PALM experiments. In some aspects, the Janus fluorescent protein can be used as a molecule counting probe.

Ignis Fluorescent Protein. The Ignis photoconvertible fluorescent protein has the highest green state pKa reported for any green to red photoconvertible fluorescent protein currently available, and a resultant increase in the absorbance of UV/Violet light by the neutral phenol form of its chromophore (peak ~385 nm). This translates to more rapid photoconversion by UV/Violet light. Despite its remarkably elevated green state pKa, its red state pKa remains below 7. As a result, the majority of photoconverted red chromophores are fluorescent at or above physiological pH.

The extreme green state pKa was unexpected. Because of this unexpected property, in some aspects, the Ignis photoconvertible fluorescent protein can be used as a genetically-encoded photocleavable protein for protein purification and optogenetics applications as it is extremely sensitive to photoconversion by UV/violet illumination. cpIgnis is a circularly permutated form of Ignis that can be used as a genetically-encoded tag for photocleavage/optogenetics applications, divided at amino acid position 74/75 such that the N- and C-termini of Ignis have been relocated to asparagine 75 (Asn75, new N-terminus) and aspartate 74 (Asp74, new C-terminus). In cpIgnis, the chromophore is therefore at position His222-Tyr223-Gly224, and photoconversion induces a cleavage at between Phe221 and His223, liberating a twelve amino acid fragment inclusive of His222-Asp233.

Also disclosed herein are monoclonal antibodies or nanobodies to the His222-Asp233 "chromotag" epitope to permit biochemical/immunological detection of photocleaved products. In some aspects, the antibodies or nanobodies can be used in applications where near-instantaneous protein cleavage and subsequent tracking via biochemical or optical means are desirable.

The Ignis fluorescent protein has advantages over other commercially available products in that it has the highest recorded green state pKa in green-to-red photoconvertible fluorescent proteins. This means the cleavage of His63-Tyr62 proceeds efficiently at physiological pH due to abundance of violet/UV-absorbing neutral chromophores. It requires lower doses of potentially damaging violet/UV light, which is a distinct advantage in live-cell imaging and optogenetics applications.

In some aspects, Ignis fluorescent proteins can be used in photocleavable protein purification and optogenetics applications; super-resolution photoactivated localization microscopy (PALM); and as the basis for developing a chromotag epitope that can be used as a photocleavage-dependent epitope tag.

Compositions

Disclosed herein are photoconvertible fluorescent proteins or variants thereof comprising one or more mutations or substitutions of the mEos4b protein coding sequence. The mEos4b protein sequence corresponds to (SEQ ID NO: 1).

Disclosed herein are photoconvertible fluorescent proteins or variants thereof, wherein the photoconvertible fluorescent proteins or variants thereof comprise the coding region of the mEos4b protein. In some aspects, the coding region can comprise at least one or more mutations or substitutions.

of the mEos4b protein coding sequence. In some aspects, the photoconvertible fluorescent protein having mutations or substitutions at residues 41, 70 and 197 of the mEos4b protein coding sequence can have the amino acid sequence corresponding to SEQ ID NO: 3. In some aspects, the mutation or substitution at residue 41 can be a substitution of a methionine residue. In some aspects, the mutation or substitution at amino acid residue 41 can be a methionine to an isoleucine residue mutation or substitution (Met41Ile). In some aspects, the mutation or substitution at residue 70 can be a substitution of a valine residue. In some aspects, the mutation or substitution at residue 70 can be a valine to a threonine residue mutation or substitution (Val70Thr). In some aspects, the mutation or substitution at residue 41 can be a methionine to an isoleucine residue mutation or substitution (Met41Ile) and the mutation or substitution at residue 70 can be a valine to a threonine residue mutation or substitution (Val70Thr). In some aspects, the mutation or substitution at residue 197 can be a substitution of an isoleucine residue. In some aspects, the mutation or substitution at residue 197 can be an isoleucine to a methionine residue mutation or substitution (Ile197Met). In some aspects, the mutation or substitution at residue 41 can be a methionine to an isoleucine residue mutation or substitution (Met41Ile); and the mutation or substitution at residue 70 can be a valine to a threonine residue mutation or substitution (Val70Thr); and the mutation or substitution at residue 197 can be an isoleucine to a methionine residue mutation or substitution (Ile197Met).

TABLE 1

Amino acid sequences.

| SEQ ID NO: | Sequence | Name |
|---|---|---|
| 1 | MVSAIKPDMRIKLRMEGNVNGHHFVIDGDGTGKPYEGKQT<br>MDLEVKEGGPLPFAFDILTTAFHYGNRVFVKYPDNIQDYFK<br>QSFPKGYSWERSLTFEDGGICNARNDITMEGDTFYNKVRFY<br>GTNFPANGPVMQKKTLKWEPSTEKMYVRDGVLTGDIEMAL<br>LLEGNAHYRCDFRTTYKAKEKGVKLPGAHFVDHAIEILSHD<br>KDYNKVKLYEHAVAHSGLPDNARR | mEos4b |
| 2 | MVSAIKPDMRIKLRMEGNVNGHHFVIDGDGTGKPYEGKQT<br>IDLEVKEGGPLPFAFDILTTAFHYGNRVFTKYPDNIQDYFKQ<br>SFPKGYSWERSLTFEDGGICNARNDITMEGDTFYNKVRFYG<br>TNFPANGPVMQKKTLKWEPSTEKMYVRDGVLTGDIEMALL<br>LEGNAHYRCDFRTTYKAKEKGVKLPGAHFVDHAIEILSHDK<br>DYNKVKLYEHAVAHSGLPDNARR | Janus |
| 3 | MVSAIKPDMRIKLRMEGNVNGHHFVIDGDGTGKPYEGKQT<br>IDLEVKEGGPLPFAFDILTTAFHYGNRVFTKYPDNIQDYFKQ<br>SFPKGYSWERSLTFEDGGICNARNDITMEGDTFYNKVRFYG<br>TNFPANGPVMQKKTLKWEPSTEKMYVRDGVLTGDIEMALL<br>LEGNAHYRCDFRTTYKAKEKGVKLPGAHFVDHAMEILSHD<br>KDYNKVKLYEHAVAHSGLPDNARR | Ignis |

In some aspects, the one or more mutations or substitutions can be at residue 41 or 70 of the mEos4b protein coding sequence. In some aspects, the one or more mutations or substitutions can be at residues 41 and 70 of the mEos4b protein coding sequence. In some aspects, the photoconvertible fluorescent protein having mutations or substitutions at residues 41 and 70 of the mEos4b protein coding sequence can have the amino acid sequence corresponding to SEQ ID NO: 2. In some aspects, the one or more mutations or substitutions can be at residue 41, 70 or 197 of the mEos4b protein coding sequence. In some aspects, the one or more mutations or substitutions can be at residues 41, 70 and 197

Disclosed herein are photoconvertible fluorescent proteins, wherein the photoconvertible fluorescent proteins comprise the coding region of the mEos4b protein, wherein the coding region can comprise a mutation or substitution at mutation or substitution at residues 41 and 70, wherein the mutation or substitution at residue 41 can be a methionine to an isoleucine residue mutation or substitution (Met41Ile); and the mutation or substitution at residue 70 can be a valine to a threonine residue mutation or substitution (Val70Thr). In some aspects, the protein can have an excitation maximum at 571 mm. In some aspects, the protein can have an emission maximum at 585 nm. In some aspects, the excitation and emission spectra of the photoconvertible fluorescent protein or variants disclosed herein can be blue-shifted relative to mEos4b.

Disclosed herein are photoconvertible fluorescent proteins, wherein the photoconvertible fluorescent proteins comprise the coding region of the mEos4b protein, wherein the coding region can comprise a mutation or substitution at mutation or substitution at residues 41, 70 and 197, wherein the mutation or substitution at residue 41 can be a methionine to an isoleucine residue mutation or substitution (Met41Ile); and the mutation or substitution at residue 70 can be a valine to a threonine residue mutation or substitution (Val70Thr); and the mutation or substitution at residue 197 can be an isoleucine to a methionine residue mutation or substitution (Ile197Met). In some aspects, the protein can be in a circularly-permutated form. In some aspects, the circularly-permutated form can be a photocleavable tag. In some aspects, the photoconvertible fluorescent protein can be divided at residues 74 and 75, such that the N- and C-termini of the photoconvertible fluorescent protein g are relocated. In some aspects, the asparagine of residue 75 can be at the N-termini and the aspartate residue of residue 74 can be at the C-termini.

In some aspects, any of the photoconvertible fluorescent proteins or variants thereof disclosed herein can have an absorbance of UV/violet light around 385 nm. In some aspects, any of the photoconvertible fluorescent proteins or variants thereof disclosed herein have no mutations or substitutions that are located at surface residues of mEos4b that confer monomeric character.

Disclosed herein are molecule probes. In some aspects, the molecular probes can comprise any of the photoconvertible fluorescent proteins or variants thereof described herein.

Disclosed herein are monomers, dimers or tetramers of any of the photoconvertible fluorescent proteins or variants thereof described herein. Disclosed herein are monomers of any of the photoconvertible fluorescent proteins or variants thereof described herein.

Also disclosed herein, are compositions comprising any of the photoconvertible fluorescent proteins or variants thereof described herein.

Methods

Disclosed herein are methods for analyzing a physiologically active substance in a cell. In some aspects, any of the photoconvertible fluorescent proteins or variants thereof described herein can be expressed in the cell. In some aspects, the physiologically active substance can be a protein, a vector or a transformant. In some aspects, the methods can comprise analyzing localization or dynamic situation of a protein in the cell.

Disclosed herein are methods of performing live cell imaging. In some aspects, any of the photoconvertible fluorescent proteins or variants thereof described herein can be expressed in the cell. In some aspects, the methods can comprise analyzing localization or dynamic situation of a protein in the cell.

Disclosed herein are methods of identifying and localizing an individual fluorescent molecule. In some aspects, the fluorescent molecule can be one or more of the photoconvertible fluorescent proteins or variants thereof described herein. In some aspects, the method can comprise photoactivated localization microscopy or stochastic optical reconstruction microscopy.

EXAMPLES

Example 1: Ensemble Characterization of mEos4b

Introduction. A wide range of photoconvertible proteins are available to measure dynamic processes or conduct single molecule photo-activated localization microscopy (PALM) experiments (see, Table 2). However, these probes often exhibit drawbacks that limit their use across disciplines, such that optical highlighters with excellent bulk photoconversion properties do not perform as well as fusion tags or single molecule probes. For example, the EosFP derivative, mEos2, is a bright single molecule probe but yields lower photoconversion contrast than mMaple and retains residual dimerization tendency. Popular PALM probes mEos3.2 and mMaple3 both exhibit high photoblinking rates that complicate quantitation of single proteins in situ. Low photoblinking probes such as PAmCherry and Dendra2 are dimmer at the single molecule level and PAmCherry tends to oligomerize. The high pKa of mMaple3 and its derivatives reduces the brightness of its green state and red states 227, though there is conflicting evidence about its single molecule brightness; some studies report comparable photon yields to mEos3.2 (~103 photons per localization), while others demonstrate about half the brightness (~5×102 photons) consistent with its reportedly lower red state extinction coefficient. Hence, there exists a need for a more generally-applicable PC-FP that exhibits desirable characteristics such as low photoblinking, high single molecule photon yield and photoconversion contrast, and demonstrated fusion tolerance. Additionally, fluorescent proteins can be sensitive to chemical fixatives used in specimen preservation (Sanders, D. W. et al. Distinct tau prion strains propagate in cells and mice and define different tauopathies. *Neuron* 82, 1271-1288 (2014)), including dose-dependent reduction in single molecule localizations after formaldehyde fixation (Subach, F. V. et al. Photoactivation mechanism of PAmCherry based on crystal structures of the protein in the dark and fluorescent states. *Proc. Natl. Acad. Sci. U S. A.* 106, 21097-21102 (2009)) development due to the two distinct absorbance maxima at 396 and 475 nm. The identities of these peaks were quickly ascribed to the neutral and anionic forms of the p-mEos4b was engineered to resist harsh chemical fixation through the removal of surface exposed residues that may react with aldehydes and osmium tetroxide (Paez Segala, M. G. et al. Fixation-resistant photoactivatable fluorescent proteins for correlative light and electron microscopy. *Nat. Methods* 12, 215-218 (2015)). The protein is highly monomeric and exhibits exceptionally high green state brightness among Kaede-like PC-FPs due to its extinction coefficient (78,170 M$^{-1}$cm$^{-1}$) and appreciably high quantum yield (0.84). Overall, mEos4b is a highly refined and robust PC-FP with desirable optical characteristics. However, mEos4b is incompletely characterized as both a PALM probe and optical highlighter. As described herein, mEos4b was analyzed at the ensemble level using a variety of in vitro and in cellulo assays and it was found that it exhibits sub-optimal photoconversion properties.

TABLE 2

Properties of Photocontrollable Fluorescent Proteins

| Protein | Structure | PDB | PC λ | Before Activation/Conversion | | | | | | | After Activation/Conversion | | | | | | |
|---|---|---|---|---|---|---|---|---|---|---|---|---|---|---|---|---|---|
| | | | | State | pKa | Bright. | Ex λ | Em λ | ε | Φ | State | pKa | Bright. | Ex λ | Em λ | ε | Φ |
| PA-GFP | Monomer | n/a | 400 | Off | n/a | n/a | n/a | n/a | n/a | n/a | On | n/a | 13.75 | 504 | 517 | 17400 | 0.79 |
| PAm-Cherry 1 | Monomer* | n/a | 405 | Off | n/a | n/a | n/a | n/a | 6500 | n/a | On | 6.3 | 8.28 | 564 | 595 | 18000 | 0.46 |
| PAmKate | Monomer* | n/a | 405 | Off | n/a | n/a | n/a | n/a | n/a | n/a | On | 5.6 | 4.50 | 586 | 628 | 25000 | 0.18 |
| Kaede-Like PC-FPs | | | | | | | | | | | | | | | | | |
| Kaede | Tetramer | n/a | 380 | Green | 5.6 | 86.94 | 508 | 518 | 98800 | 0.88 | Red | 5.6 | 19.93 | 572 | 580 | 60400 | 0.33 |
| EosFP | Tetramer | 2BTG, 1ZUX | 390 | Green | n/a | 50.40 | 506 | 516 | 72000 | 0.70 | Red | n/a | 22.55 | 571 | 581 | 41000 | 0.55 |
| mEosFP | Monomer* | 3P8U | 400 | Green | 5.3 | 43.01 | 505 | 516 | 67200 | 0.64 | Red | 6.5 | 22.94 | 569 | 581 | 37000 | 0.62 |
| mEos2 | Monomer* | 3S05 | 405 | Green | 5.6 | 47.04 | 506 | 519 | 56000 | 0.84 | Red | 6.4 | 30.36 | 573 | 584 | 46000 | 0.66 |
| mEos2-A69T | Monomer | 5DTL | 405 | Green | 8.2 | 15.31 | 495 | 509 | 24300 | 0.63 | Red | 7.4 | 7.59 | 565 | 580 | 11500 | 0.66 |
| mEos3.1 | Monomer | n/a | 405 | Green | 5.2 | 73.37 | 505 | 513 | 88400 | 0.83 | Red | 6.0 | 20.77 | 570 | 580 | 33500 | 0.62 |
| mEos3.2 | Monomer | n/a | 405 | Green | 5.4 | 53.26 | 507 | 516 | 63400 | 0.84 | Red | 5.8 | 17.71 | 572 | 580 | 32200 | 0.55 |
| mEos4a | Monomer | n/a | 405 | Green | 5.3 | 71.84 | 505 | 515 | 83530 | 0.86 | Red | 5.7 | 43.31 | 571 | 580 | 61000 | 0.71 |
| mEos4b | Monomer | n/a | 405 | Green | 5.5 | 65.66 | 505 | 516 | 78170 | 0.84 | Red | 5.8 | 39.41 | 570 | 580 | 55500 | 0.71 |
| DendFP | Tetramer | n/a | 405 | Green | 6.5 | 58.50 | 492 | 508 | 90000 | 0.65 | Red | 5.2 | 23.80 | 557 | 575 | 35000 | 0.68 |
| Dendra | Monomer | n/a | 405 | Green | 6.6 | 14.70 | 488 | 505 | 21000 | 0.70 | Red | 6.9 | 14.40 | 556 | 575 | 20000 | 0.72 |
| Dendra2 | Monomer | 2VZX | 480 | Green | 6.6 | 22.50 | 490 | 507 | 45000 | 0.50 | Red | 6.9 | 19.25 | 553 | 573 | 35000 | 0.55 |
| Dendra2-T69A | Monomer | n/a | 405 | Green | 6.0 | 23.80 | 502 | 518 | 42500 | 0.56 | Red | 7.0 | 22.66 | 563 | 578 | 35400 | 0.64 |
| KikGR1 | Tetramer | 4P76 | 365 | Green | 7.8 | 37.59 | 507 | 517 | 53700 | 0.70 | Red | 5.5 | 22.82 | 583 | 593 | 35100 | 0.65 |
| mKikGR | Monomer* | n/a | 390 | Green | 6.6 | 33.81 | 505 | 515 | 49000 | 0.69 | Red | 5.2 | 17.64 | 580 | 591 | 28000 | 0.63 |
| mClav-GR2 | Monomer* | n/a | 405 | Green | 8.0 | 14.63 | 488 | 504 | 19000 | 0.77 | Red | 7.3 | 16.96 | 566 | 583 | 32000 | 0.53 |
| mMaple | Monomer* | n/a | 380 | Green | 8.2 | 11.10 | 489 | 505 | 15000 | 0.74 | Red | 7.3 | 16.80 | 566 | 583 | 30000 | 0.56 |
| mMaple2 | Monomer* | n/a | 405 | Green | n/a | n/a | 492 | 506 | n/a | n/a | Red | n/a | n/a | 570 | 582 | n/a | n/a |
| mMaple3 | Monomer | n/a | 405 | Green | n/a | 5.83 | 491 | 506 | 15760 | 0.37 | Red | n/a | 12.46 | 568 | 583 | 23970 | 0.52 |
| mox-Dendra2 | Monomer | n/a | 405 | Green | n/a | 25.15 | 490 | 504 | 50300 | 0.50 | Red | n/a | 17.16 | 551 | 571 | 31200 | 0.55 |
| mox-Maple3 | Monomer | n/a | 405 | Green | n/a | 5.48 | 490 | 506 | 14800 | 0.37 | Red | n/a | 12.60 | 569 | 584 | 24230 | 0.52 |
| Non-Kaede-Like PC-FPs | | | | | | | | | | | | | | | | | |
| PS-CFP | Monomer | n/a | 405 | Cyan | 4.0 | 5.44 | 402 | 468 | 34000 | 0.16 | Green | 6.0 | 5.13 | 490 | 511 | 27000 | 0.19 |
| PS-CFP2 | Monomer | n/a | 405 | Cyan | n/a | 8.60 | 400 | 468 | 43000 | 0.20 | Green | n/a | 10.81 | 490 | 511 | 47000 | 0.23 |
| PSm-Orange | Monomer | 4Q7T | 480 | Orange | 6.2 | 57.78 | 548 | 565 | 113300 | 0.51 | Far-red | 5.6 | 9.16 | 634 | 662 | 32700 | 0.28 |
| PSm-Orange2 | Monomer | 4Q7U | 489 | Orange | 6.6 | 31.11 | 546 | 561 | 51000 | 0.61 | Far-red | 5.4 | 7.18 | 619 | 651 | 18900 | 0.38 |

To better characterize mEos4b, a 6×-His tagged form of the protein was purified in *E. coli*. Mass spectrometry confirmed the presence of peak at ~30,025.97 Da consistent with the predicted molecular mass of 30,026 Da, though several additional species were also present near this mass including a species of ~30,007.95 Da. These peaks may be consistent with dehydration of the chromophore or other intermediates formed during chromophore cyclization (Wachter, R. M. Chromogenic Cross-Link Formation in Green Fluorescent Protein. *Acc. Chem. Res.* 40, 120-127 (2007)), but additional studies are required to firmly assign their identities.

Figure 10A:
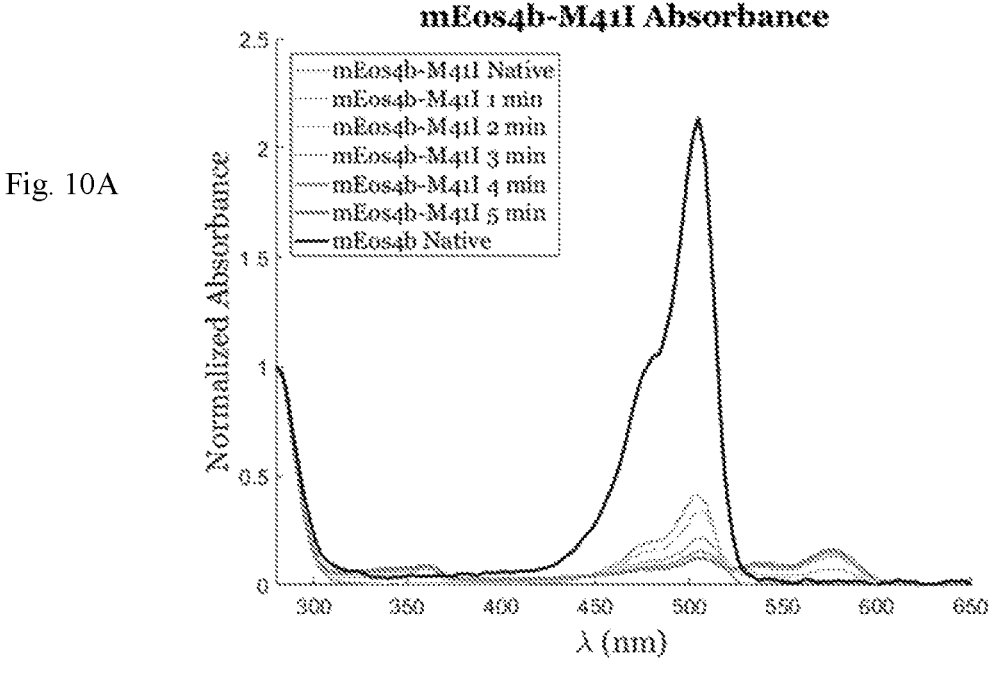
FIGS. 10A-B show the photochemical and photoconversion characteristics of mEos4b-M41I.
Figure 10B:
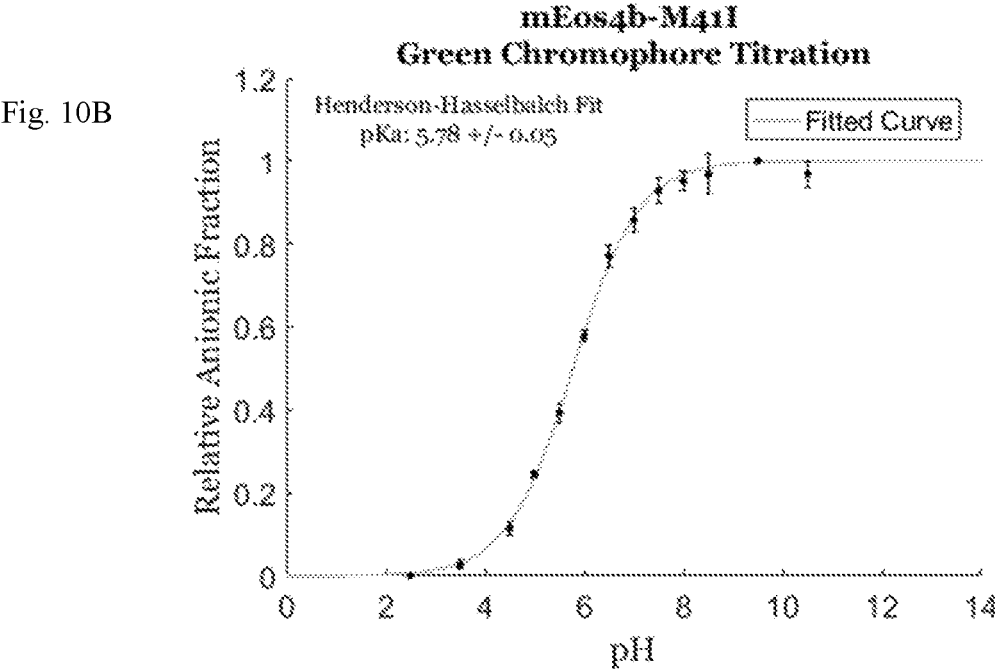

The excitation and emission spectra of purified mEos4b are given in FIG. 10. The green spectrum demonstrates an excitation peak at ~503 nm and emission peak at 516 nm (FIG. 10A). Photoconversion of mEos4b solutions with 385 nm LED illumination produces a red species with excitation and emission maxima at 568 nm and 579 nm, respectively (FIG. 10B). Low-resolution absorbance spectra (3 nm spectral resolution) was also collected to characterize large scale changes in absorbance of mEos4b solutions during photoconversion.

Figure 12A:
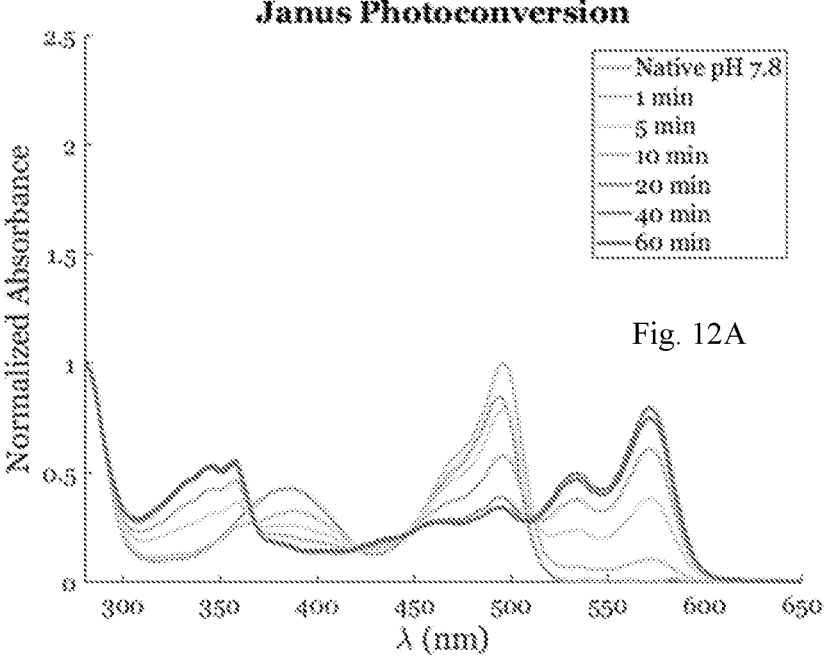
FIGS. 12A-B show Janus photoconversion vs. mEos4b photoconversion in vitro.
Figure 12B:
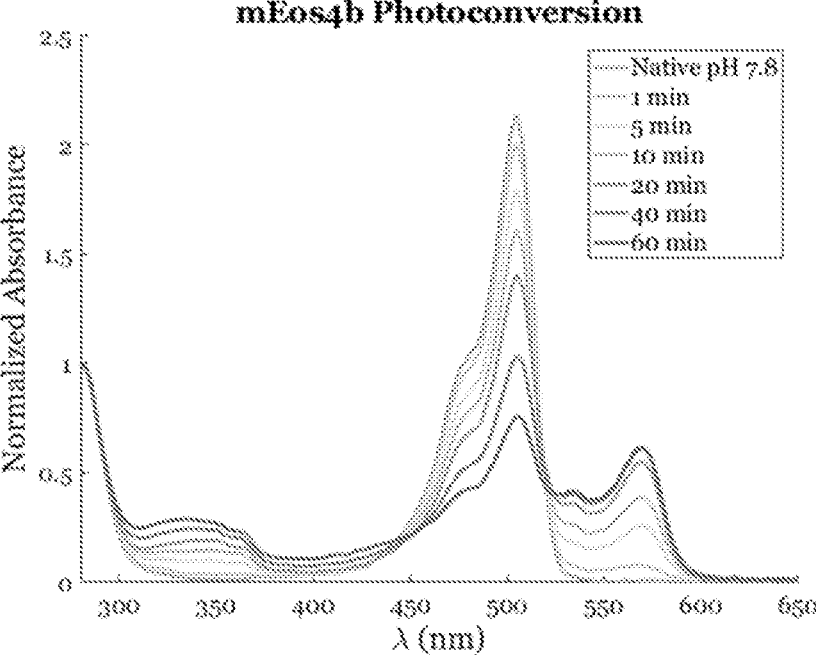

Ensemble Fluorescence Properties of mEos4b in vitro. Consistent with a predominantly anionic p-HBI chromophore, mEos4b shows a strong absorbance band that peaks near 505 nm in the native state (FIG. 11A). It was observed that the absorbance of freshly-purified mEos4b steadily increases when left at room temperature in the dark, suggestive of incomplete chromophore formation under our expression conditions. Therefore, freshly-purified mEos4b was flash frozen and its absorbance spectrum was examined over the course of four days post-thaw (FIG. 11B). At 96 hours post-purification, the green state molar extinction coefficient of 78,000 $M^{-1}cm^{-1}$ was calculated at 505 nm (relative to concentration calculated from absorbance at 280 nm with an estimated extinction coefficient of 35,870 $M^{-1}cm^{-1}$). The green mEos4b extinction coefficient was also estimated according to the method of Chudakov et al. (Chudakov, D. M. et al. Photoswitchable cyan fluorescent protein for protein tracking. *Nat. Biotechnol.* 22, 1435-1439 (2004)), by comparing the native absorbance at 505 nm to the absorbance of the alkali-denatured p-HBI chromophore, which absorbs characteristically at 446 nm with an extinction coefficient of 44,000 $M^{-1}cm^{-1}$ (FIG. 11A). Using this method, which accounts for mature chromophore (as opposed to total protein), a greater extinction coefficient of 95,810 $M^{-1}cm^{-1}$ was calculated. Importantly, measurements were taken immediately upon denaturing of the solution as the alkali-denatured chromophore absorbance decays within minutes. Upon illumination with 385 nm light, the absorbance spectrum evolves a new peak at 568-570 nm concomitant with a reduction of the 505 nm green peak (FIG. 11C), and this is assigned to the anionic red chromophore. In agreement with literature values, titration of the anionic green and red peaks revealed pKa values of 5.60±0.03 and 5.74±0.06, respectively (FIG. 12A-B) (Paez Segala, M. G. et al. Fixation-resistant photoactivatable fluorescent proteins for correlative light and electron microscopy. *Nat. Methods* 12, 215-218 (2015)). At low pH, mEos4b demonstrates a peak at ~385 nm and titration spectra reveal an isosbestic point at ~433 nm characteristic of two species in equilibrium (FIG. 12A, inset). Therefore the 385 nm peak can be confidently assigned to the protonated/neutral state of the p-HBI chromophore tyrosine.

Figure 13A:
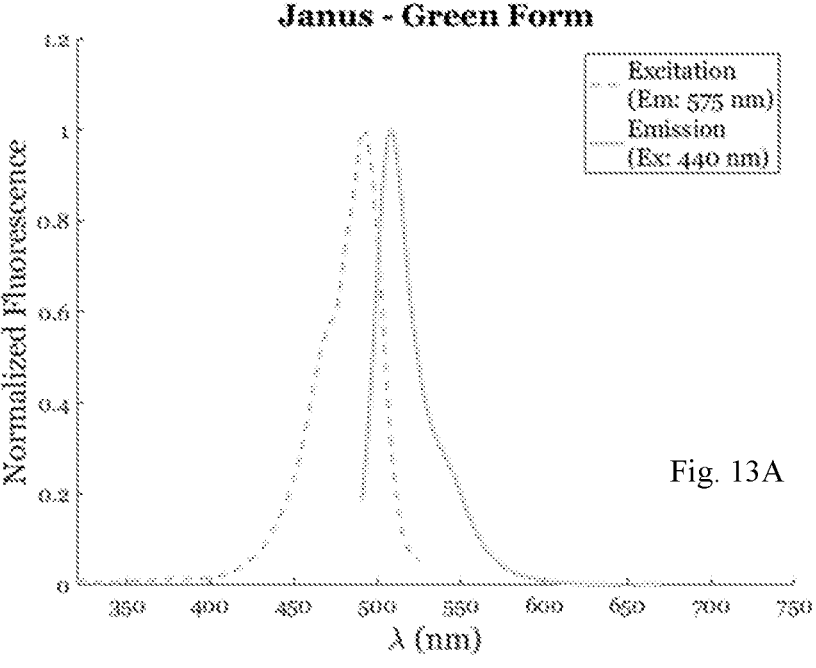
FIGS. 13A-B show the fluorescence spectra of Janus.

Ensemble Photoconversion of mEos4b in cellulo. To examine the performance of mEos4b as an optical highlighter and fusion partner, the protein was genetically tagged to the C-terminus of a membrane-targeted, N-myristoylated DmrB (FKBP/F36V) domain and assayed its photoconversion properties with wide-field epifluorescence microscopy. HeLa cells on glass bottom dishes were transfected with N-Myr-DmrB:mEos4b, or controls N-Myr-DmrB mEos3.2 and N-Myr-DmrB:Dendra2 and observed live 24 hours later. Brightly fluorescent cells were photoconverted under a DAPI-filtered Xenon lamp and imaged in green and red channels to assess wide-field photoconversion. Surprisingly, the photoconversion properties of mEos4b were noticeably inferior to those of Dendra2 and mEos3.2 under identical illumination conditions (FIG. 11). The observed photoconversion contrast of mEos4b (i.e., the fraction of red to green fluorescence at a given time point) was reduced compared to Dendra2 and mEos3.2 (FIG. 13A). Curiously, the photoconversion contrast of mEos3.2 did not appear to have peaked under these conditions, though it was noted that contrast reflects the combined contributions of green-to-red photoconversion, red photobleaching, and green photobleaching. No further brightening of the mEos3.2 red state beyond ~5 minutes of photoconversion was observed. Consistent with prior arguments in the literature, Dendra2 demonstrated more rapid photoconversion than either mEos3.2 or mEos4b (FIG. 13B), though the variability and time points employed in this assay precluded formal kinetic measurements. It was also noted that the green forms of mEos4b and mEos3.2— but not Dendra2—brightened considerably upon the initial 30 second photoconversion period, revealing the presence of a dark subpopulation of proteins that exhibit photoactivation to the green state.

Figure 13B:
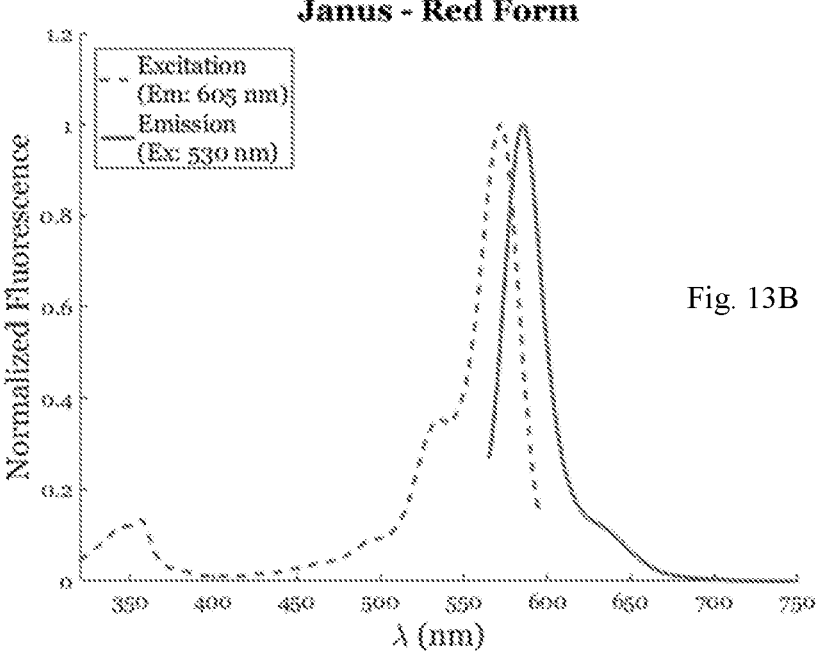

The results suggest that Dendra2 exhibits greater photoconversion efficiency—that is, the number of molecules that successfully convert to a fluorescent red state—than mEos3.2 than mEos4b in wide-field epifluorescence applications. However, such a conclusion is complicated by the variable brightness and excitation efficiency of each probe under widefield illumination, which reflect the sum their photophysical/spectral properties. The FPbase fluorophore efficiency report tool (www.FPbase.org) (Lambert, T. J. FPbase: a community-editable fluorescent protein database. *Nat. Methods* 16, 277 (2019)) was used and the excitation efficiency and brightness of each probe was estimated under wide-field excitation with green FITC (Ex: 480/30, Em: 535/50) and red TRITC (Ex: 540/25, Em: 605/55) filter sets. The order of theoretical green brightness rounded to two digits is mEos4b (21.28)>mEos3.2 (16.20)>Dendra2 (8.38). The order of red brightness is mEos4b (16.47)>Dendra2 (7.47)>mEos3.2 (5.87). Hence, if the conversion were unitary, mEos4b might be expected to yield ~0.77 units of red fluorescence per one unit of green (16.47/21.28=0.77). Similarly, mEos3.2 should yield ~0.36, Dendra2~0.89 units of red fluorescence per unit of green. The order of predicted photoconversion yield is Dendra2 (0.89)>mEos4b (0.77)>mEos3.2 (0.36). To test these ratios, measurements of red fluorescence of each probe after 30 seconds and 5 minutes of photoconversion was correlated to the initial green state fluorescence before photoconversion (FIG. 13A, C, E). However, because both mEos3.2 and mEos4b demonstrated significant fluorescence brightening, the 5-minute red fluorescence of each protein was also correlated to the 30-second green state brightness (FIG. 13D, F) where both mEos3.2 and mEos4b demonstrate peak intensity (FIG. 13B). The expectation in both cases is that a value less than the unitary conversion efficiency should be attained (as less than 100% of the green protein is converted), but the order of conversion yields should be maintained.

The slopes of regression curves are given in Table 3. The photoconversion yields inferred from the regressions are progressive between 30 seconds and 5 minutes, as expected. However, the overall yield at 5 minutes is higher than expected given the incomplete depletion of the green states observed. This may reflect some error in the estimated hypothetical brightness, photoconversion from a dark state to the red state (which would under-estimate the green fluorescence intensity), or other causes of reduced green state fluorescence in the experiment such as photobleaching prior to image acquisition. Nonetheless if it is assumed that these factors are consistent across samples, the order of wide-field photoconversion yields places mEos4b last, in contrast to expectations. Relative to initial green intensity, the order was Dendra2 (1.0970)>mEos3.2 (0.8688)>mEos4b (0.6208). When mEos3.2 and mEos4b yields were instead correlated relative to peak green intensity, the order was Dendra2 (1.0970)>mEos3.2 (0.3667)>mEos4b (0.3308).

Discussion. The experiments described herein provide baseline optical and photoconversion properties of mEos4b. Consistent with literature results, these findings show a high green state extinction coefficient, green-to-red photoconversion upon 385 nm illumination, and low acid sensitivity as evidenced by pKa values of 5.6 and 5.74 for the green and red states (respectively) (Paez Segala, M. G. et al. Fixation-resistant photoactivatable fluorescent proteins for correlative light and electron microscopy. *Nat. Methods* 12, 215-218 (2015)). However, an unreported slow maturation of the protein was also characterized in vitro. A likely source of this slow maturation is incomplete maturation in *E. coli* prior to purification. In this regard, it is noted that the purification scheme involves a short IPTG induction at 32-34 C (to enhance soluble protein yield), followed by immediate column purification, whereas others have expressed the protein in autoinduction media for prolonged periods at 37° C. (Paez Segala, M. G. et al. Fixation-resistant photoactivatable fluorescent proteins for correlative light and electron microscopy. *Nat. Methods* 12, 215-218 (2015); and Studier, F. W. Protein production by auto-induction in high density shaking cultures. *Protein Expr. Purif.* 41, 207-234 (2005)). It was suspected that prolonged expression at higher temperature increases the fraction of fully-matured molecules. However, it was found that lower temperatures to be important for mEos4b and mEos3.2 expression in the cells (NiCO2 Bl21), and hence have not directly tested this possibility.

TABLE 3

| | | | | | Vs. Peak Green | |
| --- | --- | --- | --- | --- | --- | --- |
| Linear Regression Statistics for Fig. 14 | | | | | | |
| | Vs. Initial Green | | | | | |
| | 0:00:30 | | 0:05:00 | | 0:05:00 | |
| Protein | Slope | $R^2$ | Slope | $R^2$ | Slope | $R^2$ |
| Dendra2 | 0.5166 ± 0.0236 | 0.9795 | 1.0970 ± 0.1067 | 0.9135 | n/a | n/a |
| mEos3.2 | 0.2665 ± 0.0391 | 0.7951 | 0.8688 ± 0.0974 | 0.8689 | 0.3667 ± 0.0451 | 0.8466 |
| mEos4b | 0.3954 ± 0.0436 | 0.8285 | 0.6208 ± 0.1142 | 0.6348 | 0.3308 ± 0.0268 | 0.8998 |

Wide-field photoconversion in live HeLa cells revealed unexpectedly poor photoconversion performance of mEos4b relative to popular Kaede-like PC-FPs, mEos3.2 and Dendra2. It is noted that the photoconversion contrast of mEos4b deviates from that of mEos3.2 at later time points in FIG. 13A. The cause of this plateau is unclear, as both mEos3.2 and mEos4b show similar green state decay profiles (due to combined photobleaching and photoconversion), it is possible that mEos4b red state bleaches more quickly than mEos3.2, limiting its accumulation in this assay.

Figure 14A:
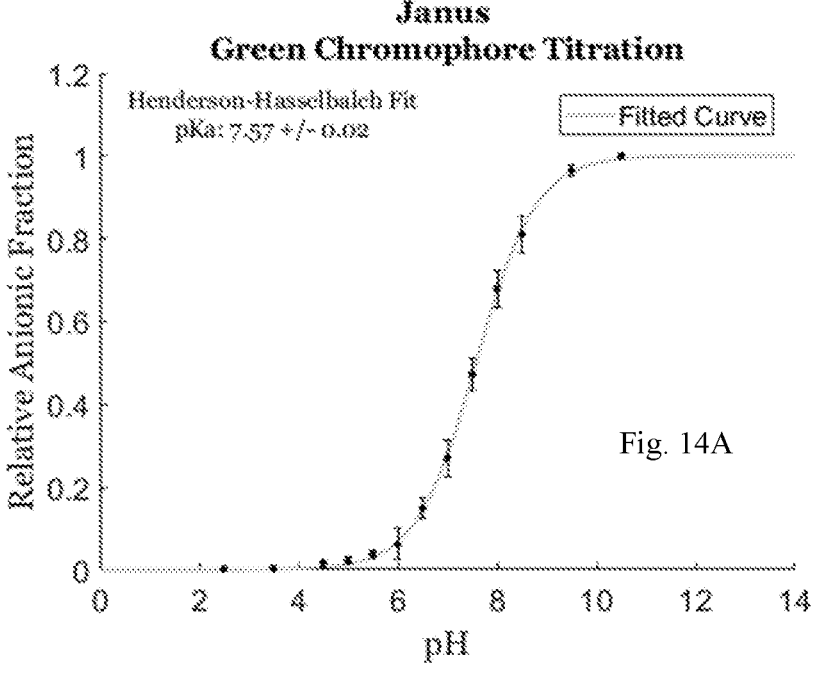
FIGS. 14A-B show chromophore acidities of green and red Janus.
Figure 14B:
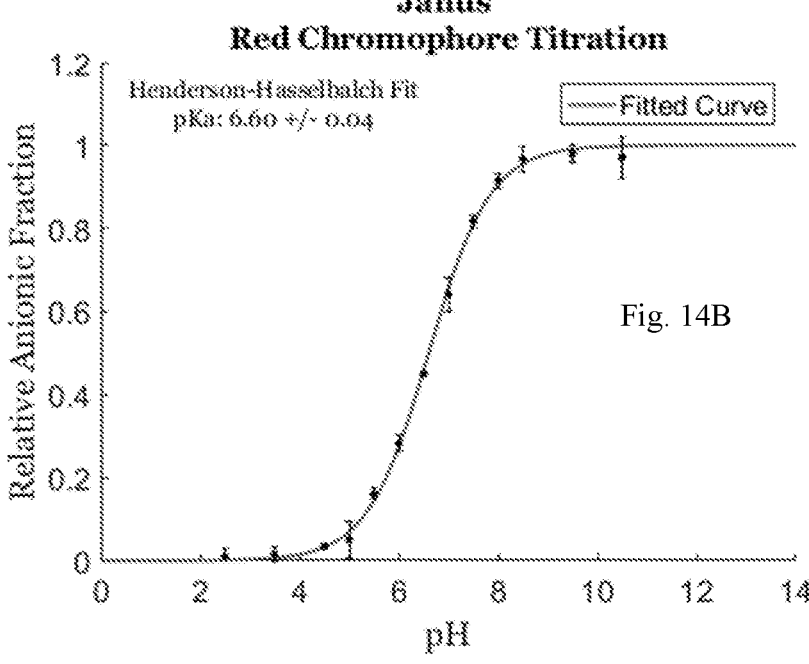

The remarkable increase in mEos3.2 and mEos4b green states upon initial UV/Violet photoconversion revealed the existence of a dark, photoactivatable pool of proteins in live cells. This pool may be composed of proteins with mature (cyclized), but conformationally-strained or isomerized chromophores. Consistent with this possibility, it was recently shown that green mEos2 molecules can be driven into a dark state by illumination with green light (Thédié, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)), and both mEos4b green and red states exhibit reversible photoswitching between dark and fluorescent states (Paez Segala, M. G. et al. Fixation-resistant photoactivatable fluorescent proteins for correlative light and electron microscopy. *Nat. Methods* 12, 215-218 (2015)); and (De Zitter, E. et al. Mechanistic investigation of mEos4b reveals a strategy to reduce track interruptions in sptPALM. *bioRxiv* 475939 (2018)). It is tempting to speculate that the dark pool of mEos3.2 and mEos4b molecules observed in this study is a similar chemical species. Alternatively, this dark pool could be related to the slow maturation of observed for mEos4b in vitro, though this seems unlikely, because the recombinant protein does not demonstrate any appreciable increase in the absorbance of its 505 nm peak upon initial photoconversion with 385 nm light (FIG. 11C), though it is noted that this may occur on a shorter time scale than was analyzed. It is also unclear if this dark fraction can directly yield red chromophore, or if it must first pass through the green intermediate (FIG. 14B).

Example 2: Engineering the mEos4b Chromophore Environment

Introduction. The results of wide-field mEos4b photoconversion experiments raised the question of how to improve the photoconversion properties of mEos4b in order to produce a fixation-resistant and high-contrast PC-FP. The results suggested that both the photoconversion rate and overall red fluorescence yield of mEos4b are low, and both characteristics may negatively impinge on the use of mEos4b in quantitative localization microscopy. The green chromophore pKa of Kaede-like PC-FPs influences the photoconversion rate by increasing the fraction of molecules with protonated, neutral chromophores that absorb in the UV/violet range. A higher green pKa is therefore desirable. However, a high red stake pKa is undesirable as it will favor non-fluorescent, protonated red chromophores.

The currently-available Kaede-like PC-FPs may be categorized based on the shift in their chromophore pKa upon photoconversion from green to red. "Natural" PC-FPs, Kaede, EosFP-derivatives (mEos2, mEos3.2, mEos4b) and Dendra derivatives generally exhibit a positive, "ascending" pKa shift, with greater red pKa than green. In contrast, the synthetically-derived PC-FPs, mClavGR2, mMaple, mMaple2, mMaple3, KikGR, mKikGR each exhibit a "descending" shift in their chromophore pKa after photoconversion No monomeric Kaede-like PC-FP exists in the "descending" category with a pKa below physiological pH. mKikGR is the closest example (green pKa: 6.6; red pKa: 5.2), but its green state pKa is not exceptionally high, it exhibits undesirable oligomerization tendency (Wang, S., Moffitt, J. R., Dempsey, G. T., Xie, X. S. & Zhuang, X. Characterization and development of photoactivatable fluorescent proteins for single-molecule-based superresolution imaging. *Proc. Natl. Acad. Sci. U.S.A.* 111, 8452-8457 (2014)) and has not been developed to resist chemical fixation.

It was tested whether the direction and magnitude of pKa shift during photoconversion is central to efficient acquisition of a bright red state, and that a descending shift across the physiological pH range may yield an enhanced PC-FP. If true, the photoconversion properties of mEos4b could be improved through rational engineering of the chromophore environment to promote a high green state pKa and low red state pKa. Described herein are several mEos4b variants engineered for improved chromophore pKa characteristics.

Figure 15A:
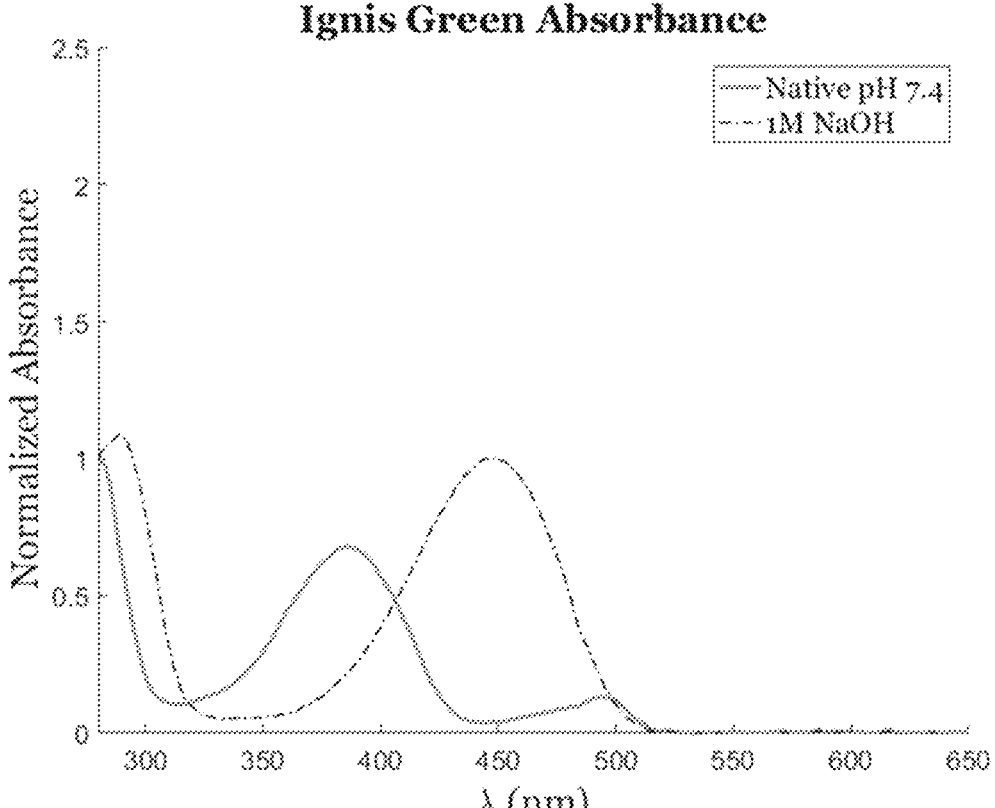

Rational Selection of Target Sites for Mutagenesis in mEos4b. An alignment of mEos4b with monomeric PC-FPs is provided in FIG. 15, with sites selected for mutagenesis indicated with arrows. Experiments were carried out to identify sites within mEos4b that may influence chromophore photochemistry. Although tremendous directed evolution efforts have revealed general sites of interest, few single-residue effects on chromophore photochemistry are clearly defined in PC-FPs. However, the starting point is Val70, the mEos4b homolog of mEos2 Ala69 and Dendra2 T69 (numbering relative to mEos2). A threonine at this position is known to increase the green chromophore pKa in mEos2 by repositioning the nearby Arg66 (Shown in FIG. 16 A,B), rendering chromophore photochemistry similar to Dendra2 (Adam, V., Nienhaus, K., Bourgeois, D. & Nienhaus, G. U. Structural Basis of Enhanced Photoconversion Yield in Green Fluorescent Protein-like Protein Dendra2. *Biochemistry* 48, 4905-4915 (2009)); and (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). Likewise, mEos4b-V70T is reported to have an elevated green state pKa of 7.7 (V69T, numbering relative to mEos2 in the original publication) (Turkowyd Bartosz et al. A General Mechanism of Photoconversion of Green-to-Red Fluorescent Proteins Based on Blue and Infrared Light Reduces Phototoxicity in Live—Cell Single—Molecule Imaging. *Angew. Chem. Int. Ed.* 56, 11634-11639 (2017)), though a lower green pKa of ~7.2 was calculated for this variant.

Figure 16A:
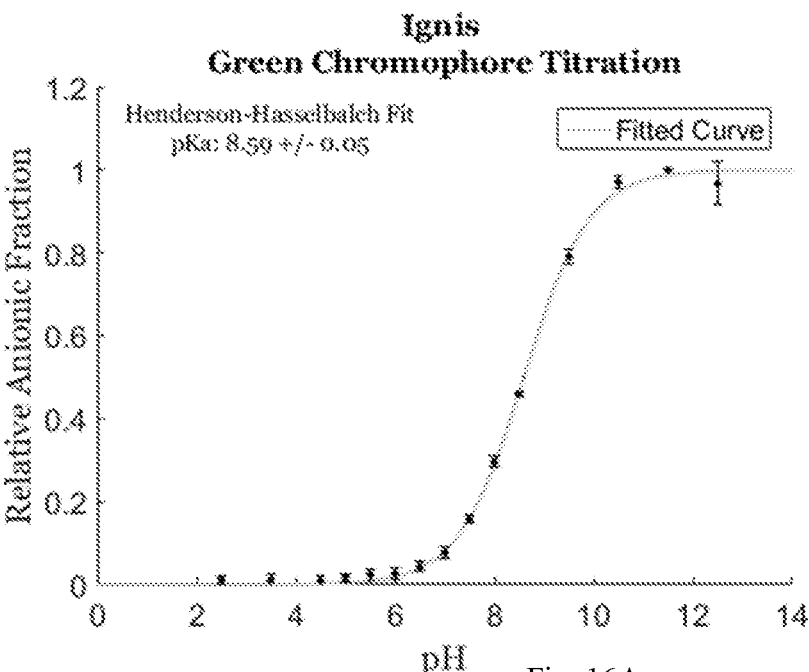
FIGS. 16A-B show the chromophore acidities of green and red Ignis.
Figure 16B:
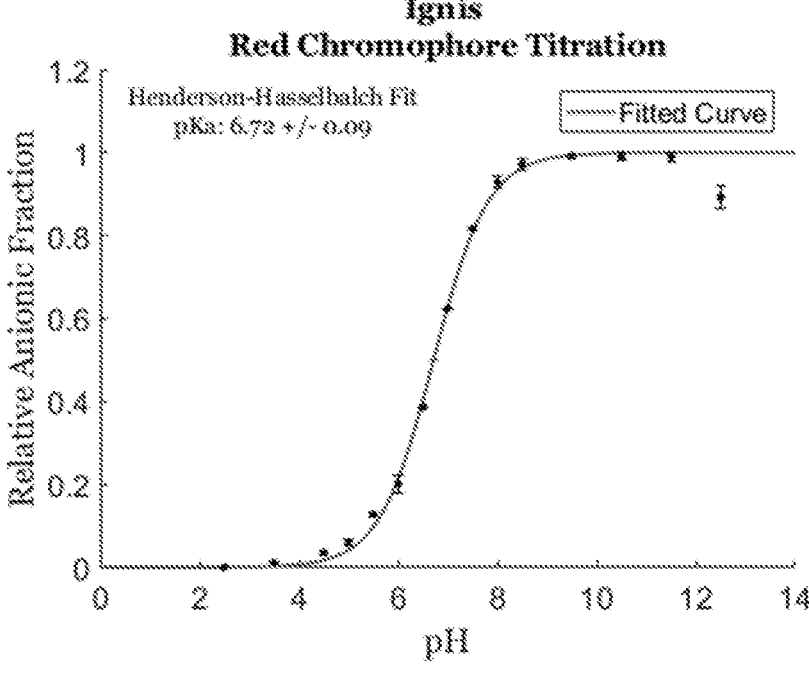

It was noted the conspicuous presence of methionine at position 40 in the PC-FPs with ascending pKa values. In contrast, PC-FPs with descending pKa values have a bulky nonpolar aliphatic residue (valine or isoleucine) in the equivalent position. In the structures of mEos2 and KikGR these residues are found immediately adjacent to the chromophore histidine imidazole moiety (FIG. 14 B). Despite being oriented away from the chromophore, the thioether of methionine is located within 4.4-5.8 Å of the imidazole atoms in the ancestral green mEos2 crystal structure. Alternative conformations bring the M40 thioether to within 3.1-4.5 Å (FIG. 16 E). These distances are compatible with thioether-aromatic interactions found in many proteins (Lewis, A. K. et al. Oxidation increases the strength of the methionine-aromatic interaction. *Nat. Chem. Biol.* 12, 860-866 (2016)); (Reid, K. S. C., Lindley, P. F. & Thornton, J. M. Sulphur-aromatic interactions in proteins. *FEBS Lett.* 190, 209-213 (1985)); (Valley, C. C. et al. The Methionine-aromatic Motif Plays a Unique Role in Stabilizing Protein Structure. *J. Biol. Chem.* 287, 34979-34991 (2012)); and (Pal, D. & Chakrabarti, P. Non-hydrogen bond interactions involving the methionine sulfur atom. *J. Biomol. Struct. Dyn.* 19, 115-128 (2001)). Additionally, the thioether sulphur may behave as a weak nucleophile and to interact with the more electrophilic imidazole N—H (Pal, D. & Chakrabarti, P. Non-hydrogen bond interactions involving the methionine sulfur atom. *J. Biomol. Struct. Dyn.* 19, 115-128 (2001)). Therefore it was reasoned that M41 in mEos4b may interact with the red chromophore histidine in mEos4b. Since this histidine is conjugated in the red, but not green chromophore, it was tested whether that substitution with a branched-chain aliphatic residue as found in mMaple and KikGR could selectively alter the photochemical properties of the red state. To this end, mEos4b-M41I, and mEos4b-M41I/V70T were generated.

Another structural difference between mEos2 and KikGR is the alternative identity of residue 196 (197 in mEos4b), which resides near the chromophore tyrosine phenol ring (FIG. 16 C, D). In the EosFP derivatives, this position is occupied by an isoleucine, but it is instead a methionine in KikGR. This position may therefore influence the photochemistries of both green and red chromophores, though the hydrogen bonding network near the chromophore tyrosine is complex, and it is difficult to predict the impact of either methionine or isoleucine at this position. To explore this interest, mEos4b variants were prepared with the I197M substitution.

A third position of interest that varies between PC-FPs with ascending and descending chromophore pKa values is residue 142, which is invariantly proline in EosFP derivatives, Dendra2, and mKikGR, but valine in the mMaple family. Residue 142 precedes the conserved Ser143, which forms well-documented hydrogen bonds with the chromophore tyrosine hydroxyl in anthozoan fluorescent proteins (Shu, X., Shaner, N. C., Yarbrough, C. A., Tsien, R. Y. & Remington, S. J. Novel Chromophores and Buried Charges Control Color in mFruits, *Biochemistry* 45, 9639-9647 (2006)); (Subach, F. V. & Verkhusha, V. V. Chromophore Transformations in Red Fluorescent Proteins. *Chem. Rev.* 112, 4308-4327 (2012)); and (Adam, V., Nienhaus, K., Bourgeois, D. & Nienhaus, G. U. Structural basis of enhanced photoconversion yield in green fluorescent protein-like protein Dendra2. *Biochemistry* 48, 4905-4915 (2009)). The cyclized side chain of homologous Pro141 in mEos2 is oriented toward the solvent and may speculatively impose some rigidity on the early residues of the β7 strand (including homologous Ser142), which passes immediately over the chromophore tyrosine in the PC-FPs. Therefore, it was tested whether the amino acid at position 142 in mEos4b may alter the conformation and hydrogen bonding of Ser143 to the chromophore, which may in turn differentially stabilize the anionic chromophore and alter its acidity.

Valine at the equivalent position of Pro142 in mMaple-family proteins is interesting due to its hydrophobicity and solvent exposure, and it is unclear how this residue impacts PC-FP photochemistry as it was introduced randomly alongside several other mutations during directed evolution of mMaple from mClavGR2. Unfortunately, no crystal structures of either protein are available. However, both were derived from a synthetic mTFP1 template (McEvoy, A. L. et al. mMaple: A Photoconvertible Fluorescent Protein for Use in Multiple Imaging Modalities. *PLoS ONE* 7, (2012)); and (Hoi, H. et al. A Monomeric Photoconvertible Fluorescent Protein for Imaging of Dynamic Protein Localization. *J. Mol. Biol.* 401, 776-791 (2010)), and it is noted that in the crystal structures of mTFP0.7, Ser146 (homolog of Ser143 in mEos4b) can be found in two conformations—one oriented outward from the beta barrel and one oriented inward toward the chromophore tyrosine (Henderson, J. N., Ai, H., Campbell, R. E. & Remington, S. J. Structural basis for reversible photobleaching of a green fluorescent protein homologue. *Proc. Natl. Acad. Sci.* 104, 6672-6677 (2007)), suggesting some plasticity in this region of β7. In mTFP1 and mClavGR2, the preceding residue (and homolog to Pro142 in mEos4b) is an alanine. Valine exhibits greater beta-strand preference than alanine, and hence the valine found in mMaple at this position may improve beta strand stability (Bhattacharjee, N. & Biswas, P. Position-specific propensities of amino acids in the β-strand. *BMC Struct. Biol.* 10, 29 (2010)). In support of this possibility, β7 rigidity and proper orientation of Ser143 homolog H148 was the important factor in development of the CFP derivative mTurquoise2 (Goedhart, J. et al. Structure-guided evolution of cyan fluorescent proteins towards a quantum yield of 93%. *Nat. Commun.* 3, 751 (2012)). If true, then an isosteric threonine substitution may be better tolerated at this position as it has similarly high beta-strand preference (Bhattacharjee, N. & Biswas, P. Position-specific propensities of amino acids in the β-strand. *BMC Struct. Biol.* 10, 29 (2010)) but would interact better with the bulk solvent due to its polar hydroxyl group. Therefore, to better understand the role of position 142 and potentially improve the folding/structural integrity of mEos4b variants, the effects of P142V and P142T were also examined.

Figure 17A:
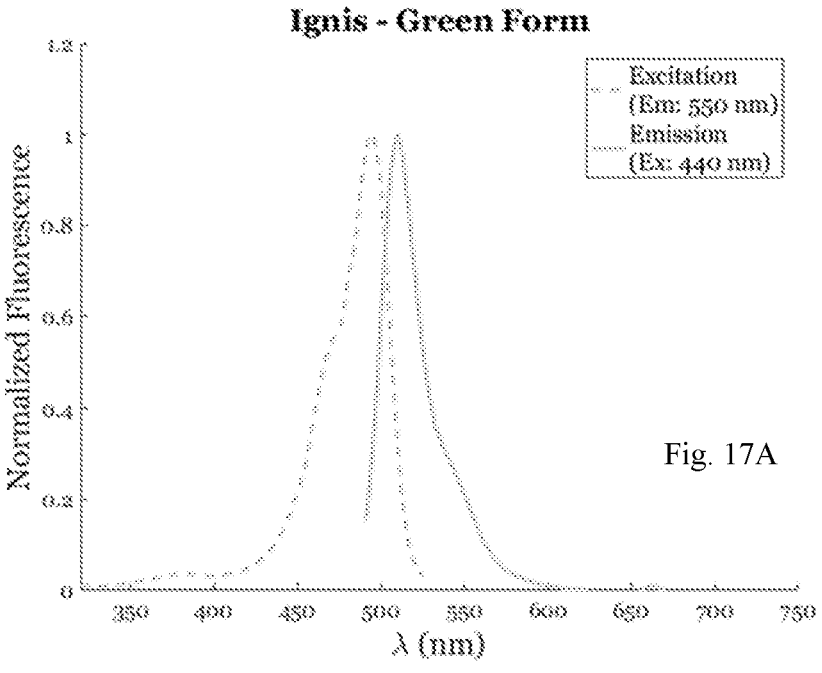
FIGS. 17A-B show the fluorescence spectra of Ignis.
Figure 17B:
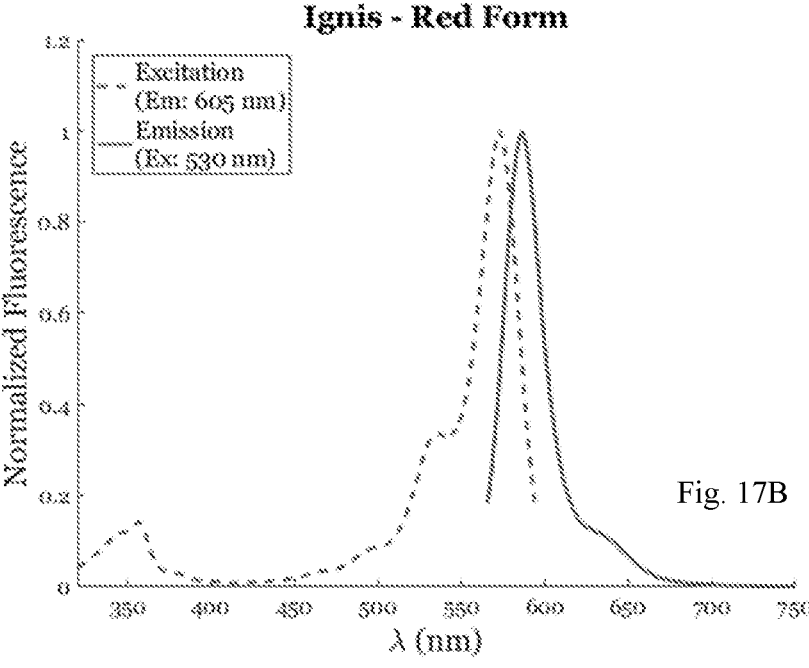
Figure 18:
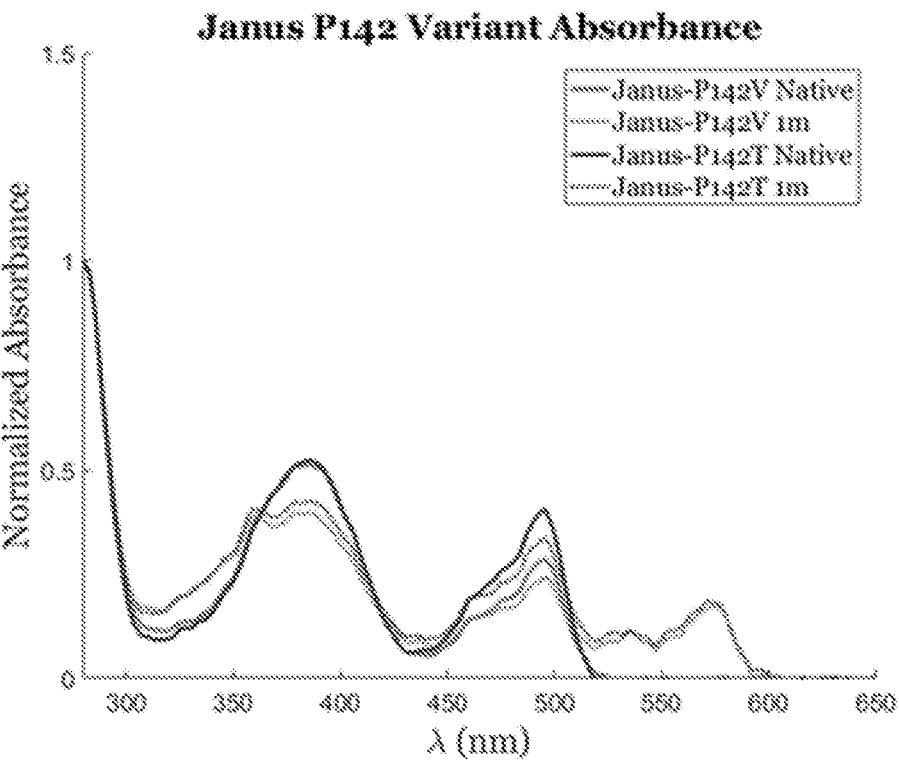
FIG. 18 shows the absorbance spectra of Janus proline 142 Variants. Normalized absorbance spectra of native and photoconverted Janus-P142V (magenta) and Janus P142T (blue). Note that both variants exhibit similar absorbance of their neutral chromophores, yet Janus-P142T demonstrates substantially greater absorbance of its anionic chromophore (solid lines). Both variants photoconvert similarly after 1 minute of 385 nm LED illumination in vitro (dotted lines).

Chromophore Characteristics of mEos4b Variants. mEos4b-V70T. As noted above, the A69T substitution has well-documented effects in mEos2 and mEos3.2, and its analogous substitution in mEos4b (V70T) demonstrates similar impacts on chromophore photochemistry (Turkowyd Bartosz et al. A General Mechanism of Photoconversion of Green-to-Red Fluorescent Proteins Based on Blue and Infrared Light Reduces Phototoxicity in Live—Cell Single—Molecule Imaging. *Angew. Chem. Int. Ed.* 56, 11634-11639 (2017)); and (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). Thus, mEos4b photochemistry with mEos4b and mEos4b-V70T as guide templates was assessed. To complement the measurements of mEos4b chromophore acidity, the mEos4b-V70T pKa values were measured. In contrast to literature, a green pKa of $7.21 \pm 0.03$ and red pKa of $6.96 \pm 0.05$ for this variant was found (FIG. 17). It is noted that the pKa values are calculated from at least three highly-consistent independent titrations over thirteen pH values, whereas previous reported value was inferred from fluorescence intensity over eight pH values with an unstated sample size. Titration of additional residues may influence fluorescence intensity independent of the protonation status of the chromophore tyrosine. The results also show a lower extinction coefficient for mEos4b-V70T chromophore than reported in literature, at 34,435 $M^{-1}cm^{-1}$ (alkali-denaturation) and 28,749 $M^{-1}cm^{-1}$ (total protein) (Turkowyd Bartosz et al. A General Mechanism of Photoconversion of Green-to-Red Fluorescent Proteins Based on Blue and Infrared Light Reduces Phototoxicity in Live—Cell Single—Molecule Imaging. Angew. Chem. Int. Ed. 56, 11634-11639 (2017)). Absorbance spectra of mEos4b-V70T are provided in FIG. 18. Consistent with its high green state pKa, mEos4b-V70T exhibits a prominent peak at 385 nm from to its neutral chromophore, reminiscent of Dendra2. Since Dendra2 exhibited noticeably faster photoconversion and greater yield than mEos4b at early time points in cellulo, photoconversion of recombinant mEos4b and mEos4b-V70T side-by-side was tested after brief 385 nm LED illumination. Interestingly, mEos4b-V70T did not photoconvert noticeably better than mEos4b in vitro at these early time points (FIG. 18B), despite its higher green pKa and the prominent increase in neutral chromophore in its absorbance spectrum at physiological pH.

Figures 19A, 19B, 19C, 19D:
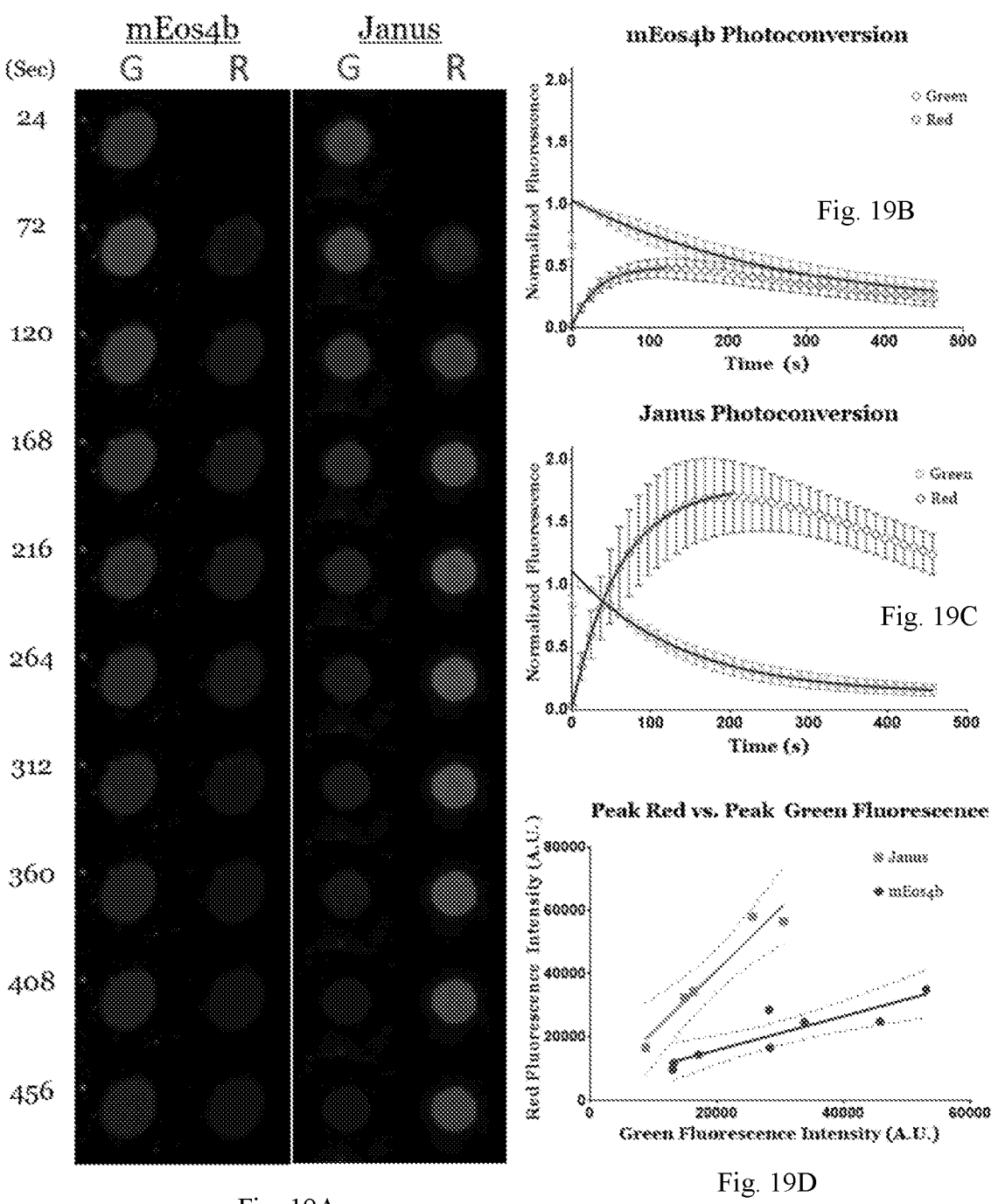
FIGS. 19A-D show the superior fluorescence yield of Janus upon photoconversion in vitro.

Substitutions at Position 41 in mEos4b and mEos4b-V70T It was tested whether Met41 may interact with the chromophore histidine in mEos4b, and whether an introduction of a bulky, aliphatic side chain such as valine or isoleucine (observed in KikGR and mMaple-family proteins) could therefore specifically influence characteristics of the red chromophore. To examine the role of M41 in mEos4b photochemistry, an isoleucine was introduced at this position in mEos4b and mEos4b-V70T, as it presumably imposes the greatest steric and hydrophobic influence on the chromophore environment among nonpolar, aliphatic amino acids. It was found that mEos4b-M41I has an absorbance peak at 505 nm. However, purified solutions of this variant were dim to the eye and exhibited substantially reduced absorbance relative to mEos4b. Nonetheless, mEos4b-M41I did photoconvert under 385 nm LED illumination (FIG. 17 A). The red state revealed a ~5 nm bathochromic shift in its peak absorbance relative to mEos4b (~575 nm vs. ~570 nm, respectively). The longer wavelength presumably reflects a more electronically stable red chromophore. The mEos4b-M41I chromophore demonstrates a green state pKa of 5.78 (FIG. 19B). Unfortunately, given the weak absorbance of this variant, no satisfactory pKa determination could be made for the red state chromophore using the standard protocol. Overall, the results suggest that the folding and/or chromophore maturation of mEos4b-M41 is compromised it was not characterized further.

Figure 20A:
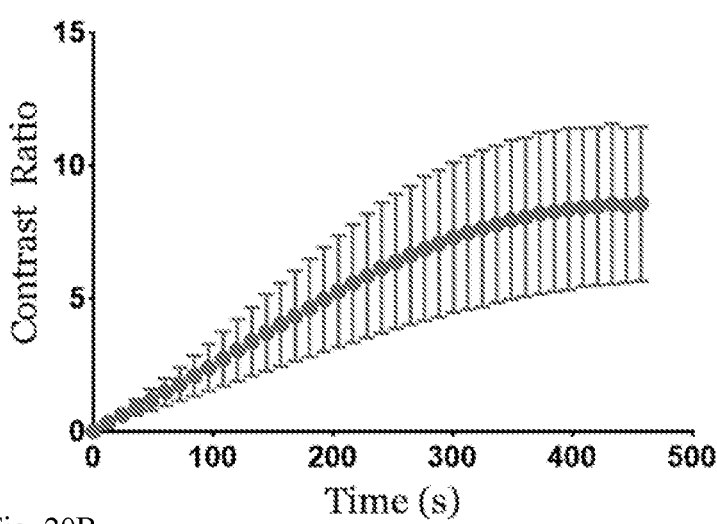
FIGS. 20A-B show the photoconversion contrast of Janus and mEos4b in vitro.
Figure 20B:
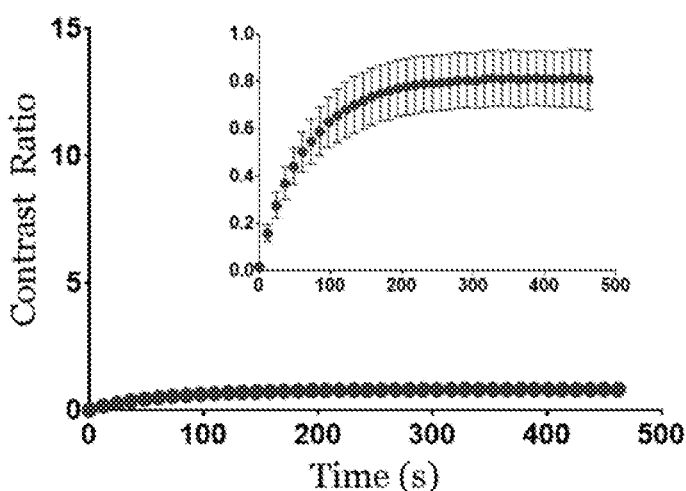
Figures 21A, 21B, 21C:
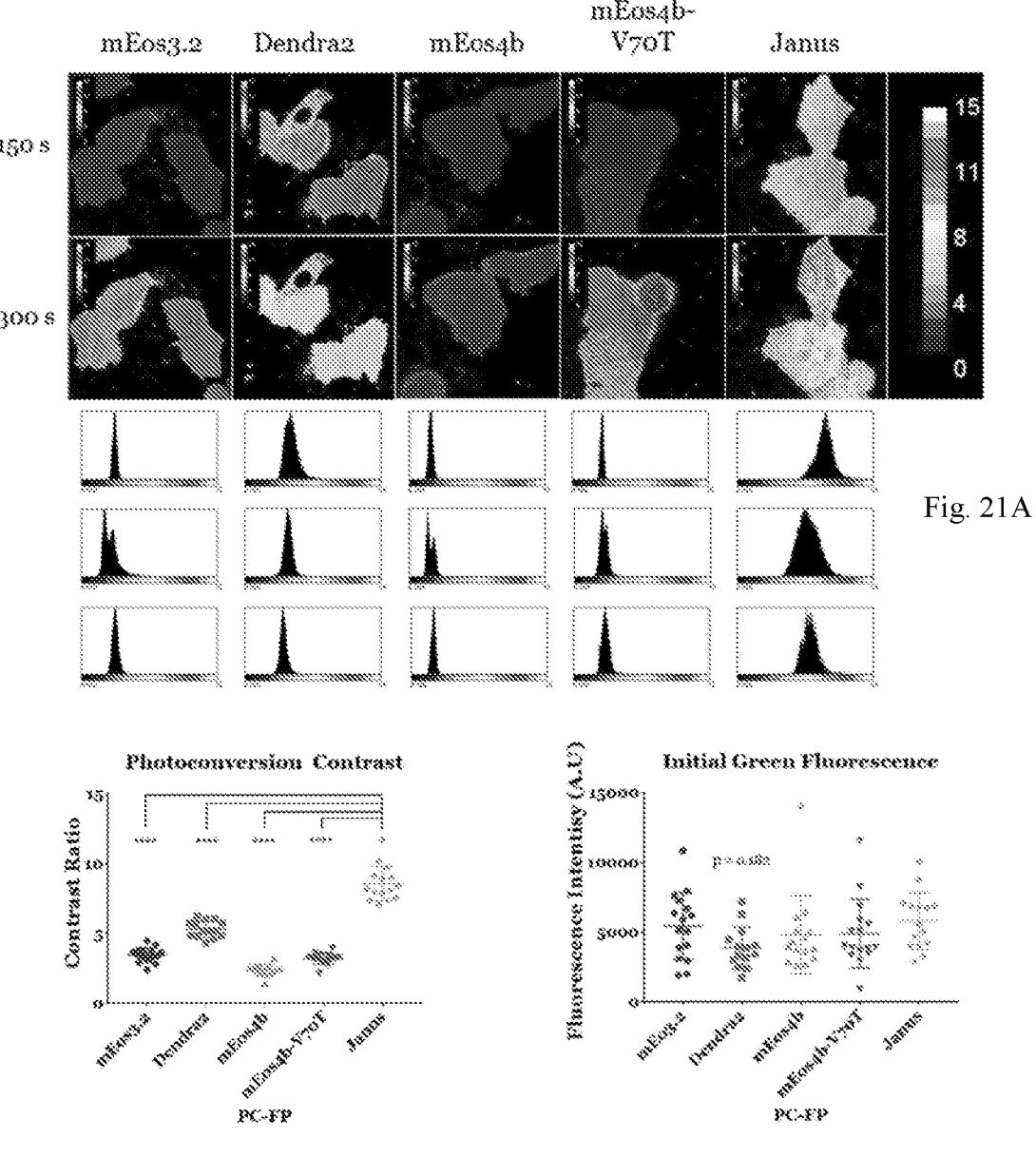
FIGS. 21A-C show the photoconversion contrast of mEos4b variants in cellulo.

Despite the generally disappointing results of mEos4b-M41I, the M41I substitution produced a brightly fluorescent variant with improved photoconversion properties when introduced into the mEos4b-V70T template. The initial photoconversion tests were so encouraging that the mEos4b-M41I/V70T variant was named "Janus"—after the two-faced Roman god of transitions. Like mEos4b-V70T, the absorbance spectrum of native Janus at pH 7.4 features a prominent peak at 385 nm indicating substantial chromophore protonation (FIG. 20A). Unlike mEos4b-V70T, Janus rapidly accumulates red chromophore under 385 nm LED illumination and outperformed mEos4b in side-by-side tests (FIG. 20B, insets). It is also noted that the green anionic peak at ~493 shifts upward and to about 496 nm at the earliest photoconversion time points. This effect is clearly observed in the representative progressive photoconversion experiment provided in FIG. 21A. The yield of red mEos4b and Janus species plateaus at later photoconversion time points, presumably due to competition between photobleaching and photoconversion processes, but Janus reaches this plateau in half the time of mEos4b (and attains a higher red absorbance peak).

Figure 22:
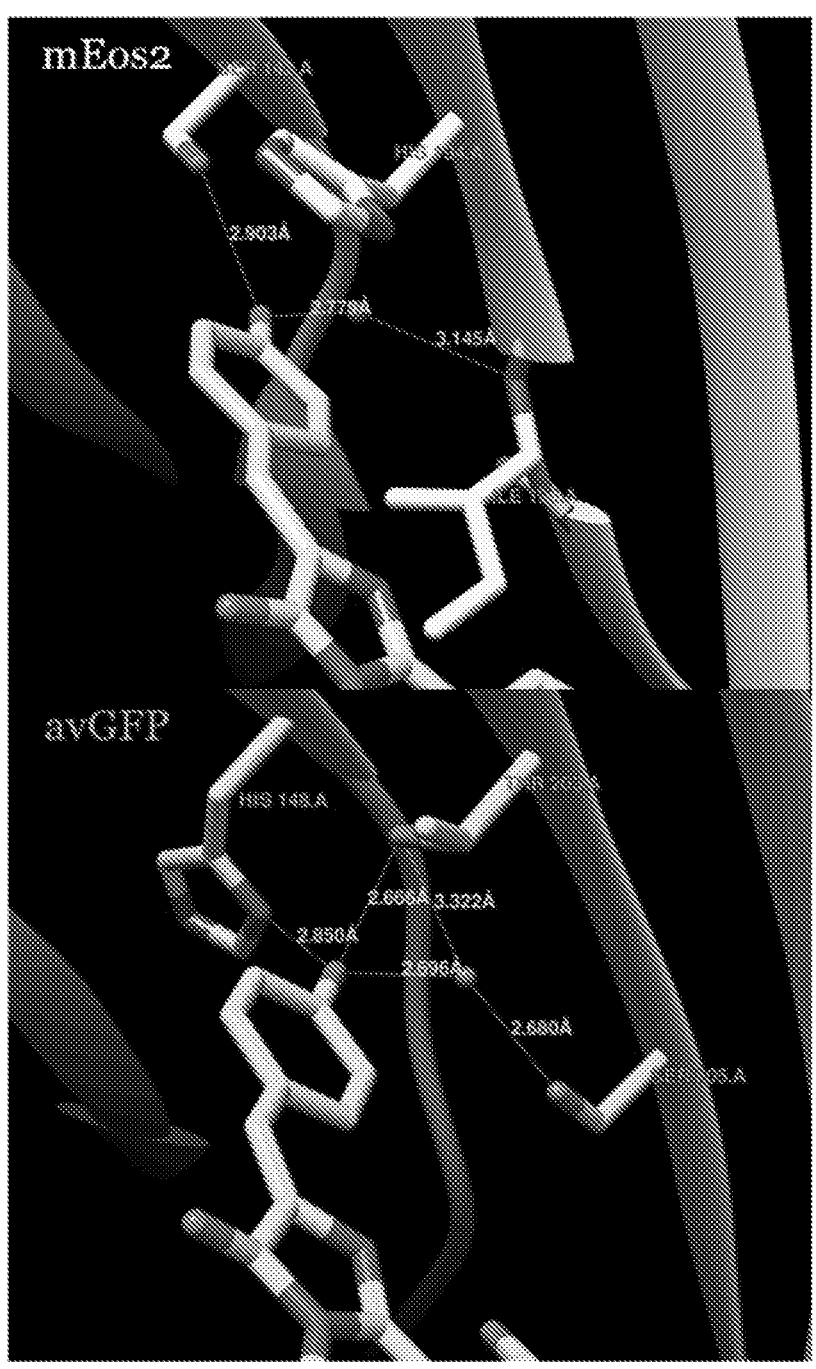
FIG. 22 shows the comparative positions of Ile196 and Thr203 in mEos2 and AvGFP. The hydrogen bonding networks near the chromophore tyrosine residue in mEos2 (PDB code: 3S05) and AvGFP-S65T (PDB code: 1EMA) appear configured to stabilize the anionic chromophore. Introduction of methionine at position 197 of Janus (equivalent to 196 in mEos2) yields Ignis, which exhibits an absorption spectrum similar to AvGFP-T203I.
Figure 23B:
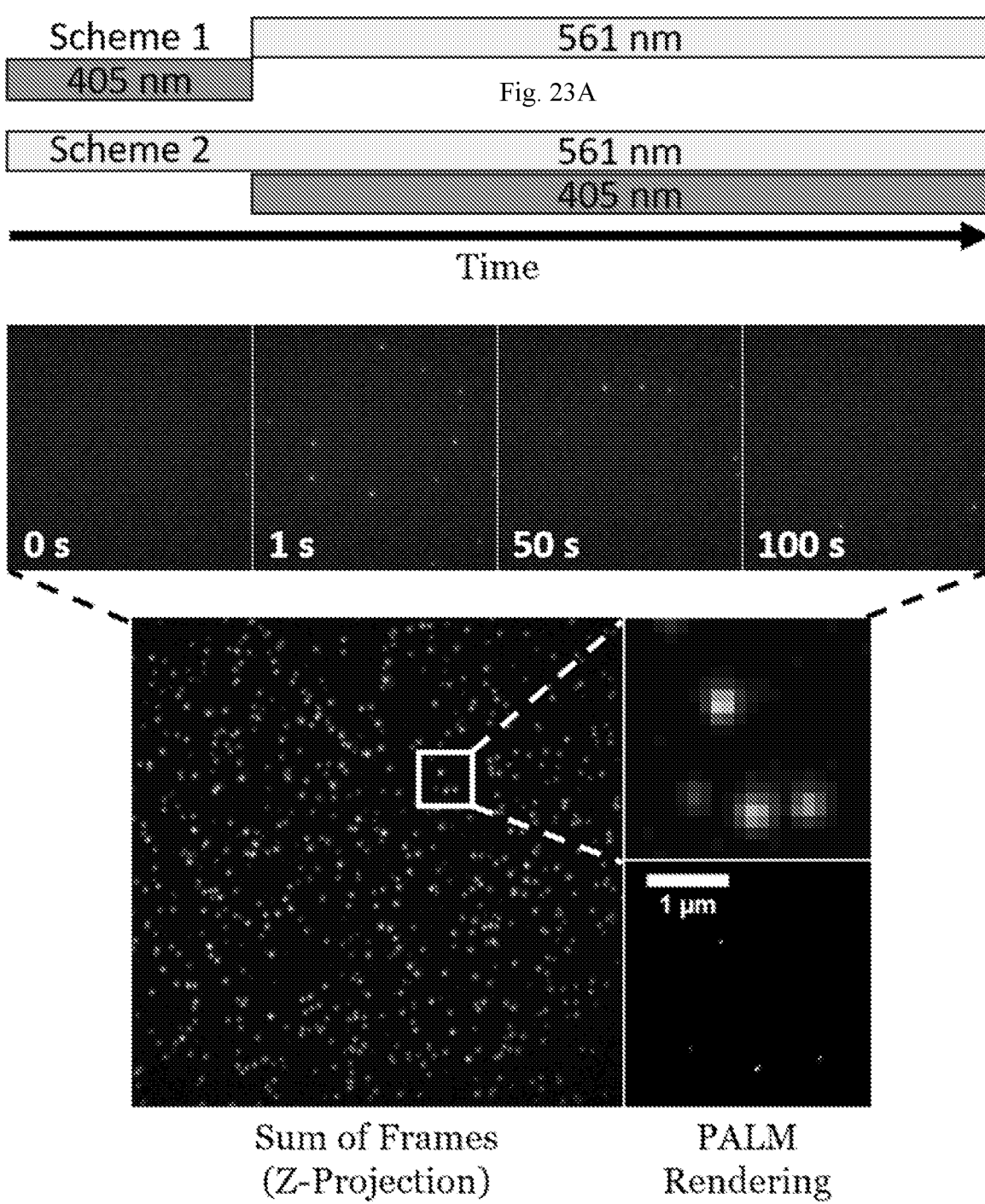

Like mEos4b-V70T and Dendra2, Janus exhibits a hypsochromic shift in its green fluorescence spectrum relative to mEos4b, with excitation and emission maxima at 493 nm and 509 nm, respectively (FIG. 22 A). Upon photoconversion, the red state excitation spectrum resembles red mEos4b with a peak at 571 nm, but the red emission maximum is red-shifted by ~5 nm to 585 nm (FIG. 22B). The pKa values of Janus in its green and red states were calculated at 7.57±0.02 and 6.60±0.04, respectively (FIG. 23), revealing a descent of nearly one full pH unit upon photoconversion. It was estimated that the extinction coefficient of the green Janus chromophore at ~30,520 $M^{-1}cm^{-1}$ (alkali-denaturation method) and ~25,800 $M^{-1}cm^{-1}$ (total protein method), similar to the bright cyan fluorescent protein mTurquoise (Goedhart, J. et al. Bright cyan fluorescent protein variants identified by fluorescence lifetime screening. Nat. Methods 7, 137-139 (2010)).

Methionine Substitution at Position 197 in mEos4b and Janus. Kaede-like PC-FPs except KikGR and mKikGR feature an isoleucine at position 197 (numbering relative to mEos4b). In KikGR and mKikGR, the homologous residue is instead a methionine (Met199). Given the proximity of Met199 to the chromophore tyrosine in KikGR (FIG. 14 D), it was tested whether the flexible, potentially nucleophilic thioether side chain of methionine might alter both the green and red state fluorescence properties of the chromophore. Thus, a methionine was introduced at position 197 in mEos4b and Janus to explore the effect of this residue.

mEos4b-I197M was not clearly fluorescent and this variant was not further characterized. This negative result suggested that Kaede-like PC-FPs do not tolerate a methionine at both positions 41 and 197, since KikGR family proteins have a valine at position 41 and no known Kaede-like PC-FPs have methionine in both positions. Alternatively, I197M may fundamentally hinder chromophore formation in mEos4b independent of other chromophore-proximal residues. To discriminate between these possibilities, I197M was introduced into the Janus variant (isoleucine at position 41) to generate mEos4b-M41I/V70T/I197M. Surprisingly, solutions of this mutant were faintly green to the eye but formed a deep red color within mere seconds of 385 nm LED illumination. The rapidity of photoconversion from an initially muted, indistinct material conjured the image of an igniting flame, and this variant was named "Ignis."

Figure 24A:
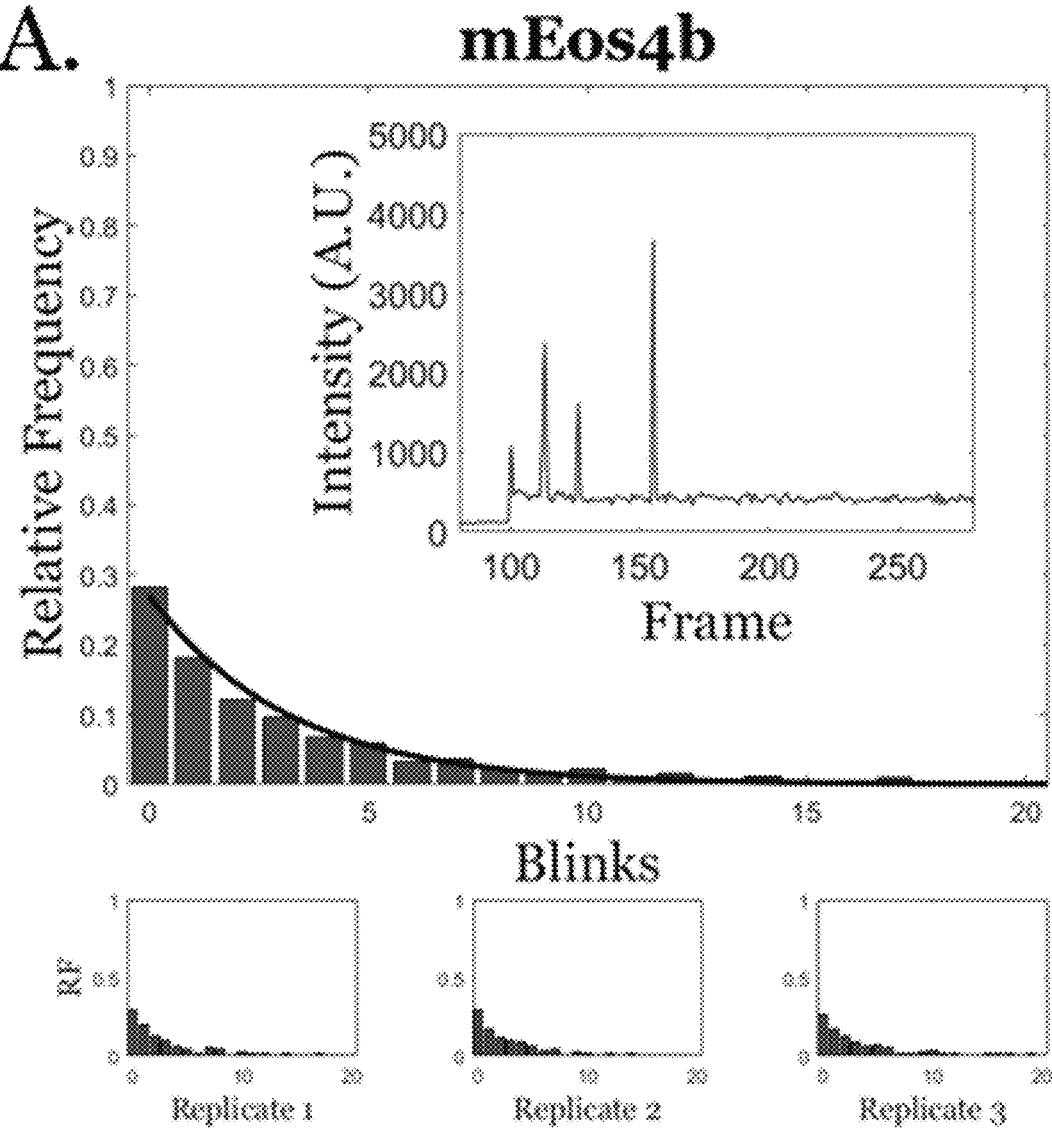
FIGS. 24A-D show the PC-FP blinking distributions (pH 7.4). PC-FP blinking distributions at pH 7.4 with geometric fit (black curve), representative replicates (miniature plots), and representative single molecule intensity trace (inset), for A) mEos4b (N=615), B) mEos4b-V70T (N=455), C) Janus (N=873), and D) Ignis (N=1283).
Figure 24B:
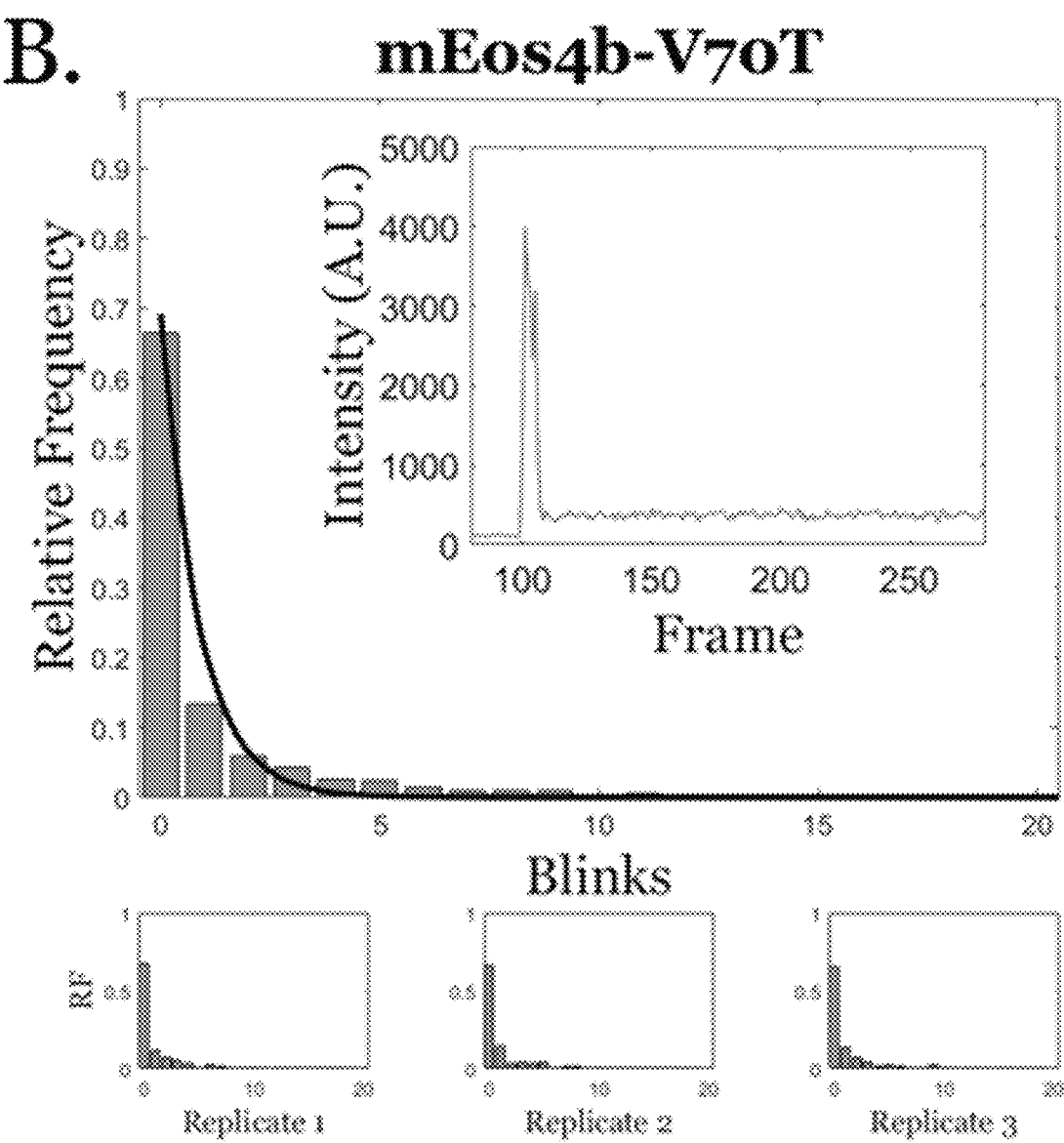
Figure 24C:
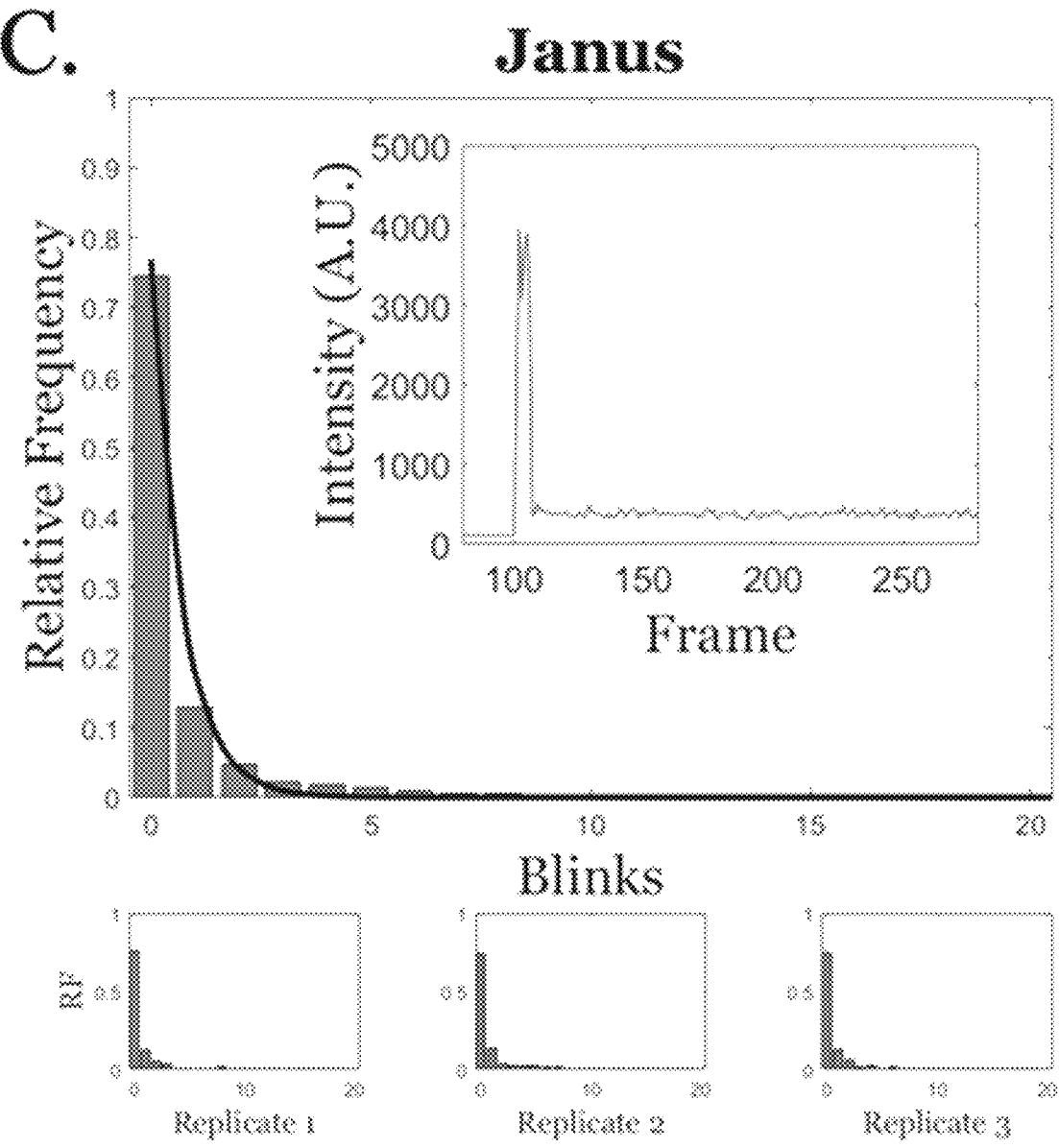
Figure 24D:
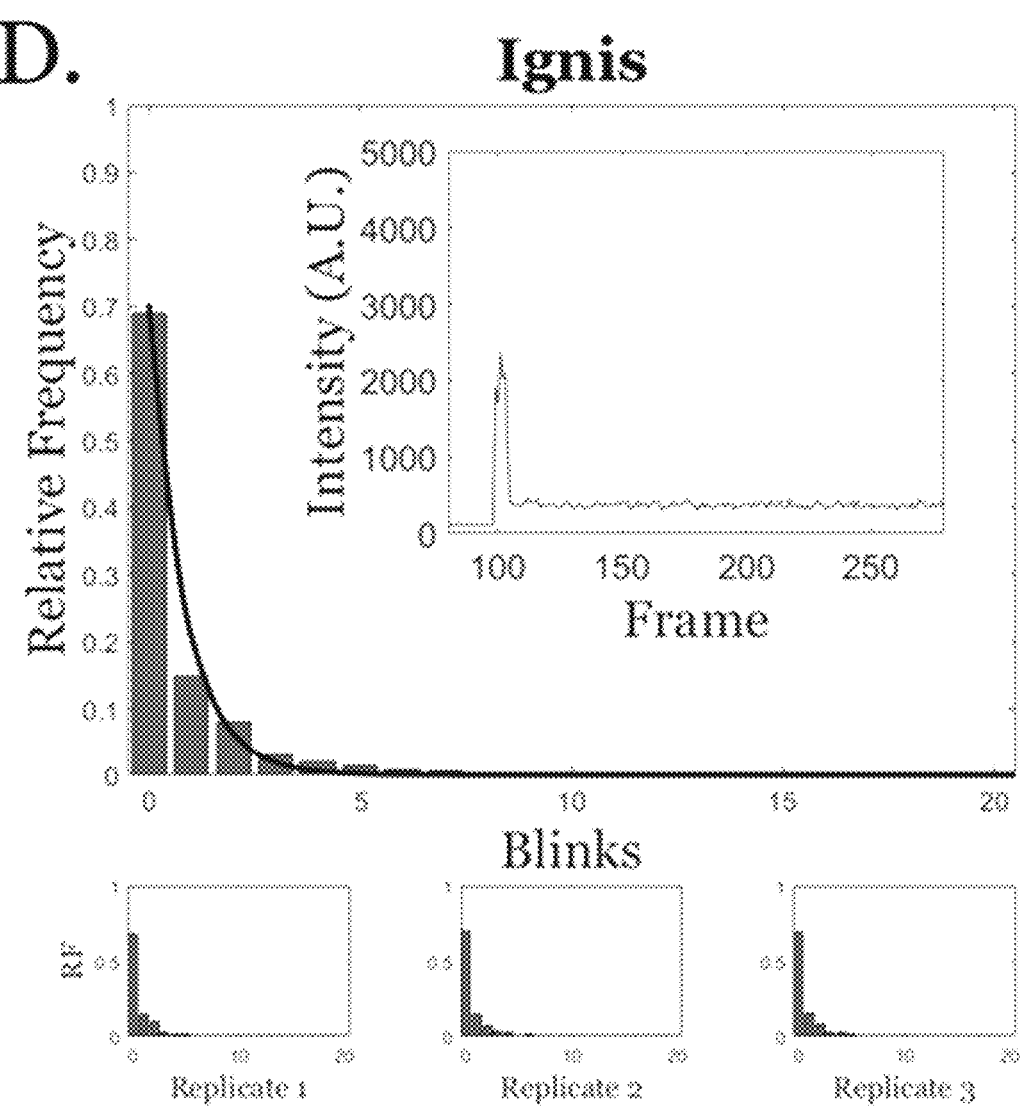
Figure 25:
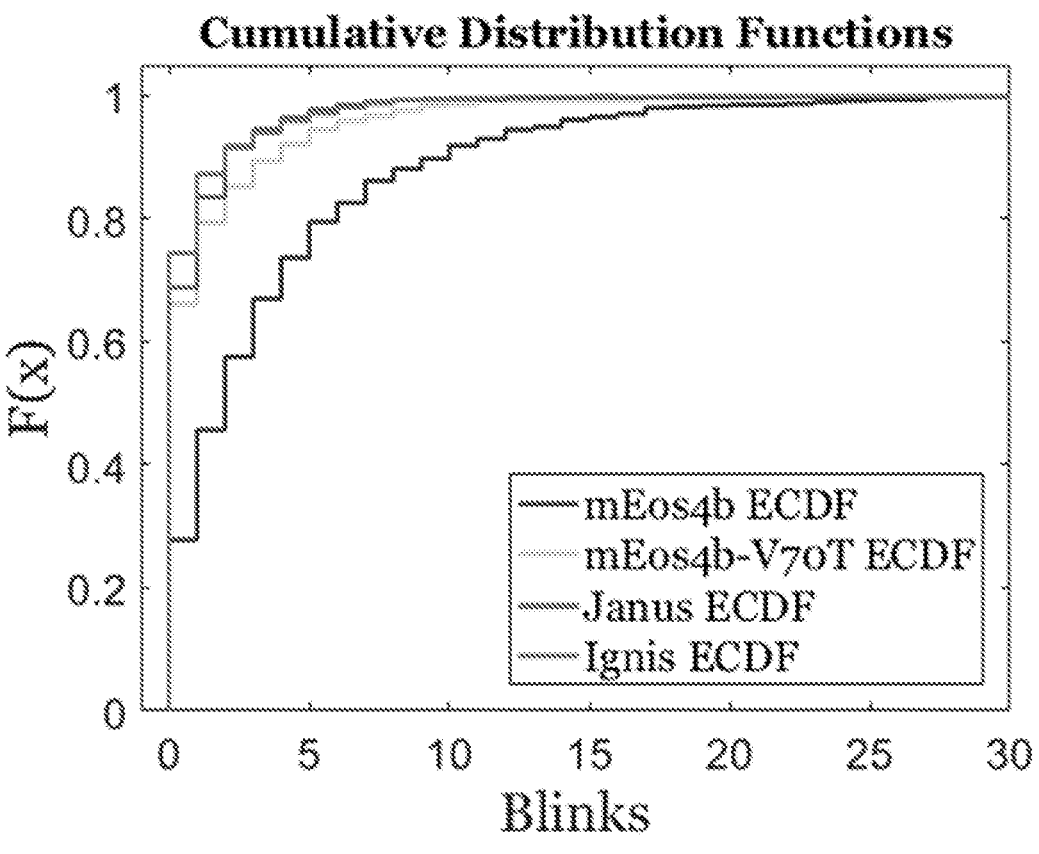
FIG. 25 shows PC-FP blinking empirical cumulative distribution functions. ECDFs of the blinking behavior for each PC-FP examined at pH 7.4, in the absence of 405 nm light. F(x) represents value of the ECDF (the fractional sum of molecules) at each corresponding blink value.
Figure 26A:
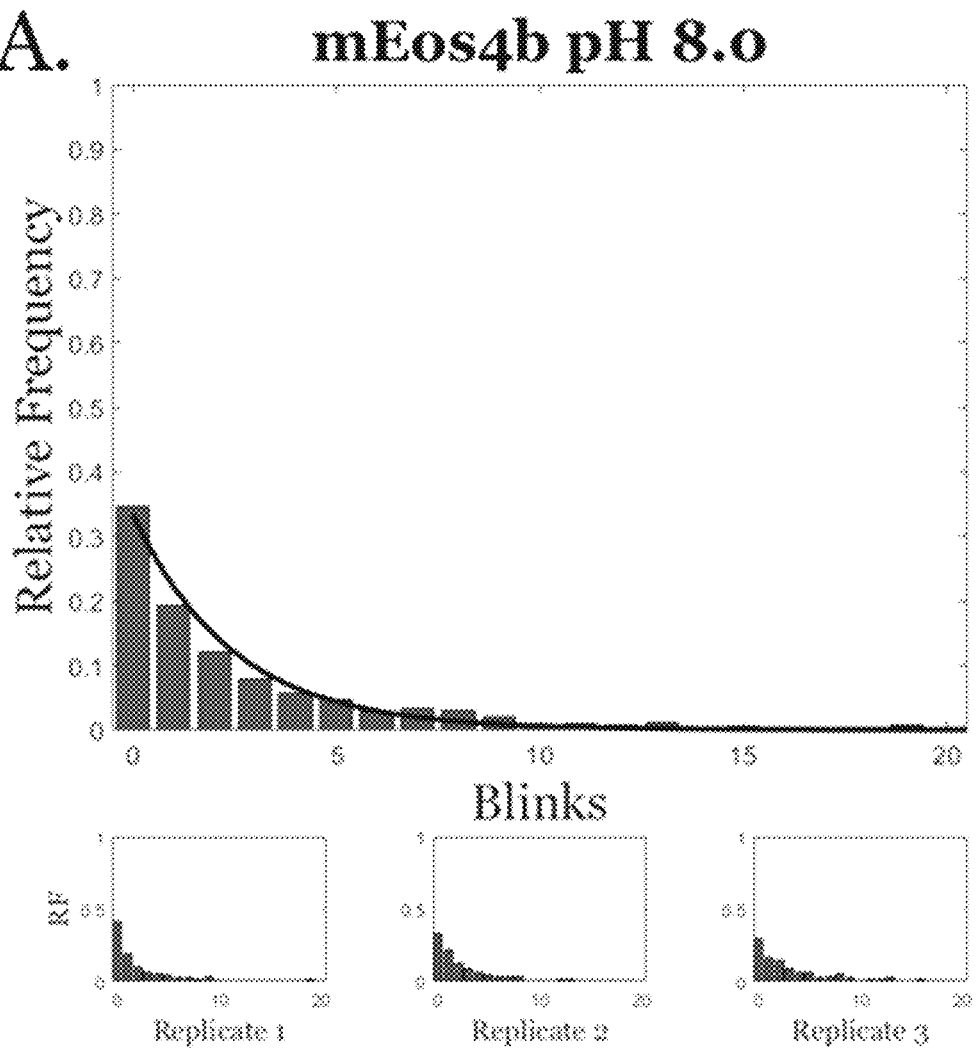
FIGS. 26A-D show PC-FP blinking distributions (pH 8.0). PC-FP blinking distributions at pH 8.0 with geometric fit (black curve), representative replicates (miniature plots) for A) mEos4b (N=653), B) mEos4b-V70T (N=388), C) Janus (N=529), and D) Ignis (N=1245).
Figure 26B:
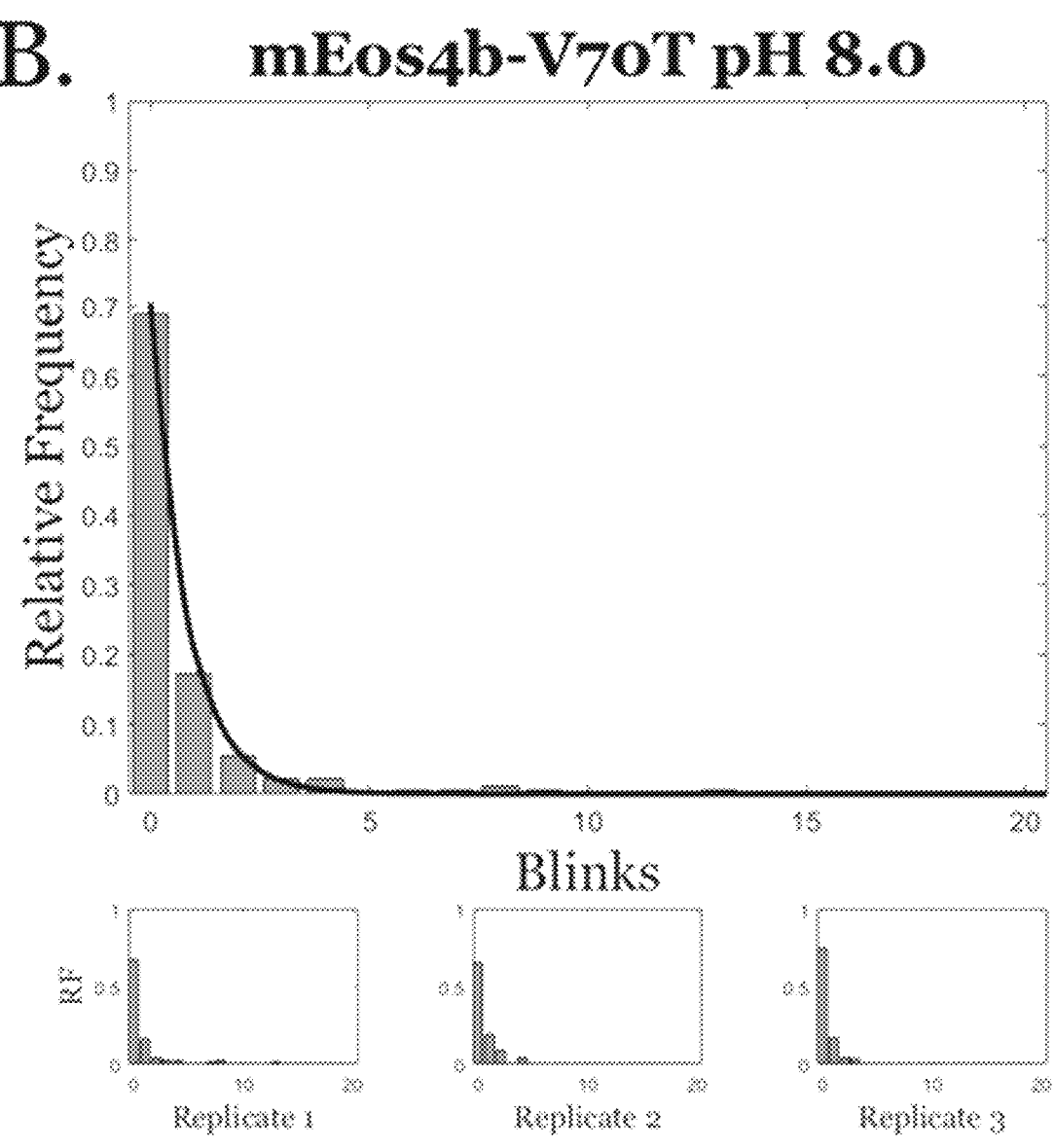
Figure 26C:
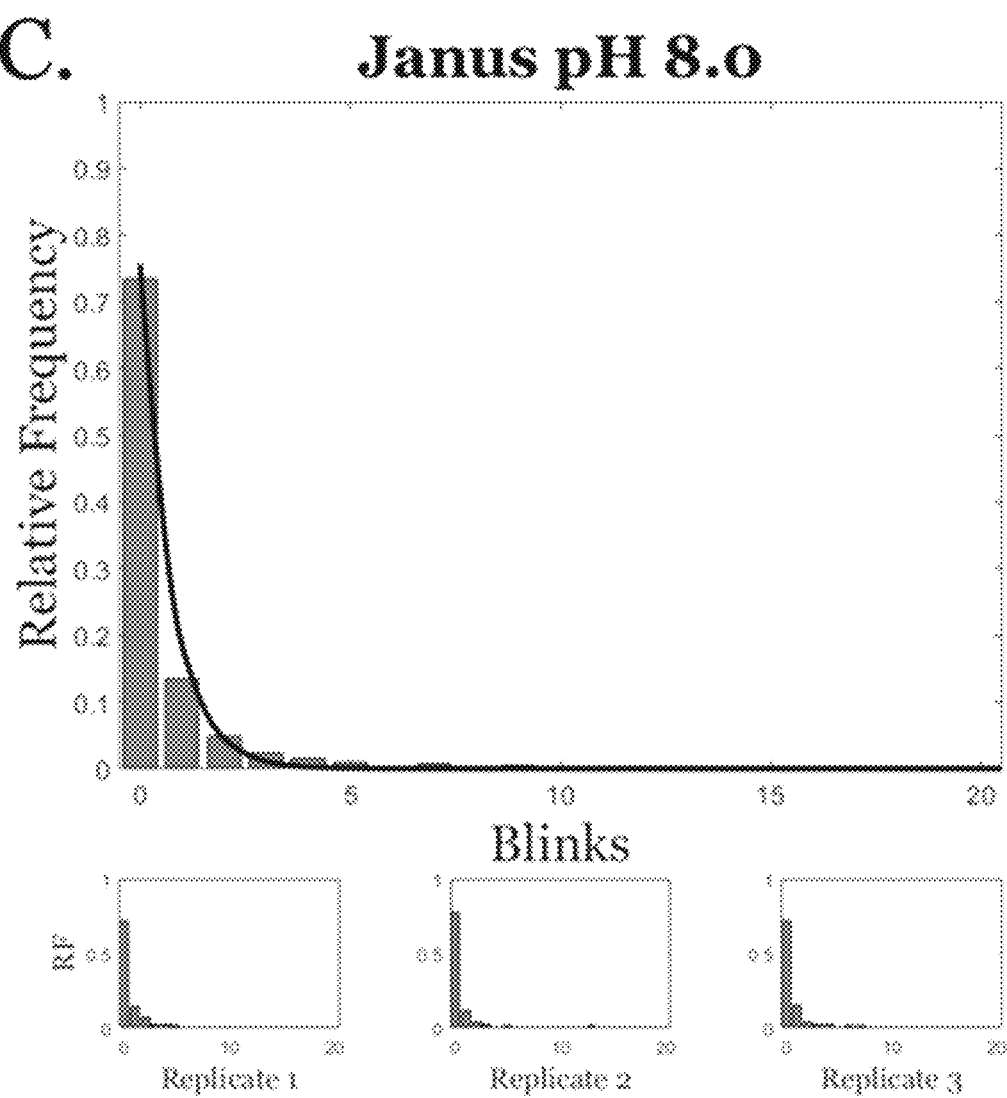
Figure 26D:
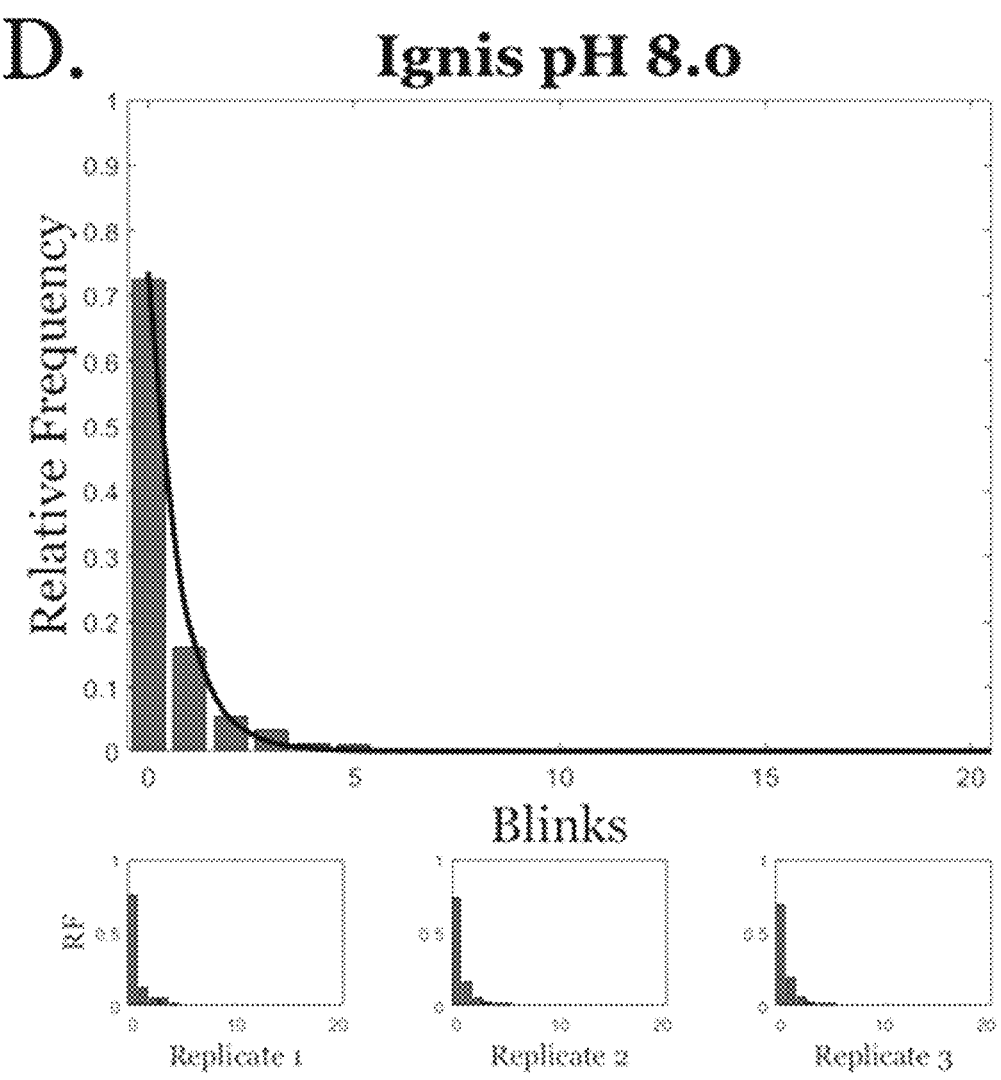

Like the mEos4b variants examined herein, Ignis forms a p-HBI chromophore as indicated by a broad absorbance band with peak at 446 nm in 1M NaOH. However, the native chromophore is almost entirely protonated at pH 7.4 (FIG. 24A). Under 385 nm LED illumination, equimolar solutions of Ignis photoconverted almost four times faster than mEos4b (FIG. 24B, insets), producing a prominent red peak at ~573 nm. Titration of the green chromophore revealed an astonishingly high pKa of 8.59±0.05—the highest known of in any PC-FP to date (FIG. 25A). Yet despite this extreme green state pKa, the red chromophore pKa was modestly shifted to 6.72±0.09 (FIG. 25B). The green-to-red pKa descent is therefore nearly two full pH units in magnitude.

The fluorescence spectra of Ignis are provided in FIG. 26. The green excitation maximum occurs at ~495 nm, with peak emission at ~509 nm. In its red form, Ignis excites maximally at 573 nm and emits with a peak at 586 nm—the farthest red-shifted emission of any mEos4b variants so far examined.

Valine and Threonine Substitutions at Position 142 of Janus. Characterization of P142V and P142T variants is described herein. Given the improved performance of Janus relative to mEos4b and mEos4b-V70T, P142V and P142T were introduced into this variant in lieu of mEos4b to improve folding or pKa characteristics of the probe. The absorbance spectra of Janus-P142V and Janus-P142T are provided in FIG. 27. Both variants showed increased absorbance of the neutral green chromophore band compared to Janus, indicative of a higher green state pKa. The green state peak is ~496 nm, and a red peak appears to evolve at ~575 nm. One difference is that the anionic peak of Janus-P142T absorbs more strongly than Janus-P142V. It is currently unclear if this reflects a difference in the intrinsic molar absorptivity of the green anionic states, or a difference in chromophore pKa between the two variants which is obscured due to the broad neutral chromophore absorbance band. Measurement of each variant's green pKa will largely resolve this question.

Ensemble Fluorescence Photoconversion of mEos4b and Janus in vitro. The absorbance spectra of Janus solutions photoconverted under 385 nm LED illumination prompted examination of the photoconversion rate as measured via fluorescence. Droplets of mEos4b and Janus were prepared as emulsions in 8-octanol and photoconversion time courses of single isolated droplets were measured with confocal laser scanning microscopy (Kremers, G.-J. & Piston, D. Photoconversion of Purified Fluorescent Proteins and Dual-probe Optical Highlighting in Live Cells. *JOVE J. Vis. Exp.* e1995 (2010)). Here 405 nm laser scans were used to photoconvert each protein, followed by 488 nm and 561 nm laser scans to readout fluorescence from the green and red forms, respectively (FIG. 28 A). Green and red fluorescence intensities at each time point were then normalized to the peak green intensity of each droplet permitting the information about photoconversion kinetics from both the red and green fluorescence data to be interpreted.

Figure 28A:
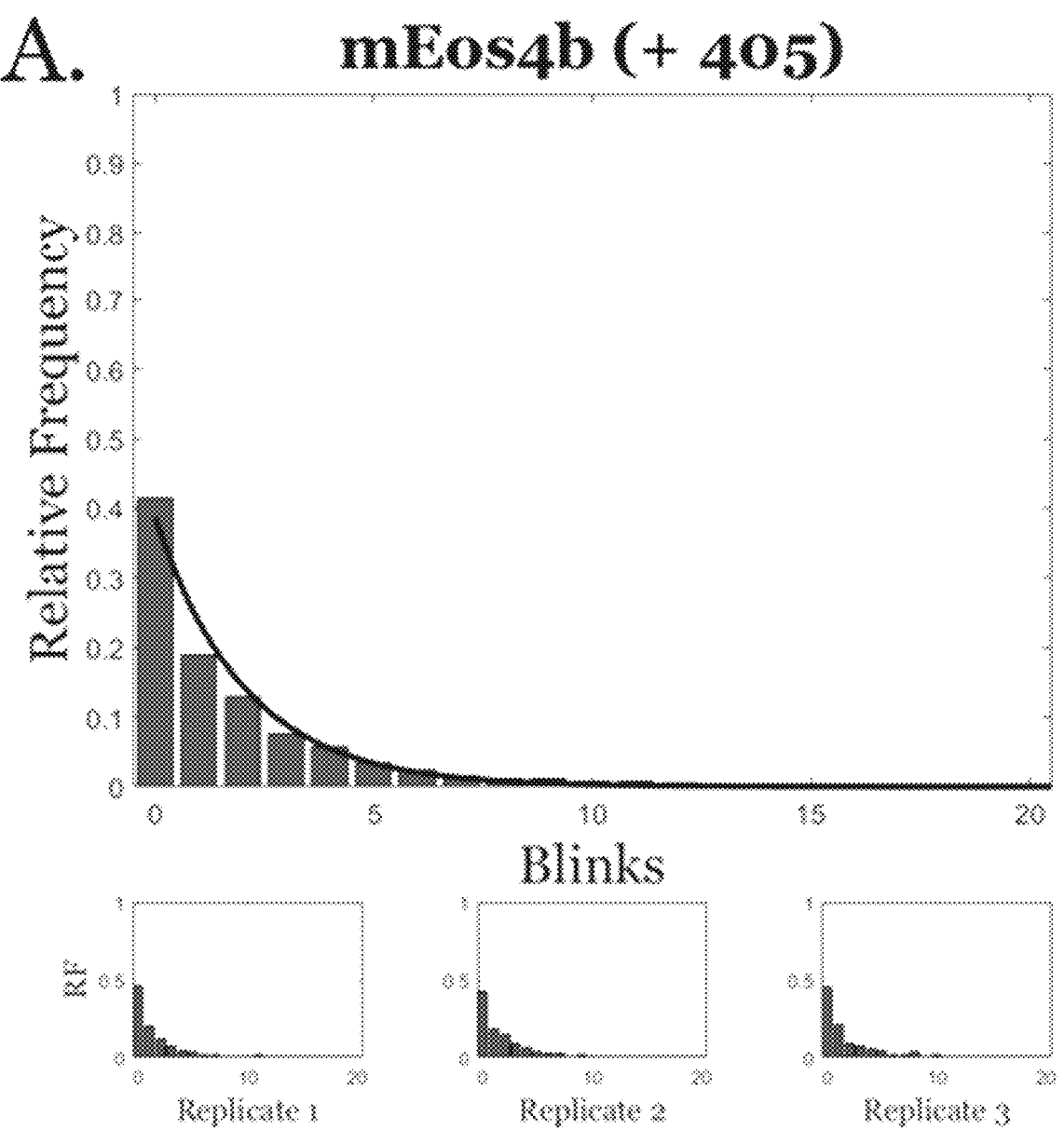
FIGS. 28A-D show PC-FP blinking distributions with 405 nm Light (pH 7.4). PC-FP blinking distributions at pH 8.0 with geometric fit (black curve), representative replicates (miniature plots) for A) mEos4b (N=4454), B) mEos4b-V70T (N=4973), C) Janus (N=4852), and D) Ignis (N=4874).
Figure 28B:
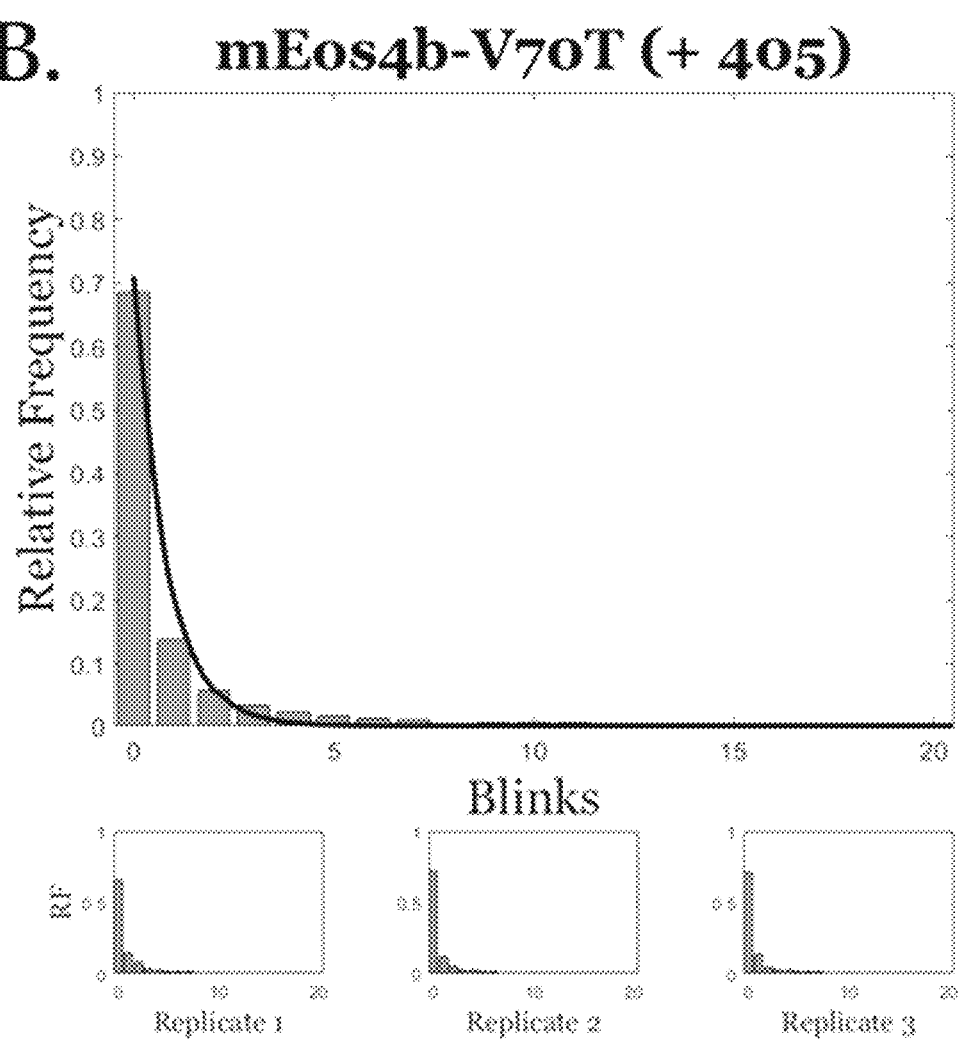
Figure 28C:
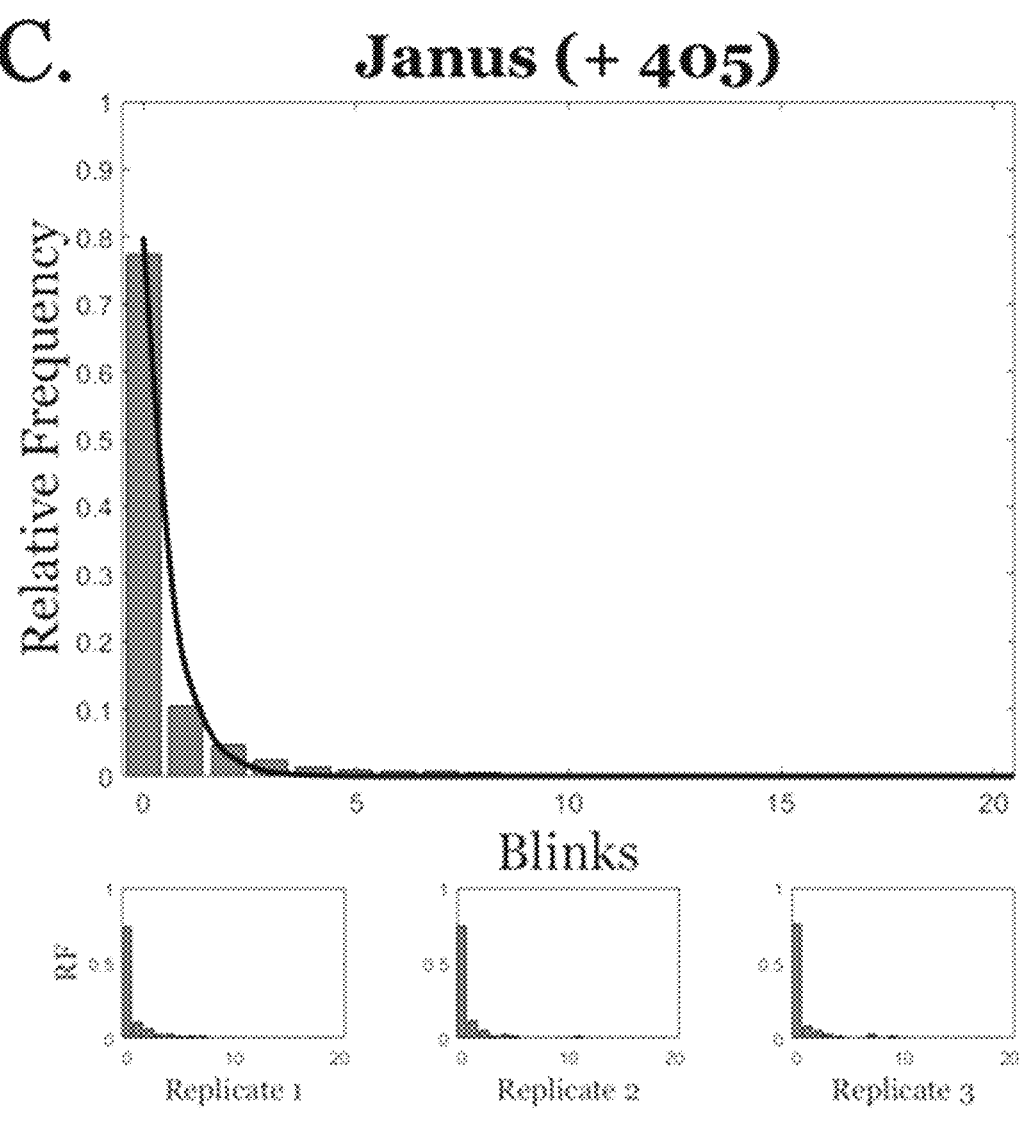
Figure 28D:
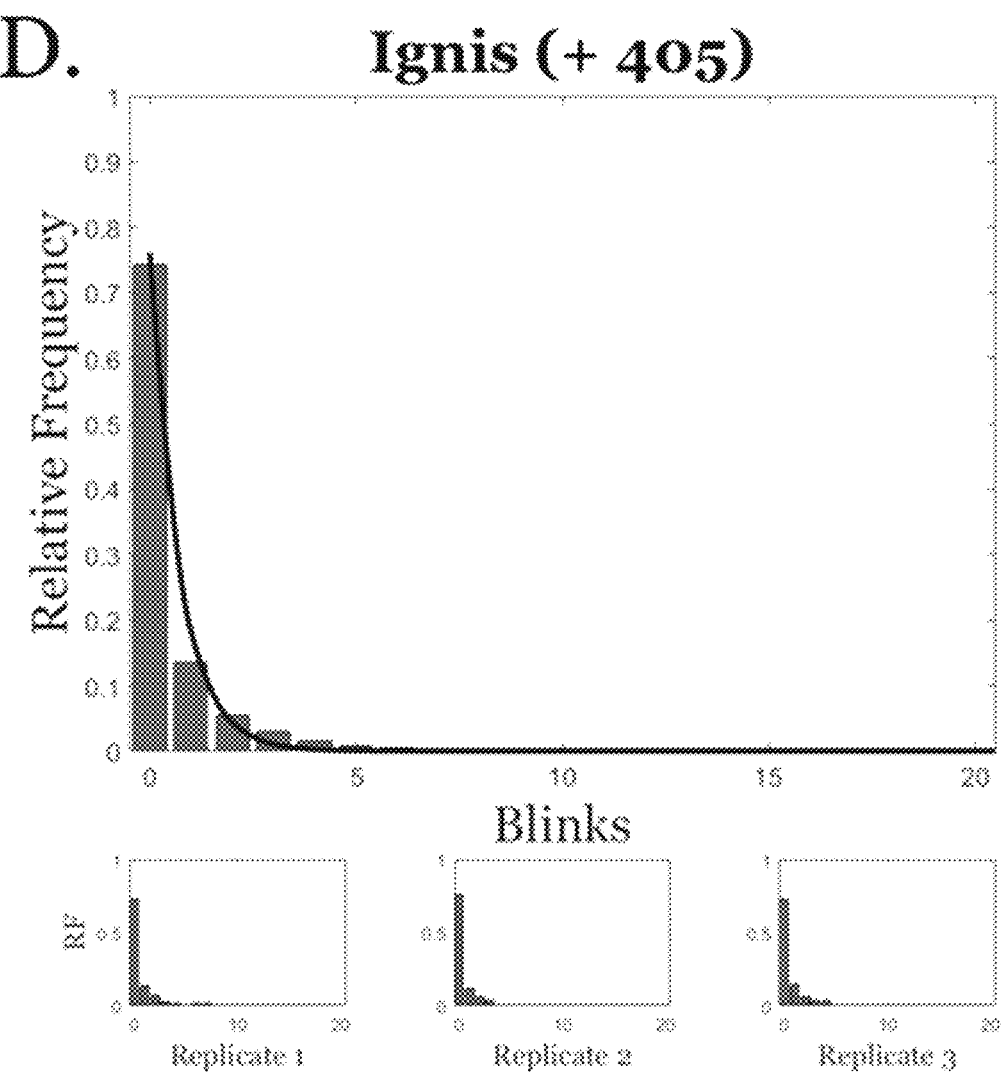
Figure 29A:
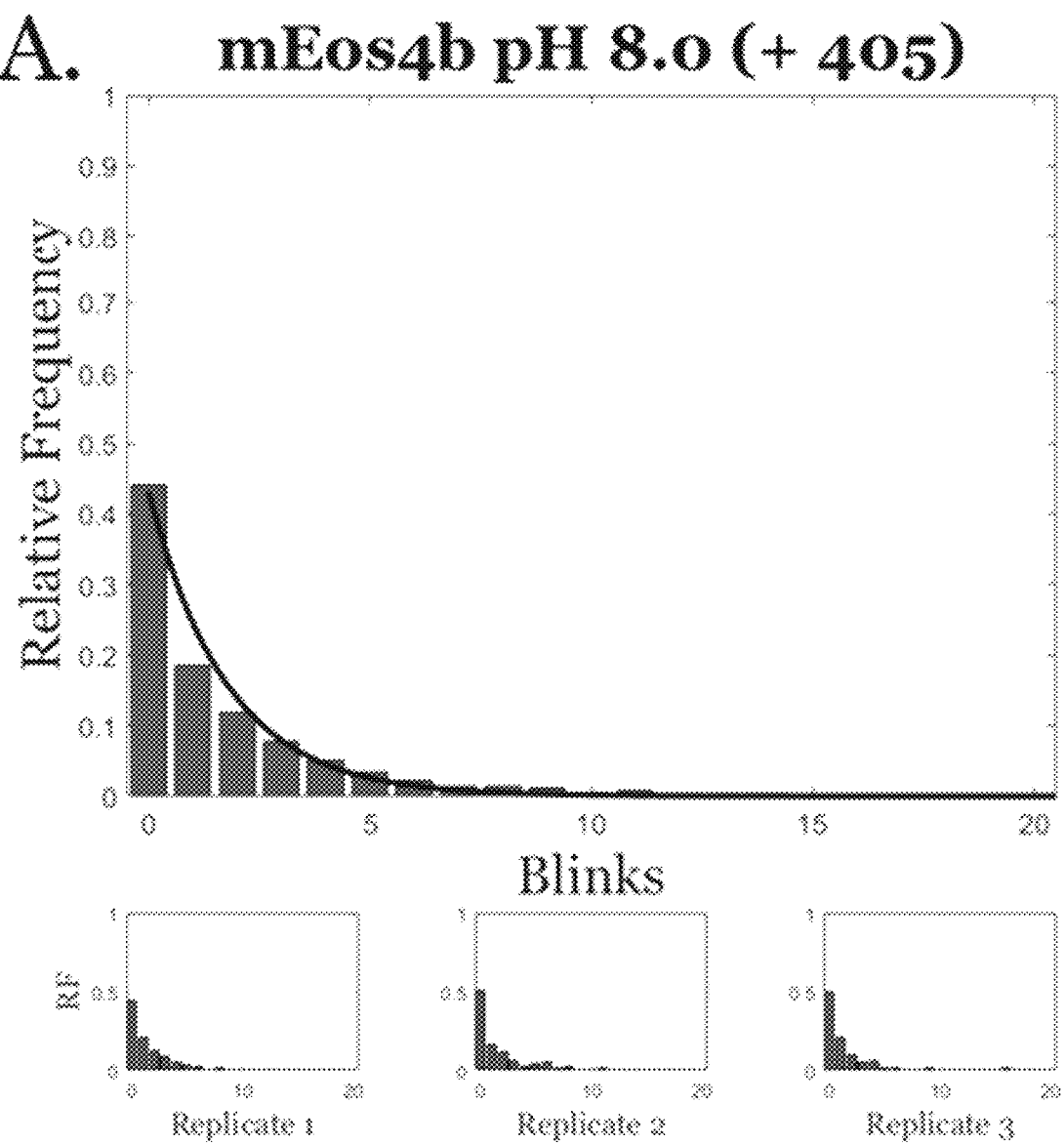
FIGS. 29A-D show PC-FP blinking distributions with 405 nm Light (pH 8.0). PC-FP blinking distributions at pH 8.0 with geometric fit (black curve), representative replicates (miniature plots) for A) mEos4b (N=2643), B) mEos4b-V70T N=3464), C) Janus (N=4417), and D) Ignis (N=5450).
Figure 29B:
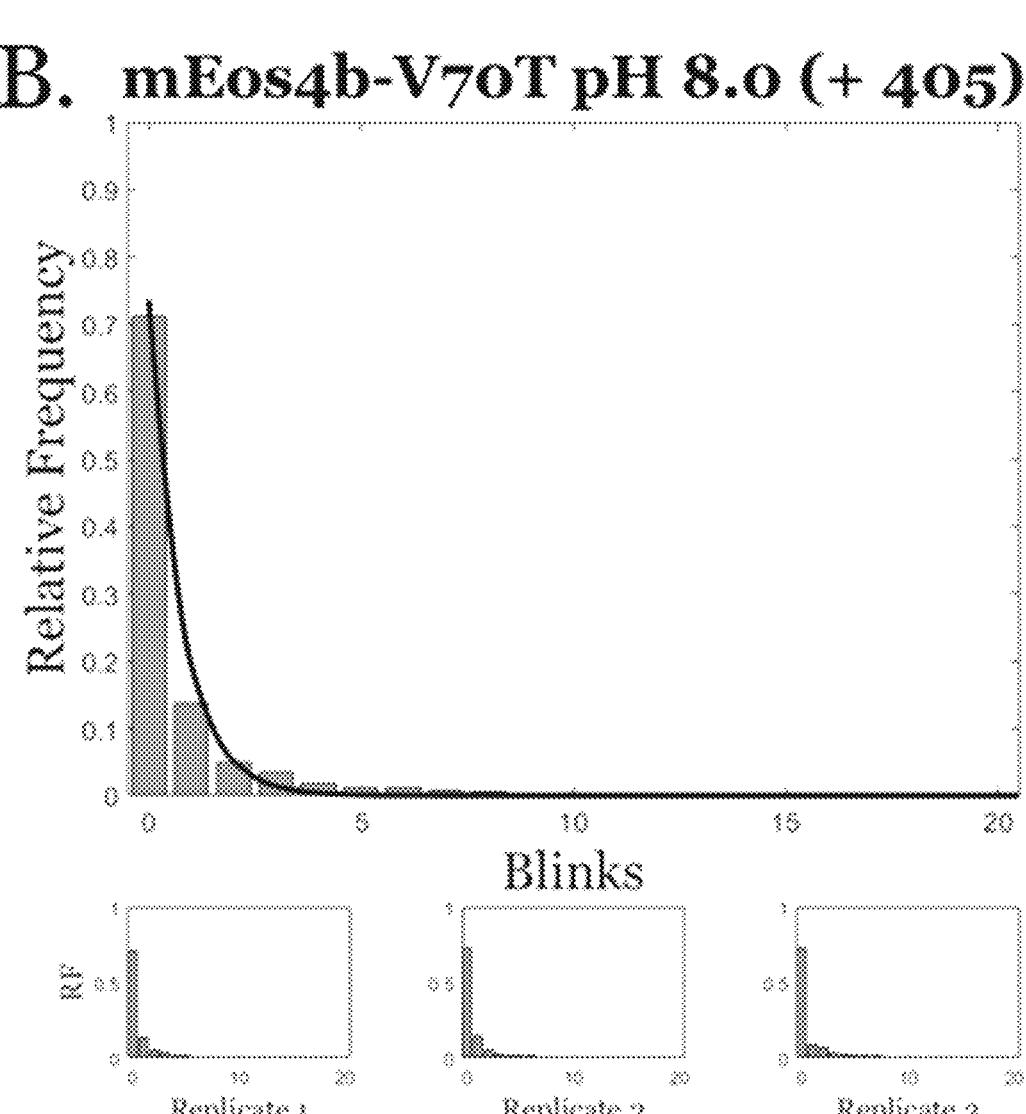
Figure 29C:
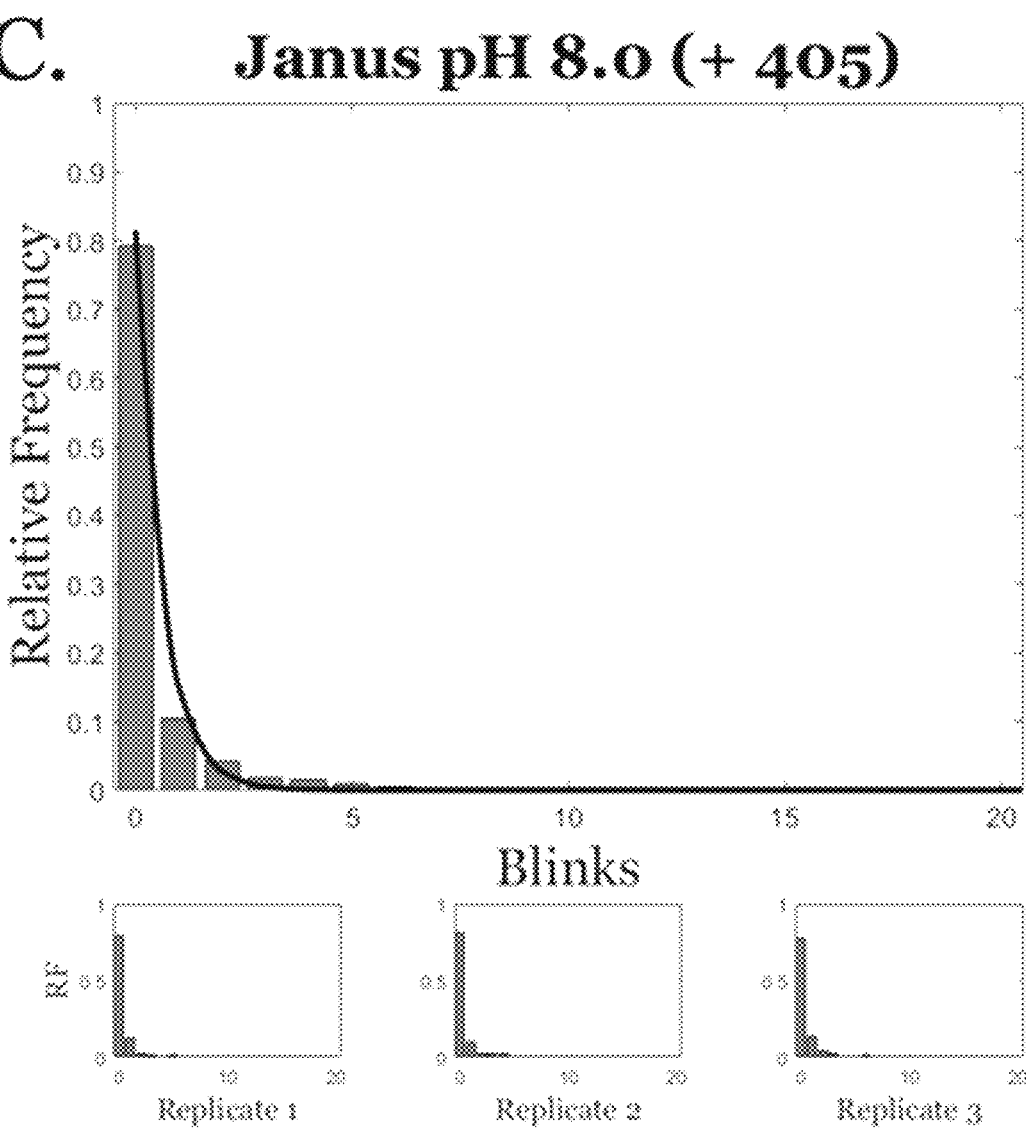
Figure 29D:
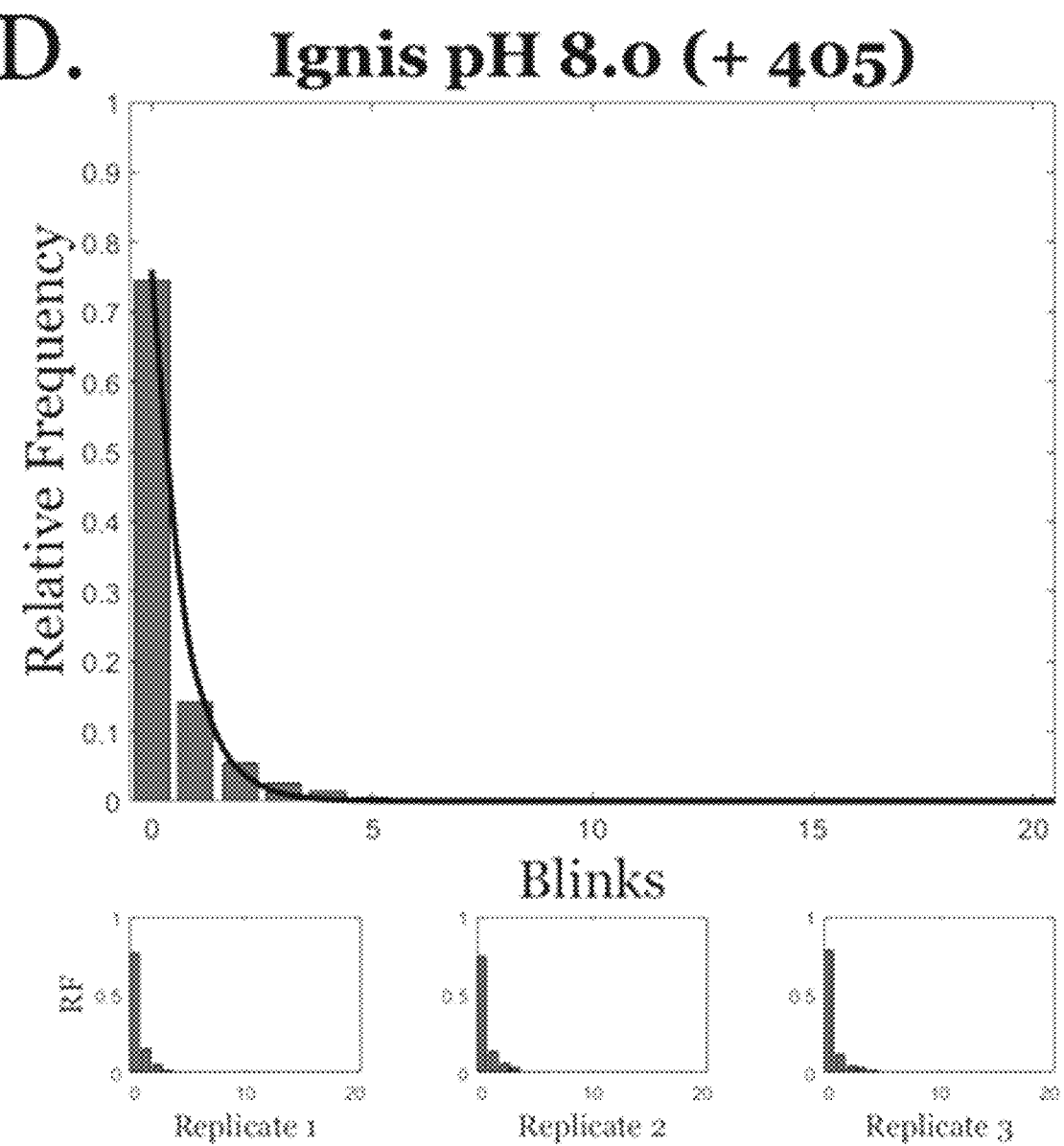

Overall, Janus photoconverted much more efficiently than mEos4b. Single exponential fits through the red fluorescent maxima revealed that Janus reaches a plateau at ~1.79±0.09×the initial green intensity, whereas mEos4b reached ~0.50±0.02 times the initial green intensity (FIG. 28B, C). Also, the rate constant for mEos4b was about twice that of Janus ($0.031\pm0.004$ s$^{-1}$ vs. $0.017\pm0.003$ s$^{-1}$) under these conditions. Green state decays were well fit by a single exponential model, and here Janus decayed more quickly with a half-life of 93.5 seconds, whereas mEos4b required 194 seconds. Next, it was assessed how red fluorescence yields correlated with initial green state fluorescence intensities. Janus produced nearly four times more red fluorescence per unit green than mEos4b with a slope of 1.95±0.28 vs. 0.53±0.11 for mEos4b (FIG. 28D). The photoconversion contrast between red and green channels was also analyzed at each time point and it was found that Janus vastly outperformed mEos4b in this assay, though with larger variation (FIG. 29). On that note, it is important to note the much larger range of red pixel intensities sampled for Janus protein droplets (FIG. 28D).

These results also revealed an initial increase in green fluorescence intensity for both proteins at the first post-conversion time points analyzed (FIG. 28B, C) This contrasts with absorbance measurements where the peak anionic absorbance of mEos4b did not increase upon 385 nm LED-mediated photoconversion (FIG. 19B), but is consistent with the wide-field photoconversion experiments in cellulo described earlier.

Figure 30A:
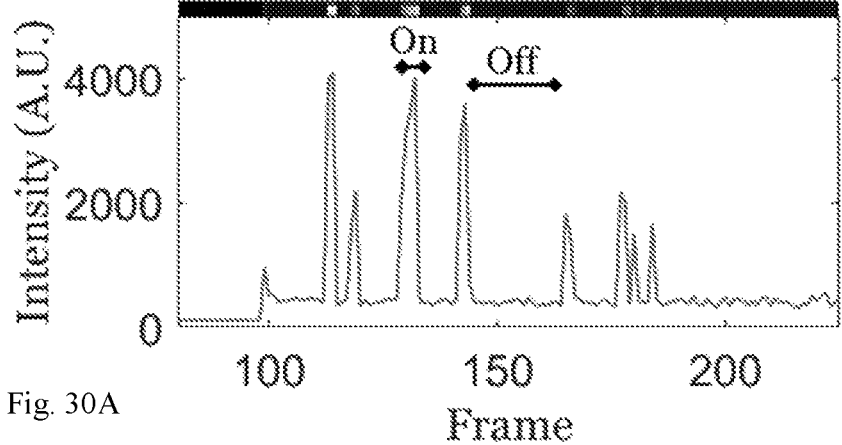
FIG. 30A-B show the dynamics of single molecule fluorescence.
Figure 30B:
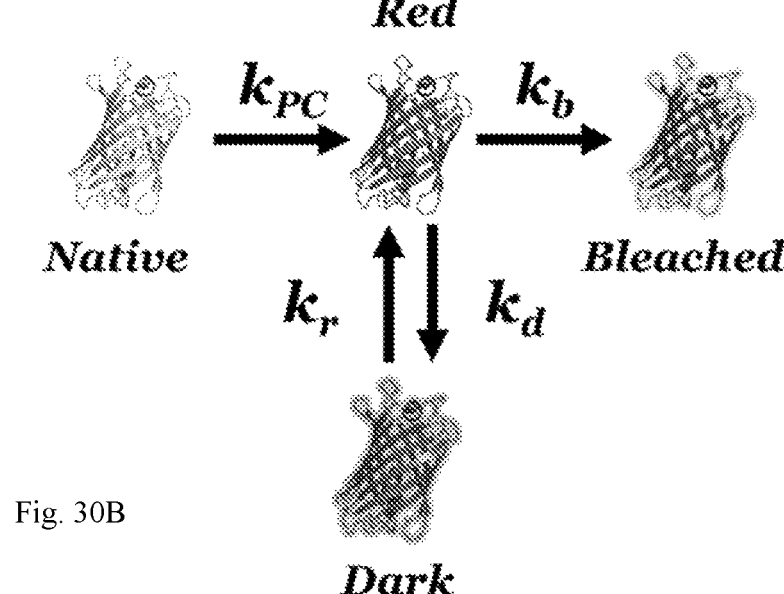

Benchmarking mEos4b Variants as Optical Highlighters. To better establish the performance of mEos4b, mEos4b-V70T and Janus in practical conditions, live cell confocal photoconversion experiments were performed and the photoconversion contrast of each probe was compared to Dendra2 and mEos3.2. N-myristoylated DmrB:PCFP fusions were expressed in HeLa cells and progressively photoconverted with 15-second pulses of low intensity 405 nm laser illumination. Contrast values after 10 and 20 pulses (150 and 300 seconds, respectively) are given in FIG. 30A, with representative 300-second field histograms from three separate imaging sessions given for each PC-FP. Consistent with the in vitro results, Janus gave the greatest photoconversion contrast among the probes tested (FIG. 30B). Mean contrast differences for Janus were 3.2 vs. Dendra2, 5.12 vs. mEos3.2, 6.2 vs. mEos4b, and 5.4 vs. mEos4b-V70T ($p<0.001$ in each case, corrected for multiple comparisons). A statistical difference in the average initial green fluorescence intensity of cells analyzed (FIG. 30C) was observed, though there was a very weak trend toward dimmer Dendra2 signal ($p=0.182$). Occasional biphasic distributions of contrast values was also observed in ratiometric images of each probe (FIG. 30A, histograms), likely reflecting different rates of green state decay from photobleaching/photoconversion between cells within each field.

Discussion. This Example examined residue-specific effects on the chromophore acidity and photoconversion properties of mEos4b. The principle conclusions of this study concern the influence of specific residues on chromophore pKa in mEos4b, and the resulting impact of altered chromophore photochemistry on photoconversion performance.

A Nuanced View of Threonine 70 and Green Chromophore pKa. The data indicate that mEos4b-V70T can be classified as a PC-FP with descending pKa upon photoconversion, though the magnitude of this descent (~0.2 pH units) is modest in comparison to other PC-FPs. Under monoprotic Henderson-Hasselbalch behavior, green mEos4b-V70T chromophores should be ~40% protonated, and red mEos4b-V70T chromophores ~73% deprotonated at physiological pH. If photoconversion is largely dependent on the fraction of available neutral green chromophores, mEos4b-V70T should convert quickly and yield a majority population of anionic (fluorescent) chromophores. However, it was found that both mEos4b and mEos4b-V70T photoconverted similarly in vitro at early time points under 385 nm LED illumination. In contrast, Janus and Ignis proteins photoconvert efficiently in vitro as indicated by the accumulation of red anionic chromophore in their absorbance spectra upon 385 nm mediated illumination. Recombinant Janus outperforms mEos4b in fluorescence photoconversion assays despite revealing a lower photoconversion rate constant in the protein droplet assay. These results, however, do not report on the molecular quantum yield of photoconversion (i.e., how many molecules reach a red state per photon absorbed) without correcting for protein extinction coefficient and molecular brightness (McEvoy, A. L. et al. mMaple: A Photoconvertible Fluorescent Protein for Use in Multiple Imaging Modalities. PLoS ONE 7, (2012)); and (Habuchi, S., Tsutsui, H., Kochaniak, A. B., Miyawaki, A. & Oijen, A. M. van. mKikGR, a Monomeric Photoswitchable Fluorescent Protein. PLOS ONE 3, e3944 (2008)). The measurements of single molecule photoconversion kinetics as disclosed herein can provide additional measurements of this property. Nonetheless, these data provide a functional assessment of PC-FP performance under commonly used illumination conditions. Moreover, the recombinant data are remarkably consistent with in cellulo photoconversion results, which establish Janus as superior to mEos4b, mEos4b-V70T, mEos3.2 and Dendra2 as an optical highlighter.

The photoconversion performance of mEos4b derivatives tested here are at first perplexing because mEos4b-V70T, Janus, and Ignis each possess the V70T substitution that is known to elevate the green state chromophore pKa of EosFP family PC-FPs (Turkowyd Bartosz et al. A General Mechanism of Photoconversion of Green-to-Red Fluorescent Proteins Based on Blue and Infrared Light Reduces Phototoxicity in Live-Cell Single-Molecule Imaging. *Angew. Chem. Int. Ed.* 56, 11634-11639 (2017)); and (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)), rendering them more similar to Dendra2 (Adam, V., Nienhaus, K., Bourgeois, D. & Nienhaus, G. U. Structural basis of enhanced photoconversion yield in green fluorescent protein-like protein Dendra2. *Biochemistry* 48, 4905-4915 (2009)). Indeed, green pKa values were measured at 7.21, 7.57 and 8.59 for these proteins, respectively. Yet the results indicate that the higher green state pKa conferred by V70T is insufficient to substantially improve photoconversion in mEos4b derivatives in vitro. In this light, it is significant that KikGR and mKikGR both have elevated green state pKa values and reportedly efficient photoconversion (Tsutsui, H., Karasawa, S., Shimizu, H., Nukina, N. & Miyawaki, A. Semi-rational engineering of a coral fluorescent protein into an efficient highlighter. *EMBO Rep.* 6, 233-238 (2005)); and (Turkowyd Bartosz et al. A General Mechanism of Photoconversion of Green-to-Red Fluorescent Proteins Based on Blue and Infrared Light Reduces Phototoxicity in Live-Cell Single-Molecule Imaging. *Angew. Chem. Int. Ed.* 56, 11634-11639 (2017)), yet neither contain substitutions equivalent to V70T. Indeed, both proteins contain a valine at the equivalent position 70, like mEos4b. This observation challenges an explicit role of a Thr70-Arg67 interaction in mediating photoconversion efficiency in mEos4b—as has been suggested from work in Dendra2 and mEos2-A69T—despite the clear effect that this interaction has on chromophore pKa in the three proteins. Therefore, one interpretation of these studies is that elevated green pKa is important but not sufficient for green-to-red photoconversion in Kaede-like PC-FPs.

Alternative Factors in Photoconversion: Red pKa and pKa Descent? The poor photoconversion of mEos4b-V70T raises the question of what additional factors must be present to increase photoconversion rate and/or yield? One factor appears to be a sufficiently low red chromophore pKa, since photoconversion to a protonated red state would manifest as impaired photoconversion yield and lower photoconversion contrast. Both Janus and Ignis have a lower red state chromophore pKa (6.57, 6.72) than mEos4b-V70T (6.96), which result in ~87% and ~82% deprotonated red chromophores vs. 73% in mEos4b-V70T. It seems unlikely that 14% and 9% differences in chromophore protonation state can explain the superior photoconversion of Janus and Ignis alone, but it is likely important when coupled with the higher green state pKa (and therefore a greater availability of neutral, photo-convertible chromophore). These data are consistent with a model in which both the magnitude of pKa descent between green and red states, and the final red pKa, dictate photoconversion efficiency in Kaede-like PC-FPs.

How then does one explain the low photoconversion contrast and apparent plateau of red mEos4b chromophore observed in three independent experimental systems (live widefield photoconversion, swept-field confocal photoconversion, and confocal photoconversion of recombinant proteins in vitro)? First, a slower rate of photoconversion might be expected due to mEos4b's low green pKa (5.6), since less than 2% of chromophores are available for photoconversion at pH 7.4. However, this predicts a slow rate of continuous accumulation and not a plateau. The rapid halt in red chromophore accumulation suggests additional photochemistry at play. Two possible explanations include: (1) rapid photobleaching of the red state; and (2) an alternative photoconversion pathway that yields a long-lived or permanently dark chromophore product instead of a fluorescent red chromophore. The possible existence of an alternative photoconversion pathway/product is attractive since the 505 nm green absorbance peak of mEos4b continues to decline at time points beyond the plateau in red chromophore accumulation (FIG. 19B, 20-60-minute time points). Likewise, green state fluorescence decay continued after red fluorescence reached a plateau in both recombinant protein and cellular photoconversion time courses. Another potential factor recently demonstrated in mEos2 is green-state shelving by 561 nm illumination used to read out red fluorescence, which transiently depletes the available pool of photoconvertible green proteins (Thedie, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)). Discrimination between these different possibilities requires further investigation.

Figures 31A, 31B, 31C, 31D:
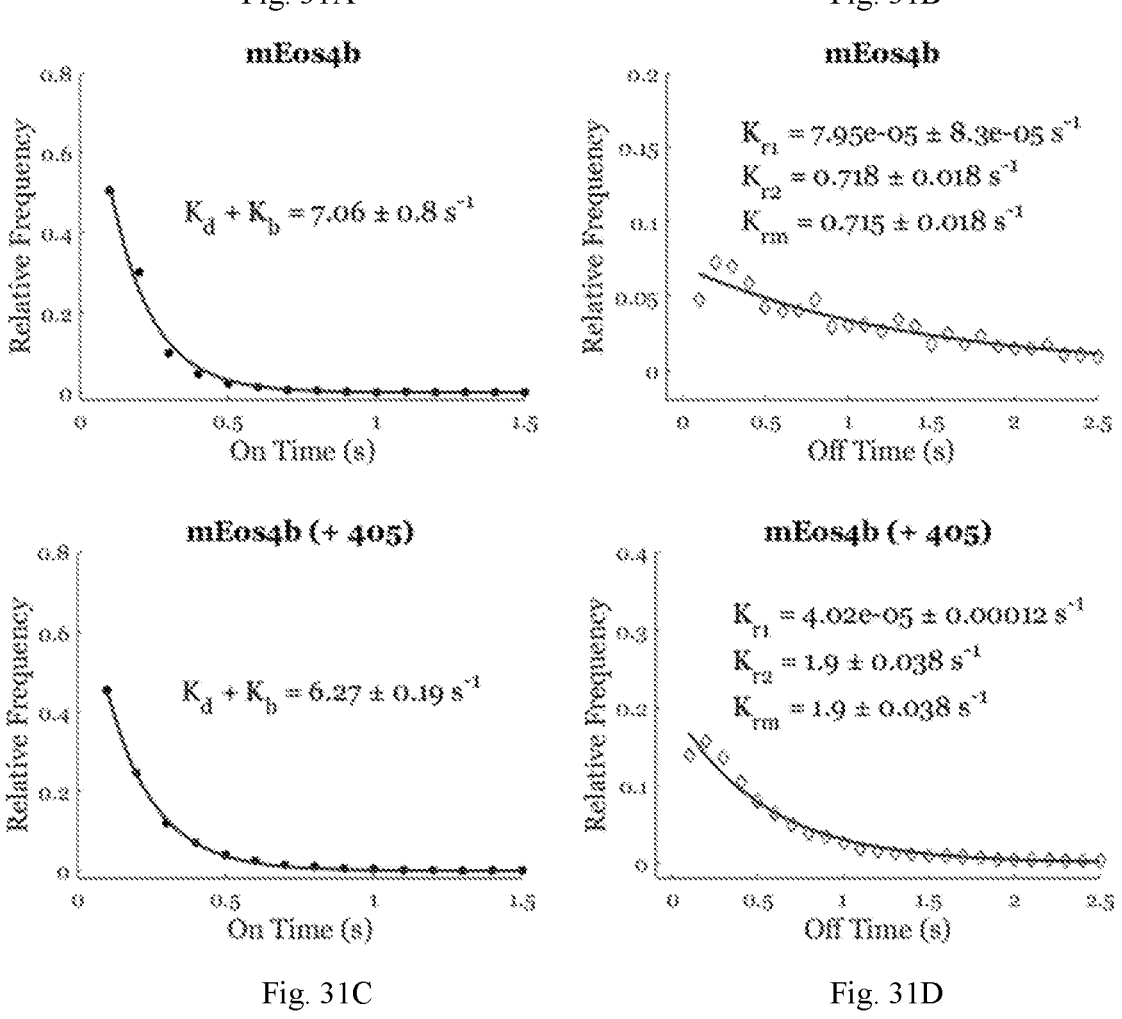
FIGS. 31A-D show the distributions of mEos4b on and off times (pH 7.4).

The Green Chromophore pKa of Ignis. The development of Ignis via reciprocal methionine/isoleucine substitutions on opposite ends of the chromophore (Met41Ile, and Ile197Met) is a particularly interesting result. The absorbance spectrum of Ignis is reminiscent of the T203I mutant of AvGFP (Heim, R., Prasher, D. C. & Tsien, R. Y. Wavelength mutations and posttranslational autoxidation of green fluorescent protein. *Proc. Natl. Acad. Sci. U.S.A.* 91, 12501-12504 (1994)); and (Ehrig, T., O'Kane, D. J. & Prendergast, F. G. Green-fluorescent protein mutants with altered fluorescence excitation spectra. *FEBS Lett.* 367, 163-166 (1995)). Like AvGFP T203I, the chromophore of Ignis is mostly protonated at pH 7.4 (about 94% assuming monoprotic behavior). It is noted that Thr203 occupies an influential position just above the chromophore tyrosine hydroxyl on the tenth beta strand (β10) of AvGFP (here "above" means nearer the N-terminus). Along with His148 and Ser205, Thr203 forms an intricate hydrogen bond network with the chromophore tyrosine phenolate and a water molecule, partially stabilizing the chromophore in its anionic state. In mEos2, Ile196 (homolog of Ile197 in mEos4b and Met197 in Ignis) is also located on β10, at the same position as Ser205 in AvGFP (FIG. 31). However, the hydrogen bonding landscape looks different in mEos2, where the chromophore tyrosine accepts a bond from Ser142 and a nearby water molecule that is itself positioned to serve as a hydrogen bond acceptor from the backbone amide of Ile196. Introduction of a more electron-donating thioether from Met197 in Ignis could alter the hydrogen bonding landscape considerably. It is tempting to speculate that hydrogen bond-donating water molecule in mEos2 is instead a hydrogen bond acceptor in Ignis, as this would favor the neutral chromophore. In support of this basic mechanistic explanation, recent subatomic resolution structures of AvGFP-T203I reveal the chromophore tyrosine donating a hydrogen bond to a nearby water molecule, confirming the plasticity of this local environment (Takaba, K. et al. Sub-atomic resolution X-ray structures of green fluorescent protein. *IUCrJ* 6, 387-400 (2019)). Though the mechanism will require additional structural insight, the anionic chromophore is indisputably destabilized in Ignis.

Initial Insight into the Role of Proline 142. Characterization of Janus-P142V and Janus-P142T support the role of Pro142 in stabilizing the green anionic chromophore as both valine and threonine substitutions result in a decreased absorbance of the anionic chromophore peak and substantial absorbance of the broad neutral chromophore peak at 385 nm. The consequences of valine substitution appear more severe than threonine, as evidenced by the clear difference in anionic absorbance bands between Janus-P142V and Janus-P142T. This may be consistent with a more stable conformation of β7 conferred by threonine due to its polarity and solvent exposure, as opposed to valine. This is an example of isosteric substitution on the surface of a fluorescent protein yielding a measurable impact on the properties of the buried chromophore, ostensibly due to the change in polarity of the side chain. How other polar residues at this position may influence the absorbance and fluorescence properties of Kaede-like PC-FPs is contemplated.

These data suggest that the green pKa values of both variants will be positively shifted relative to Janus. If true, it may partially explain the differences between mMaple from mClavGR2 achieved by directed evolution, since an alanine-to-valine substitution was introduced at this position in mMaple, and mMaple has a higher green pKa than mClavGR2 (McEvoy, A. L. et al. mMaple: A Photoconvertible Fluorescent Protein for Use in Multiple Imaging Modalities. *PLoS ONE* 7, (2012)).

Other modifications are introduced at internal sites that should have little impact on the self-association of the highly monomeric mEos4b. However, introduction of valine could pose a problem due to its hydrophobicity. It is noted that despite the presence of this valine in mMaple3, it is highly monomeric, and its monomerization was achieved through the incorporation of the same amino acid substitutions that rendered mEos3.2 and mEos4a/mEos4b monomeric relative to mEos2 (Wang, S., Moffitt, J. R., Dempsey, G. T., Xie, X. S. & Zhuang, X. Characterization and development of photoactivatable fluorescent proteins for single-molecule-based superresolution imaging. *Proc. Natl. Acad. Sci. U.S.A.* 111, 8452-8457 (2014)). Therefore, it is not anticipated that this mutation will have an effect on oligomerization propensity of Janus-P142V.

Example 3: Single Molecule Characterization of mEos4b Derivatives

Introduction. The ensemble fluorescence properties of fluorescent proteins reflect an average of population-wide single molecule emissions. Measurements of fluorescence at the single-molecule level therefore affords greater understanding of fluorescent proteins. PC-FPs exhibit substantial diversity in their single molecule fluorescence characteristics. Differences between PC-FPs should be considered carefully when selecting a probe for single molecule experiments to avoid inappropriate experimental or analytical approaches. Unfortunately, the single molecule properties of new fluorescent proteins are not routinely characterized alongside bulk fluorescence properties. Hence, PC-FPs were adopted for use before their characteristics were fully understood—leading to post-hoc discoveries such as photoblinking in mEos2.

Single molecule techniques such as PALM permit sensitive dissection of photophysical behaviors of individual PC-FPs. including blinking statistics, photoconversion kinetics, and photon yields. The photoconversion properties of mEos4b, mEos4b-V70T, Janus and Ignis suggested differences in the photophysics of the green-to-red chromophore transformation, as well as possible variations in the fluorescence properties of the red chromophore. PALM is well-suited to measure these properties. As described herein, PALM was used to measure single molecule fluorescence from populations of each PC-FP in vitro. The results reveal the photophysical origins of differences observed in preceding ensemble fluorescence experiments.

Two principle illumination schemes were utilized in the in vitro PALM experiments (FIG. 32 A). The first scheme involves pre-illumination of samples with low-intensity 405 nm light ($<25$ W/cm$^2$) to photoconvert fluorescent proteins, followed by removal of 405 nm light and illumination with high-intensity 561 nm excitation laser (~500 W/cm$^2$) to read out fluorescence from single molecules. This first scheme permits analysis of the red chromophore under photoexcitation absent any interference from concomitant 405 nm light, which is known to influence photophysics in vitro (Annibale, P., Scarselli, M., Kodiyan, A. & Radenovic, A. Photoactivatable Fluorescent Protein mEos2 Displays Repeated Photoactivation after a Long-Lived Dark State in the Red Photoconverted Form. *J. Phys. Chem. Lett.* 1, 1506-1510 (2010)); (De Zitter, E. et al. Mechanistic investigation of mEos4b reveals a strategy to reduce track interruptions in sptPALM. *bioRxiv* 475939 (2018)); (Thédié, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)); and (Avilov, S. et al. In cellulo Evaluation of Phototransformation Quantum Yields in Fluorescent Proteins Used As Markers for Single-Molecule Localization Microscopy. *PLoS ONE* 9, (2014)), and is therefore appropriate for measuring intrinsic properties of the red chromophore. The second scheme involves illumination with 561 nm readout laser followed by concurrent illumination with 405 nm photoconversion light at a constant power. This permits comparison of photoconversion kinetics and analysis of the interaction between 561 nm and 405 nm light which are often used concurrently in biological PALM experiments.

Blinking Propensity of mEos4b Derivatives. Photoblinking of PC-FPs is a common phenomenon that must be characterized and properly accounted for in PALM experiments. Although the precise mechanism(s) that govern photoblinking in PC-FPs are incompletely understood, the A69T substitution in mEos2 reduces the molecule's intrinsic photoblinking probability (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). Because the low-blinking PC-FP, Dendra2, also possesses a threonine at the equivalent position (Thr74), it was tested whether this residue might control photoblinking in Kaede-like PC-FPs. However, this hypothesis is challenged by the fact that both mMaple and mMaple3 exhibit high blinking propensities despite the presence of a threonine at position 78 (equivalent to positions 69 in mEos2 and 74 in Dendra2; see FIG. 15) (Wang, S., Moffitt, J. R., Dempsey, G. T., Xie, X. S. & Zhuang, X. Characterization and development of photoactivatable fluorescent proteins for single-molecule-based superresolution imaging. *Proc. Natl. Acad. Sci. U.S.A.* 111, 8452-8457 (2014)); (McEvoy, A. L. et al. mMaple: A Photoconvertible Fluorescent Protein for Use in Multiple Imaging Modalities. *PLoS ONE* 7, (2012)); and (Baldering, T. N. et al. Synthetic and genetic dimers as quantification ruler for single-molecule counting with PALM. *Mol. Biol. Cell* mbcE18100661 (2019)).

Figures 33A, 33B, 33C, 33D:
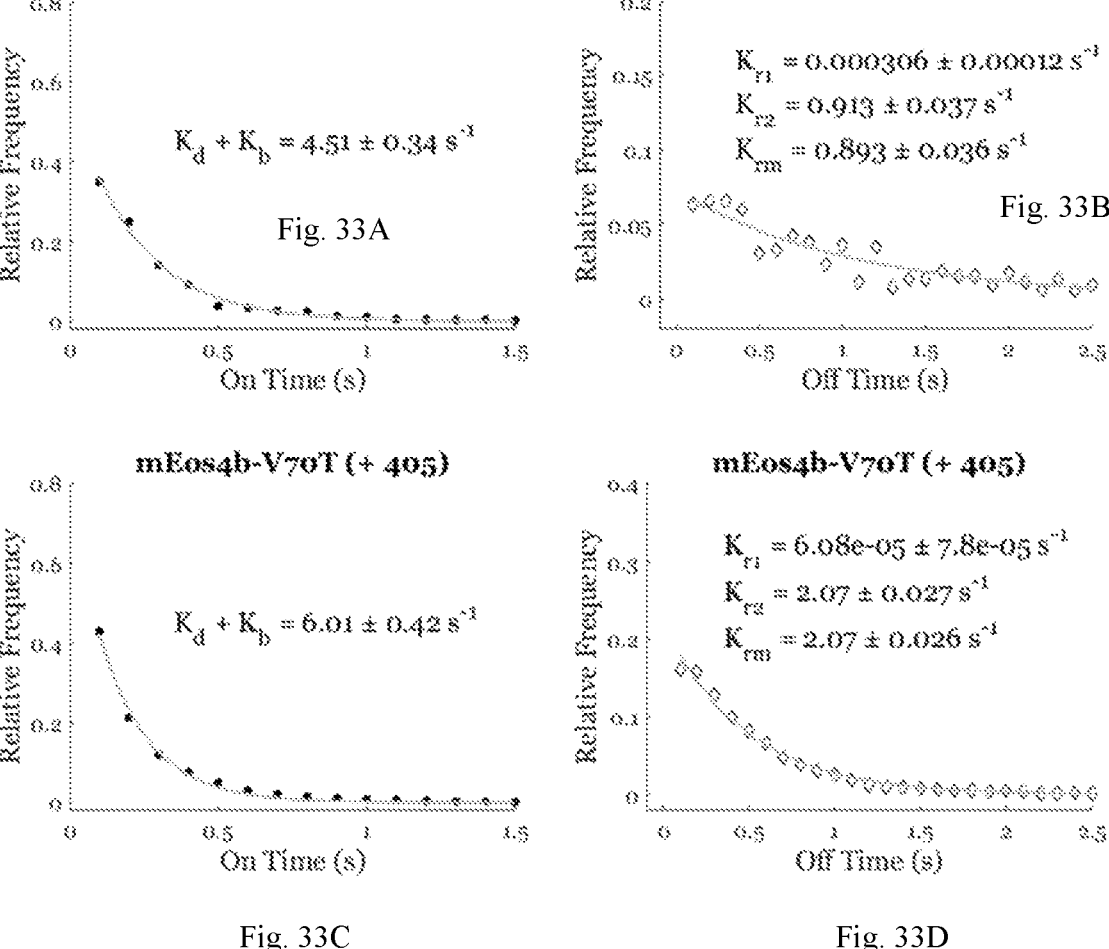
FIGS. 33A-D show the distributions of mEos4b-V70T on and off times (pH 7.4).

In contrast to mEos4b, mEos4b-V70T, Janus, and Ignis each possess threonine at position 70. A such, it was reasoned that mEos4b-V70T should exhibit reduced blinking propensity relative to mEos4b (like mEos2-A69T relative to mEos2) since the chromophore-oriented mutation introduced into mEos2 during the engineering of mEos4b was A70V (meant to improve chromophore packing) (Paez Segala, M. G. et al. Fixation-resistant photoactivatable fluorescent proteins for correlative light and electron microscopy. *Nat. Methods* 12, 215-218 (2015)). However, it was not clear how Janus and Ignis might blink since both contain additional Met41Ile substitutions relative to mEos4b and mEos4b-V70T, and the equivalent residue to Ile41 in high-blinking mMaple3 is also an isoleucine. As noted herein, this ability (1-p) of 0.73 and a mean of 2.7 blinks per molecule (FIG. 33A), consistent with reported blinking rates of mEos2 and mEos3.2 under similar illumination conditions (Fricke, F., Beaudouin, J., Eils, R. & Heilemann, M. One, two or three? Probing the stoichiometry of membrane proteins by single-molecule localization microscopy. *Sci. Rep.* 5, 14072 (2015)); and (Baldering, T. N. et al. Synthetic and genetic dimers as quantification ruler for single-molecule counting with PALM. *Mol. Biol. Cell* mbcE18100661 (2019)). The blinking rate of mEos4b-V70T was reduced compared to mEos4b (FIG. 33B), with a 0.31 blink probability and mean of 0.45 blinks per molecule. Surprisingly, Janus blinked even less than mEos4b-V70T with an average of 0.30 blinks per molecule, and blinking probability of 0.23 (FIG. 33C). The geometric fit to Ignis blinking data was similar to mEos4b-V70T, with 0.30 blink probability and an average of 0.42 blinks per molecule (FIG. 33D). Empirical cumulative distributions for each protein supported the distinct behaviors of mEos4b, mEos4b-V70T and Janus indicated by the geometric fits, but instead revealed similar blinking between Janus and Ignis (FIG. 34). This may be explained by a longer tail in the mEos4b-V70T blinking distribution, which is not observed for either Ignis or Janus.

TABLE 4

| | Summary of Blinking Statistics | | | | | | | |
|---|---|---|---|---|---|---|---|---|
| | Without 405 | | | | | | | |
| | pH 7.4 | | | | pH 8.0 | | | |
| | $p^{Geo}$ | $B_0$ RF | Mean | $N_{Mol}$ | $p^{Geo}$ | $B_0$ RF | Mean | $N_{Mol}$ |
| mEos4b | 0.27 ± 0.01 | 0.28 | 2.7 | 615 | 0.33 ± 0.02 | 0.345 | 2.0 | 653 |
| mEos4b-V70T | 0.69 ± 0.04 | 0.66 | 0.45 | 455 | 0.70 ± 0.02 | 0.69 | 0.42 | 388 |
| Janus | 0.77 ± 0.02 | 0.745 | 0.30 | 873 | 0.76 ± 0.02 | 0.735 | 0.32 | 529 |
| Ignis | 0.70 ± 0.03 | 0.69 | 0.42 | 1283 | 0.74 ± 0.02 | 0.72 | 0.36 | 1245 |
| mEos4b | 0.40 ± 0.02 | 0.415 | 1.5 | 4454 | 0.43 ± 0.03 | 0.44 | 1.3 | 2643 |
| mEos4b-V70T | 0.71 ± 0.03 | 0.68 | 0.40 | 4973 | 0.73 ± 0.03 | 0.71 | 0.36 | 3464 |
| Janus | 0.80 ± 0.03 | 0.77 | 0.25 | 4852 | 0.82 ± 0.02 | 0.79 | 0.23 | 4417 |
| Ignis | 0.76 ± 0.02 | 0.74 | 0.31 | 4874 | 0.76 ± 0.02 | 0.745 | 0.31 | 5450 | isoleucine resides near the imidazole of His63 in the red chromophore and may therefore influence its excited state dynamics.

To understand the intrinsic blinking behavior of each protein, picomolar solutions in PBS pH 7.4 were deposited on clean glass coverslips and imaged with PALM. After washing to remove unattached molecules, the sparsely adhered molecules were exposed to ten seconds of low-power 405 laser illumination ($\sim$2 W/cm$^2$). The 405 nm laser was then switched off and a high-power 561 nm readout laser ($\sim$500 W/cm$^2$) was turned on to excite red state fluorescence (FIG. 32A, Scheme 2). Clusters of localizations within 45 nm were identified with "simplified" DBSCAN without a density threshold, (i.e. minpts=1 and $\varepsilon$=45 nm) and the number of transient off states (i.e. the number of blinks) was calculated as the number of discontinuous localizations per cluster minus one. Blinking distributions may then be fit to a geometric distribution.

Figures 35A, 35B, 35C, 35D:
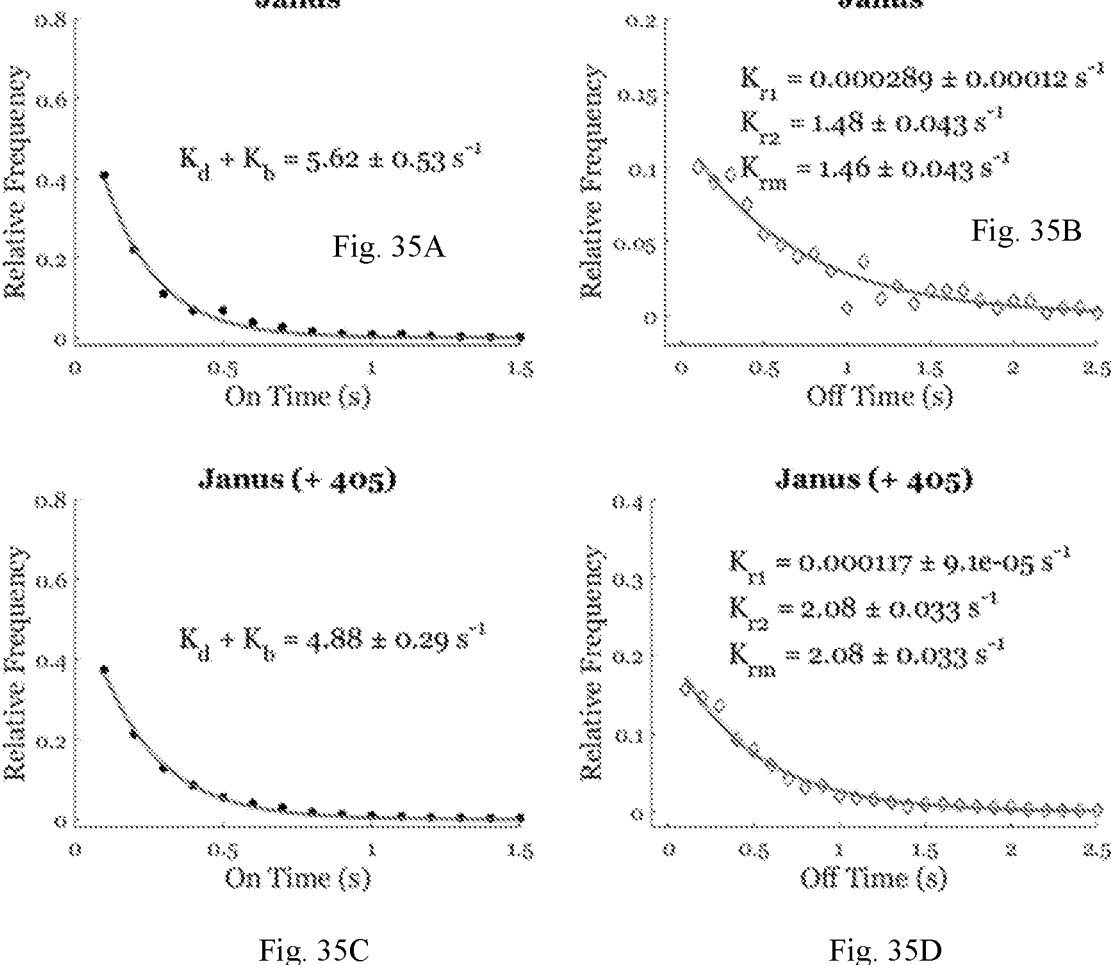
FIGS. 35A-D show the distributions of Janus on and off times (pH 7.4).
Figures 36A, 36B, 36C, 36D:
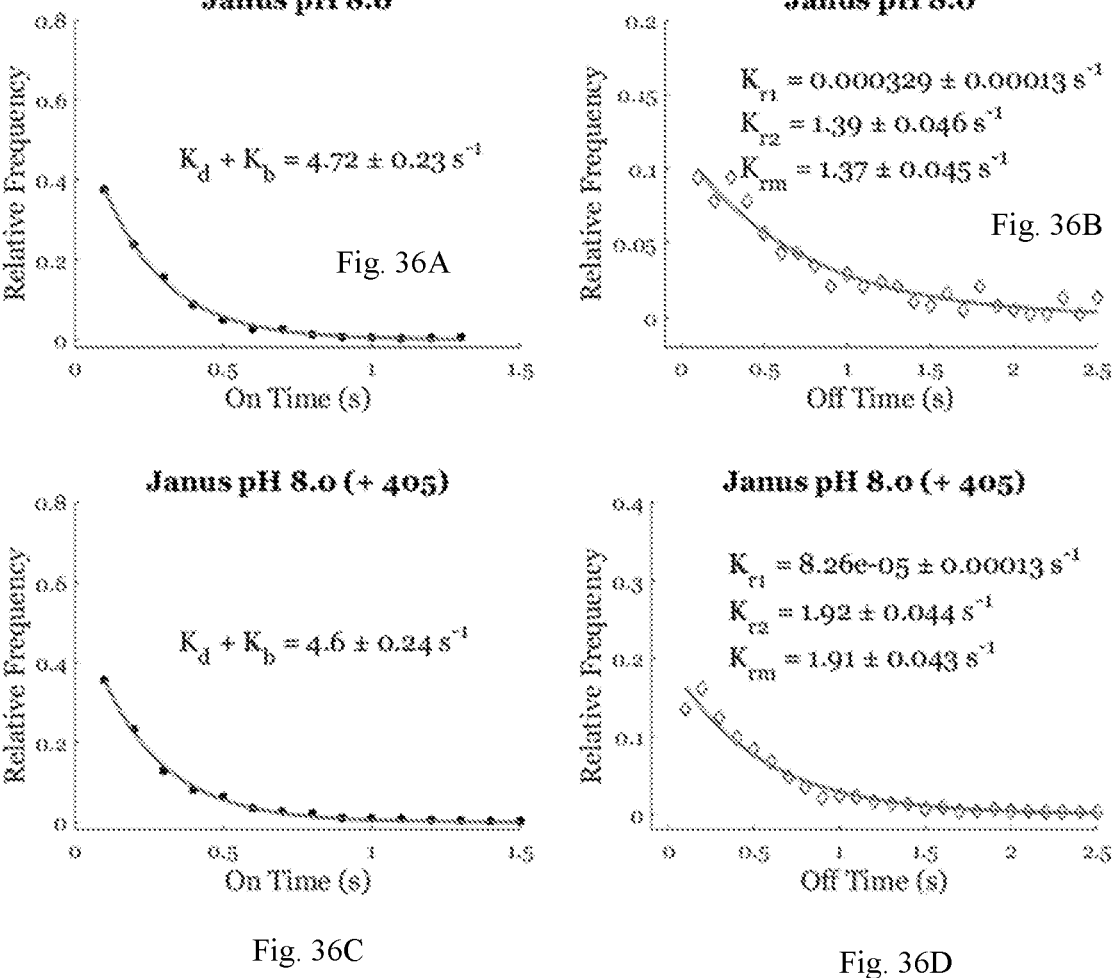
FIGS. 36A-D show the distributions of Janus on and off times (pH 8.0).

A summary of blinking statistics is provided in Table 4. The mEos4b blinking distribution revealed a blinking prob- Buffer pH influences the protonation state of the HYG chromophore, but the effect of pH on blinking is unclear. It was also tested whether alkaline pH might reduce photoblinking by favoring the anionic state of the chromophore. At pH 8.0 there was a strong trend toward less photoblinking for mEos4b (p=0.0527, two sample Kolmogorov-Smirnov test). The geometric fit to the data indicated a mean of 2.0 blinks per molecule (FIG. 35A). Fits also suggested modestly reduced blinking of mEos4b-V70T and Ignis (means of 0.42 and 0.36, respectively). ECDFs were plotted for each protein from blinking data at pH 7.4 and pH 8.0 (FIG. 36). A weaker trend toward reduced blinking was observed for Ignis (p=0.0957), but mEos4b-V70T and Janus blinked similarly at both pH 7.4 and pH 8.0 (p=0.2873 and p=0.999, FIG. 36B-C).

Figures 37A, 37B, 37C, 37D:
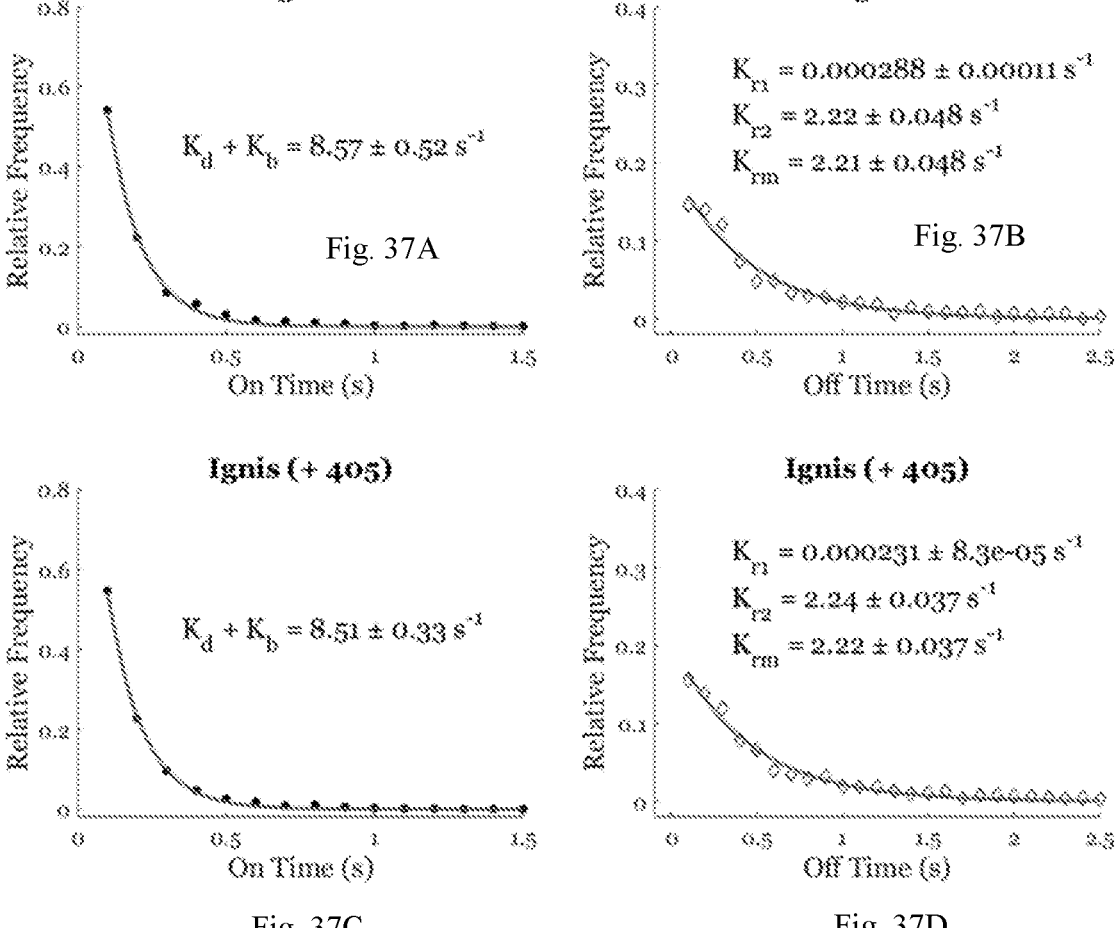
FIGS. 37A-D show the distributions of Ignis on and off times (pH 7.4).
Figures 38A, 38B, 38C, 38D:
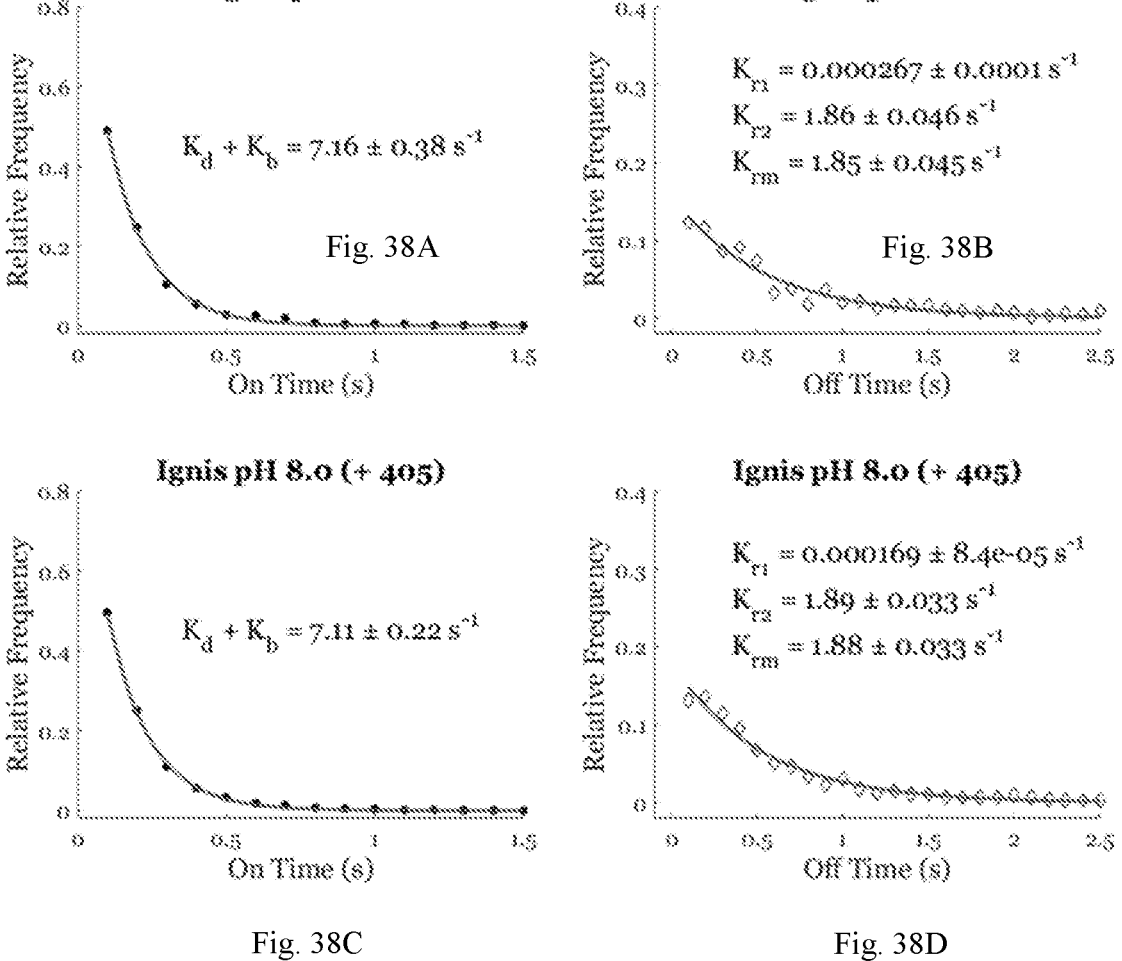
FIGS. 38A-D show the distributions of Ignis on and off times (pH 8.0).

PALM experiments are normally run in the presence of pulsed or continuous UV/violet illumination that gradually increases in intensity over the course of an experiment (in order to maintain a steady photoactivation rate). Therefore, next, the effect of concurrent illumination with 561 nm and 405 nm laser light on PC-FP blinking propensity was examined (see Scheme 2 in FIG. 32). A power density of ~1.9 W/cm² was selected, on order with moderate literature power densities (0.03-10 W/cm²) (Fricke, F., Beaudouin, J., Eils, R. & Heilemann, M. One, two or three? Probing the stoichiometry of membrane proteins by single-molecule localization microscopy. *Sci. Rep.* 5, 14072 (2015)); (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)); (Baldering, T. N. et al. Synthetic and genetic dimers as quantification ruler for single-molecule counting with PALM. *Mol. Biol. Cell* mbcE18100661 (2019)); (Annibale, P., Scarselli, M., Kodiyan, A. & Radenovic, A. Photoactivatable Fluorescent Protein mEos2 Displays Repeated Photoactivation after a Long-Lived Dark State in the Red Photoconverted Form. *J. Phys. Chem. Lett.* 1, 1506-1510 (2010)); and (Thédié, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)). (This power density also facilitated practical comparisons of single molecule photoactivation rates, see below). The addition of continuous 405 nm laser illumination substantially reduced photoblinking of mEos4b (FIGS. 37A and 38A). At pH 7.4 and 8.0, an average of 1.5 and 1.3 blinks per molecule was found in the presence of 405 nm light, down from 2.7 and 2.0 measured in the absence of 405 nm illumination, respectively. Similar trends were observed for mEos4b-V70T, Janus, and Ignis (FIGS. 37 and 38B-D). Notably, Janus revealed a low probability of photoblinking (0.18) and only 0.23 blinks per molecule on average the presence of 405 nm illumination at pH 8.0 (FIG. 38C).

Figure 39A:
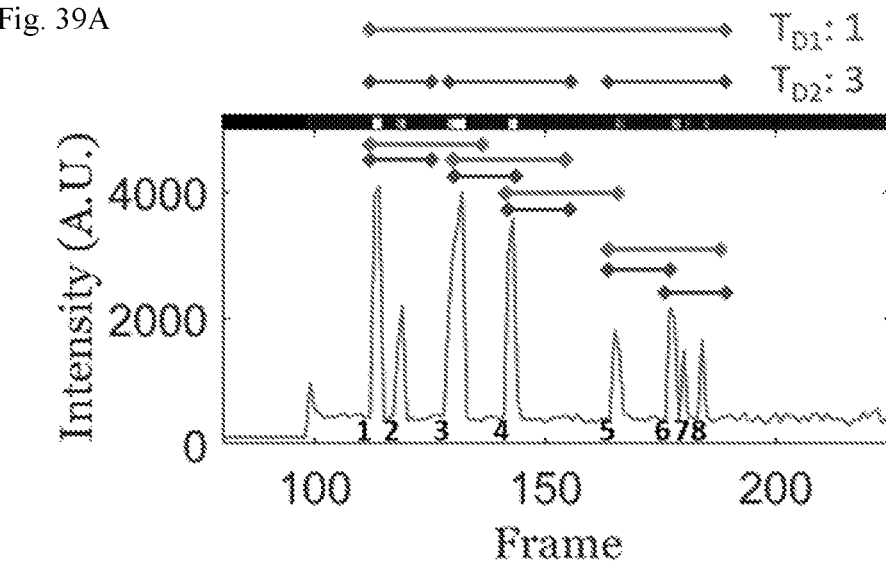
FIGS. 39A-B show the dark time ($T_D$) parameter in spatio-temporal grouping.
Figure 39B:
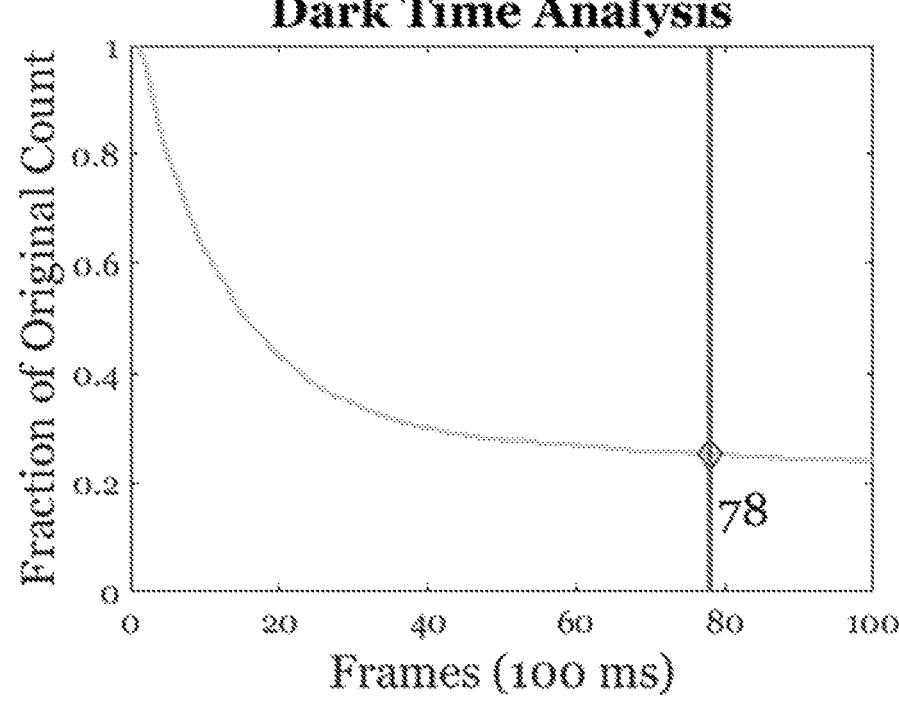

On/Off-Times of mEos4b Derivatives. Blinking is the manifestation of physical transitions between fluorescent "on" and non-fluorescent "off" states (FIG. 39A). Alongside blinking frequencies, the on- and off-time distributions of fluorescence bursts were analyzed from single PC-FP molecules and they were fit to a simple kinetic model of PC-FP dark state transitions (FIG. 39B). This model has been successfully employed in studies of both mEos2 and Dendra2, which are reference proteins for comparisons drawn in this work (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)); and (Avilov, S. et al. In cellulo Evaluation of Phototransformation Quantum Yields in Fluorescent Proteins Used As Markers for Single-Molecule Localization Microscopy. *PLoS ONE* 9, (2014)). As described by Lee and colleagues (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)), this kinetic model accounts for transitions between dark and fluorescent state(s) with three rate constants: (1) the dark state transition rate constant, $k_d$, describing transitions to dark state(s) from a fluorescent state; (2) the photobleaching rate constant, $k_b$, describing irreversible loss of fluorescence due to photodamage; and (3) the dark state return rate constant, $k_r$, describing the rate at which molecules return to the fluorescent state from transient dark state(s) during a photoblinking cycle. (The fourth constant in FIG. 39B, $k_{PC}$, represents the green-to-red photoconversion rate).

The decay rate of on-time distributions, $k_{on}$, may be fit to the single exponential relationship in Equation 4.3.1.

$$f(t) = ae^{-k_{on}t} \tag{0.1}$$

Here, $k_{on}$ is the sum of dark state transition rate, $k_d$, and the bleaching rate, $k_b$, and the average on time can be calculated as $1/k_{on}$. Additionally, the instantaneous probability of blinking is equal to the fraction of total off state transitions, $(k_d + k_b)$ attributable to the dark state transition rate, $k_d$ (Equation 4.3.2). Note that this latter probability is equivalent to $(1-p)$, where p is the zero-blink probability calculated from geometric fits to the blinking distribution.

$$P_{Blink} = \frac{k_d}{k_d + k_b} \tag{0.2}$$

Off-times can be fit to monophasic (Avilov, S. et al. In cellulo Evaluation of Phototransformation Quantum Yields in Fluorescent Proteins Used As Markers for Single-Molecule Localization Microscopy. *PLoS ONE* 9, (2014)) or biphasic (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)); and (Annibale, P., Vanni, S., Scarselli, M., Rothlisberger, U. & Radenovic, A. Quantitative Photo Activated Localization Microscopy: Unraveling the Effects of Photoblinking. *PLOS ONE* 6, e22678 (2011)) exponential decay equations (Equations 4.3.2 and 4.3.3) to obtain the return rate(s) from nonfluorescent dark state(s). Two return rates (slow $k_{r1}$ and fast $k_r2$) with a ratio $\alpha = k_{r2}/k_{r1}$ were observed for mEos2 and may reflect two dark states or modes of fluorescence reacquisition, whereas a single monophasic return rate ($k_{rm}$) instead suggests a single type of transition.

$$f(t) = be^{k_{rm}t} \tag{0.3}$$

$$f(t) = \frac{(k_{r1}e^{-k_{r1}t} + \alpha k_{r2}e^{-k_{r2}t})}{(1 + \alpha)} \tag{0.4}$$

The on- and off-time distributions of mEos4b derivatives were examined at pH 7.4 and pH 8.0 in both the presence and absence of 405 nm illumination. Kinetic parameters derived from fits are summarized in Table 5. On-times were well fit to the single exponential of equation 4.3.1, but in contrast to some prior studies, off-time distributions were suitably fit by monophasic exponential equations (standard error/RMSE<0.01) and did not support the involvement of a slow return rate described by $k_{r1}$ (though this may relate to different integration times, see Discussion). In each case examined, the fast rate constant fit to Equation 4.3.4, $k_{r2}$, was nearly equivalent to the monophasic rate constant, $k_{rm}$, fit by equation 4.3.3, and $k_{r1}$ was three to four order of magnitude smaller than $k_{r2}$. Unless otherwise specified the monophasic fit parameter, $k_{rm}$ is discussed below.

TABLE 5

| | Photokinetic Statistics of mEos4b and Derivatives | | | | | | | | | | |
|---|---|---|---|---|---|---|---|---|---|---|---|
| | Without 405 | | | | | | | | | | |
| | pH 7.4 | | | | | | pH 8.0 | | | | |
| | $k_{on}$ | $k_d$ | $k_b$ | $k_{r1}$ ($\times 10^{-5}$) | $k_{r2}$ | $k_{rm}$ | $k_{on}$ | $k_d$ | $k_b$ | $k_{r1}$ ($\times 10^{-5}$) | $k_{r2}$ | $k_{rm}$ |
| mEos4b | 7.06 ± 0.80 | 5.15 | 1.91 | 7.95 ± 8.3 | 0.718 ± 0.018 | 0.715 ± 0.018 | 7.59 ± 0.94 | 5.05 | 2.54 | 9.55 ± 8.7 | 0.71 ± 0.018 | 0.705 ± 0.017 |
| mEos4b-V70T | 4.51 ± 0.34 | 1.39 | 3.12 | 30.6 ± 12 | 0.913 ± 0.037 | 0.893 ± 0.036 | 5.33 ± 0.54 | 1.57 | 3.76 | 23.7 ± 13 | 0.58 ± 0.31 | 0.567 ± 0.030 |
| Janus | 5.62 ± 0.53 | 1.30 | 4.32 | 28.9 ± 12 | 1.48 ± 0.043 | 1.46 ± 0.043 | 4.72 ± 0.23 | 1.15 | 3.57 | 32.9± 13 | 1.39± 0.046 | 1.37± 0.045 |
| Ignis | 8.57 ± 0.52 | 2.54 | 6.03 | 28.8 ± 11 | 2.22 ± 0.048 | 2.21 ± 0.048 | 7.15 ± 0.38 | 1.88 | 5.27 | 26.7 ± 10 | 1.86 ± 0.046 | 1.85 ± 0.045 |
| | With 405 | | | | | | | | | | |
| mEos4b | 6.27 ± 0.19 | 3.73 ± 6.21 | 2.54 | 4.02 ± 12 | 1.90 ± 0.038 | 1.9 ± 0.038 | 6.21 ± 0.16 | 3.53 | 2.68 | 3.32 ± 19 | 2.11 ± 0.052 | 2.10± 0.052 |
| mEos4b-V70T | 6.01 ± 0.42 | 1.74 | 4.27 | 6.08 ± 7.8 | 2.07 ± 0.027 | 2.07 ± 0.026 | 5.34 ± 0.31 | 1.41 | 3.92 | 2.66 ± 15 | 1.88 ± 0.043 | 1.88 ± 0.043 |
| Janus | 4.88 ± 0.29 | 0.97 | 3.91 | 11.7 ± 9.1 | 2.08 ± 0.033 | 2.08 ± 0.033 | 4.60 ± 0.24 | 0.85 | 3.75 | 8.26± 13 | 1.92± 0.044 | 1.91 ±0.043 |
| Ignis | 8.51 ± 0.33 | 2.03 | 6.48 | 23.1 ± 8.3 | 2.24 ± 0.037 | 2.22 ± 0.037 | 7.11 ± 0.22 | 1.70 | 5.41 | 16.9 ± 8.4 | 1.89 ± 0.033 | 1.88 ± 0.033 |

Figure 40A:
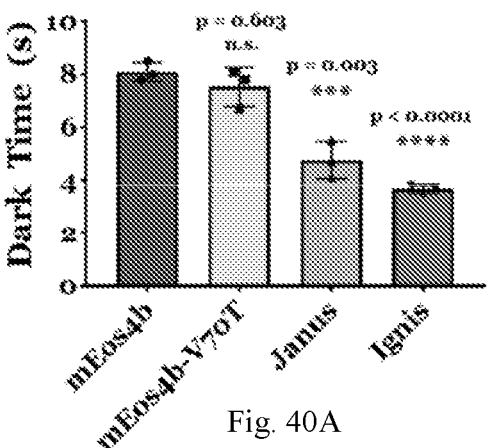
FIGS. 40A-D show PC-FP 95% dark times.
Figure 40B:
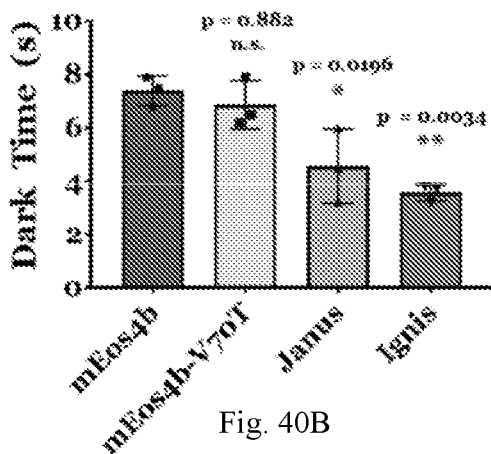
Figure 40C:
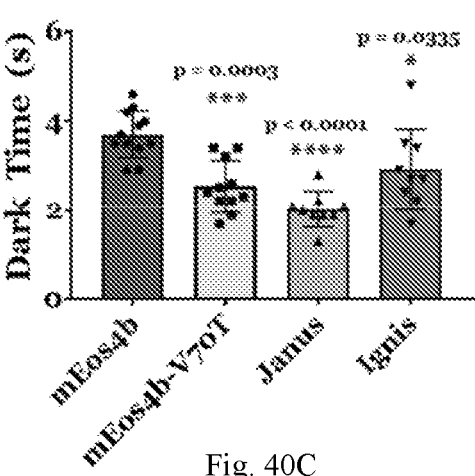
Figure 40D:
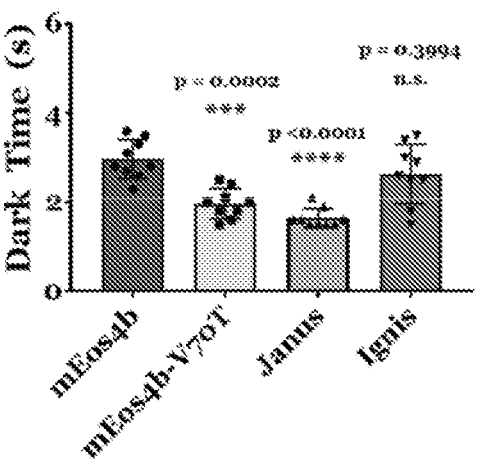
Figures 41C, 41D:
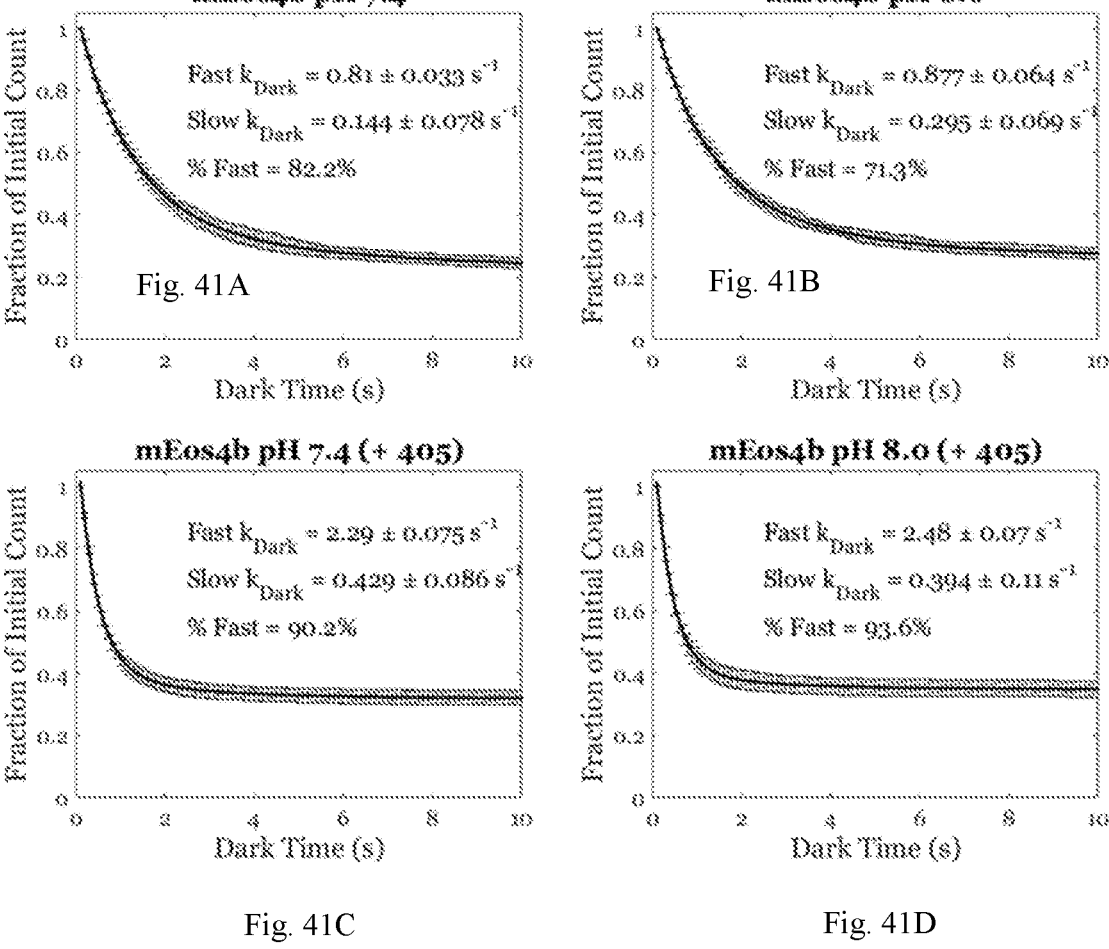

At pH 7.4, mEos4b shows an average on time of ~0.14 seconds ($k_{on}$=7.06±0.80 s$^{-1}$, error reported as 95% confidence interval). In the presence of 405 nm light, $k_{on}$ was fit to a lower value of 6.27±0.19 s$^{-1}$ (FIG. 40A, C). Consistent with prior results, 405 nm light increased the off-time return rate, $k_{rm}$, from 0.715±0.0018 s$^{-1}$ to 1.9±0.038 s$^{-1}$ (FIG. 40B, D). At pH 8.0, the on-time decay rates were 7.59±0.94 s$^{-1}$ (without 405 nm light) and 6.21±0.0.16 s$^{-1}$ (with 405 nm light, yielding average on times of 0.13 and 0.16 seconds, respectively (FIG. 41A, C). At both pH values examined, the on-time decay was mostly described by dark state transition rate, $k_d$, which reflects the large number of blinks per mEos4b molecule. The corresponding off-time distributions indicated return rates of 0.705±0.0.017 s$^{-1}$ and 2.10±0.052 s$^{-1}$, respectively, highlighting a stronger effect of 405 nm illumination at pH 8.0 (FIG. 41B, D). Average off state dwell times were on the order of 0.47-1.4 seconds.

The on-time distribution of mEos4b-V70T at pH 7.4 indicates an average on-time of ~0.22 seconds ($k_{on}$=4.51±0.34 s$^{-1}$)—about 63% of the value of mEos4b under the same conditions. Unlike mEos4b, 405 nm light increased the $k_{on}$ of mEos4b-V70T (6.01±0.19 s$^{-1}$), such that the average on time was reduced to ~0.17 seconds. Given the lower blinking rate of mEosb-V70T, most of the on-time decay is attributable to the photobleaching rate, $k_b$, which was substantially increased by 405 nm irradiation.

In the absence of 405 nm light, the dark state return rate of mEos4b-V70T was 0.893±0.036 s$^{-1}$, and this increased to 2.07±0.026 s$^{-1}$ with 405 nm irradiation (FIG. 42B, D). The $k_{on}$ values of mEos4b-V70T at pH 8.0 similar under 405 illumination, at 4.93±0.85 s$^{-1}$ and 4.61±0.25 s$^{-1}$ (FIG. 43A, C). The $k_{rm}$ of mEos4b-V70T was reduced to 0.567±0.030 s$^{-1}$ at pH 8.0, and 405 nm light raised this to 1.88±0.043 s$^{-1}$ (FIG. 43B, D). Across the measured conditions, the dark state return rates translate to average dark state dwell times of 0.48-1.76 seconds (with shorter values under 405 nm irradiation). It is noted that despite their different blinking propensities, mEos4b and mEos4b-V70T share similarly long dark state dwell times absent 405 nm light.

Figures 44A, 44B, 44C, 44D:
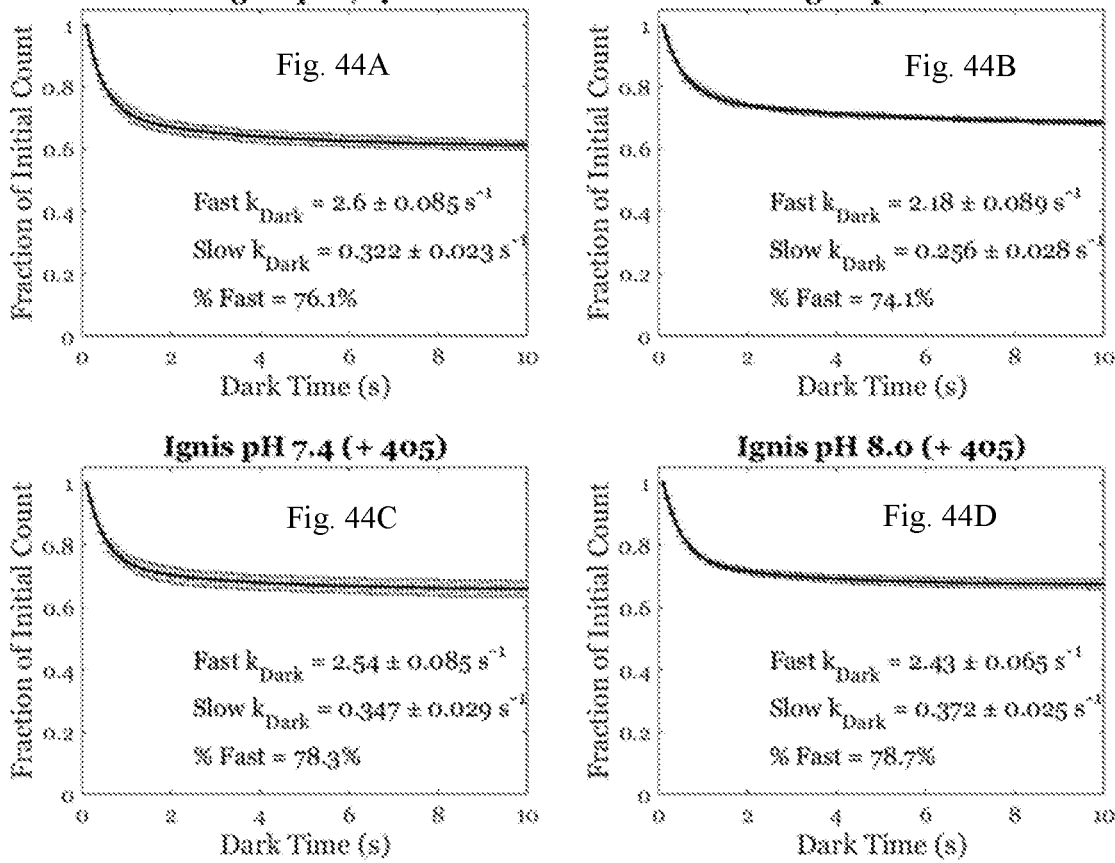
FIGS. 44A-D show Ignis molecule counts vs. dark time ($T_D$). Plots of total Ignis molecule counts vs. $T_D$ (normalized to the count at $T_D$=0), with biphasic exponential fit (black curve) and fit parameters.
Figures 45A, 45B:
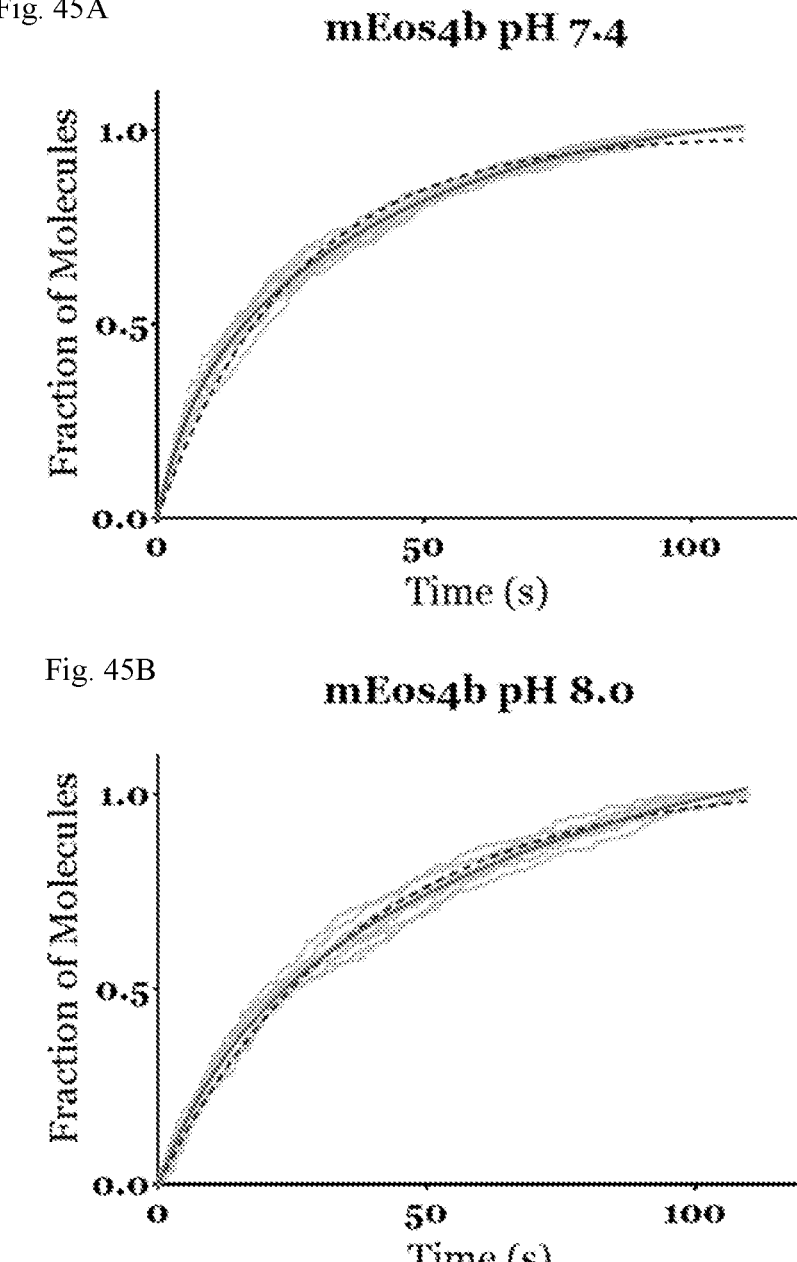
FIGS. 45A-B show the single molecule photoconversion of mEos4b. Cumulative single molecule photoconversion curves for mEos4b, along with monophasic exponential association model (blue dashed curve) and biphasic association model (red curve). Individual experiments are plotted in grey.

Janus exhibited intermediate pH 7.4 on times with a $k_{on}$ of 5.61±0.53 s$^{-1}$. Unlike mEos4b-V70T, $k_{on}$ was lower with concurrent 405 nm illumination, at 4.88±0.29 s$^{-1}$ (FIG. 44A, C). Janus off-time distributions indicated faster basal dark state recovery than either mEos4b or mEos4b-V70T (FIGS. 44B, D, and 45B, D), with shorter average dark state dwell times of 0.68-0.73 seconds. With moderate intensity 405 nm irradiation, the recovery rates rose to 2.08±0.033 (pH 7.4) and 1.89±0.044 s$^{-1}$, with average dark state dwell times of 0.48-0.52 seconds, in line with mEos4b and mEos4b-V70T.

Figures 46A, 46B:
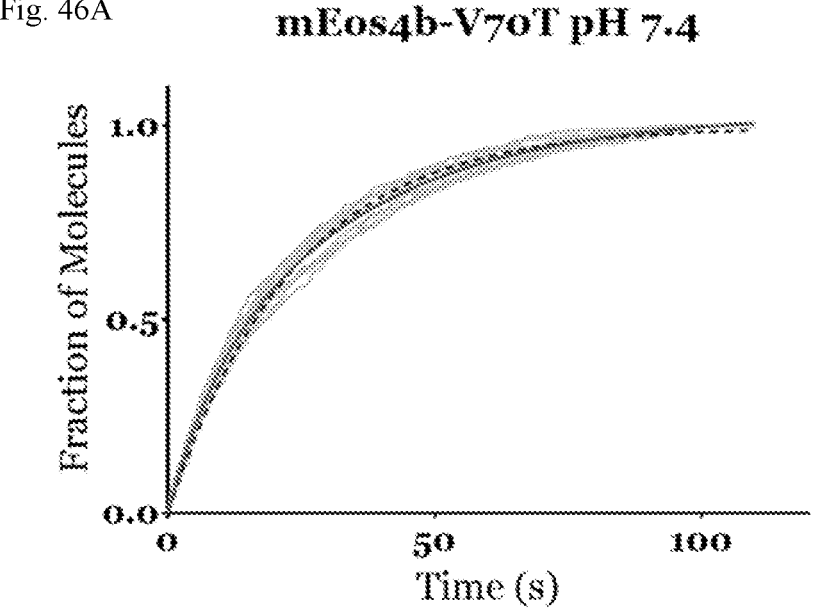
FIGS. 46A-B show the single molecule photoconversion of mEos4b-V70T. Cumulative single molecule photoconversion curves for mEos4b-V70T, along with monophasic exponential association model (blue dashed curve) and biphasic association model (red curve). Individual experiments are plotted in grey.
Figures 47A, 47B:
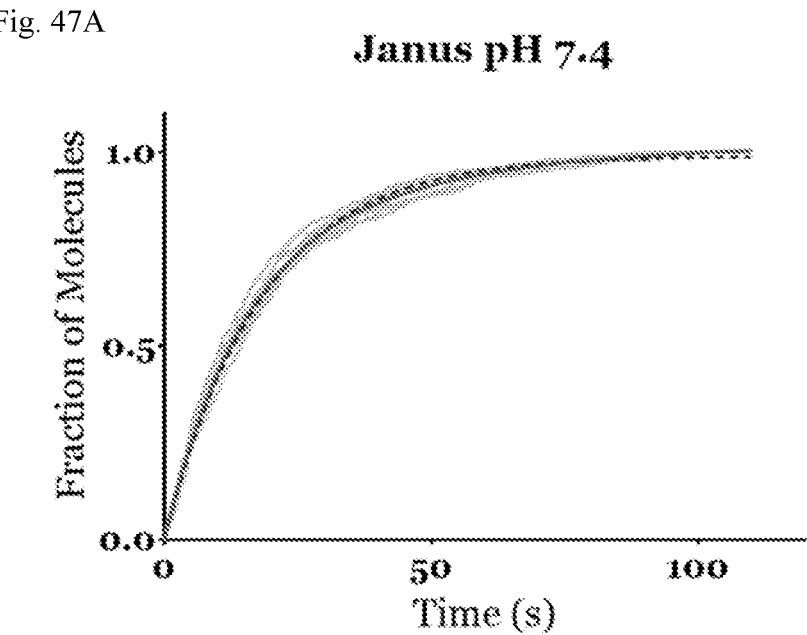
FIGS. 47A-B show the single molecule photoconversion of Janus. Cumulative single molecule photoconversion curves for Janus, along with monophasic exponential association model (blue dashed curve) and biphasic association model (red curve). Individual experiments are plotted in grey.

Ignis on times at pH 7.4 were the shortest of the four proteins tested, with $k_{on}$ values fit to 8.57±0.52 s$^{-1}$ and 8.51±0.60 s$^{-1}$ in the absence and presence of 405 nm illumination, respectively (FIG. 46A, C). At pH 8.0, $k_{on}$ was fit to 7.15±0.38 s$^{-1}$ and this was relatively unchanged by concurrent 405 nm illumination (FIG. 47A, C).

Given its low blinking rate, the on state decay rates of Ignis are mostly described by the bleaching rate, $k_b$, which were the highest of the tested PC-FPs regardless of pH or illumination scheme. Off-time distributions generally revealed return rates between 1.86±0.046 and 2.24±0.037 s$^{-1}$. Like other PC-FPs examined, these rates were slightly lower at pH 8.0, but insensitive to 405 nm laser light (FIGS. 46B, D and 47B, D).

Spatio-Temporal Grouping and Dark Time, $T_D$. Overcounting due to photoblinking can be corrected by grouping together temporally distinct, but spatially adjacent emissions that originate from the same molecule (e.g. "spatio-temporal grouping"). In the case of a single PC-FP (or obligate monomer fused to a PC-FP) this is relatively simple, because the emissions within close spatial proximity to the initial emission may be assumed to arise from the same molecule. In this case, accurate grouping requires knowledge of the average spread between sub-pixel localizations (usually about 45-90 nm), because the localized emission events may be grouped together within this distance regardless of the temporal gap between their appearances in the experiment. However, when multiple molecules occupy the same space within the resolution of a PALM experiment, one cannot assume that every emission originates from the same molecule. Hence, grouping of nearby emissions across the entire time course of an experiment will result in under-counting by merging emissions that actually originate from independent molecules.

PALM experiments separate the emissions of spatially overlapping molecules in the temporal dimension, so it should be possible to discriminate between molecules that photoactivate/photoconvert at different time points if the rate of photoactivation of new molecules occurs on a larger time scale than the duration of a molecule's photoblinking period. This raises the question of how much "dark" time ($T_D$) must elapse between sequential (spatially overlapping) emissions in a PALM experiment before the next emission can be confidently assigned as the first emission of a new, independent molecule.

Figures 48A, 48B:
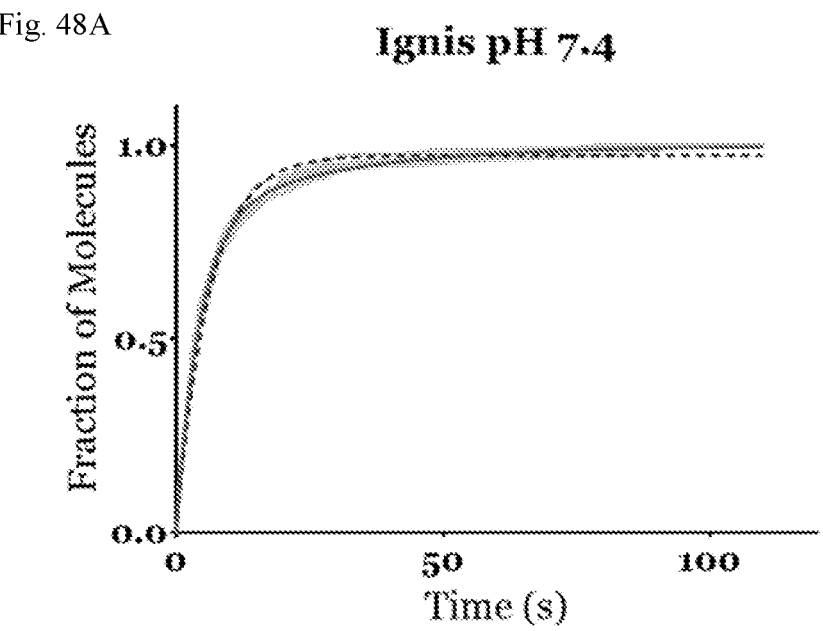
FIGS. 48A-B show the single molecule photoconversion of Ignis. Cumulative single molecule photoconversion curves for Ignis, along with monophasic exponential association model (blue dashed curve) and biphasic association model (red curve). Individual experiments are plotted in grey.
Figures 54A, 54B, 54C, 54E, 54F:
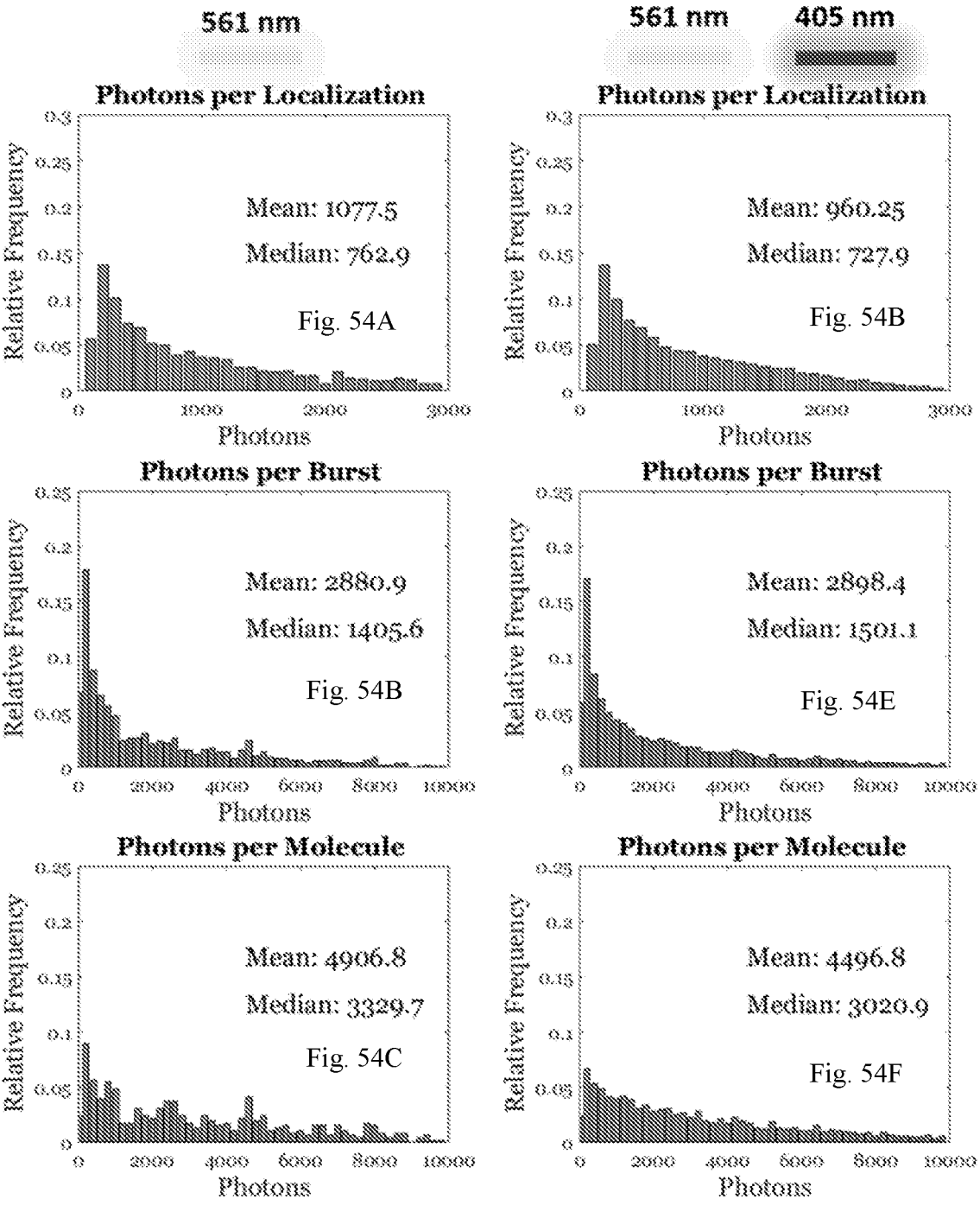

This question can be examined empirically by measuring how the number of ungrouped localizations decays with increasing values of $T_D$. With no dark time, every continuous burst of fluorescence is counted as an independent molecule. As $T_D$ is increased, the number of estimated molecules decreases as more emissions are grouped together (FIG. 48A). On average, an appropriate $T_D$ should link together temporal emissions from a single molecule and accommodate a range of potential dark state dwell times. It was found that most PC-FPs decay asymptotically within $T_D$ values of ten seconds or less (FIG. 48B), though the magnitude of normalized decay varies by protein (consistent with blinking rates). To quantify the gross effect of varying $T_D$ values in mEos4b and its derivatives, we measured the $T_D$ where normalized counts decayed to within 95% of this asymptotic ten second value. It was surprising to find that both mEos4b and mEos4b-V70T exhibit similarly long 95% dark times in the absence of 405 nm light (FIG. 49A, B). At pH 7.4, these values were 8.10±0.36 seconds for mEos4b and 7.53±0.74 seconds for mEos4b-V70T (mean±standard deviation). The values were slightly lower at pH 8.0, at 7.40±0.56 seconds for mEos4b and 6.87±0.91 seconds for mEos4b-V70T. This similarity is unexpected given the 2.3-2.6× larger dark state return rate constants ($k_{rm}$) obtained for mEos4b-V70T vs. mEos4b.

The 95% dark times of Janus and Ignis at pH 7.4 and pH 8.0 are significantly shorter than those of mEos4b and mEos4b-V70T. Janus required 4.8±0.70 seconds of dark time at pH 7.4, and 4.57±1.4 seconds of dark time at pH 8.0. Ignis required 3.66±0.15 seconds and 3.57±0.32 seconds of dark time at pH 7.4 and pH 8.0, respectively. This is consistent with both the lower blinking and the faster dark state return rates of Janus and Ignis vs. mEos4b. The longer 95% dark time required by mEos4b-V70T absent 405 nm light relates to its slower dark state return rates and longer dark state dwell times than Janus or Ignis (1.2-1.76 vs. 0.45-0.73 seconds, respectively).

In response to 405 nm light, 95% dark times were reduced for mEos4b, meos4b-V70T and Janus. At pH 7.4 and 8.0, mEos4b was reduced from 8.1±0.36 sec and 7.4±0.56 sec to 3.7±0.53 sec and 3.67±0.15 sec, respectively. Likewise, mEos4b-V70T transitioned from 7.53±0.74 sec and 6.87±0.91 sec to 2.53±0.58 sec and 1.97±0.33 sec. Janus required the shortest $T_D$ values with 405 illumination at 2.02±0.39 sec and 1.64±0.21 sec. In contrast, Ignis resembled mEos4b, particularly at pH 8.0 though the data were much more variable (FIG. 49C, D). Importantly, the 95% dark time did not substantially change for Ignis upon 405 illumination at either pH 7.4 (3.67±0.15 sec vs. 2.922±0.90 sec, p=0.1259) or pH 8.0 (3.57±0.32 s vs. 2.63±0.67 s, p=0.1920) using a one-way ANOVA with Sidak test for multiple comparisons. It is noted that the 95% dark times of Janus under 405 nm illumination were consistently smaller than those of mEos4b-V70T (p=0.0192 and 0.0270 by two-tailed unpaired t-test), though the statistical significance of these differences is eliminated by correction for multiple comparisons in the one-way ANOVA analysis, which compared the measurements at greater risk of type II error.

The unexpected divergence between mEos4b/mEos4b-V70T and Janus/Ignis dark times prompted the shapes of $T_D$ decay curves to be examined for each PC-FP. Overall, the curves were well fit by biphasic exponential decay models and revealed the contributions of both fast and slow decay rates. The magnitude of contribution by the slow rate was suppressed by 405 nm laser illumination for the probes tested except Ignis (which remained unchanged), such that the fast decay rate dominated the decay profiles ("% Fast" in FIGS. 50-53). Both the fast and slow decay rate constants of mEos4b-V70T $T_D$ curves were lower than those of Janus and Ignis, and the fractional contribution of the fast decay rate was greater for Janus and Ignus at pH 7.4 and pH 8.0. In the presence of moderate-intensity 405 nm photoconversion light, fast dark time decay rate constants were larger and notably similar for mEos4b, mEos4b-V70T, and Janus.

Photoconversion Kinetics of mEos4b Derivatives. As described herein, the photoconversion of mEos4b and its engineered derivatives were monitored by the ensemble absorbance or fluorescence intensity of the photoconverted red chromophore. However, measurements of absorption and fluorescence intensity may not directly reveal the molecular photoconversion rate (e.g., how many individual proteins convert from green to red per unit time) without knowledge of the extinction coefficient and quantum yield of the red species being measured. In principle, if photoconversion goes to completion, then the moles of native green species could be neatly related to the moles of resulting red chromophore simply by comparing the extinction coefficients or relative fluorescence yields of each species. However, this is impractical for several reasons highlighted in preceding experiments: (1) The presence of residual green chromophore signal indicates incomplete photoconversion vitro and in cellulo; (2) Excitation maxima (and therefore excitation efficiencies) vary between each PC-FP, which influences fluorescence intensity independent of chromophore content; (3) Photobleaching reduces measured fluorescence intensities; and (4) The red chromophore content reaches a plateau prior to green chromophore depletion. Together these factors complicate the interpretation of photoconversion rates and limit mechanistic insight into the differences observed between each PC-FP.

The substantial improvements in photoconversion contrast and red chromophore accumulation in Janus and Ignis might be explained by improved photoconversion rates at the single molecule level. To this end, the rate at which new red molecules appeared during a PALM experiment was measured. Samples were illuminated first with a 561 nm laser, and then a 405 nm laser at constant power to stimulate photoconversion (Scheme 2, FIG. 32A). The deposition of molecules was carefully developed to guarantee fewer than 1.5 molecules per $\mu m^2$, thereby effectively eliminating overlapping PSFs and allowing unambiguous assignment of emissions to individual molecules. To account for blinking, the initial appearance of a new molecule was counted.

Cumulative single molecule photoconversion plots were fit with mono- and biphasic exponential association models to extract photoconversion rate constants (Thédié, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)) (FIGS. 54-57). Biphasic models with fast and slow rate constants ($k_1$ and $k_2$, respectively) accounted for the data marginally better, but both fits revealed differences in photoconversion kinetics between each PC-FP. Kinetic photoconversion parameters are summarized in Tables 6 and 7.

Figure 57:
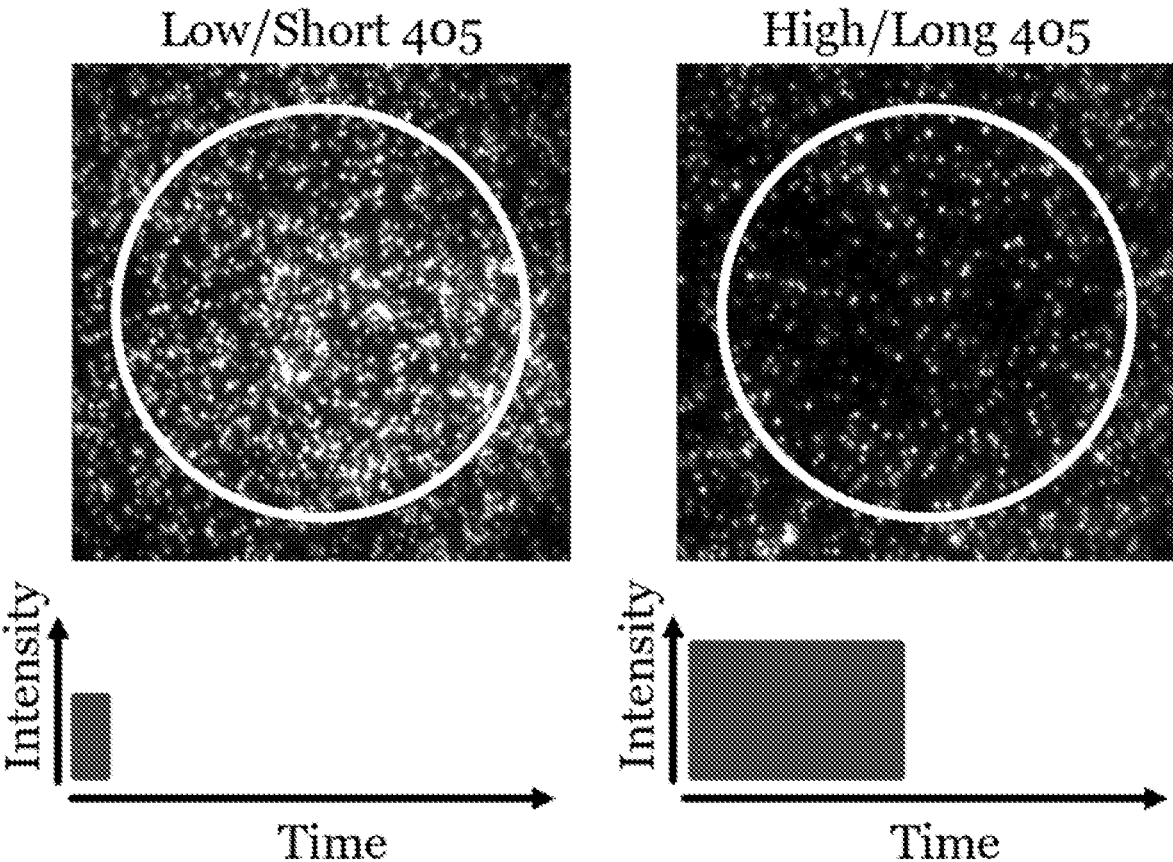
FIG. 57 shows photobleaching by 405 nm irradiation. TIRF micrographs demonstrating the photobleaching of immobilized PC-FPs. Left: Brief, low-intensity 405 nm illumination photoconverts PC-FPs deposited on a clean coverslip within the circular beam profile (inscribed circle). Right: Prolonged higher intensity 405 nm light not only photoconverts but also photobleaches PC-FPs in a similar pattern.

At pH 7.4, the monophasic fits revealed rate constants of $3.865\pm0.017\times10^{-2}$ $s^{-1}$ (mEos4b), $4.250\pm0.014\times10^{-2}$ $s^{-1}$ (mEos4b-V70T), $5.250\pm0.014\times10^{-2}$ $s^{-1}$ (Janus), and $16.21\pm0.08\times10^{-2}$ $s^{-1}$ (Ignis). Since the mutations that produced Janus and Ignis from mEos4b also substantially altered the pKa values of their green and red state chromophores, it was tested whether the solution pH might impact photoconversion kinetics. Since the green state pKa determines the fraction of fluorescent proteins in the neutral, photoconvertible state, it was assessed whether a more alkaline imaging buffer should reduce the rate of photoconversion observed for mEos4b-V70T, Janus, and Ignis, but have less impact on mEos4b since it is almost fully deprotonated at pH 7.4. Monophasic fits indicated rate constants of $2.656\pm0.015\times10^{-2}$ $s^{-1}$ (mEos4b), $2.712\pm0.011\times10's^{-1}$ (mEos4b-V70T), $3.318\pm0.012\times10's^{-1}$ (Janus), and $12.21\pm0.07\times10's^{-1}$ (Ignis). Hence, photoconversion rates were reduced by 31% for mEos4b, 36% for mEos4b-V70T, 37% for Janus and 25% for Ignis pH 8.0 vs. 7.4 (FIGS. 54-57). The cumulative photoconversion curve of mEos4b at pH 7.4 demonstrates a weak "L" bend (FIG. 51A). This suggested the possible contribution of two rate constants, which can be fit with a biphasic exponential model, as previously reported for mEos2 under high-intensity 561 nm illumination (Thédié, D., Berardozzi, R., Adam, V. & Bourgeois, D. Photoswitching of Green mEos2 by Intense 561 nm Light Perturbs Efficient Green-to-Red Photoconversion in Localization Microscopy. *J. Phys. Chem. Lett.* 8, 4424-4430 (2017)). Across the proteins, biphasic fast rate constants were between three and seven times greater than slow rate constants. Unexpectedly, mEos4b exhibits a greater "fast" photoconversion rate constant, $k_1$, than either mEos4b-V70T or Janus (Table 5). In fact, the fast rate constant of Janus was the lowest among these PC-FPs at $0.0696\pm0.001$ $s^{-1}$. However, unlike mEos4b and mEos4b-V70T, Janus photoconversion is mostly accounted for by the fast rate constant (~74%), whereas mEos4b and mEos4b-V70T fast rate constants account for ~24% and ~23% of cumulative photoconversion plots, respectively. Ignis stood out among the four PC-FPs with both the highest $k_1$ ($0.2315\pm0.0008$ $s^{-1}$) and the greatest percent of photoconversion attributed to $k_1$ (~80%), which are consistent with its substantially more rapid photoconversion in vitro. Overall, a larger fraction of mEos4b and mEos4b-V70T molecules photoconvert at the slower rate described by $k_2$ than in Janus and Ignis, which mostly photoconvert at the faster rate described by $k_1$. This is easily seen in the prolonged initial "steep" slope of the Janus and Ignis cumulative photoconversion plots (FIGS. 56A and 57A, respectively). At pH 8.0, the fast mEos4b rate constant, $k_1$, was approximately half that observed at pH 7.4 ($0.0801$ $s^4$ vs. $0.1675$ $s^1$), whereas this constant was modestly different for mEos4b-V70T, Janus and Ignis (FIGS. 55B-57B). However, in each of these proteins the percent of photoconversion attributed to the fast rate constant was reduced. For mEos4b-V70T, $k_1$ accounts for 23% of the cumulative photoconversion at pH 7.4, but ~16% at pH 8.0. For Janus, the effect was more dramatic, with ~13% of photoconversion explained by $k_1$ at pH 8.0, in contrast to ~74% at pH 7.4. Less dramatically, $k_1$ explains ~72% of Ignis photoconversion at pH 8.0, as opposed to ~80% at pH 7.4.

42

TABLE 6

| | Single Molecule Photoconversion Statistics | | | | | |
| --- | --- | --- | --- | --- | --- | --- |
| | Biphasic Exponential Association Model | | | | | |
| | pH 7.4 | | | pH 8.0 | | |
| | $k_1$ (s$^{-1}$) | $k_2$(s$^{-1}$) | % $k_1$ | $k_1$ (s$^{-1}$) | $k_2$(s$^{-1}$) | % $k_1$ |
| mEos4b | 0.1675 ± 0.0023 | 0.0232 ± 0.0001 | 24.23 ± 0.25 | 0.0801 ± 0.0028 | 0.0135 ± 0.0005 | 23.51 ± 0.88 |
| mEos4b-V70T | 0.1191± 0.0037 | 0.0310 ± 0.0004 | 22.65 ± 0.92 | 0.0928 ± 0.0037 | 0.0194 ± 0.0003 | 15.76 ± 0.79 |
| Janus | 0.0696 ± 0.0010 | 0.0222 ± 0.0016 | 74.05 ± 1.91 | 0.07359 ± 0.0099 | 0.0286 ± 0.0009 | 13.71 ± 4.05 |
| Ignis | 0.2315 ± 0.0008 | 0.0381 ± 0.0005 | 79.67 ± 0.21 | 0.1885 ± 0.0016 | 0.0410 ± 0.0008 | 71.83 ± 0.56 |
| | Monophasic Exponential Association Model | | | | | |
| | pH 7.4 | | | pH 8.0 | | |
| | $k_{PC}$(s$^{-1}$) | Green OH | Red O- | $k_{PC}$ (s$^{-1}$) | Green OH | Red O- |
| mEos4b | 0.0387 ± 0.0002 | 1.56 | 97.86 | 0.0266 ± 0.0002 | 0.36 | 99.45 |
| mEos4b-V70T | 0.0425 ± 0.0001 | 39.23 | 73.36 | 0.0271 ± 0.0001 | 13.95 | 91.64 |
| Janus | 0.0547 ± 0.0001 | 59.66 | 86.32 | 0.0332 ± 0.0001 | 27.09 | 96.17 |
| Ignis | 0.1621 ± 0.0008 | 93.94 | 82.71 | 0.1221 ± 0.0007 | 79.55 | 95.01 |

Photon Yields of mEos4b Derivatives. The single-molecule photon yield of a PC-FP is a major determinant of its utility in PALM, since localization uncertainty is inversely proportional to the photons detected per molecule. Therefore, the single molecule photon yields of mEos4b, mEos4b-V70T, Janus and Ignis were analyzed under the same pH and laser illumination schemes described herein. The analysis was stratified into three categories: (1) photons per frame/localization; (2) photons per burst (for emissions spanning multiple consecutive frames); and (3) photons per molecule (the sum of the emissions per blinking molecule).

Histograms of the analyzed molecules along with the median and mean photon yields of each distribution to central tendency and skew of the data are summarized in Table 7. Generally, the order of photon yields was mEos4b>Janus>mEos4b-V70T>Ignis. The median (and mean) photon yield per mEos4b localization was 909.07 (mean: 1274.2) at pH 7.4, and slightly reduced to 762.71 (mean: 1131.2) in the presence of 405 nm light (FIG. 58A, D). At pH 8.0, photon yields were modestly higher at 977.53 (mean: 1352 photons per burst, but again lower in the presence of 405 nm laser illumination. When "bursts" of continuous emissions were analyzed, the mean photon yield was approximately twice as large, consistent with the bulk of on-times being between 0.1-0.5 seconds (1-5 frames, FIG. 40-41). The distribution of photons per molecule are 3-4× higher, again consistent with an average number of continuous emissions of 2.3-3.7 per molecule (the mean number of blinks+1, see, Table 4), depending on the pH and illumination condition analyzed. As previously reported for mEos2, the distribution of molecular photon yields exhibits a long tail toward higher values (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)).

TABLE 7

| | Photons per Localization | | | | Photons per Burst | | | | Photons per Molecule | | | |
|---|---|---|---|---|---|---|---|---|---|---|---|---|
| | pH 7.4 | | pH 8.0 | | pH 7.4 | | pH 8.0 | | pH 7.4 | | pH 8.0 | |
| | (−405) | (+ 405) | (−405) | (+ 405) | (−405) | (+ 405) | (−405) | (+ 405) | (−405) | (+ 405) | (−405) | (+ 405) |
| mEos4b | 909.07 | 762.71 | 977.53 | 667.74 | 1530.9 | 1183.2 | 1548.9 | 1076.9 | 7687.1 | 4769.4 | 6261 | 4181.3 |
| | (1274.2) | (1131.2) | (1352) | (1075.4) | (2442.5) | (2625) | (2533.7) | (2518.8) | (11037) | (8405.2) | (9929.1) | (7435.6) |
| mEos4b-V7OT | 545.89 | 513.63 | 788.85 | 597.71 | 1089 | 804.33 | 1424.9 | 1053.5 | 2712.4 | 2660.5 | 3138.4 | 2582.7 |
| | (731.52) | (686.72) | (989.48) | (806.2) | (2139.9) | (1864.1) | (2553.3) | (2238.4) | (4600.1) | (4062) | (4757.8) | (4294) |
| Janus | 753.67 | 621.51 | 762.9 | 727.9 | 1262.7 | 1231.3 | 1405.5 | 1501.1 | 2872.2 | 2929 | 3329.7 | 3020.9 |
| | (930.3) | (826.25) | (1077.5) | (960.25) | (2553.9) | (2501.6) | (2880.9) | (2898.4) | (4319) | (4225.2) | (4906.8) | (4496.8) |
| | 402.72 | 413.48 | 501.09 | 476.66 | 579.22 | 595.25 | 803.77 | 762.46 | 1128.3 | 997.62 | 1374.1 | 1292.8 |
| Ignis | (528.27) | (540.04) | (657.31) | (639.07) | (1141.4) | (1115.7) | (1489.9) | (1379.3) | (1978.8) | (1735.1) | (2289.4) | (2104.2) | mEos4b-V70T was consistently about 60% as bright as mEos4b on a per-frame basis, in agreement with the reportedly reduced photon yields in Dendra2 and mEos2-A69T vs. mEos2 and Dendra2-T69 Å (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). However, when shifted into pH 8.0 buffer, the mean photon yield was increased by about 35% and the median by 31%. The median photon yield per burst at pH 7.4 was about 70% that of mEos4b (1089 photons), and the mean was nearly 88% of mEos4b at 2139.9 photons per burst. Excitingly, the photon yield per burst at pH 8.0 were close to mEos4b. Unfortunately, like mEos4b, mEos4b-V70T showed a noticeable loss in photon yields upon concurrent illumination with 405 nm light. Interestingly, the median photon yields were much more affected by 405 nm light at pH 8.0 than pH 7.4, as could be clearly seen in the shape the distribution of photons per localization.

Janus provided brighter single frame localizations than mEos4b-V70T at pH 7.4, with a median of 753.67 and a mean of 930.30 photons, while still being dimmer than mEos4b. Bursts were also brighter with a median 1262.7 and a mean 2553.9 photons, while molecular brightness was comparable to mEos4b-V70T. It is noted that these results are consistent with the slightly lower blinking probability of Janus vs. mEos4b-V70T and indicate that its similar molecular photon budget is delivered in a fewer number of brighter emission events. At pH 8.0, the median photon yields of Janus and mEos4b-V70T were similar at the level of localizations (762 vs. 788.85 photons) and bursts (1405.6 vs. 1424.9 photons), though the mean photon yields were modestly larger for Janus in each case (1077.50 vs. 989.48 and 2880.9 vs. 2553.3)—suggesting a greater skew toward bright localizations and bursts among Janus molecules.

One of the most remarkable findings of this study is that Janus retains its per burst and per molecule photon yields in the presence of 405 nm illumination, whereas both mEos4b and mEos4b-V70T exhibit substantial reductions in photon yields with 405 nm light. Although the numbers of photons per localization were modestly reduced, the per burst and per molecule photon yields were steady or even slightly increased upon 405 illumination. In fact, Janus molecules were, on average, as bright or brighter than mEos4b molecules at both pH 7.4 and 8.0 under concurrent illumination with 561 nm and 405 nm light.

Ignis is unambiguously dimmer than mEos4b, mEos4b-V70T and Janus. At pH 7.4 and pH 8.0, photon yields per localization were about half as large as mEos4b (localization means: 528.27 and 657.31, localization medians: 402.72 and 501.09). Photon yield per burst and per molecule were similarly about half that of mEos4b. Ignis was maximally bright at pH 8.0 with median brightness of 803 photons per molecule (median: 1489.9). Like Janus, the photon yields of Ignis were resilient to concurrent 405 nm laser illumination, despite be substantially lower overall.

Discussion. This work represents the first thorough single molecule characterization of mEos4b and its derivatives, and therefore provides an important reference point for applications that employ these probes in cellulo. This is important because, as a class, fixation-resistant PC-FPs stand to significantly improve ultrastructural analysis in applications such as correlative light and electron microscopy (CLEM) and tomography, where photophysical information may become important for proper experimental design and interpretation of ultrastructural information. Additionally, the photophysical analyses here provide insight into the residue-specific effects of substitutions that enhance photoconversion contrast and performance of each PC-FP in ensemble applications.

Blinking Propensity of mEos4b Derivatives. Blinking distributions rank Janus as the lowest-blinking PC-FP analyzed, offering 5-10% lower probability of blinking than mEos4b-V70T and ~50% lower than mEos4b.

The low intrinsic photoblinking of Janus immediately suggests utility in single molecule counting experiments, since the degree of overcounting is inherently lower than many other PC-FPs (in fact, PA-mCherry is known to achieve a comparably low blinking rate under similar conditions (Baldering, T. N. et al. Synthetic and genetic dimers as quantification ruler for single-molecule counting with PALM. *Mol. Biol. Cell* mbcE18100661 (2019))). This contention is supported by the analyses of molecule count vs. $T_D$ for each protein, which found overcounting to be routinely lower for Janus than mEos4b or mEos4b-V70T, and similar to Ignis. These results further revealed that moderate intensity 405 nm light reduces photoblinking and the 95% dark time for each PC-FP. This has important consequences for quantitation, since the intensity of 405 nm light is gradually increased in most in cellulo PALM experiments in order to maintain a steady photoconversion/photoactivation rate (Betzig, E. et al. Imaging intracellular fluorescent proteins at nanometer resolution. *Science* 313, 1642-1645 (2006)); (Fricke, F., Beaudouin, J., Eils, R. & Heilemann, M. One, two or three? Probing the stoichiometry of membrane proteins by single-molecule localization microscopy. *Sci. Rep.* 5, 14072 (2015)); and (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441

(2012)). If 405 nm light reduces photoblinking and dark time requirements, then one might expect that molecules activated later in a PALM experiment (where 405 nm intensity is higher) will blink less than molecules activated earlier in the imaging sequence and require less dark time for accurate spatio-temporal grouping.

An unexpected result of these experiments was that mEos4b-V70T required longer 95% dark time than Janus and Ignis in the absence of 405 nm light. This is surprising given its lower blinking propensity since the most well-characterized low-blinking PC-FP, Dendra2, requires short merging intervals (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)). However, this result is adequately explained by the low dark state recovery rate of mEos4b-V70T, $k_{rm}$, which resembles that of mEos4b. The 95% dark time result reveals a clear distinction between Met41-containing PC-FPs (mEos4b and mEos4b-V70T), and Ile41 PC-FPs (Janus and Ignis) when imaged independently under green (561 nm) laser light vs. concurrently with green and violet (405 nm) wavelengths.

Photokinetics of mEos4b Derivatives. Single molecule data were generally compatible with the simple kinetic model in FIG. 39B. On-time distributions were characteristically mono-exponential. Generally, the presence of Thr70 appears to enhance photobleaching of the red chromophore, as evidenced by the higher $k_b$ values of mEos4b-V70T, Janus, and Ignis (Table 6). It is noted that consistency with the results of Berardozzi et al., who showed that the analogous A69T mutation increased photobleaching quantum yields in mEos2 (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). The results herein show that 405 nm illumination apparently accentuates this effect at pH 7.4 for mEos4b-V70T, as $k_b$ increased from 3.12 to 4.27 s$^{-1}$ in the presence of 405 nm light. This may partially explain the poor photoconversion contrast of mEos4b-V70T in cellulo, despite a predicted improvement over mEos4b by virtue of its elevated green state pKa. The 405 nm photoconversion pulses used to generate red chromophores may also bleach the protein in live cells and contribute to a premature plateau in red fluorescence. On this note, PC-FPs are susceptible to 405 nm-mediated photobleaching even in the absence of concurrent 561 nm excitation (FIG. 66).

Off-time distributions were principally mono-exponential and did not support the contribution of two dark states with independent return rates ($k_{r1}$ and $k_{r2}$), in agreement with work from Avilov and colleagues on Dendra2 (Avilov, S. et al. In cellulo Evaluation of Phototransformation Quantum Yields in Fluorescent Proteins Used As Markers for Single-Molecule Localization Microscopy. *PLoS ONE* 9, (2014)). However, these results differ from at least three prior studies that examined dark state transitions in Kaede-like PC-FPs (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012))(Annibale, P., Scarselli, M., Kodiyan, A. & Radenovic, A. Photoactivatable Fluorescent Protein mEos2 Displays Repeated Photoactivation after a Long-Lived Dark State in the Red Photoconverted Form. *J. Phys. Chem. Lett.* 1, 1506-1510 (2010)); and (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). In these prior reports, PC-FP off-time distributions were fit to biphasic exponential decay models, indicating clear contributions of both fast and slow rates of return to the red fluorescent state. How may these discrepancies between studies be explained? First, it is possible that the red chromophores of mEos2 and mEos4b (or its derivatives) are photophysically distinct due to inherent variations in their chromophore environments.

However, given the otherwise similar behaviors of mEos2 and mEos4b—including blinking distributions characterized in this work and bulk fluorescence characteristics reported by others (Paez Segala, M. G. et al. Fixation-resistant photoactivatable fluorescent proteins for correlative light and electron microscopy. *Nat. Methods* 12, 215-218 (2015)); and (Turkowyd Bartosz et al. A General Mechanism of Photoconversion of Green-to-Red Fluorescent Proteins Based on Blue and Infrared Light Reduces Phototoxicity in Live-Cell Single-Molecule Imaging. *Angew. Chem. Int. Ed.* 56, 11634-11639 (2017))—this possibility seems relatively unsupported. Instead, the experimental design and instrumentation (particularly the illumination schemes and detection methods employed) are considered to be likely sources of variation between off time distributions. The present work utilized a 561 nm power density of ~0.5 kW/cm$^2$ and a 10 Hz frame rate (100 ms integration time). In contrast, the power densities in studies where mEos2 or Dendra2 showed biphasic off-time distributions varied between 0.25-4 kW/cm$^2$ (most >1 kW/cm$^2$), and were recorded at 33.3-20 Hz (30-50 ms integration times). Available evidence indicates that the short time constant of mEos2 ($1/k_{r1}$) is inversely related to 561 nm laser intensity (though less is known about the impact of 561 nm intensity on the slow return rate) (Annibale, P., Scarselli, M., Kodiyan, A. & Radenovic, A. Photoactivatable Fluorescent Protein mEos2 Displays Repeated Photoactivation after a Long-Lived Dark State in the Red Photoconverted Form. *J. Phys. Chem. Lett.* 1, 1506-1510 (2010)). Speculatively, the lower 561 nm laser intensity and slower frame rates described herein might not adequately resolve $k_{r1}$ from the slow state, $k_{r2}$. However, Avilov et al. utilized an even shorter integration time of 30 ms and still observed mono-exponential behavior, though they employed substantially higher 561 nm intensities (5-7 kW/cm$^2$) (Avilov, S. et al. In cellulo Evaluation of Phototransformation Quantum Yields in Fluorescent Proteins Used As Markers for Single-Molecule Localization Microscopy. *PLoS ONE* 9, (2014)). Although short dark states might ostensibly become vanishingly short under such intense excitation, the source of this discrepancy is unclear and requires further study of photokinetics under a variety of frame rates and illumination schemes. Nonetheless, despite the lack of a fast dark state recovery component ($k_{r1}$) in the data, the mono-exponential recovery rates are remarkably similar to the slow $k_{r2}$ values reported by others (between 0.4 and 1.6 for mEos2 and Dendra2, respectively) (Lee, S.-H., Shin, J. Y., Lee, A. & Bustamante, C. Counting single photoactivatable fluorescent molecules by photoactivated localization microscopy (PALM). *Proc. Natl. Acad. Sci. U.S.A.* 109, 17436-17441 (2012)); and (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)). By comparison, the $k_{rm}$ values were between 0.567 and 2.22 s$^{-1}$. Ultimately, although the short-lived dark state and fast recovery rate are of biophysical interest, the long-lived dark state and slow recovery rate described by $k_{r2}$ or $k_{rm}$ is most relevant to the analysis of PALM data as it influences the selection of an appropriate M.

Photoconversion Rates. The examination of PC-FP photoconversion with PALM provides a highly controlled, direct measurement of molecular photoconversion rate independent of molecular brightness and photobleaching effects. The results point to two principle conclusions: First, the overall order of photoconversion rates was Ignis>Janus>mEos4b-V70T>mEos4b. Although the data were generally well-described by single exponential association models ($R^2$>0.96), it was clear that single rate constants under-estimated the initial photoconversion rate in several experiments. This led to the observation that, when explained as the result of fast and slow rate constants, mEos4b and mEos4b-V70T photoconversion is mostly attributed to a slower rate constant, whereas a fast photoconversion rate dominates for both Janus and Ignis. The second principle conclusion is that unlike in ensemble photoconversion experiments, the molecular photoconversion rate of each PC-FP tracks more closely with green chromophore pKa (though not proportionally). This is further substantiated by the observation that single molecule photoconversion rates were decreased at pH 8.0 vs. pH 7.4. It is interesting to note that despite the increased photoconversion rate of mEos4b-V70T relative to mEos4b, it still does not exhibit greater photoconversion contrast in cells. This stands in contrast to Dendra2, which has a similar green pKa (Fron, E. et al. Revealing the Excited-State Dynamics of the Fluorescent Protein Dendra2. *J. Phys. Chem. B* 117, 2300-2313 (2013)); and (Adam, V., Nienhaus, K., Bourgeois, D. & Nienhaus, G. U. Structural basis of enhanced photoconversion yield in green fluorescent protein-like protein Dendra2. *Biochemistry* 48, 4905-4915 (2009)). Overall this challenges the assumption that green pKa and photoconversion rate are principle determinants of photoconversion contrast, supporting involvement of other factors.

Photon Statistics. mEos4b has the largest per-molecule photon budget of PC-FPs examined herein. However, this can be misleading in the context of PALM, as the per-frame photon count is the principle determinant of localization precision and most of the photons generated per mEos4b molecule originate from blinking events after initial emissions. An ideal PALM probe for quantitative localization microscopy would deliver a high photon budget per localization, and blink infrequently. With this in mind, it is noted that Ignis is likely a poor PALM probe despite its low blinking rate due to its low brightness per frame and apparently high sensitivity to photobleaching. If the model of Berardozzi et al. is correct, and photobleaching pathways compete with photoblinking pathways (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)), then a sufficiently high photobleaching rate will fundamentally limit photon yield of PC-FPs. This may explain the low brightness of Ignis relative to the other PC-FPs tested.

In contrast to Ignis, Janus offers a low-blinking and bright PC-FP with several attractive trends in its photon statistics. Most notably, Janus maintains overall high photon yields per localization and per burst at pH 7.4 (in contrast to mEos4b-V70T), and nearly matches the photon yields of mEos4b when imaged at pH 8.0. Janus and mEos4b-V70T were similarly brightened at pH 8.0—presumably the result of a shift toward greater occupation of the anionic chromophore state. More importantly, Janus does not produce substantially fewer photons in response to moderate intensity 405 nm illumination at pH 8.0, unlike both mEos4b-V70T and mEos4b. In fact, at pH 8.0, Janus was the overall brightest PC-FP in the presence of 405 nm light, despite having the lowest blinking probability. This strongly supports the use of Janus as a PALM probe at pH 8.0, as blinking is minimized by continuous 405 nm illumination while photon yield and localization precision are both improved.

The Influence of Residues 70, 41, and 197 on mEos4b Photophysics. These single molecule data provide a strong means for understanding the roles of three residues in photophysical behaviors of mEos4b derivatives. Compared to mEos4b, the successive incorporation of V70T, M41I, and I197M substantially altered blinking, on/off state kinetics, photoconversion kinetics and photon statistics of each PC-FP examined. Consistent with the results of Berardozzi et al., the results described herein indicate that Thr70 shifts the dominant dark state transition pathway from photoblinking ($k_d$) and toward photobleaching ($k_b$) while simultaneously increasing the rate of 405-mediated photoconversion ($k_{PC}$). The effect on photoconversion rate is likely the result of an increased green pKa and larger fraction of neutral chromophore. Consistently, the photoconversion rate of mEos4b-V70T was substantially reduced at pH 8.0 vs. pH 7.4 (FIG. 55, Table 6).

Unlike the effects of Thr70, the impact(s) of Met41Ile and Ile197Met in Janus and Ignis are more nuanced at the single molecule level. The clearest result of the M41I substitution is an increased dark state recovery rate in the absence of 405 nm light. This is distinct from V70T, which appears to principally limit entry to the dark state (and therefore photo-blinking). Instead, M41I appears to antagonize occupation of the dark state. This effect can be clearly seen in the off-time distributions and 1.6-2.4× larger dark state recovery rates ($k_{rm}$) of Janus vs. mEos4b-V70T (FIGS. 42B-45B, Table 5). Notably, the dark state transition rate constant ($k_d$) of Janus is also lower than mEos4b-V70T in every condition tested, suggesting a modest additional impact on dark state entry. How does the data for mEos4b-V70T compare to those of Berardozzi et al., who compared slow dark state recovery rates in the nearest PC-FP analogue, mEos2-A69T? Unfortunately, slow dark state recovery rates were reported in the presence of 3 W/cm² 405 light, so no direct comparison of basal dark state recovery can be made. However, their reported rate in the presence of 405 nm light was 1.4±1.6 s⁻¹ (their Table 1) (Berardozzi, R., Adam, V., Martins, A. & Bourgeois, D. Arginine 66 Controls Dark-State Formation in Green-to-Red Photoconvertible Fluorescent Proteins. *J. Am. Chem. Soc.* 138, 558-565 (2016)), in reasonable agreement with the measurement of 1.88-2.07 s⁻¹ for mEos4b-V70T. It is noted that Berardozzi and colleagues did observe slower dark state recovery rates (below 1 s⁻¹) for mEos2 in the absence of 405 light (their Figure S8), and it is predicted that a similar value might be observed for mEos2-A69T. Met41Ile and I197M also appear to impinge upon photobleaching properties of the red chromophore in addition to their documented effects on chromophore pKa described herein. Although photobleaching rates need to be directly measured and compared to the fit-derived rate constants, it is currently postulated that 405 nm photobleaching occurs in both the presence and the absence of 561 nm light, and that Janus is more resistant than mEo4b or mEos4b-V70T to putative 405 nm photobleaching. In contrast, Ignis is apparently sensitized to photobleaching by 561 nm light but not 405 nm light. Hence, the contributions of 405 nm and 561 nm mediated photobleaching should be considered independently. These differences ascribe functional roles to the residues targeted in the engineering effort. Overall, these suggestions are supported by at least three lines of evidence: (1) the kinetic data and photon yields demonstrating differential effects of 561 nm and 405 nm illumination on Janus and Ignis vs. mEos4b-V70T; (2) the wide-field and confocal photoconversion results compared to Dendra2; and (3) literature evidence implicating chromophore proximal methionine residues in oxidative photobleaching processes.

First, examination of the $k_{on}$ fits indicate trends suggestive of independent effects of 561 nm and 405 nm irradiation on the photokinetics of mEos4b derivatives, and these appear to relate neatly to single-residue substitutions. In the absence of 405 nm light, trends in $k_{on}$ are mainly the result of 561 nm light mediated photobleaching and dark state transitions (though residual photodamage from 405 nm pre-illumination should be considered, according to Scheme 1 in FIG. 32A). At pH 8.0, PC-FPs with Met41 exhibit a slight positive change in $k_{on}$. In contrast, PC-FPs with Ile41 show a clear reduction in $k_{on}$. This cannot be due to 405 nm effects, and the majority of the $k_{on}$ shift in each case is ascribed to $k_b$, indicating that Met41 and Ile41 containing proteins have different, pH-dependent sensitivities to 561 nm illumination. The additional Ile197Met substitution in Ignis sensitizes the chromophore even further to 561 nm mediated photobleaching. However, Met197 does not appear to increase sensitivity of $k_b$ to 405 nm light. Even more remarkably, 405 nm light appreciably reduces the photon yields of both mEos4b and mEos4b-V70T while sparing those of Ignis and Janus. This appears compatible with the shortened on-times and larger $k_b$ of mEos4b-V70T under 405 nm irradiation at pH 7.4. Likewise, 405 nm light increased $k_b$ in mEos4b, despite slightly longer on-times due to concomitantly smaller $k_d$ and larger $k_{rm}$. Overall, the photon yield and kinetic data support different effects of 561 and 405 nm light on PC-FPs with Met41 (mEos4b and mEos4b-V70T) vs. those engineered with Ile41 (Janus and Ignis).

Secondly, the single molecule results should also be considered alongside the in cellulo widefield and confocal photoconversion experiments described herein. Based on its enhanced photoconversion rate and presence of Thr70, it is expected that mEos4b-V70T will perform similarly to Dendra2. Indeed, the protein exhibits several photochemical similarities to Dendra2, including its absorbance spectrum, a hypsochromic shift in its excitation and emission spectra relative to mEos4b, and a low blinking rate. Nonetheless, mEos4b-V70T demonstrates poor photoconversion contrast much like its parent molecule, mEos4b. This is likely due to the presence of Met41 in mEos4b-V70T, because the analogous residue in Dendra2 is not a methionine, but rather alanine (Ala45, see FIG. 13). In Janus, replacement of Met41 with Ile41 simultaneously increased green pKa (from 7.21 to 7.57), decreased red pKa (from 6.96 to 6.60), increased the basal dark state recovery rate ($k_{rm}$), and apparently spared photon yields under concurrent 561/405 nm laser illumination, so its improved performance relative to mEos4b-V70T reflects, in part, a sum of these effects. The specific single molecule impact of Met41 could be further explored by introducing its equivalent into Dendra2. It is predicted that this hypothetical PC-FP, Dendra2-A45M, should have similarly poor photoconversion contrast to mEos4b-V70T, and a slow dark state return rate in the absence of 405 nm light. Conversely, it is also predicted that mEos4b-M41I should exhibit faster dark state recovery times in the absence of 405 light, though this may be difficult to test given this derivative's apparently poor maturation (see, FIG. 19). Nonetheless, mEos4b does form chromophore, so despite its poor ensemble maturation, this variant may yet be amenable to single molecule measurements.

Third, the presence or absence of chromophore-proximal methionine residues may have consequences compatible with the observations disclosed herein. The data permit two points of comparison, as methionine residues were removed and introduced on opposite sides of the mEos4b chromophore (Met41Ile in Janus, and Ile197Met in Ignis). Met41Ile "unlocked" greater photoconversion contrast in Janus vs. mEos4b-V70T, whereas addition of Met197 to generate Ignis from Janus resulted in a dimmer protein with 1.4-1.7× greater $k_b$, indicative of rapid photobleaching. Although at first these results seem unrelated, they may be different manifestations of similar phenomena involving oxidative modification of methionine residues (Met41 in mEos4b and mEos4b-V70T, and Met197 in Ignis). Studies by Duan and coworkers of the EosFP derivative, IrisFP, suggest that sulfur-containing residues (methionine, cysteine) contribute to photobleaching of the chromophore through oxidative modifications at low illumination intensities $\leq 10$ W/cm$^2$ (commonly used for ensemble excitation and also PALM photoconversion) (Duan, C. et al. Structural Evidence for a Two-Regime Photobleaching Mechanism in a Reversibly Switchable Fluorescent Protein. *J. Am. Chem. Soc.* 135, 15841-15850 (2013)); and (Duan, C. et al. Rational design of enhanced photoresistance in a photoswitchable fluorescent protein. *Methods Appl. Fluoresc.* 3, 014004 (2015)). In IrisFP, the side chains of Met159 and Cys171 are photo-oxidized to sulfoxides, and this provokes several conformational changes in the chromophore pocket that ultimately lock the chromophore in a non-fluorescent, neutral state with characteristic absorbance peak at 385 nm (Duan, C. et al. Structural Evidence for a Two-Regime Photobleaching Mechanism in a Reversibly Switchable Fluorescent Protein. *J. Am. Chem. Soc.* 135, 15841-15850 (2013)). Notably, photobleaching of IrisFP was performed with 405 nm and 488 nm lasers, and green-to-red photoconversion was evident in the crystal structures as negative electron density between Phe61 and His62 (Reference 242, their FIGS. 2C and S12). Hence, their photobleached "green" states may also provide a glimpse into the photobleached red state of Kaede-like PC-FPs mediated by higher energy 488 and 405 nm light. In this regard, mass spectra revealed oxidation of the Met41 analogue, Met40, in IrisFP, though the consequences of Met40 oxidation are unknown. It is tempting to speculate that photo-oxidation of Met41 during 405 or 488 nm illumination limits photoconversion of mEos4b and mEos4b-V70T, and that this is avoided in Janus by virtue of the M41I substitution. The unambiguous impact of I197M on photobleaching of Ignis highlights the relevance of chromophore-proximal methionines in PC-FP performance.

In summary the single molecule examination of mEos4b derivatives revealed surprising characteristics of high contrast PC-FPs, Janus and Ignis, which may be attributed to reciprocal methionine-isoleucine substitutions at positions 41 and 197 of mEos4b. Among the PC-FPs tested, these data support the use of Janus as a PALM probe due to its robust photon yields (even in the presence of 405 nm light), rapid photoconversion rate, low photoblinking propensity, and rapid dark state recovery rate.

What is claimed is:

1. A photoconvertible fluorescent protein comprising the amino acid sequence as set forth in SEQ ID NO: 2 or SEQ ID NO: 3.

2. The photoconvertible fluorescent protein of claim 1, wherein the amino acid sequence of SEQ ID NO: 2 is red at an excitation maximum at 571 mm.

3. The photoconvertible fluorescent protein of claim 1, wherein the amino acid sequence of SEQ ID NO: 2 is red at an emission maximum at 585 nm.

4. The photoconvertible fluorescent protein of claim 1, wherein the amino acid sequence of SEQ ID NO: 3 has an absorbance of UV/violet light around 385 nm.

5. The photoconvertible fluorescent protein of claim 1, wherein the protein is in a circularly-permutated form.

6. The photoconvertible fluorescent protein of claim 5, wherein the photoconvertible fluorescent protein is divided at residue 74 and 75, such that the N- and C-termini of the photoconvertible fluorescent protein are relocated.

7. The photoconvertible fluorescent protein of claim 5, wherein the circularly-permutated form is a photocleavable tag.

8. A method for analyzing a physiologically active substance in a cell, comprising attaching the physiological substance to the photoconvertible fluorescent protein of claim 1, expressing the attached photoconvertible fluorescent protein in the cell and observing the fluorescence of the protein.

9. A method of performing live cell imaging, wherein the photoconvertible fluorescent protein claim 1 is expressed in the cell and the cell is then subjected to imaging.

10. The method of claim 8, wherein the physiologically active substance is a protein or a vector.

11. The method of claim 8, comprising analyzing localization or dynamic situation of a protein in the cell that is attached to photoconvertible fluorescent protein.

12. A method of identifying and localizing an individual fluorescent molecule, wherein the fluorescent molecule is one or more of the photoconvertible fluorescent proteins of claim 1 and wherein said one or more photoconvertible fluorescent proteins is subjected to fluorescent imaging.

13. The method of claim 12, wherein the method comprises photo-activated localization microscopy or stochastic optical reconstruction microscopy.

* * * * *

SEQUENCE LISTING

<160> NUMBER OF SEQ ID NOS: 35

<210> SEQ ID NO 1
<211> LENGTH: 227
<212> TYPE: PRT
<213> ORGANISM: Artificial Sequence
<220> FEATURE:
<223> OTHER INFORMATION: Synthetic construct

<400> SEQUENCE: 1

```
Met Val Ser Ala Ile Lys Pro Asp Met Arg Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe His Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Leu Thr Phe
                85                  90                  95

Glu Asp Gly Gly Ile Cys Asn Ala Arg Asn Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Ile Glu Met
145                 150                 155                 160

Ala Leu Leu Leu Glu Gly Asn Ala His Tyr Arg Cys Asp Phe Arg Thr
                165                 170                 175

Thr Tyr Lys Ala Lys Glu Lys Gly Val Lys Leu Pro Gly Ala His Phe
            180                 185                 190

Val Asp His Ala Ile Glu Ile Leu Ser His Asp Lys Asp Tyr Asn Lys
        195                 200                 205

Val Lys Leu Tyr Glu His Ala Val Ala His Ser Gly Leu Pro Asp Asn
    210                 215                 220

Ala Arg Arg
225
```

<210> SEQ ID NO 2
<211> LENGTH: 227
<212> TYPE: PRT
<213> ORGANISM: Artificial Sequence
<220> FEATURE:
<223> OTHER INFORMATION: Synthetic construct

<400> SEQUENCE: 2

```
Met Val Ser Ala Ile Lys Pro Asp Met Arg Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Ile Asp Leu Glu Val Lys Glu Gly
            35                  40                  45

Gly Pro Leu Pro Phe Ala Phe Asp Ile Leu Thr Thr Ala Phe His Tyr
        50                  55                  60
```

-continued

```
Gly Asn Arg Val Phe Thr Lys Tyr Pro Asp Asn Ile Gln Asp Tyr Phe
65                  70                  75                  80

Lys Gln Ser Phe Pro Lys Gly Tyr Ser Trp Glu Arg Ser Leu Thr Phe
                85                  90                  95

Glu Asp Gly Gly Ile Cys Asn Ala Arg Asn Asp Ile Thr Met Glu Gly
            100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Thr Gly Asp Ile Glu Met
145                 150                 155                 160

Ala Leu Leu Leu Glu Gly Asn Ala His Tyr Arg Cys Asp Phe Arg Thr
                165                 170                 175

Thr Tyr Lys Ala Lys Glu Lys Gly Val Lys Leu Pro Gly Ala His Phe
            180                 185                 190

Val Asp His Ala Ile Glu Ile Leu Ser His Asp Lys Asp Tyr Asn Lys
            195                 200                 205

Val Lys Leu Tyr Glu His Ala Val Ala His Ser Gly Leu Pro Asp Asn
        210                 215                 220

Ala Arg Arg
225

<210> SEQ ID NO 3
<211> LENGTH: 227
<212> TYPE: PRT
<213> ORGANISM: Artificial Sequence
<220> FEATURE:
<223> OTHER INFORMATION: Synthetic construct

<400> SEQUENCE: 3

Met Val Ser Ala Ile Lys Pro Asp Met Arg Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Ile Asp Leu Glu Val Lys Glu Gly
            35                  40                  45

Gly Pro Leu Pro Phe Ala Phe Asp Ile Leu Thr Thr Ala Phe His Tyr
        50                  55                  60

Gly Asn Arg Val Phe Thr Lys Tyr Pro Asp Asn Ile Gln Asp Tyr Phe
65                  70                  75                  80

Lys Gln Ser Phe Pro Lys Gly Tyr Ser Trp Glu Arg Ser Leu Thr Phe
                85                  90                  95

Glu Asp Gly Gly Ile Cys Asn Ala Arg Asn Asp Ile Thr Met Glu Gly
            100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Thr Gly Asp Ile Glu Met
145                 150                 155                 160

Ala Leu Leu Leu Glu Gly Asn Ala His Tyr Arg Cys Asp Phe Arg Thr
                165                 170                 175

Thr Tyr Lys Ala Lys Glu Lys Gly Val Lys Leu Pro Gly Ala His Phe
            180                 185                 190
```

```
Val Asp His Ala Met Glu Ile Leu Ser His Asp Lys Asp Tyr Asn Lys
        195                 200                 205

Val Lys Leu Tyr Glu His Ala Val Ala His Ser Gly Leu Pro Asp Asn
    210                 215                 220

Ala Arg Arg
225
```

<210> SEQ ID NO 4
<211> LENGTH: 52
<212> TYPE: PRT
<213> ORGANISM: Artificial Sequence
<220> FEATURE:
<223> OTHER INFORMATION: Synthetic construct

<400> SEQUENCE: 4

```
Met Val Ser Ala Ile Lys Pro Asp Met Arg Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro
    50
```

<210> SEQ ID NO 5
<211> LENGTH: 51
<212> TYPE: PRT
<213> ORGANISM: Artificial Sequence
<220> FEATURE:
<223> OTHER INFORMATION: Synthetic construct

<400> SEQUENCE: 5

```
Met Ser Ala Ile Lys Pro Asp Met Lys Ile Lys Leu Arg Met Glu Gly
1               5                   10                  15

Asn Val Asn Gly His His Phe Val Ile Asp Gly Asp Gly Thr Gly Lys
            20                  25                  30

Pro Phe Glu Gly Lys Gln Ser Met Asp Leu Glu Val Lys Glu Gly Gly
        35                  40                  45

Pro Leu Pro
    50
```

<210> SEQ ID NO 6
<211> LENGTH: 51
<212> TYPE: PRT
<213> ORGANISM: Artificial Sequence
<220> FEATURE:
<223> OTHER INFORMATION: Synthetic construct

<400> SEQUENCE: 6

```
Met Ser Ala Ile Lys Pro Asp Met Lys Ile Lys Leu Arg Met Glu Gly
1               5                   10                  15

Asn Val Asn Gly His His Phe Val Ile Asp Gly Asp Gly Thr Gly Lys
            20                  25                  30

Pro Phe Glu Gly Lys Gln Ser Met Asp Leu Glu Val Lys Glu Gly Gly
        35                  40                  45

Pro Leu Pro
    50
```

<210> SEQ ID NO 7
<211> LENGTH: 56
<212> TYPE: PRT

```
<213> ORGANISM: Artificial Sequence
<220> FEATURE:
<223> OTHER INFORMATION: Synthetic construct

<400> SEQUENCE: 7

Met Asn Thr Pro Gly Ile Asn Leu Ile Lys Glu Asp Met Arg Val Lys
1               5                   10                  15

Val His Met Glu Gly Asn Val Asn Gly His Ala Phe Val Ile Glu Gly
            20                  25                  30

Glu Gly Lys Gly Lys Pro Tyr Glu Gly Thr Gln Thr Ala Asn Leu Thr
        35                  40                  45

Val Lys Glu Gly Ala Pro Leu Pro
    50                  55

<210> SEQ ID NO 8
<211> LENGTH: 60
<212> TYPE: PRT
<213> ORGANISM: Artificial Sequence
<220> FEATURE:
<223> OTHER INFORMATION: Synthetic construct

<400> SEQUENCE: 8

Met Val Ser Lys Gly Glu Glu Thr Ile Met Ser Val Ile Lys Pro Asp
1               5                   10                  15

Met Lys Ile Lys Leu Arg Met Glu Gly Asn Val Asn Cys His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro
    50                  55                  60

<210> SEQ ID NO 9
<211> LENGTH: 60
<212> TYPE: PRT
<213> ORGANISM: Artificial Sequence
<220> FEATURE:
<223> OTHER INFORMATION: Synthetic construct

<400> SEQUENCE: 9

Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro
    50                  55                  60

<210> SEQ ID NO 10
<211> LENGTH: 52
<212> TYPE: PRT
<213> ORGANISM: Artificial Sequence
<220> FEATURE:
<223> OTHER INFORMATION: Synthetic construct

<400> SEQUENCE: 10

Met Val Ser Val Ile Thr Ser Glu Met Lys Ile Glu Leu Arg Met Glu
1               5                   10                  15

Gly Ser Val Asn Gly His Lys Phe Val Ile Thr Gly Lys Gly Ser Gly
            20                  25                  30

Arg Pro Tyr Glu Gly Thr Gln Thr Val Asp Leu Thr Val Ile Glu Gly
```

```
        35              40              45

Gly Pro Leu Pro
    50

<210> SEQ ID NO 11
<211> LENGTH: 60
<212> TYPE: PRT
<213> ORGANISM: Artificial Sequence
<220> FEATURE:
<223> OTHER INFORMATION: Synthetic construct

<400> SEQUENCE: 11

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Val Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro
    50                  55                  60

<210> SEQ ID NO 12
<211> LENGTH: 60
<212> TYPE: PRT
<213> ORGANISM: Artificial Sequence
<220> FEATURE:
<223> OTHER INFORMATION: Synthetic construct

<400> SEQUENCE: 12

Phe Ala Phe Asp Ile Leu Thr Thr Ala Phe His Tyr Gly Asn Arg Val
1               5                   10                  15

Phe Val Lys Tyr Pro Asp Asn Ile Gln Asp Tyr Phe Lys Gln Ser Phe
            20                  25                  30

Pro Lys Gly Tyr Ser Trp Glu Arg Ser Leu Thr Phe Glu Asp Gly Gly
        35                  40                  45

Ile Cys Asn Ala Arg Asn Asp Ile Thr Met Glu Gly
    50                  55                  60

<210> SEQ ID NO 13
<211> LENGTH: 60
<212> TYPE: PRT
<213> ORGANISM: Artificial Sequence
<220> FEATURE:
<223> OTHER INFORMATION: Synthetic construct

<400> SEQUENCE: 13

Phe Ala Phe Asp Ile Leu Thr Thr Ala Phe His Tyr Gly Asn Arg Val
1               5                   10                  15

Phe Ala Lys Tyr Pro Asp Asn Ile Gln Asp Tyr Phe Lys Gln Ser Phe
            20                  25                  30

Pro Lys Gly Tyr Ser Trp Glu Arg Ser Leu Thr Phe Glu Asp Gly Gly
        35                  40                  45

Ile Cys Ile Ala Arg Asn Asp Ile Thr Met Glu Gly
    50                  55                  60

<210> SEQ ID NO 14
<211> LENGTH: 60
<212> TYPE: PRT
<213> ORGANISM: Artificial Sequence
<220> FEATURE:
<223> OTHER INFORMATION: Synthetic construct
```

```
<400> SEQUENCE: 14

Phe Ala Phe Asp Ile Leu Thr Thr Ala Phe His Tyr Gly Asn Arg Val
1               5                   10                  15

Phe Ala Lys Tyr Pro Asp Asn Ile Gln Asp Tyr Phe Lys Gln Ser Phe
            20                  25                  30

Pro Lys Gly Tyr Ser Trp Glu Arg Ser Leu Thr Phe Glu Asp Gly Gly
        35                  40                  45

Ile Cys Asn Ala Arg Asn Asp Ile Thr Met Glu Gly
        50                  55                  60

<210> SEQ ID NO 15
<211> LENGTH: 60
<212> TYPE: PRT
<213> ORGANISM: Artificial Sequence
<220> FEATURE:
<223> OTHER INFORMATION: Synthetic construct

<400> SEQUENCE: 15

Phe Ser Tyr Asp Ile Leu Thr Thr Ala Val His Tyr Gly Asn Arg Val
1               5                   10                  15

Phe Thr Lys Tyr Pro Glu Asp Ile Pro Asp Tyr Phe Lys Gln Ser Phe
            20                  25                  30

Pro Glu Gly Tyr Ser Trp Glu Arg Thr Met Thr Phe Glu Asp Lys Gly
        35                  40                  45

Ile Cys Thr Ile Arg Ser Asp Ile Ser Leu Glu Gly
        50                  55                  60

<210> SEQ ID NO 16
<211> LENGTH: 60
<212> TYPE: PRT
<213> ORGANISM: Artificial Sequence
<220> FEATURE:
<223> OTHER INFORMATION: Synthetic construct

<400> SEQUENCE: 16

Phe Ala Tyr Asp Ile Leu Thr Thr Ala Phe His Tyr Gly Asn Arg Val
1               5                   10                  15

Phe Thr Lys Tyr Pro Glu Asp Ile Pro Asp Tyr Phe Lys Gln Ser Phe
            20                  25                  30

Pro Glu Gly Tyr Ser Trp Glu Arg Ser Met Thr Tyr Glu Asp Gly Gly
        35                  40                  45

Ile Cys Ile Ala Thr Asn Asp Ile Thr Met Glu Glu
        50                  55                  60

<210> SEQ ID NO 17
<211> LENGTH: 60
<212> TYPE: PRT
<213> ORGANISM: Artificial Sequence
<220> FEATURE:
<223> OTHER INFORMATION: Synthetic construct

<400> SEQUENCE: 17

Phe Ala Tyr Asp Ile Leu Thr Thr Ala Phe His Tyr Gly Asn Arg Val
1               5                   10                  15

Phe Thr Lys Tyr Pro Arg Lys Ile Pro Asp Tyr Phe Lys Gln Ser Phe
            20                  25                  30

Pro Glu Gly Tyr Ser Trp Glu Arg Ser Met Thr Tyr Glu Asp Gly Gly
        35                  40                  45

Ile Cys Asn Ala Thr Asn Asp Ile Thr Met Glu Glu
        50                  55                  60
```

-continued

<210> SEQ ID NO 18
<211> LENGTH: 60
<212> TYPE: PRT
<213> ORGANISM: Artificial Sequence
<220> FEATURE:
<223> OTHER INFORMATION: Synthetic construct

<400> SEQUENCE: 18

Phe Ala Phe Asp Ile Leu Thr Thr Ala Phe His Tyr Gly Asn Arg Val
1               5                   10                  15

Phe Val Glu Tyr Pro Glu Glu Ile Val Asp Tyr Phe Lys Gln Leu Phe
                20                  25                  30

Pro Glu Gly Tyr Ser Trp Glu Arg Ser Met Ser Tyr Glu Asp Gly Gly
            35                  40                  45

Ile Cys Leu Ala Thr Asn Asn Ile Thr Met Lys Lys
        50                  55                  60

<210> SEQ ID NO 19
<211> LENGTH: 60
<212> TYPE: PRT
<213> ORGANISM: Artificial Sequence
<220> FEATURE:
<223> OTHER INFORMATION: Synthetic construct

<400> SEQUENCE: 19

Phe Thr Trp Asp Ile Leu Ser Pro Gln Phe Met Tyr Gly Ser Asn Ala
1               5                   10                  15

Tyr Val Lys His Pro Ala Asp Ile Pro Asp Tyr Phe Lys Leu Ser Phe
                20                  25                  30

Pro Glu Gly Phe Lys Trp Glu Arg Val Met Lys Phe Glu Asp Gly Gly
            35                  40                  45

Val Val Thr Val Thr Gln Asp Ser Ser Leu Gln Asp
        50                  55                  60

<210> SEQ ID NO 20
<211> LENGTH: 56
<212> TYPE: PRT
<213> ORGANISM: Artificial Sequence
<220> FEATURE:
<223> OTHER INFORMATION: Synthetic construct

<400> SEQUENCE: 20

Thr Phe Tyr Asn Lys Val Arg Phe Tyr Gly Thr Asn Phe Pro Ala Asn
1               5                   10                  15

Gly Pro Val Met Gln Lys Lys Thr Asp Arg Trp Glu Pro Ser Thr Glu
                20                  25                  30

Lys Met Tyr Val Arg Asp Gly Val Leu Thr Gly Asp Ile Glu Met Ala
            35                  40                  45

Leu Leu Leu Glu Gly Asn Ala His
        50                  55

<210> SEQ ID NO 21
<211> LENGTH: 56
<212> TYPE: PRT
<213> ORGANISM: Artificial Sequence
<220> FEATURE:
<223> OTHER INFORMATION: Synthetic construct

<400> SEQUENCE: 21

Thr Phe Tyr Asn Lys Val Arg Phe Tyr Gly Thr Asn Phe Pro Ala Asn
1               5                   10                  15

```
Gly Pro Val Met Gln Lys Lys Thr Leu Lys Trp Glu Pro Ser Thr Glu
            20                  25                  30

Lys Met Tyr Val Arg Asp Gly Val Leu Thr Gly Asp Ile His Met Ala
        35                  40                  45

Leu Leu Leu Glu Gly Asn Ala His
    50                  55
```

```
<210> SEQ ID NO 22
<211> LENGTH: 56
<212> TYPE: PRT
<213> ORGANISM: Artificial Sequence
<220> FEATURE:
<223> OTHER INFORMATION: Synthetic construct

<400> SEQUENCE: 22

Thr Phe Tyr Asn Lys Val Arg Phe Tyr Gly Thr Asn Phe Pro Ala Asn
1               5                   10                  15

Gly Pro Val Met Gln Lys Lys Thr Leu Lys Trp Glu Pro Ser Thr Glu
            20                  25                  30

Lys Met Tyr Val Arg Asp Gly Val Leu Thr Gly Asp Ile Glu Met Ala
        35                  40                  45

Leu Leu Leu Glu Gly Asn Ala His
    50                  55
```

```
<210> SEQ ID NO 23
<211> LENGTH: 55
<212> TYPE: PRT
<213> ORGANISM: Artificial Sequence
<220> FEATURE:
<223> OTHER INFORMATION: Synthetic construct

<400> SEQUENCE: 23

Cys Phe Gln Asn Val Arg Phe Lys Gly Thr Asn Phe Pro Pro Asn Gly
1               5                   10                  15

Pro Val Met Gln Lys Lys Thr Leu Lys Trp Glu Pro Ser Thr Glu Lys
            20                  25                  30

Leu His Val Arg Asp Gly Leu Leu Val Gly Asn Ile Asn Met Ala Leu
        35                  40                  45

Leu Leu Glu Gly Gly Gly His
    50              55
```

```
<210> SEQ ID NO 24
<211> LENGTH: 56
<212> TYPE: PRT
<213> ORGANISM: Artificial Sequence
<220> FEATURE:
<223> OTHER INFORMATION: Synthetic construct

<400> SEQUENCE: 24

Ser Phe Ile Asn Lys Ile His Phe Lys Gly Thr Asn Phe Pro Pro Asn
1               5                   10                  15

Gly Pro Val Met Gln Lys Arg Thr Val Gly Trp Glu Val Ser Thr Glu
            20                  25                  30

Lys Met Tyr Val Arg Asp Gly Val Leu Lys Gly Asp Val Lys Met Lys
        35                  40                  45

Leu Leu Leu Lys Gly Gly Ser Tyr
    50                  55
```

```
<210> SEQ ID NO 25
<211> LENGTH: 56
```

```
<212> TYPE: PRT
<213> ORGANISM: Artificial Sequence
<220> FEATURE:
<223> OTHER INFORMATION: Synthetic construct

<400> SEQUENCE: 25

Ser Phe Ile Asn Lys Ile His Phe Lys Gly Thr Asn Phe Pro Pro Asn
1               5                   10                  15

Gly Pro Val Met Gln Lys Arg Thr Val Gly Trp Glu Val Ser Thr Glu
            20                  25                  30

Lys Met Tyr Val Arg Asp Gly Val Leu Lys Gly Asp Val Lys Met Lys
        35                  40                  45

Leu Leu Leu Lys Gly Gly Ser His
    50                  55

<210> SEQ ID NO 26
<211> LENGTH: 60
<212> TYPE: PRT
<213> ORGANISM: Artificial Sequence
<220> FEATURE:
<223> OTHER INFORMATION: Synthetic construct

<400> SEQUENCE: 26

Asp Gly Ser Asn Thr Phe Val Asn Glu Ile Arg Phe Asp Gly Thr Asn
1               5                   10                  15

Phe Pro Ala Asn Gly Pro Val Met Gln Arg Lys Thr Val Lys Trp Glu
            20                  25                  30

Pro Ser Thr Glu Lys Met Tyr Val Arg Asp Gly Val Leu Lys Gly Asp
        35                  40                  45

Val Glu Met Ala Leu Leu Leu Glu Gly Gly Gly His
    50                  55                  60

<210> SEQ ID NO 27
<211> LENGTH: 56
<212> TYPE: PRT
<213> ORGANISM: Artificial Sequence
<220> FEATURE:
<223> OTHER INFORMATION: Synthetic construct

<400> SEQUENCE: 27

Glu Phe Ile Tyr Lys Val Lys Leu Arg Gly Thr Asn Phe Pro Ser Asp
1               5                   10                  15

Gly Pro Val Met Gln Lys Lys Thr Met Gly Trp Glu Ala Leu Ser Glu
            20                  25                  30

Arg Met Tyr Glu Pro Asp Gly Ala Leu Lys Gly Glu Val Lys Pro Arg
        35                  40                  45

Val Lys Leu Lys Asp Gly Gly His
    50                  55

<210> SEQ ID NO 28
<211> LENGTH: 58
<212> TYPE: PRT
<213> ORGANISM: Artificial Sequence
<220> FEATURE:
<223> OTHER INFORMATION: Synthetic construct

<400> SEQUENCE: 28

Tyr Arg Cys Asp Phe Arg Thr Thr Tyr Lys Ala Lys Glu Lys Gly Val
1               5                   10                  15

Lys Leu Pro Gly Ala His Phe Val Asp His Ala Ile Glu Ile Leu Ser
            20                  25                  30
```

-continued

```
His Asp Lys Asp Tyr Asn Lys Val Lys Leu Tyr Glu His Ala Val Ala
        35                  40                  45

His Ser Gly Leu Pro Asp Asn Ala Arg Arg
    50                  55

<210> SEQ ID NO 29
<211> LENGTH: 58
<212> TYPE: PRT
<213> ORGANISM: Artificial Sequence
<220> FEATURE:
<223> OTHER INFORMATION: Synthetic construct

<400> SEQUENCE: 29

Tyr Arg Cys Asp Phe Arg Thr Thr Tyr Lys Ala Lys Glu Lys Gly Val
1               5                   10                  15

Lys Leu Pro Gly Tyr His Phe Val Asp His Cys Ile Glu Ile Leu Ser
            20                  25                  30

His Asp Lys Asp Tyr Asn Lys Val Lys Leu Tyr Glu His Ala Val Ala
        35                  40                  45

His Ser Gly Leu Pro Asp Asn Ala Arg Arg
    50                  55

<210> SEQ ID NO 30
<211> LENGTH: 58
<212> TYPE: PRT
<213> ORGANISM: Artificial Sequence
<220> FEATURE:
<223> OTHER INFORMATION: Synthetic construct

<400> SEQUENCE: 30

Tyr Arg Cys Asp Phe Arg Thr Thr Tyr Lys Ala Lys Glu Lys Gly Val
1               5                   10                  15

Lys Leu Pro Gly Ala His Phe Val Asp His Cys Ile Glu Ile Leu Ser
            20                  25                  30

His Asp Lys Asp Tyr Asn Lys Val Lys Leu Tyr Glu His Ala Val Ala
        35                  40                  45

His Ser Gly Leu Pro Asp Asn Ala Arg Arg
    50                  55

<210> SEQ ID NO 31
<211> LENGTH: 57
<212> TYPE: PRT
<213> ORGANISM: Artificial Sequence
<220> FEATURE:
<223> OTHER INFORMATION: Synthetic construct

<400> SEQUENCE: 31

Tyr Leu Cys Asp Phe Lys Thr Thr Tyr Lys Ala Lys Lys Val Val Gly
1               5                   10                  15

Leu Pro Asp Ala His Phe Val Asp His Arg Ile Glu Ile Leu Gly Asn
            20                  25                  30

Asp Ser Asp Tyr Asn Lys Val Lys Leu Tyr Glu His Ala Val Ala Arg
        35                  40                  45

Tyr Ser Pro Leu Pro Ser Gln Val Trp
    50                  55

<210> SEQ ID NO 32
<211> LENGTH: 60
<212> TYPE: PRT
<213> ORGANISM: Artificial Sequence
<220> FEATURE:
<223> OTHER INFORMATION: Synthetic construct
```

<400> SEQUENCE: 32

```
Tyr Arg Cys Asp Phe Arg Thr Thr Tyr Lys Val Lys Gln Lys Ala Val
1               5                   10                  15

Lys Leu Pro Asp Tyr His Phe Val Asp His Arg Ile Glu Ile Leu Ser
            20                  25                  30

His Asp Lys Asp Tyr Asn Lys Val Lys Leu Tyr Glu His Ala Val Ala
        35                  40                  45

Arg Asn Ser Thr Glu Ser Met Asp Glu Leu Tyr Lys
    50                  55                  60
```

<210> SEQ ID NO 33
<211> LENGTH: 60
<212> TYPE: PRT
<213> ORGANISM: Artificial Sequence
<220> FEATURE:
<223> OTHER INFORMATION: Synthetic construct

<400> SEQUENCE: 33

```
Tyr Arg Cys Asp Phe Arg Thr Thr Tyr Lys Val Lys Gln Lys Ala Val
1               5                   10                  15

Lys Leu Pro Lys Ala His Phe Val Asp His Arg Ile Glu Ile Leu Ser
            20                  25                  30

His Asp Lys Asp Tyr Asn Lys Val Lys Leu Tyr Glu His Ala Val Ala
        35                  40                  45

Arg Asn Ser Thr Asp Ser Met Asp Glu Leu Tyr Lys
    50                  55                  60
```

<210> SEQ ID NO 34
<211> LENGTH: 59
<212> TYPE: PRT
<213> ORGANISM: Artificial Sequence
<220> FEATURE:
<223> OTHER INFORMATION: Synthetic construct

<400> SEQUENCE: 34

```
Tyr Arg Cys Asp Phe Arg Thr Thr Tyr Lys Ala Lys Lys Val Val Gln
1               5                   10                  15

Leu Pro Asp Tyr His Tyr Val Asp His Gln Met Glu Ile Thr Ser His
            20                  25                  30

Asp Lys Asp Tyr Asn Lys Val Lys Ala Tyr Glu His Ala Lys Ala Tyr
        35                  40                  45

Ser Gly Thr Tyr Arg Gly Ala Lys Tyr Glu Phe
    50                  55
```

<210> SEQ ID NO 35
<211> LENGTH: 59
<212> TYPE: PRT
<213> ORGANISM: Artificial Sequence
<220> FEATURE:
<223> OTHER INFORMATION: Synthetic construct

<400> SEQUENCE: 35

```
Tyr Asp Ala Glu Val Lys Thr Thr Tyr Lys Ala Lys Lys Pro Val Gln
1               5                   10                  15

Leu Pro Gly Ala Tyr Asn Val Asn Arg Lys Leu Asp Ile Thr Ser His
            20                  25                  30
```

-continued

```
Asn Glu Asp Tyr Thr Ile Val Glu Gln Tyr Glu Arg Ala Glu Gly Arg
        35                  40                  45

His Ser Thr Gly Gly Met Asp Glu Leu Tyr Lys
    50                  55
```